US011352601B2

(12) United States Patent
Ding et al.

(10) Patent No.: US 11,352,601 B2
(45) Date of Patent: Jun. 7, 2022

(54) CYANOBACTERIAL HOSTS AND METHODS FOR PRODUCING CHEMICALS

(71) Applicant: University of Florida Research Foundation, Incorporated, Gainesville, FL (US)

(72) Inventors: Yousong Ding, Gainesville, FL (US); Guang Yang, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 16/634,027

(22) PCT Filed: Jul. 27, 2018

(86) PCT No.: PCT/US2018/043993

§ 371 (c)(1),
(2) Date: Jan. 24, 2020

(87) PCT Pub. No.: WO2019/023524

PCT Pub. Date: Jan. 31, 2019

(65) Prior Publication Data

US 2021/0087522 A1 Mar. 25, 2021

Related U.S. Application Data

(60) Provisional application No. 62/611,634, filed on Dec. 29, 2017, provisional application No. 62/537,516, filed on Jul. 27, 2017.

(51) Int. Cl.
*C12N 15/52* (2006.01)
*C12N 1/12* (2006.01)
(Continued)

(52) U.S. Cl.
CPC ................ *C12N 1/12* (2013.01); *C12N 9/12* (2013.01); *C12N 1/125* (2021.05); *C12R 2001/89* (2021.05)

(58) Field of Classification Search
CPC ..................................................... C12N 15/52
See application file for complete search history.

(56) References Cited

U.S. PATENT DOCUMENTS

2007/0220634 A1 9/2007 Metz
2010/0298612 A1 11/2010 Behrouzian et al.

FOREIGN PATENT DOCUMENTS

WO WO 2015/200335 A1 12/2015
WO WO-2015200335 A1 * 12/2015 ........... C12P 7/6409

OTHER PUBLICATIONS

International Search Report and Written Opinion dated Jan. 15, 2019 in connection with PCT/US2018/042993.

* cited by examiner

*Primary Examiner* — Rosanne Kosson
(74) *Attorney, Agent, or Firm* — Wolf, Greenfield & Sacks, P.C.

(57) ABSTRACT

The present invention relates to recombinant cyanobacterial cells for the production of a chemical compound of interest. In particular, the present invention relates to genetic modifications that introduce one or more heterologous phosphopantetheinyl transferases (PPTases) into a cyanobacterial cell. These cells can, optionally, further comprise heterologous carrier protein and nucleic acid constructs that provide the cyanobacterial cells with the capability of producing chemicals of interest or compounds of interest, such secondary metabolites polyketides, nonribosomal peptides and their hybrids, the three major families of bioactive natural
(Continued)

products, of cyanobacteria and other bacterial phyla, secondary metabolites analogs, and unnatural compounds.

14 Claims, 38 Drawing Sheets

Specification includes a Sequence Listing.

(51) Int. Cl.

| | |
|---|---|
| ***C12N 9/12*** | (2006.01) |
| *C12R 1/89* | (2006.01) |

| | FAS | | PKS | | | NRPS | | NRPS/PKS | | | |
|---|---|---|---|---|---|---|---|---|---|---|---|
| | SFACP | AFACP | APACP | ScACP | SsPCP | FNPCP | FisPCP | MACP | APNPCP | FNsACP | AprACP |
| SPPT | 100.0 | 98.8 | 79.3 | 0.0 | 8.3 | 96.1 | 87.8 | 16.1 | 71.6 | 79.2 | 79.3 |
| MPPT | 94.8 | 99.6 | 84.6 | 18.8 | 24.0 | 96.2 | 97.4 | 100.0 | 93.9 | 93.5 | 93.2 |
| SePPT | 99.5 | 94.9 | 11.9 | 0.0 | 0.0 | 30.5 | 47.3 | 0.0 | 0.0 | 43.6 | 11.9 |
| APPT | 99.1 | 100.0 | 100.0 | 64.9 | 28.8 | 75.4 | 100.0 | 89.7 | 100.0 | 100.0 | 100.0 |
| AvPPT | 98.3 | 98.7 | 22.0 | 28.5 | 32.8 | 81.9 | 93.7 | 88.5 | 98.8 | 94.5 | 93.7 |
| FPPT | 96.1 | 94.5 | 10.1 | 0.0 | 29.0 | 100.0 | 78.5 | 0.0 | 0.0 | 91.0 | 89.9 |
| Sfp | 98.6 | 96.2 | 98.0 | 100.0 | 100.0 | 82.8 | 25.1 | 97.1 | 53.3 | 92.9 | 99.6 |

FIGURE 3

| Accession Number | Gene name/locus tag | Organisms | Length (aa) |
|---|---|---|---|
| ABA22212.1 | PPTase[a] | *Anabaena variabilis ATCC 29413* | 237 |
| WP_044522635.1 | PPTase | *Nostoc sp. PCC 7120* | 237 |
| WP_004163140.1 | PPTase | *Microcystis aeruginosa NIES-843* | 220 |
| ABB57835.1 | HetI protein-like | *Synechococcus elongatus PCC 7942* | 259 |
| WP_012307697.1 | PPTase | *Synechococcus sp. PCC 7002* | 227 |
| WP_010873553.1 | PPTase | *Synechocystis sp. PCC 6803* | 246 |
| WP_017309026.1 | PPTase | *Fischerella sp. PCC 9339* | 240 |
| ACG68433.1 | Sfp | *Bacillus subtilis* | 224 |
| WP_009782852.1 | PPTase | *Lyngbya sp. PCC 8106* | 239 |
| WP_026092908.1 | PPTase | *Calothrix sp. PCC 7103* | 241 |
| WP_016950943.1 | PPTase | *Anabaena sp. PCC 7108* | 240 |
| AAW67221.1 | PPTase | *Nodularia spumigena NSOR10* | 239 |
| WP_015186867.1 | PPTase | *Gloeocapsa sp. PCC 7428* | 253 |
| EHJ11403.1 | PPTase | *Crocosphaera watsonii WH 0003* | 248 |
| WP_006529694.1 | PPTase | *Gloeocapsa sp. PCC 73106* | 242 |
| WP_051044566.1 | hypothetical protein | *Pleurocapsa sp. PCC 7319* | 243 |
| WP_006511535.1 | PPTase | *Xenococcus sp. PCC 7305* | 255 |
| BAU66329.1 | PPTase | *Stanieria sp. NIES-3757* | 250 |
| WP_017660318.1 | hypothetical protein | *Geitlerinema sp. PCC 7105* | 226 |
| CUR17315.1 | PPTase | *Planktothrix sp. PCC 11201* | 249 |
| WP_015112227.1 | PPTase | *Nostoc sp. PCC 7107* | 243 |
| SCY12562.1 | PPTase | *Nitrosospira sp. Nsp13* | 246 |
| WP_017306450.1 | PPTase | *Spirulina subsalsa* | 235 |
| WP_029633554.1 | hypothetical protein | *Scytonema hofmanni UTEX B 1581* | 235 |
| OCQ99688.1 | PPTase | *Oscillatoriales cyanobacterium USR001* | 254 |
| WP_057178475.1 | PPTase | *Cylindrospermopsis sp. CR12* | 240 |
| WP_041933312.1 | PPTase | *Cyanothece sp. PCC 7822* | 240 |
| WP_054469188.1 | hypothetical protein | *Planktothricoides sp. SR001* | 247 |
| WP_059000742.1 | hypothetical protein | *Leptolyngbya sp. NIES-2104* | 235 |
| WP_015127290.1 | PPTase | *Calothrix sp. PCC 7507* | 234 |
| ZP_00107102.1 | PPTase | *Nostoc punctiforme PCC 73102* | 239 |
| ACN96032.1 | holo-acyl-carrier-protein | *Fischerella sp. MV11* | 128 |
| WP_015181769.1 | PPTase | *Microcoleus sp. PCC 7113* | 139 |
| AFY89096.1 | PPTase | *Chroococcidiopsis thermalis PCC 7203* | 137 |
| WP_006519439.1 | holo-ACP synthase | *Leptolyngbya sp. PCC 7375* | 129 |
| NP_926954.1 | ACP synthase | *Gloeobacter violaceus PCC 7421* | 132 |
| AFY65439.1 | holo-acyl-carrier-protein | *Geitlerinema sp. PCC 7407* | 148 |
| WP_006634204.1 | holo-ACP synthase | *Microcoleus vaginatus* | 157 |
| WP_015187908.1 | holo-ACP synthase | *Gloeocapsa sp. PCC 7428* | 129 |
| BAL39319.1 | holo-acyl-carrier-protein | *Escherichia coli str. K-12 substr. MDS42* | 126 |
| AAH75207.1 | MGC84206 protein | *Xenopus laevis* | 302 |
| XP_040785.1 | PPTase | *Homo sapiens* | 309 |
| AGP54231.1 | PPTase | *Streptomyces rapamycinicus NRRL 5491* | 247 |

[a]: PPTase is an abbreviation of 4'-phosphopantetheinyl transferase.

FIGURE 9

| CPs | Strains | Metabolites | Biosynthetic pathway | Apo-form MW | Holo-form MW | | GenBank accession number |
|---|---|---|---|---|---|---|---|
| | | | | | Calculated | Observed | |
| SFACP | *Synechocystis* sp. PCC6803 | Fatty acid | FAS | 9655.69 | 9995.69 | 9997.78 | ssl2084 |
| AFACP | *Anabaena* sp. PCC7120 | Fatty acid | FAS | 10282.20 | 10622.20 | 10622.65 | WP_010997493.1 |
| APACP | *Anabaena* sp. PCC7120 | Glycolipid | PKS | 10804.09 | 11144.09 | 11012.84[a] | WP_010999481.1 |
| APNPCP | *Anabaena* sp. PCC7120 | Unknown | NRPS/PKS | 12115.69 | 12455.69 | 12455.54 | WP_010996791.1 |
| FNPCP | *Fischerella* sp. PCC9339 | Unknown | NRPS | 10699.21 | 11039.21 | 10908.39[a] | WP_017308667.1 |
| FisPCP | *Fischerella* sp. PCC9339 | Shinorine | NRPS | 12475.06 | 12815.06 | 12683.13[a] | WP_017312907.1 |
| FNsACP | *Fischerella* sp. PCC9339 | Unknown[b] | NRPS/PKS | 15215.20 | 15555.20 | 15422.01[a] | WP_017308557.1 |
| AprACP | *Moorea bouillonii* | Apratoxin | NRPS/PKS | 10693.38 | 11033.38 | 11035.41 | ctg1_8[c] |
| MACP | *Microcystis aeruginosa* NIES843 | Unknown | NRPS/PKS | 11106.54 | 11446.54 | 11314.81[a] | WP_012265828.1 |
| ScACP | *Streptomyces coelicolor* A(3)2 | Concanamycin | PKS | 11186.50 | 11526.50 | 11526.67 | WP_011030786.1 |
| SsPCP | *Streptomyces scabiei* 87.22 | Thaxtomin | PKS | 8240.44 | 8580.44 | 8580.49 | CBG75339.1 |

[a]Values corresponded to the proteins without the *N*-terminal *methionine residue*; [b]FNsACP is a homolog of NdaC from *Nodularia spumigena* NSOR10; [c]gene sequence is provided in the supporting information.

FIGURE 10

| PPTase | CPs | | | | | | | | | | |
|---|---|---|---|---|---|---|---|---|---|---|---|
| | SFACP | AFACP | APNPCP | FNPCP | FisPCP | AprACP | APACP | MACP | FNsACP | ScACP | SsPCP |
| APPT | 99.1 ± 1.1 | 100 ± 2.0 | 100 ± 1.4 | 75.4 ± 2.9 | 100 ± 1.5 | 100 ± 1.4 | 100 ± 1.6 | 89.7 ± 3.9 | 100 ± 1.4 | 64.9 ± 3.1 | 28.8 ± 3.8 |
| AvPPT | 98.3 ± 2.4 | 98.7 ± 0.6 | 98.6 ± 2.6 | 81.9 ± 1.4 | 93.7 ± 3.2 | 93.7 ± 1.2 | 22 ± 2.3 | 88.5 ± 2.5 | 94.5 ± 0.6 | 28.6 ± 2.1 | 32.8 ± 2.7 |
| MPPT | 94.8 ± 1.3 | 99.6 ± 1.7 | 93.9 ± 1.3 | 96.2 ± 0.6 | 97.4 ± 3.6 | 93.2 ± 1.9 | 84.6 ± 3.8 | 100 ± 2.1 | 93.5 ± 1.3 | 18.8 ± 0.6 | 24 ± 3.9 |
| FPPT | 96.1 ± 2.1 | 94.5 ± 0.8 | 0.0 | 100 ± 0.7 | 78.5 ± 3.1 | 89.9 ± 2.1 | 10.1 ± 1.0 | 0.0 | 91.0 ± 2.4 | 0.0 | 29 ± 3.2 |
| SePPT | 99.5 ± 0.8 | 94.9 ± 2.2 | 0.0 | 30.5 ± 2.7 | 47.3 ± 2.8 | 11.9 ± 1.1 | 11.9 ± 0.8 | 0.0 | 43.6 ± 3.3 | 0.0 | 0.0 |
| SPPT | 100 ± 1.6 | 98.8 ± 3.1 | 71.6 ± 2.3 | 96.1 ± 1.5 | 87.8 ± 1.3 | 79.3 ± 2.7 | 79.3 ± 4.1 | 16.1 ± 1.7 | 79.2 ± 3.2 | 0.0 | 8.3 ± 0.8 |
| Sfp | 98.6 ± 1.7 | 96.2 ± 1.3 | 53.3 ± 3.8 | 82.8 ± 1.9 | 25.1 ± 1.5 | 99.6 ± 2.2 | 98 ± 3.3 | 97.1 ± 2.9 | 92.9 ± 2.0 | 100 ± 1.7 | 100 ± 1.0 |

[a]The data represented mean ± SD of three independent experiments.

FIGURE 11

| | Sequence 5'-3' | Function |
|---|---|---|
| Sfp-Fw | CATGCCATGGAAATTTATGGGATTTAC | Sfp expression |
| Sfp-Rv | CCGCTCGAGCTACAACAGTTCTTCATAG | Sfp expression |
| MPPT-Fw | CATGCCATGGTTATATCTACCGATGA | MPPT expression |
| MPPT-Rv | CCGCTCGAGTAGATCAGAAAGGCCA | MPPT expression |
| SPPT-Fw | CATGCCATGGTCCCCCAGCCCCAAAT | SPPT expression |
| SPPT-Rv | CCGCTCGAGGGGCAATGAATCAAGG | SPPT expression |
| SePPT-Fw | CATGCCATGGAACGCCCCAACCCTAG | SePPT expression |
| SePPT-Rv | CCGCTCGAGATGATTTTTCCGGATTATG | SePPT expression |
| APPT-Fw | CATGCCATGGTGCAGCATACTTGGC | APPT expression |
| APPT-Rv | CCGCTCGAGATAATGCCAGAATTTTG | APPT expression |
| AvPPT-Fw | CATGCCATGGTGCAGCATACTTGGCTAC | AvPPT expression |
| AvPPT-Rv | CCGCTCGAGATACTGCCAGAATTTTGGC | AvPPT expression |
| FPPT-Fw | CATGCCATGGGGTCTGAGACTAATCA | FPPT expression |
| FPPT-Rv | CCGCTCGAGATACTGCCAGTACTTTAA | FPPT expression |
| SFACP-Fw | CATGCCATGGATCAGGAAATTTTTGA | SFACP expression |
| SFACP-Rv | CCGCTCGAGTTTACTTTCGATATGCTC | SFACP expression |
| AFACP-Fw | GGAATTCCATATGAGCCAATCAG | AFACP expression |
| AFACP-Rv | CCGCTCGAGAGCTGATGCGGCAACTTG | AFACP expression |
| APACP-Fw | CATGCCATGGGTCTAAAACAAAATTATAG | APACP expression |
| APACP-Rv | CCGCTCGAGAGATTGTTCTTCCAATTCTTC | SFACP expression |
| APNPCP-Fw | CATGCCATGGAACAATCTACAACTAATC | APNPCP expression |
| APNPCP-Rv | CCGCTCGAGATCAGTAATAGGCGATTG | APNPCP expression |
| FNPCP-Fw | CATGCCATGGCCCAACGCCCTATCATTATC | FNPCP expression |
| FNPCP-Rv | CCGCTCGAGTTCAACTTCATCACTATC | FNPCP expression |
| FisPCP-Fw | CATGCCATGGGATCGCTTCCCAAACCTG | FisPCP expression |
| FisPCP-Rv | CCGCTCGAGTGAATTGGGAAAAACATC | FisPCP expression |
| FNsACP-Fw | CATGCCATGGCTTTTCTAGAAGATGTC | FNsACP expression |
| FNsACP-Rv | CCGCTCGAGGGAATTACCTAGAAAAGC | FNsACP expression |
| AprACP-Fw | CATGCCATGGAAATTTTTGAACAGGAAT | AprACP expression |
| AprACP-Rv | CCGCTCGAGACTAAAATTAATATCTTC | AprACP expression |
| MACP-Fw | CATGCCATGGTGACAACTGTTCAATC | MACP expression |
| MACP-Rv | CCGCTCGAGAAGATATAATTCCCCT | MACP expression |
| ScACP-Fw | CATGCCATGGAGCAGCGGCTGGCTC | ScACP expression |
| ScACP-Rv | CCGCTCGAGCTCCTGCTCGCCGAAC | ScACP expression |
| SSPCP-Fw | CATGCCATGGAGGAGATCCTCGCC | SSPCP expression |
| SSPCP-Rv | CCGCTCGAGGGTACGCCCGGCCAGGC | SSPCP expression |
| Ptrc-F | GGATCCATTCTGAAATGAGCTGTTGAC | Shinorine Cloning |
| SHI-F | CTCGAGATGGGTACACCTCACGCTAC | Shinorine Cloning |
| SHI-R | AGATCTTCAGCACAAACATTTCTG | Shinorine Cloning |
| PRNPB-F | AGATCTTTCAATGCGGTCCAATAC | PPT cloning |
| PRNPB-R | GTTGATGCCTACCATCATATGTTTTTCTAGTGTGCCATTG | PPT cloning |
| FPPT-F | TGGCACACTAGAAAAACATATGATGGTAGGCATCAACTAT | FPPT cloning |
| F PPT-R | GAGCTCTCACTCTGGCCACCGCCAAC | FPPT cloning |
| APPT-F | TGGCACACTAGAAAAACATATGATGTTGCAGCATACTTGG | APPT cloning |
| APPT-R | GAGCTCATAATGCCAGAATTTTGGCTG | APPT cloning |
| SPPT-Up-F | CCAAGCTT CCTGGCAGTAGTGTTGGTG | Integration vector |
| SPPT-Up-R | GGTAACGAAAACTAGTCGTACGAGGTCAGTTTAAACAGCG | Integration vector |
| SPPT-Dn-F | AAACTGACCTCGTACG ACTAGTTTTCGTTACCTTGGGCCG | Integration vector |
| SPPT-Dn-R | GTGAATTC GGGCTACACCGTCGCTAC | Integration vector |
| Syn-APPT-F | TAAAGAGGTATATATTAATGTTGCAGCATACTTGG | Integration vector |
| Syn-APPT-R | CATAGCTGTTTCCTGTGTCAAAAAACCCCTCAAGACCCGTTTAG AGGCCCCAAGGGGTTATGCTAGTCAATAATGCCAGAATTTTG | Colony PCR |

FIGURE 12

| Primer | Sequence 5'-3' | Function |
|---|---|---|
| Syn-MPPT-F | TAAAGAGGTATATATTAATGTTTATATCTACCGATG | Colony PCR |
| Syn-MPPT-R | CATAGCTGTTTCCTGTGTCAAAAAACCCCTCAAGACCCGTTTAGA GGCCCCAAGGGGTTATGCTAGTCATAGATCAGAAAGGCC | Colony PCR |
| Syn-SFP-F | TAAAGAGGTATATATTAATGAAAATTTATGGGATTTAC | Colony PCR |
| Syn-SFP-R | CATAGCTGTTTCCTGTGTCAAAAAACCCCTCAAGACCCGTTTAGA GGCCCCAAGGGGTTATGCTAGCTACAACAGTTCTTCATAG | Colony PCR |
| Ptrc-F | CTCGTACGATTCTGAAATGAGCTGTTG | Colony PCR |
| Ptrc-APPT-R | CCAAGTATGCTGCAACATTAATATATACCTCTTTA | Colony PCR |
| Ptrc-MPPT-R | CATCGGTAGATATAAACATTAATATATACCTCTTTA | Colony PCR |
| Ptrc-SFP-R | GTAAATCCCATAAATTTTCATTAATATATACCTCTTTA | Colony PCR |
| Kana-F | GTCTTGAGGGGTTTTTTG ACACAGGAAACAGCTATG | Colony PCR |
| Kana-R | AAACTAGTAAACGACGGCCAGTGAAT | Colony PCR |
| RT-rnpB-F | CGTGAGGACAGTGCCACAG | RT-PCR |
| RT-rnpB-R | CGCTCTTACCGCACCTTTG | RT-PCR |
| RT-SPPT-F | TTTGATTGGCTTAAGTAC | RT-PCR |
| RT-SPPT-R | AATGCTTCCTTCGCTGTC | RT-PCR |
| RT-APPT-F | ATCTAGTGACGAATTAGC | RT-PCR |
| RT-APPT-R | AATAAACCACTCTCGGC | RT-PCR |
| RT-MPPT-F | GTATTAACTATCAATTGC | RT-PCR |
| RT-MPPT-R | AAGCTATCTAAATCTTTC | RT-PCR |
| RT-Sfp-F | TAGTCATTCTGGTCGCTG | RT-PCR |
| RT-Sfp-R | ATAAATCAGAGTATTCGG | RT-PCR |

FIGURE 12 (continued)

```
Sfp     ------------------------------------------MKIYGIYMDRPLSQEENE     18
SePPT   MQRPNPSDAVPVPSIPSCDRGPIPNPVTWRTSPEPLFLSAQTVHLWRCSLTRSLSSAE--     58
SPPT    --------------------------------------MLPQPQIWLCPTDRPL--IP--     18
MPPT    -----------------------------------MFISTDEVHLYFISLDPSGDRLE--     23
FPPT    --------------------MGSETNHLWLTAPTNLTLLPDDVHVWRISLDRPESELQ--     38
AvPPT   -----------------------MLQHTWLPKPPNLTLLSDEVHLWRIPLDRPESQLQ--     35
APPT    -----------------------MLQHTWLPKPPNLTLLSDEVHLWRIPLDQPESQLQ--     35

Sfp     RFMTFISPEKREKCRRFYHKEDAHRTLLGDVLVRSVISRQYQLDKSDIRFSTQEYGKPCI     78
SePPT   QAI---VAADCDRAQA-YGSNRRHQFLCGRWWLRQLLSLYLPEEPADFRFQLSPTGKPEL     114
SPPT    GYQALLSSEEMARGERYQRPQDKQRFLTMRLALRILLARQLDCLPQQLQFTYGPQGKPEL     78
MPPT    TLASLLSEDEIIRANRYHFPEHKRRFLVARGCLREILGSYLAISPEKIEFIYSERGKPSI     83
FPPT    ALQTTLSSDEIARAQRFYFEQHRQRFVAGRGILRTILGRYLGVEPQAVEFTYELRGKPLL     98
AvPPT   HLAATLSSDELARANRFYFPEHRQRFTAGRGILRSILGLYLGVEPKQVKFEYESRGKPVL     95
APPT    DLAATLSSDELARANRFYFPEHRRRFTAGRGILRSILGGYLGVEPGQVKFDYESRGKPIL     95

                                        * *
Sfp     PDL---PDAHFNISHSGRWVIGAFD-SQPIGIDIEKTKPI--SLEIAKRFFSKTEYSDLL     132
SePPT   PQ----SNLCFNLSHSGSTLLIAIAW-QPVGVDVEQPRSR-SWLALARRYFPSAELAAMQ     168
SPPT    VDRERR-SPWFNVAHSGNYGLIGLSTEGEIGVDLQIMLPKPHYLKLAKRFFAPQEVQQLE     137
MPPT    NY-----QLQFNLSHSEEMAICGLTLTARIGVDLEKMRQMKDLDSLTKRFFCAREHELVE     138
FPPT    ADRFADSGVSFNLSHSQDLALCGVSRNRKIGIDVEYMRSVSDVEALAERFFAPREYEVVR     158
AvPPT   GDRFADSGLLFNLSHSQNLGLCAVNYTRQIGIDLEYLRPTSDLESLAKRFFLPREYELLR     155
APPT    GDRFAESGLLFNLSHSQNLALCAVNYTRQIGIDLEYLRPTSDLESLAKRFFLPREYELLR     155

                          *
Sfp     AKDKDEQTLYFYHLWSMKESFIKQEGKGLSLPLDSFSVRLHQDGQVSIELPDSHSPCYIK     192
SePPT   Q--STDCDRWGLASWVCKEAWIKAQGRTLANSLRHLQCAWTANGQPRLSGLGSEES-QVQ     225
SPPT    SLEGEKRTKLFYQLWTAKEAFLKATGKGISGGLNQVIPDENLAKYQYLPDS----G-DTN     192
MPPT    K--SAEKEKLFFQLWTAKEAYLKAVGTGISGGLDRVEVGLNPLKLD--NVA----G-EWQ     189
FPPT    SLPSNQQQQVFFRYWTCKEAYLKAIGVGIVQ-LEKVEISLTLEQPAKLITD----E-EWS     212
AvPPT   SLPDEQKQKIFFRYWTCKEAYLKATGDGIAK-LEEIEIALTPTEPAKLQTT----P-AWS     209
APPT    SLPDEQKQKIFFRYWTCKEAYLKATGDGIAK-LEEIEIALTPTEPAKLQTA----P-AWS     209

Sfp     TYEVDPGYK--MAVCAAHPDFPEDIT---MVSYEELL-----------------------     224
SePPT   LLQVDPQEQLWAAI-AMPAGWNYQTWTAAIIRKNH-------------------------     259
SPPT    HWRLSSQ------PLLADQGSNDNYWMAIAWCTNEVNQVESNYLPNIQPFQWPRNLDSLP     246
MPPT    LWTAAIGDNYRATVVIEGSDRVIKTF-----GLSDL------------------------     220
FPPT    LIELVPGDHYLGAVAIAGQNLDLKYW-----QY---------------------------     240
AvPPT   LLELVPDDNCVAAVAVAGFGWQPKFW-----QY---------------------------     237
APPT    LLELVPDDNCVAAVAVAGFGWQPKFW-----HY---------------------------     237
```

FIGURE 14

*SFACP*

ATGGATCAGGAAATTTTTGAAAAAGTAAAAAAAATCGTCGTGGAACAGTTGGAAGTGGATCCTGAC
AAAGTGACCCCCGATGCCACCTTTGCCGAAGATTTAGGGGCTGATTCCCTCGATACAGTGGAATTGG
TCATGGCCCTGGAAGAAGAGTTTGATATTGAAATTCCCGATGAAGTGGCGGAAACCATTGATACCGT
GGGCAAAGCCGTTGAGCATATCGAAAGTAAA

*AFACP*

ATGGGCCAATCAGAAACTTTTGAAAAAGTCAAAAAAATTGTTATCGAACAACTAAGTGTGGAGAAC
CCTGACACAGTAACTCCAGAAGCTAGTTTTGCCAACGATTTACAGGCTGATTCCCTCGATACAGTAG
AACTAGTAATGGCTTTGGAAGAAGAATTTGATATCGAAATTCCCGATGAAGCCGCAGAGAAAATTA
CCACTGTTCAAGAAGCGGTGGATTACATCAATAACCAAGTTGCCGCATCAGCT

*APACP*

ATGGGTCTAAAACAAAATTATAGTGCAGCAGATATTCAAGCTTGGATGATATCTAATCTAGCTGAAT
TGTTGGGAGTAGATGGTGATGAAATCGATGCTACTGTCAATTTAGAAAGCTATGGTTTGGATTCGGC
ACAGGCAATGGTACTAGTTAGTAAACTAGAGCAATTGTTGGGATTTCAACCATCACCTTTGTTGTTGT
GGCATTACCCCACTATTGAATCGTTGTCTGAACGTTTAGCTGAAGAATTGGAAGAACAATCT

*APNPCP*

ATGGAACAATCTACAACTAATCACGCCCGCCCCCAAATTACCGCTACCTACCTTCCCCCCAGCAATG
AAATTGAAGCCAGAGTCACCCAAGTAATGGAGAGTTTATTGGGAATCGCTCCTATTGGGGTTAATGA
TAACTTCTTTGAGTTAGGAGGACATTCCCTGTTAGCAATTCAAGCAGTTTCACAGCTACGGGAAGAA
TTTCAAGTAGAATTACCCATGCGACAATTTTTATTTGAGTCACCCACAATTGGGGGGATAGCCAAAA
TTATCATTGAAAATCAATCGCCTATTACTGAT

*FNPCP*

ATGGCCCAACGCCCTATCATTATCCCTCGTACAAATACTGAACAGCGAATAGGCGAGATTTGGAAGA
AGGCGATGAAGTGGGATTCTGTCTCGATATGTGATGATTTCTTTGAATCTGGCGGAAATTCACTTATT
GCTGTGAGAATAATCAACGCTATCAACAAAGAATTTCATTGTGCCTTGCCTTTACATGCTCTTTTTGA
AGCTCCAAGCATTGAAAAGCTCGCTCATAAGGTTGATAGTGATGAAGTTGAA

*FNsACP*

ATGGCTTTTCTAGAAGATGTCCCTCCAACAGAACGTCGAGAACACTTATTAGAATATCTTGGAAAA
GAAGTAGCAAAAATCTTAGGAATAAAACATATACCCGACCCAGAACAAGGATTTATAGAAATGGG
AATTGACTCTTTGCTTTCCATTGAATTCAAAAATCGTTTAGAAAAAGGATTAGAAATTGCTTTACC
ATCTACTTTAATATTTGATTTTCCGAATATTAGCAAATTAAATAATTATCTATTTGAGCAAATTTAT
GGTTGGGAAGTAAATACTACCGTGGAGACAACTGTTGATATTGTAGAAGTTAATGAAGATTTAATT
TTGCAAGAACTGGCAGATTTAGAAGCTTTTCTAGGTAATTCC

FIGURE 15

*FisPCP*

ATGGGATCGCTTCCCAAACCTGATTTTTCTAACTTAATCACTCATGAAGATTTTACGCCTGCACGCAA
TGATTTAGAGAGAAAAATCGCGCAGATTTGGTCAGAAATTTTACAGATTTCGGAAATTGATATTAGA
GATAACTTTTTTGAAGTTGGTGGTAATTCCCTTTTAGCATTACATTTAATGAATGCCATCGAACAAAA
ATTTGGTCGAGAGTTAGCACTGTCAACTTTACTTACTAATAACTCAATTGAAAAACTAGCAGAAATT
CTGCAAAACCCCACAGATGTTTTTCCCAATTCA

*AprACP*

ATGGAAATTTTTGAACAGGAATGTCGAAAATTATTAAAATCTCTACTGGGTGTTCAACGTATGGAGA
GATTGCCTGGTGACACACCACTAATGGAGTCAGGAATGGATTCACTGGAGTTGTTAGAATTTCGTGC
TCTTATAGAAAGAAAGTTTGGGATTAAGTTAAAGTCTACCTTCTTTTTTAGTTACAAAACTCTTATAG
CGGTAGCAGAGTATCTTTCAGAACGGGAAGATATTAATTTTAGT

*MACP*

ATGGTGACAACTGTTCAATCTCCTTGTACCGTTGAAGACATTCAAAACTGGCTCGTTGATCAGTTTGC
TCAACAACTCGATGTTGACCTTGATGACATTGATATTGAAGAACCTTTTGATAATTATGAACTCGACT
CACGAAAAGCGTTAGTTTTATTAGGACGCTTAGAAAAATGGCTCGGAAAGGAATTAAATCCTGTGGT
CATTTTTAACTATCCCACCATTGCTGAATTAGCAACCCGATTAGGGGAATTATATCTT

*ScACP*

ATGGAGCAGCGGCTGGCTCCGCTGTCCGCGGCCGAGCGCGAGCGGGCACTCACGGATCTCGTGCGC
GTCCAGGTCGCGGCGGTGCTCGGGCACTCTGACCCCGGCGCGATCGAGTCCGGCCGGGCCTTCCAGG
AGCTGGGCTTCGACTCACTGACAGCCGTCGAACTTCGCAACCAGCTGAGCACCGCGAGCGGACTGCG
CCTGCCCACCACCCTCGTCTTCGACCACCCCTCCCCCGCCGCTCTCGCCGCCCACCTCTCGGCGGAGC
TGTTCGGCGAGCAGGAG

*SsPCP*

ATGGCCCGCCGGCTCGAACCGTTGGACGAACCCGCGCGACGCCGTCTGCTGCTCGACCTGGTGTGCG
ACCACGCGGCCGCGGTCCTCGGCCACACCGGCCGCCAGGCCGTCCCGGCCGACCAGGCGTTCTCCGC
CGTCGGGTTCGACTCGATGCTCGCCGTGTCCTTCCGTAACCGGCTGCGCACCGCGACCGGCGTCCCC
GTCGCCGCGACGGTGGTGTTCGACCATCCCACCCCCGCCGCCCTCGCCGACCACCTGTACGACGGGT
TGAGCGCCCGTCCCGGACCGGCCGTT

**Codon optimized *Sfp***

ATGAAAATTTATGGGATTTACATGGATAGACCCCTGAGCCAAGAAGAAAACGAACGCTTTATGACCT
TTATTAGCCCTGAAAAACGGGAAAAATGTCGCCGTTTTTATCATAAAGAAGATGCCCATCGTACCTT
ATTGGGTGATGTGTTGGTTCGGAGTGTGATTTCTCGCCAATACCAATTGGATAAAAGTGATATTCGGT
TTTCTACTCAAGAATATGGTAAACCCTGTATTCCCGATTTGCCCGATGCCCATTTTAATATTAGTCAT
TCTGGTCGCTGGGTTATTGGTGCTTTTGATAGTCAACCCATTGGTATTGATATTGAAAAAACCAAACC
CATTTCTTTGGAAATTGCCAAACGCTTTTTCAGTAAAACCGAATACTCTGATTTATTGGCTAAAGATA
AAGATGAACAAACTGATTACTTTTACCATTTGTGGAGTATGAAAGAATCTTTTATTAAACAAGAAGG
TAAAGGTTTAAGTTTGCCCTTAGATAGTTTTTCTGTGCGGTTGCATCAAGATGGTCAAGTTAGTATTG
AATTACCCGATAGTCATTCTCCCTGTTACATTAAAACTTATGAAGTTGATCCCGGTTATAAAATGGCT
GTTTGTGCAGCACACCCCGATTTTCCAGAAGATATTACTATGGTTTCCTATGAAGAACTGTTGTAG

FIGURE 15 (continued)

| | |
|---|---|
| BBa_J23119 | ttgacagctagctcagtcctaggtataatgctagc |
| BBa_J23100 | ttgacggctagctcagtcctaggtacagtgctagc |
| BBa_J23101 | tttacagctagctcagtcctaggtattatgctagc |
| BBa_J23102 | ttgacagctagctcagtcctaggtactgtgctagc |
| BBa_J23103 | ctgatagctagctcagtcctagggattatgctagc |
| BBa_J23104 | ttgacagctagctcagtcctaggtattgtgctagc |
| BBa_J23105 | tttacggctagctcagtcctaggtactatgctagc |
| BBa_J23106 | tttacggctagctcagtcctaggtatagtgctagc |
| BBa_J23107 | tttacggctagctcagccctaggtattatgctagc |
| BBa_J23108 | ctgacagctagctcagtcctaggtataatgctagc |
| BBa_J23109 | tttacagctagctcagtcctagggactgtgctagc |
| BBa_J23110 | tttacggctagctcagtcctaggtacaatgctagc |
| BBa_J23111 | ttgacggctagctcagtcctaggtatagtgctagc |
| BBa_J23112 | ctgatagctagctcagtcctagggattatgctagc |
| BBa_J23113 | ctgatggctagctcagtcctagggattatgctagc |
| BBa_J23114 | tttatggctagctcagtcctaggtacaatgctagc |
| BBa_J23115 | tttatagctagctcagcccttggtacaatgctagc |
| BBa_J23116 | ttgacagctagctcagtcctagggactatgctagc |
| BBa_J23117 | ttgacagctagctcagtcctagggattgtgctagc |
| BBa_J23118 | ttgacggctagctcagtcctaggtattgtgctagc |

FIGURE 19

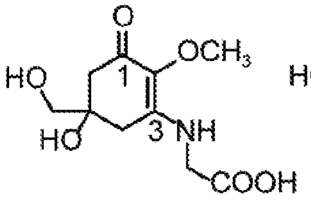
Mycosporine-glycine
(310 nm)
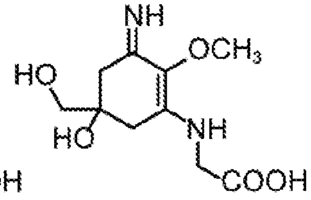
Palythine
(320 nm)
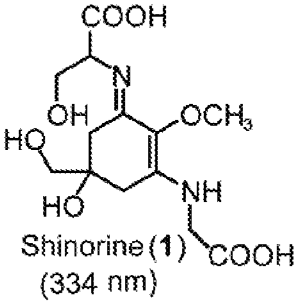
Shinorine (1)
(334 nm)
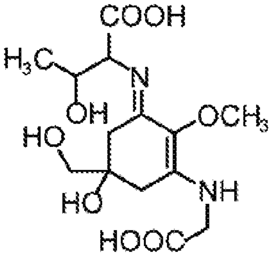
Porphyra-334
(334 nm)
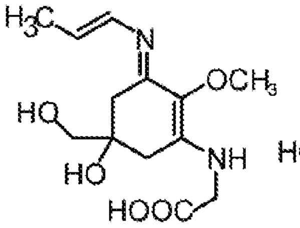
Palythene
(360 nm)
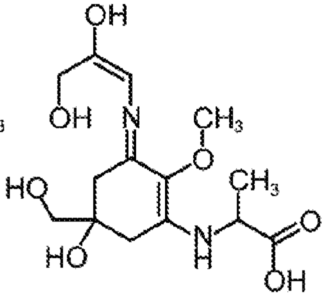
Euhalothece-362
(362 nm)
FIGURE 20

Sedoheptulose 7-phosphate (SH7-P)

3-deoxy-D-arabino-heptulosonate phosphate (DAHP)

4-Deoxygadusol (4-DG)

Glycine

Mycosporine-glycine (MG)

L-Serine

Shinorine (1)

CYANOBACTERIAL HOSTS AND METHODS FOR PRODUCING CHEMICALS

CROSS-REFERENCE TO RELATED APPLICATIONS

This application is a National Stage filing under 35 U.S.C. 371 of International Patent Application No. PCT/US2018/043993, filed Jul. 27, 2018, which claims priority to U.S. Provisional Application No. 62/537,516, filed Jul. 27, 2017 and U.S. Provisional Application No. 62/611,634, filed Dec. 29, 2017. The entire content of each of the foregoing applications is expressly incorporated by reference herein.

The Sequence Listing for this application is labeled "U119570139US02-SEQ.txt" which was created on Jan. 22, 2020 and is 207 KB. The entire content of the sequence listing is incorporated herein by reference in its entirety.

FIELD OF INVENTION

The present invention relates to recombinant cyanobacterial cells for the production of chemical compounds of interest. In particular, the present invention relates to genetic modifications that introduce one or more heterologous phosphopantetheinyl transferases (PPTases) into the cyanobacterial cells. These cells can, optionally, further comprise heterologous carrier protein and nucleic acid constructs which provide the cyanobacterial cells with the capability of producing chemicals of interest or compounds of interest, such as secondary metabolites polyketides, nonribosomal peptides and their hybrids, the three major families of bioactive natural products, of cyanobacteria and other bacterial phyla, secondary metabolites analogs, and unnatural compounds. The nucleic acid constructs can be chromosomally integrated or present in self-replicating plasmids.

BACKGROUND OF THE INVENTION

Cyanobacteria produce structurally and functionally diverse secondary metabolites polyketides, nonribosomal peptides and their hybrids. Sfp-like phosphopantetheinyl transferases (PPTases) are essential to the modular biosynthesis of these compounds via functionalizing carrier proteins (CPs) of megaenzymes. However, cyanobacterial Sfp-like PPTases remain poorly characterized, posing a significant barrier to the exploitation of cyanobacteria for biotechnological and biomedical applications.

Herein, we describe the characterization of multiple cyanobacterial Sfp-like PPTases. Biochemical characterization and kinetic analysis of these enzymes along with the prototypic enzyme Sfp from *Bacillus subtilis* demonstrated their varying specificities toward recombinant CPs from different types of biosynthetic pathways in cyanobacterial and *Streptomyces* strains. Moreover, two selected cyanobacterial PPTases along with Sfp were transiently expressed in one PPTase-deficient mutant of model cyanobacterium *Synechocystis* sp. PCC6803 and supported its growth comparable to the wild type. These enzymes in the cyanobacterial cell lysates also functionalized selected CPs in vitro.

The subject application provides new tools to synthesize cyanobacterial natural products using in vitro and in vivo synthetic biology approaches. In one embodiment, cyanobacterial cells can be engineered to express heterologous proteins or chemicals/compounds of interest (such as cyanobacterial secondary metabolites polyketides, nonribosomal peptides and their hybrids, the three major families of bioactive natural products). In one embodiment, *Synechocystis* sp. PCC6803 can be engineered for the heterologous expression of a shinorine gene cluster from the cyanobacterium *Fischerella* sp. PCC9339. After optimization, the yield of shinorine in the engineered *Synechocystis* sp. PCC6803 was higher than any known cyanobacterial producers in nature. This work demonstrates the feasibility of the *Synechocystis* sp. PCC6803 to produce cyanobacterial secondary metabolites polyketides, nonribosomal peptides and their hybrids, the three major families of bioactive natural products.

BRIEF SUMMARY OF THE INVENTION

This invention provides a recombinant, i.e. non-naturally occurring, cyanobacterial cell for the production of chemical compounds of interest. The cyanobacterial cell comprises an inactivated endogenous phosphopantetheinyl transferase(s) (PPTase(s)) and expresses one or more heterologous PPTases. These engineered cells can further comprise exogenous expression genetic constructs that permit the expression of heterologous proteins or chemicals/compounds of interest (such as cyanobacterial secondary metabolites polyketides, nonribosomal peptides and their hybrids, the three major families of bioactive natural products). The genetically engineered cells can further comprise one or more heterologous carrier proteins (CPs) activated by the heterologous PPTases.

The invention also provides a method for producing the above-mentioned cyanobacterial cell. The method comprises inactivating endogenous PPTases within a cyanobacterial cell, providing at least one transformable nucleic acid construct for the genetic modification said cyanobacterial cell that encodes a heterologous PPTase and, optionally, providing at least one transformable nucleic acid construct encoding a heterologous protein or a compound/chemical of interest. The transformable nucleic acid constructs can be transformed into a cyanobacterial cell to obtain the recombinant cyanobacterial cell of the present invention. The transformable nucleic acid constructs can be transformed into a cyanobacterial cell and then integrated into the chromosomal DNA to obtain the recombinant cyanobacterial cell of the present invention. Alternatively, the transformable nucleic acid constructs can be present within the recombinant cyanobacterial cell in the form of self-replicating plasmids or modules (see, for example, Taton, Arnaud et al. "Broad-Host-Range Vector System for Synthetic Biology and Biotechnology in Cyanobacteria." *Nucleic Acids Research* 42.17 (2014): e136. *PMC*. Web. 26 Jul. 2017, the disclosure of which is hereby incorporated by reference in its entirety).

BRIEF DESCRIPTION OF THE DRAWINGS

FIG. 3. Relative activity of seven PPTases on 11 CP substrates. For any CP, the activity of the most active PPTase was set as 100%, and those of other PPTases were normalized as shown in the heatmap. The data represent the mean of three independent experiments. Red to white color indicates the high to low relative activity of PPTases. CPs are grouped according to the biosynthetic pathways while cyanobacterial PPTases are organized by the subsections of sources.

FIG. 9. PPTases used in the phylogenetic analysis. The sequences of the PPTases can be obtained from GenBank or EMBL using the accession numbers listed in the table and these sequences are hereby incorporated by reference in their entireties.

FIG. 10. CPs used to characterize PPTases. The sequences of the CPs can be obtained from GenBank or EMBL using the accession numbers listed in the table and these sequences are hereby incorporated by reference in their entireties.

FIG. 11. Relative Activity of select PPTases in activating CPs.

FIG. 12. Oligos used in the Examples (SEQ ID NOs: 89-159).

FIG. 14. Multiple-sequence alignment of characterized cyanobacterial PPTases and Sfp. The completely conserved residues are shaded in gray. The proposed magnesium binding residues are indicated with asterisks (*). Boxed region indicates the conserved W/KEA motif. Sfp, SEQ ID NO: 7; SePPT, SEQ ID NO: 5; SPPT, SEQ ID NO: 6; MPPT, SEQ ID NO: 3; FPPT, SEQ ID NO: 4; AvPPT, SEQ ID NO: 2; and APPT, SEQ ID NO: 1.

FIG. 15. Sequences of selected CP genes and codon optimized Sfp gene. SFACP (SEQ ID NOs: 8 and 9); AFACP (SEQ ID NOs: 10 and 11); APACP (SEQ ID NOs: 12 and 13); APNPCP (SEQ ID NOs: 14 and 15); FNPCP (SEQ ID NOs: 16 and 17); FNsACP (SEQ ID NOs: 18 and 19); FisPCP (SEQ ID NOs: 20 and 21); AprACP (SEQ ID NOs: 22 and 23); MACP (SEQ ID NOs: 24 and 25); ScACP (SEQ ID NOs: 26 and 27); SsPCP (SEQ ID NOs: 28 and 29); and Codon optimized Sfp (SEQ ID NOs: 30 and 31).

FIG. 19. Exemplary promoters in the J23 library (SEQ ID NOs: 160-179).

FIG. 20. Chemical structures and absorption maxima of selected cyanobacterial mycosporine-like amino acids.

DETAILED DISCLOSURE OF THE INVENTION

Figure 1:
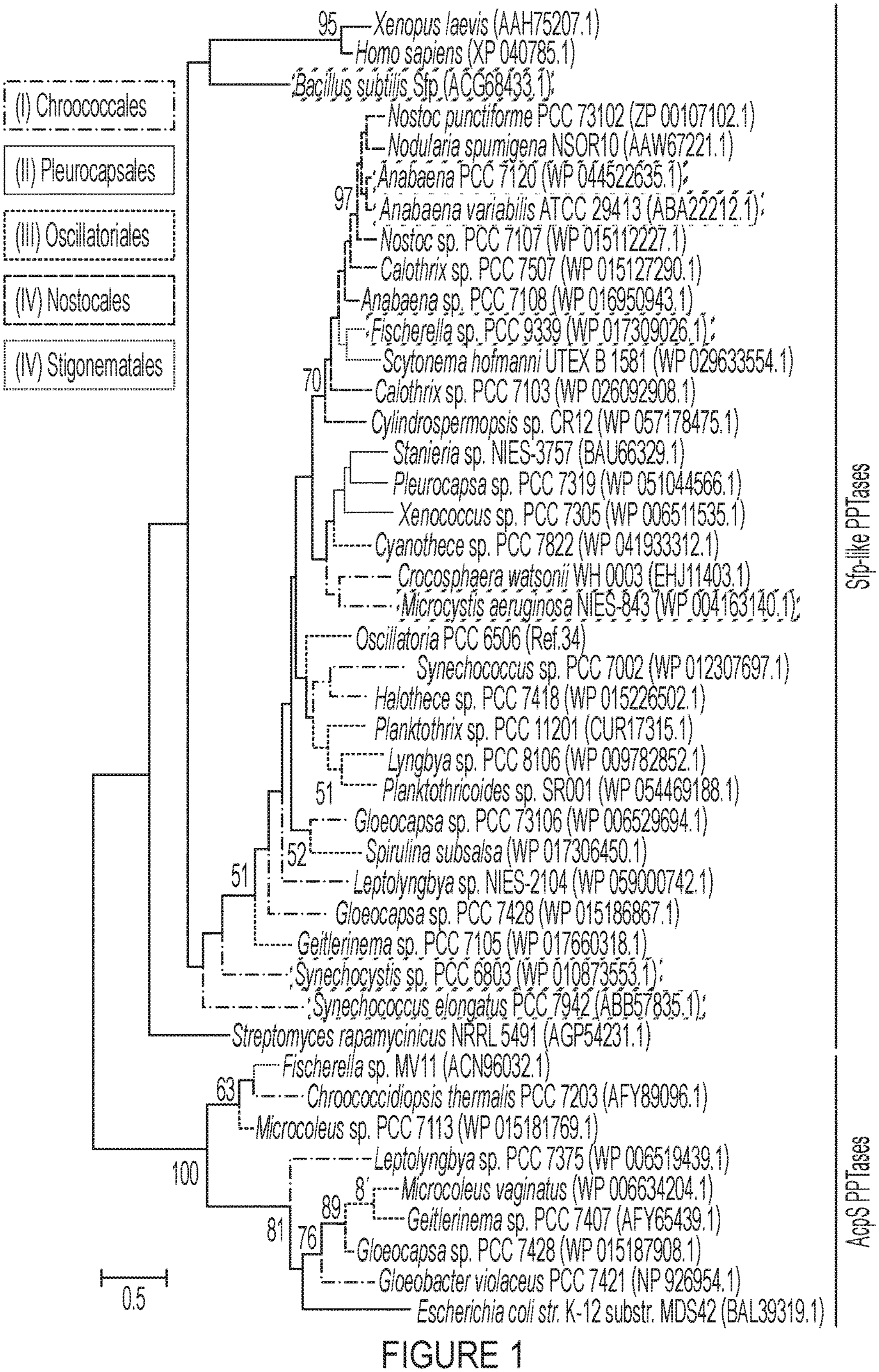
FIG. 1. A maximum-likelihood phylogeny based on selected cyanobacterial PPTases. A phylogenetic tree was generated using MEGA7 maximum-likelihood method. Enzymes are shown as the names of corresponding strains with NCBI accession numbers given in parenthesis. The *E. coli* AcpS was chosen as an outgroup for the AcpS-like PPTase clade, while the PPTases from *Streptomyces rapamycinicus* NRRL5491, *Xenopus laevis* and *Homo sapiens* were outgroups for the Sfp-like PPTase clade. Branches are color-coded according to morphological subsections of cyanobacteria. Branch length is proportional to the amount of genetic change. Significant bootstrap values (over 500 of 1,000 repeats) are shown. PPTases with shaded taxa names were selected for the characterization in this study.

In a first aspect, the subject invention provides a recombinant, i.e. non-naturally occurring, cyanobacterial cell for the production of a chemical compound of interest. The cyanobacterial cell comprises an inactivated endogenous phosphopantetheinyl transferase(s) (PPTase(s)) and expresses one or more heterologous PPTases. These engineered cells can further comprise exogenous expression cassettes or nucleic acid constructs that permit the expression of heterologous proteins or chemicals/compounds of interest (such as cyanobacterial secondary metabolites polyketides, nonribosomal peptides and their hybrids, the three major families of bioactive natural products). The genetically engineered cells can further comprise one or more heterologous carrier proteins (CPs) activated by the heterologous PPTases.

Definitions

Unless defined otherwise, all technical and scientific terms used herein have the meaning commonly understood by a person skilled in the art to which this invention belongs. As used herein, the following terms have the meanings ascribed to them unless specified otherwise.

The term "about" is used herein to mean approximately, in the region of, roughly, or around. When the term "about" is used in conjunction with a numerical value/range, it modifies that value/range by extending the boundaries above and below the numerical value(s) set forth. In general, the term "about" is used herein to modify a numerical value(s) above and below the stated value(s) by a variance of 10% (i.e., ±10%).

The term "Cyanobacterium" refers to a member from the group of photoautotrophic prokaryotic microorganisms which can utilize solar energy and fix carbon dioxide. Cyanobacteria are also referred to as blue-green algae. Exemplary cyanobacteria include, but are not limited to, *Synechocystis* sp. The cyanobacterial cell of the present invention can be selected from the group consisting of *Synechocystis, Synechococcus, Anabaena, Chroococcidiopsis, Cyanothece, Lyngbya, Phormidium, Nostoc, Spirulina, Arthrospira, Trichodesmium, Leptolyngbya, Plectonema, Myxosarcina, Pleurocapsa, Oscillatoria, Pseudanabaena, Cyanobacterium, Geitlerinema, Euhalothece, Calothrix*, and *Scytonema*. Particularly preferred is *Synechocystis* PCC6803.

The terms "host cell" and "recombinant host cell" are intended to include a cell suitable for genetic manipulation, e.g., which can incorporate heterologous polynucleotide sequences, e.g., which can be transformed. The term is intended to include progeny of the cell originally transformed. In particular embodiments, the cell is a prokaryotic cell, e.g., a cyanobacterial cell. The term "recombinant host cell" is intended to include a cell that has already been selected or engineered to have certain desirable properties and to be suitable for further genetic enhancement.

"Competent to express" refers to a host cell that provides a sufficient cellular environment for expression of endogenous and/or heterologous polynucleotides.

The terms "polynucleotide" and "nucleic acid" also refer to a polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs. It will be understood that, where required by context, when a nucleotide sequence is represented by a DNA sequence (i.e., A, T, G, C), this also includes an RNA sequence (i.e., A, U, G, C) in which "U" replaces "T."

The nucleic acids of this present invention may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages, charged linkages, alkylators, intercalators, pendent moieties, modified linkages, and chelators. Also included are synthetic molecules that mimic polynucleotides in their ability to bind to a designated sequence via hydrogen bonding and other chemical interactions.

The term "nucleic acid" (also referred to as polynucleotide) is also intended to include nucleic acid molecules having an open reading frame encoding a polypeptide, and can further include non-coding regulatory sequences and introns. In addition, the terms are intended to include one or more genes that map to a functional locus. In addition, the terms are intended to include a specific gene for a selected purpose. The gene can be endogenous to the host cell or can be an endogenous or heterologous gene that is recombinantly introduced into the host cell.

In one aspect the invention also provides nucleic acids which are at least 60%, 70%, 80% 90%, 95%, 99%, or 99.5% identical to the nucleic acids disclosed herein.

The percentage of identity of two nucleic acid sequences or two amino acid sequences can be determined using the algorithm of Thompson et al. (CLUSTALW, 1994, Nucleic Acids Research 22: 4673-4680). A nucleotide sequence or an amino acid sequence can also be used as a so-called "query sequence" to perform a search against public nucleic acid or protein sequence databases in order, for example, to identify PPTases within microorganisms, which can also be used in various embodiments of this invention for either transformation of a microorganism or inactivation of an endogenous PPTase within a microorganism.

In addition, any nucleic acid sequences or protein sequences disclosed in this patent application can also be used as a "query sequence" in order to identify yet unknown sequences in public databases, which can encode PPTases or CPs which could be useful in this invention. Such searches can be performed using the algorithm of Karlin and Altschul (1990, Proceedings of the National Academy of Sciences U.S.A. 87: 2,264 to 2,268), modified as in Karlin and Altschul (1993, Proceedings of the National Academy of Sciences U.S.A. 90: 5,873 to 5,877). Such an algorithm is incorporated in the NBLAST and)(BLAST programs of Altschul et al. (1990, Journal of Molecular Biology 215: 403 to 410). Suitable parameters for these database searches with these programs are, for example, a score of 100 and a word length of 12 for BLAST nucleotide searches as performed with the NBLAST program. BLAST protein searches are performed with the XBLAST program with a score of 50 and a word length of 3. Where gaps exist between two sequences, gapped BLAST is utilized as described in Altschul et al. (1997, Nucleic Acids Research, 25: 3,389 to 3,402).

As used herein, the term "genetically modified" refers to any change in the endogenous genome of a wild type cell or to the addition of non-endogenous (heterologous) genetic code to a wild type cell, e.g., the introduction of a heterologous gene. More specifically, such changes are made by the hand of man through the use of recombinant DNA technology or mutagenesis. The changes can involve protein coding sequences or non-protein coding sequences, including regulatory sequences such as promoters or enhancers.

The term "recombinant" refers to polynucleotides synthesized or otherwise manipulated in vitro ("recombinant polynucleotides") and to methods of using recombinant polynucleotides to produce gene products encoded by those polynucleotides in cells or other biological systems. For example, a cloned polynucleotide may be inserted into a suitable expression vector, such as a bacterial plasmid, and the plasmid can be used to transform a suitable host cell. A host cell that comprises the recombinant polynucleotide is referred to as a "recombinant host cell" or a "recombinant bacterium" or a "recombinant cyanobacterium." The gene is then expressed in the recombinant host cell to produce, e.g., a "recombinant protein." A recombinant polynucleotide may serve a non-coding function (e.g., promoter, origin of replication, ribosome-binding site, etc.) as well.

The term "homologous recombination" refers to the process of recombination between two nucleic acid molecules based on nucleic acid sequence similarity. The term embraces both reciprocal and nonreciprocal recombination (also referred to as gene conversion). In addition, the recombination can be the result of equivalent or non-equivalent cross-over events. Equivalent crossing over occurs between two equivalent sequences or chromosome regions, whereas nonequivalent crossing over occurs between identical (or substantially identical) segments of nonequivalent sequences or chromosome regions. Unequal crossing over typically results in gene duplications and deletions. For a description of the enzymes and mechanisms involved in homologous recombination see Court et al., "Genetic engineering using homologous recombination," Annual Review of Genetics 36:361-388; 2002.

The term "non-homologous or random integration" refers to any process by which DNA is integrated into the genome that does not involve homologous recombination. It appears to be a random process in which incorporation can occur at any of a large number of genomic locations.

The term "expressed endogenously" refers to polynucleotides that are native to the host cell and are naturally expressed in the host cell.

The term "operably linked" refers to a functional relationship between two parts in which the activity of one part (e.g., the ability to regulate transcription) results in an action on the other part (e.g., transcription of the sequence). Thus, a polynucleotide is "operably linked to a promoter" when there is a functional linkage between a polynucleotide expression control sequence (such as a promoter or other transcription regulation sequences) and a second polynucleotide sequence (e.g., a native or a heterologous polynucleotide), where the expression control sequence directs transcription of the polynucleotide.

The term "vector" as used herein is intended to refer to a nucleic acid molecule capable of transporting another nucleic acid to which it has been linked. One type of vector is a "plasmid," which generally refers to a circular double stranded DNA molecule into which additional DNA segments may be ligated, but also includes linear double-stranded molecules such as those resulting from amplification by the polymerase chain reaction (PCR) or from treatment of a circular plasmid with a restriction enzyme.

Certain vectors are capable of autonomous replication in a host cell into which they are introduced (e.g., vectors having an origin of replication which functions in the host cell). Other vectors can be integrated into the genome of a host cell upon introduction into the host cell, and are thereby replicated along with the host genome. Moreover, certain vectors are capable of directing the expression of genes to which they are operatively linked. Such vectors are referred to herein as "recombinant expression vectors" (or simply "expression vectors"). Thus, transformable nucleic acid constructs can be transformed into a cyanobacterial cell and then integrated into the chromosomal to obtain the recombinant cyanobacterial cell of the present invention. Alternatively, the transformable nucleic acid constructs can be present within the recombinant cyanobacterial cell in the form of self-replicating plasmids or modules (see, for example, Taton, Arnaud et al. "Broad-Host-Range Vector System for Synthetic Biology and Biotechnology in Cyanobacteria." *Nucleic Acids Research* 42.17 (2014): e136. *PMC*. Web. 26 Jul. 2017, the disclosure of which is hereby incorporated by reference in its entirety). A "promoter" is an array of nucleic acid control sequences that direct transcription of an associated polynucleotide, which may be a heterologous or native polynucleotide. A promoter includes nucleic acid sequences near the start site of transcription, such as a polymerase binding site. The promoter also optionally includes distal enhancer or repressor elements which can be located as much as several thousand base pairs from the start site of transcription. The term "promoter" is intended to include a polynucleotide segment that can transcriptionally control a gene of interest, e.g., a PPTase gene that it does or does not transcriptionally control in nature. In one embodiment, the transcriptional control of a promoter results in an increase in expression of the gene of interest. In an embodiment, a promoter is placed 5' to the gene of interest. A heterologous promoter can be used to replace the natural promoter, or can be used in addition to the natural promoter. A promoter can be endogenous with regard to the host cell in which it is used or it can be a heterologous polynucleotide sequence introduced into the host cell, e.g., exogenous with regard to the host cell in which it is used. Promoters of the invention may also be inducible, meaning that certain exogenous stimuli (e.g., chemicals, nutrient starvation, heat shock, mechanical stress, metal ions, light exposure, etc.) will induce the promoter leading to the transcription of the gene. In certain embodiments, constitutive promoters, such as ptrc, can be used to express heterologous PPTases within a recombinant cell. Other constitutive promoters that can be used in the context of this invention include Pcpc560, Ptrc, Ptrc2O-2, PA1lacO-1, L03, PnrsB, PpsbA2, PpsbA, the plastocyanin promoter and the promoters provided in the J23 library (a synthetic library of minimal and constitutive $\sigma^{70}$ promoters, examples of which are provided in FIG. 19). These and other promoters, such as inducible promoters, are disclosed in "Engineered transcriptional systems for cyanobacterial biotechnology", Camsund and Lindblad, *Frontiers in Bioengineering and Biotechnology,* 2014, 2:40, which is hereby incorporated by reference in its entirety. Endogenous and exogenous promoters can also be identified using a bioinformatics algorithm, such as bTSSfinder: a novel tool for the prediction of promoters in cyanobacteria and *Escherichia coli*, Bioinformatics. 2017; 33(3): 334-340.

The term "recombinant nucleic acid molecule" includes a nucleic acid molecule (e.g., a DNA molecule) that has been altered, modified or engineered such that it differs in nucleotide sequence from the native or natural nucleic acid molecule from which the recombinant nucleic acid molecule was derived (e.g., by addition, deletion or substitution of one or more nucleotides). The recombinant nucleic acid molecule (e.g., a recombinant DNA molecule) also includes an isolated nucleic acid molecule or gene of the present invention.

The term "gene" refers to an assembly of nucleotides that encode a polypeptide, and includes cDNA and genomic DNA nucleic acids. "Gene" also refers to a nucleic acid fragment that expresses a specific protein or polypeptide, including regulatory sequences preceding (5' non-coding sequences) and following (3' non-coding sequences) the coding sequence. In particular embodiments, the subject invention provides genes encoding PPTases disclosed herein and, optionally, CPs as disclosed herein.

The term "endogenous gene" refers to a native gene in its natural location in the genome of an organism. The terms "endogenous" and "native" can be used interchangeably within this application. A "foreign" gene, "exogenous gene" or "heterologous" gene refers to a gene not normally found in the host organism, but that is introduced into the host organism by gene transfer or transformation of the microorganism. Foreign genes can comprise native genes inserted into a non-native organism, or chimeric genes. A "transgene" is a gene that has been introduced into the genome by a transformation procedure. A "foreign gene" can also comprise an endogenous gene that is introduced into another location in the genome of an organism (i.e., moved from its natural location within the genome of the organism) which is operably linked to its naturally occurring promoter or to a heterologous promoter. A heterologous gene can also include a native gene of a microorganism that is found in its native location but which has had its native promoter substituted with a heterologous (non-native) promoter, such as the constitutive or inducible promoters discussed within this application. The terms "heterologous", "exogenous", and foreign" can be used interchangeably within this application.

The term "fragment" refers to a nucleotide sequence of reduced length relative to the reference nucleic acid and comprising, over the common portion, a nucleotide sequence substantially identical to the reference nucleic acid. Such a nucleic acid fragment according to the invention may be, where appropriate, included in a larger polynucleotide of which it is a constituent. Such fragments comprise, or alternatively consist of, oligonucleotides ranging in length from at least about 6, 50, 100, 200, 500, 1,000, to about 1,500 or more consecutive nucleotides of a polynucleotide according to the invention.

The term "open reading frame," abbreviated as "ORF," refers to a length of nucleic acid sequence, either DNA, cDNA or RNA that comprises a translation start signal or initiation codon, such as an ATG or AUG, and a termination codon and can be potentially translated into a polypeptide sequence.

The term "upstream" refers to a nucleotide sequence that is located 5' to reference nucleotide sequence. In particular, upstream nucleotide sequences generally relate to sequences that are located on the 5' side of a coding sequence or starting point of transcription. For example, most promoters are located upstream of the start site of transcription.

The term “downstream” refers to a nucleotide sequence that is located 3' to a reference nucleotide sequence. In particular, downstream nucleotide sequences generally relate to sequences that follow the starting point of transcription. For example, the translation initiation codon of a gene is located downstream of the start site of transcription.

The term “homology” refers to the percent of identity between two polynucleotide or two polypeptide moieties. The correspondence between the sequence from one moiety to another can be determined by techniques known to the art. For example, homology can be determined by a direct comparison of the sequence information between two polypeptide molecules by aligning the sequence information and using readily available computer programs. Alternatively, homology can be determined by hybridization of polynucleotides under conditions that form stable duplexes between homologous regions, followed by digestion with single-stranded-specific nuclease(s) and size determination of the digested fragments. The terms “homology” and “identity” can be used interchangeably within the subject application.

As used herein, “substantially similar” refers to nucleic acid fragments wherein changes in one or more nucleotide bases results in substitution of one or more amino acids, but do not affect the functional properties of the protein encoded by the DNA sequence.

The term “substantially similar” also refers to modifications of the nucleic acid fragments of the instant invention such as deletion or insertion of one or more nucleotide bases that do not substantially affect the functional properties of the resulting transcript.

The term “expression”, as used herein, refers to the transcription and stable accumulation mRNA derived from a nucleic acid or polynucleotide. Expression may also refer to translation of mRNA into a protein or polypeptide.

An “expression cassette” or “nucleic acid construct” or “genetic construct” refers to a series of polynucleotide elements that permit transcription of a gene in a host cell. Typically, the expression cassette or nucleic acid construct includes a promoter (native or heterologous) and a heterologous or native polynucleotide sequence that is transcribed. Expression cassettes or constructs may also include, e.g., transcription termination signals, polyadenylation signals, and enhancer elements.

The term “codon” refers to a triplet of nucleotides coding for a single amino acid.

The term “codon bias” refers to the fact that different organisms use different codon frequencies.

The term “codon optimization” refers to the modification of at least some of the codons present in a heterologous gene sequence from a triplet code that is not generally used in the host organism to a triplet code that is more common in the particular host organism. This can result in a higher expression level of the gene of interest.

The term “transformation” is used herein to mean the insertion of heterologous genetic material into the host cell. Typically, the genetic material is DNA on a plasmid vector, but other means can also be employed. General transformation methods and selectable markers for bacteria and cyanobacteria are known in the art (Wirth, Mol Gen Genet. 216:175-177 (1989); Koksharova, Appl Microbiol Biotechnol 58:123-137 (2002). Additionally, transformation methods and selectable markers for use in bacteria are well known (see, e.g., Sambrook et al, supra).

The term “knockout” generally refers to a partial or complete suppression of the expression of at least a portion of a protein encoded by an endogenous DNA sequence in a cell. As used herein, the “knockout” relates to the deletion of a target gene, such as an endogenous PPTase or CP.

The term “knockout construct” refers to a nucleic acid sequence that is designed to decrease or suppress expression of a protein encoded by endogenous DNA sequence in a cell. The knockout construct is inserted into a cell, and integrates with the genomic DNA of the cell in such a position so as to prevent or interrupt transcription of the native DNA sequence. Such insertion usually occurs by homologous recombination. The knockout construct nucleic acid sequence may comprise (1) a full or partial sequence of the gene to be suppressed, (2) a full or partial promoter sequence of the gene to be suppressed, or (3) combinations thereof. Typically, the knockout construct is inserted into a cyanobacterial host cell and is integrated into the cell genomic DNA to delete a target gene, such as an endogenous PPTase and/or CP, usually by the process of homologous recombination.

The phrases “disruption of the gene” and “gene disruption” refer to the deletion or insertion of a nucleic acid sequence into one region of the native DNA sequence and/or the promoter region of a gene so as to decrease or prevent expression of that gene in the cell as compared to the wild-type or naturally occurring sequence of the gene.

The term “plurality” means more than one.

The terms “chemical compound of interest” or “product of interest” refer to a product produced by the modified cyanobacteria. In one embodiment, the product is shinorine. In other embodiments, the product can be cyanobacterial secondary metabolites, polyketides, or non-ribosomal peptides and their hybrids. In other embodiments, the product can be analogs of cyanobacterial secondary metabolites, polyketides, or non-ribosomal peptides and their hybrids. In other embodiments, the product can be unnatural compounds of polyketides, or non-ribosomal peptides and their hybrids. In other embodiments, the product can be secondary metabolites, polyketides, or non-ribosomal peptides and their hybrids of bacterial species that do not belong to the cyanobacterium phylum.

Non-limiting examples of PPTases that can be used in the context of this invention for transformation into recombinant cells are identified in the following table. Other PPTases suitable for use in the context of the subject application can be found in FIG. 9. The sequences for these PPTases can be found, by their accession number, in various databases such as GenBank and EMBL.

| PPTases | Accession No. | SEQ ID NO: |
|---|---|---|
| APPT | WP_044522635.1 | 1 |
| AvPPT | ABA22212.1 | 2 |
| MPPT | WP_004163140.1 | 3 |
| FPPT | WP_017309026.1 | 4 |
| SePPT | ABB57835.1 | 5 |
| SPPT | WP_010873553.1 | 6 |
| Sfp | ACG68433.1 | 7 |

APPT (SEQ ID NO: 1)

```
  1   mlqhtwlpkp pnltllsdev hlwripldqp esqlqdlaat lssdelaran rfyfpehrrr
 61   ftagrgilrs ilggylgvep gqvkfdyesr gkpilgdrfa esgllfnlsh sqnlalcavn
121   ytrqigidle ylrptsdles lakrfflpre yellrslpde qkqkiffryw tckeaylkat
181   gdgiakleei eialtptepa klqtapawsl lelvpddncv aavavagfgw qpkfwhy
```

AvPPT (SEQ ID NO: 2)

```
  1   mlqhtwlpkp pnltllsdev hlwripldrp esqlqhlaat lssdelaran rfyfpehrqr
 61   ftagrgilrs ilglylgvep kqvkfeyesr gkpvlgdrfa dsgllfnlsh sqnlglcavn
121   ytrqigidle ylrptsdles lakrfflpre yellrslpde qkqkiffryw tckeaylkat
181   gdgiakleei eialtptepa klqttpawsl lelvpddncv aavavagfgw qpkfwqy
```

MPPT (SEQ ID NO: 3)

```
  1   mfistdevhl yfisldpsgd rletlaslls edeiiranry hfpehkrrfl vargclreil
 61   gsylaispek iefiysergk psinyqlqfn lshseemaic gltltarigv dlekmrqmkd
121   ldsltkrffc arehelveks aekeklffql wtakeaylka vgtgisggld rvevglnplk
181   ldnvagewql wtaaigdnyr atvviegsdr viktfglsdl
```

FPPT (SEQ ID NO: 4)

```
  1   mgsetnhlwl taptnltllp ddvhvwrisl drpeselqal qttlssdeia raqrfyfeqh
 61   rqrfvagrgi lrtilgrylg vepqavefty elrgkpllad rfadsgvsfn lshsqdlalc
121   gvsrnrkigi dveymrsysd vealaerffa preyevvrsl psnqqqqvff rywtckeayl
181   kaigvgivql ekveisltle qpaklitdee wslielvpgd hylgavaiag qnldlkywqy
```

SePPT (SEQ ID NO: 5)

```
  1   mqrpnpsdav pvpsipscdr gpipnpvtwr tspeplflsa qtvhlwrcsl trslssaeqa
 61   ivaadcdraq aygsnrrhqf lcgrwwlrql lslylpeepa dfrfqlsptg kpelpqsnlc
121   fnlshsgstl liaiawqpvg vdveqprsrs wlalarryfp saelaamqqs tdcdrwglas
181   wvckeawika qgrtlanslr hlqcawtang qprlsglgse esqvqllqvd pqeqlwaaia
241   mpagwnyqtw taaiirknh
```

SPPT (SEQ ID NO: 6)

```
  1   mlpqpqiwlc ptdrplipgy qallsseema rgeryqrpqd kqrfltmrla lrillarqld
 61   clpqqlqfty gpqgkpelvd rerrspwfnv ahsgnyglig lstegeigvd lqimlpkphy
121   lklakrffap qevqqlesle gekrtklfyq lwtakeaflk atgkgisggl nqvipdenla
181   kyqylpdsgd tnhwrlssqp lladqgsndn ywmaiawctn evnqvesnyl pniqpfqwpr
241   nldslp
```

Sfp (SEQ ID NO: 7)

```
  1   mkiygiymdr plsqeenerf mtfispekre kcrrfyhked ahrtllgdvl vrsvisrqyq
 61   ldksdirfst qeygkpcipd lpdahfnish sgrwvigafd sqpigidiek tkpisleiak
121   rffskteysd llakdkdeqt dyfyhlwsmk esfikqegkg lslpldsfsv rlhqdgqvsi
181   elpdshspcy iktyevdpgy kmavcaahpd fpeditmvsy eell
```

Non-limiting examples of carrier proteins (Cps) that can be used in the context of the subject application include: ACPs of *Synechocystis* (SFACP) and *Anabaena* (AFACP), the ACP of the glycolipid PKS in *Anabaena* (APACP), the ACP of the apratoxin (PK/NRP) gene cluster in *Lyngbya* sp. (AprACP), the PCP of the shinorine gene cluster from *Fischerella* (FisPCP), CPs from *Fischerella* (FNPCP, an NRP pathway), *Anabaena* (APNPCP, an NRP/PK pathway) and *M. aeruginosa* NIES843 (MACP, an NRP/PK pathway), $ArCP_{Np}$ from *Fischerella* (FNsACP), one ACP of a putative concanamycin gene cluster from *Streptomyces coelicolor* A(3)2 (ScACP) and one PCP of a thaxtomin cluster from plant pathogen *Streptomyces scabiei* 87.22 (SsPCP).

SFACP
(SEQ ID NOs: 8 and 9)
ATGGATCAGGAAATTTTTGAAAAAGTAAAAAAAATCGTCGTGGAACAGTT
GGAAGTGGATCCTGACAAAGTGACCCCCGATGCCACCTTTGCCGAAGATT
TAGGGGCTGATTCCCTCGATACAGTGGAATTGGTCATGGCCCTGGAAGAA
GAGTTTGATATTGAAATTCCCGATGAAGTGGCGGAAACCATTGATACCGT
GGGCAAAGCCGTTGAGCATATCGAAAGTAAA AFACP
(SEQ ID NOs: 10 and 11)
ATGGGCCAATCAGAAACTTTTGAAAAAGTCAAAAAAATTGTTATCGAACA
ACTAAGTGTGGAGAACCCTGACACAGTAACTCCAGAAGCTAGTTTTGCCA
ACGATTTACAGGCTGATTCCCTCGATACAGTAGAACTAGTAATGGCTTTG
GAAGAAGAATTTGATATCGAAATTCCCGATGAAGCCGCAGAGAAAATTAC
CACTGTTCAAGAAGCGGTGGATTACATCAATAACCAAGTTGCCGCATCAG
CT APACP
(SEQ ID NOs: 12 and 13)
ATGGGTCTAAAACAAAATTATAGTGCAGCAGATATTCAAGCTTGGATGAT
ATCTAATCTAGCTGAATTGTTGGGAGTAGATGGTGATGAAATCGATGCTA
CTGTCAATTTAGAAAGCTATGGTTTGGATTCGGCACAGGCAATGGTACTA
GTTAGTAAACTAGAGCAATTGTTGGGATTTCAACCATCACCTTTGTTGTT
GTGGCATTACCCCACTATTGAATCGTTGTCTGAACGTTTAGCTGAAGAAT
TGGAAGAACAATCT APNPCP
(SEQ ID NOs: 14 and 15)
ATGGAACAATCTACAACTAATCACGCCCGCCCCCAAATTACCGCTACCTA
CCTTCCCCCCAGCAATGAAATTGAAGCCAGAGTCACCCAAGTAATGGAGA
GTTTATTGGGAATCGCTCCTATTGGGGTTAATGATAACTTCTTTGAGTTA
GGAGGACATTCCCTGTTAGCAATTCAAGCAGTTTCACAGCTACGGGAAGA
ATTTCAAGTAGAATTACCCATGCGACAATTTTTATTTGAGTCACCCACAA
TTGGGGGGATAGCCAAAATTATCATTGAAAATCAATCGCCTATTACTGAT FNPCP
(SEQ ID NOs: 16 and 17)
ATGGCCCAACGCCCTATCATTATCCCTCGTACAAATACTGAACAGCGAAT
AGGCGAGATTTGGAAGAAGGCGATGAAGTGGGATTCTGTCTCGATATGTG
ATGATTTCTTTGAATCTGGCGGAAATTCACTTATTGCTGTGAGAATAATC
AACGCTATCAACAAAGAATTTCATTGTGCCTTGCCTTTACATGCTCTTTT -continued

TGAAGCTCCAAGCATTGAAAAGCTCGCTCATAAGGTTGATAGTGATGAAG
TTGAA

FNsACP
(SEQ ID NOs: 18 and 19)
ATGGCTTTTCTAGAAGATGTCCCTCCAACAGAACGTCGAGAACACTTATT
AGAATATCTTGGAAAAGAAGTAGCAAAAATCTTAGGAATAAAACATATAC
CCGACCCAGAACAAGGATTTATAGAAATGGGAATTGACTCTTTGCTTTCC
ATTGAATTCAAAAATCGTTTAGAAAAAGGATTAGAAATTGCTTTACCATC
TACTTTAATATTTGATTTTCCGAATATTAGCAAATTAAATAATTATCTAT
TTGAGCAAATTTATGGTTGGGAAGTAAATACTACCGTGGAGACAACTGTT
GATATTGTAGAAGTTAATGAAGATTTAATTTTGCAAGAACTGGCAGATTT
AGAAGCTTTTCTAGGTAATTCC FisPCP
(SEQ ID NOs: 20 and 21)
ATGGGATCGCTTCCCAAACCTGATTTTTCTAACTTAATCACTCATGAAGA
TTTTACGCCTGCACGCAATGATTTAGAGAGAAAAATCGCGCAGATTTGGT
CAGAAATTTTACAGATTTCGGAAATTGATATTAGAGATAACTTTTTTGAA
GTTGGTGGTAATTCCCTTTTAGCATTACATTTAATGAATGCCATCGAACA
AAAATTTGGTCGAGAGTTAGCACTGTCAACTTTACTTACTAATAACTCAA
TTGAAAAACTAGCAGAAATTCTGCAAAACCCCACAGATGTTTTTCCCAAT
TCA AprACP
(SEQ ID NOs: 22 and 23)
ATGGAAATTTTTGAACAGGAATGTCGAAAATTATTAAAATCTCTACTGGG
TGTTCAACGTATGGAGAGATTGCCTGGTGACACACCACTAATGGAGTCAG
GAATGGATTCACTGGAGTTGTTAGAATTTCGTGCTCTTATAGAAAGAAAG
TTTGGGATTAAGTTAAAGTCTACCTTCTTTTTTAGTTACAAAACTCTTAT
AGCGGTAGCAGAGTATCTTTCAGAACGGGAAGATATTAATTTTAGT MACP
(SEQ ID NOs: 24 and 25)
ATGGTGACAACTGTTCAATCTCCTTGTACCGTTGAAGACATTCAAAACTG
GCTCGTTGATCAGTTTGCTCAACAACTCGATGTTGACCTTGATGACATTG
ATATTGAAGAACCTTTTGATAATTATGAACTCGACTCACGAAAAGCGTTA
GTTTTATTAGGACGCTTAGAAAAATGGCTCGGAAAGGAATTAAATCCTGT
GGTCATTTTTAACTATCCCACCATTGCTGAATTAGCAACCCGATTAGGGG
AATTATATCTT ScACP
(SEQ ID NOs: 26 and 27)
ATGGAGCAGCGGCTGGCTCCGCTGTCCGCGGCCGAGCGCGAGCGGGCACT
CACGGATCTCGTGCGCGTCCAGGTCGCGGCGGTGCTCGGGCACTCTGACC
CCGGCGCGATCGAGTCCGGCCGGGCCTTCCAGGAGCTGGGCTTCGACTCA
CTGACAGCCGTCGAACTTCGCAACCAGCTGAGCACCGCGAGCGGACTGCG
CCTGCCCACCACCCTCGTCTTCGACCACCCCTCCCCCGCCGCTCTCGCCG
CCCACCTCTCGGCGGAGCTGTTCGGCGAGCAGGAG

```
SsPCP
                               (SEQ ID NOs: 28 and 29)
ATGGCCCGCCGGCTCGAACCGTTGGACGAACCCGCGCGACGCCGTCTGCT

GCTCGACCTGGTGTGCGACCACGCGGCCGCGGTCCTCGGCCACACCGGCC

GCCAGGCCGTCCCGGCCGACCAGGCGTTCTCCGCCGTCGGGTTCGACTCG

ATGCTCGCCGTGTCCTTCCGTAACCGGCTGCGCACCGCGACCGGCGTCCC

CGTCGCCGCGACGGTGGTGTTCGACCATCCCACCCCCGCCGCCCTCGCCG

ACCACCTGTACGACGGGTTGAGCGCCCGTCCCGGACCGGCCGTT
```

The subject invention also provides a codon optimized Sfp gene:

```
Codon optimized Sfp
                               (SEQ ID NOs: 30 and 31)
ATGAAAATTTATGGGATTTACATGGATAGACCCCTGAGCCAAGAAGAAAA

CGAACGCTTTATGACCTTTATTAGCCCTGAAAAACGGGAAAAATGTCGCC

GTTTTTATCATAAAGAAGATGCCCATCGTACCTTATTGGGTGATGTGTTG

GTTCGGAGTGTGATTTCTCGCCAATACCAATTGGATAAAAGTGATATTCG

GTTTTCTACTCAAGAATATGGTAAACCCTGTATTCCCGATTTGCCCGATG

CCCATTTTAATATTAGTCATTCTGGTCGCTGGGTTATTGGTGCTTTTGAT

AGTCAACCCATTGGTATTGATATTGAAAAAACCAAACCCATTTCTTTGGA

AATTGCCAAACGCTTTTTCAGTAAAACCGAATACTCTGATTTATTGGCTA

AAGATAAAGATGAACAAACTGATTACTTTTACCATTTGTGGAGTATGAAA

GAATCTTTTATTAAACAAGAAGGTAAAGGTTTAAGTTTGCCCTTAGATAG

TTTTTCTGTGCGGTTGCATCAAGATGGTCAAGTTAGTATTGAATTACCCG

ATAGTCATTCTCCCTGTTACATTAAAACTTATGAAGTTGATCCCGGTTAT

AAAATGGCTGTTTGTGCAGCACACCCCGATTTTCCAGAAGATATTACTAT

GGTTTCCTATGAAGAACTGTTGTAG
```

In one embodiment of the subject invention, a recombinant host cell comprising inactivated endogenous PPTase(s) and genetically modified to contain one or more exogenous PPTase. Such cells may, optionally, also be genetically modified to contain one or more exogenous CP (with or without inactivation of endogenous CPs within the recombinant host cell. Other embodiments provide for recombinant host cells that have been genetically modified to substitute a constitutive promoter for the endogenous promoter. For example, it is possible that the genetic modification causes a constitutive expression of the endogenous and/or exogenous PPTase. These cells may further comprise additional nucleic acid constructs that permit the expression of a chemical or other compound of interest.

Certain embodiments of the invention demonstrate the ability of production of a compound of interest (shinorine) by the recombinant host cells disclosed herein.

As discussed above, the invention provides for the genetic modification of a recombinant host cell in a manner that decreases or eliminates the expression of endogenous PPTases. One possibility is that the genetic modification comprises a heterologous nucleic acid sequence encoding a knockdown component that reduces or eliminates the expression of the endogenous PPTase and/or CP. As used herein, the term "heterologous" refers to an element such as a gene, part of a gene or protein in a cyanobacterium which does not naturally have this element. For example, a "heterologous nucleic acid sequence" has been inserted into the host organism by recombinant DNA technology. The term "heterologous" also means a DNA sequence which appears endogenously in the cyanobacterium but is additionally present in a non-native form, for instance by forming part of a synthetic plasmid or by artificially controlling expression of the DNA sequence by a promoter which is not naturally controlling the sequence in the cyanobacterium. The knockdown component can comprise RNA transcribed from the heterologous nucleic acid that is at least partially complementary to mRNA transcribed from a PPTase and/or CP gene for binding to the mRNA and initiating degradation and/or inhibiting translation of at least part thereof. For example, the heterologous nucleic acid can encode a small RNA (sRNA) or an antisense RNA (asRNA) to silence the expression of the PPTase gene and/or the CP gene.

The expression of the knockdown component is preferably controlled by a constitutive promoter or, as the case may be, a promoter that is at least constitutive under typical cyanobacterial culturing conditions. Suitable constitutive promoters for the various aspects of the present invention include, but are not limited to, Pcpc560, Ptrc, Ptrc2O-2, PA1lacO-1, L03, PnrsB, PpsbA2, PpsbA, the plastocyanin promoter and the promoters provided in the J23 library.

Alternatively, the genetic modification can comprise at least partial disruption or complete removal of an endogenous PPTase and/or CP gene. In this way, the gene may be translated into a protein which has an altered or reduced function or is non-functional. Preferably, the gene is not translated at all. It is possible that the genome of the cyanobacterial cell harbors more than one copy of the endogenous PPTase and/or CP gene. In such a case, it is further preferred that all copies of the gene comprise the at least partial disruption or, more preferably, have been completely removed in order to deprive the cyanobacterium of the possibility utilizing the endogenous PPTase and/or CP.

In a second aspect, this invention provides a method for producing a chemical or compound of interest with the recombinant cyanobacterial cell. The method comprises culturing the cyanobacterial cell under conditions that permit the expression of the chemical or compound of interest, thereby producing the chemical compound of interest. Typically, the cyanobacterium is exposed to light and $CO_2$ during the method steps.

In the following, certain embodiments of the invention will be explained in more detail with reference to figures and experimental data. The figures and examples are not intended to be limiting with respect to specific details.

EXAMPLES

Example 1

Methods

Reagents and Chemicals

Restriction enzymes, Taq DNA polymerase and Phusion DNA polymerase were purchased from Thermo Scientific. Chemicals and solvents were from Sigma Aldrich, Fisher Scientific or RPI Corp (USA). The GeneJET Plasmid Miniprep Kit, PCR Purification Kit and Gel Extraction Kit were from Thermo Scientific. Oligonucleotide primers were synthesized by Sigma Aldrich, while codon-optimized Sfp gene was obtained from GenScript. DNA sequencing was performed at Eurofins.

Strains and Culture Conditions

*Escherichia coli* DH5α and BL21-CodonPlus (DE3) RIPL were used for routine molecular biology studies and protein expression, respectively, and were grown in Luria-Bertani broth or Terrific broth. *Synechocystis* sp. PCC6803, *Anabaena* sp. PCC7120, *Anabaena variabilis* ATCC29413, *Fischerella* sp. PCC9339, *Microcystis aeruginosa* NIES-843, and *Synechococcus* sp. PCC7942 were purchased from UTEX or NIES (Japan) and cultured in BG11 medium with $CO_2$ bubbling. All cyanobacterial cultures were performed at 26° C. with 16 h/8 h light/dark cycle using 2000-2500 lux during lighting period. BG-11 medium supplemented with 1.0% (wt/vol) agar and 0.3% (wt/vol) sodium thiosulfate was used to grow cyanobacterial strains on the plate.

Construction of Plasmids

Figure 18:
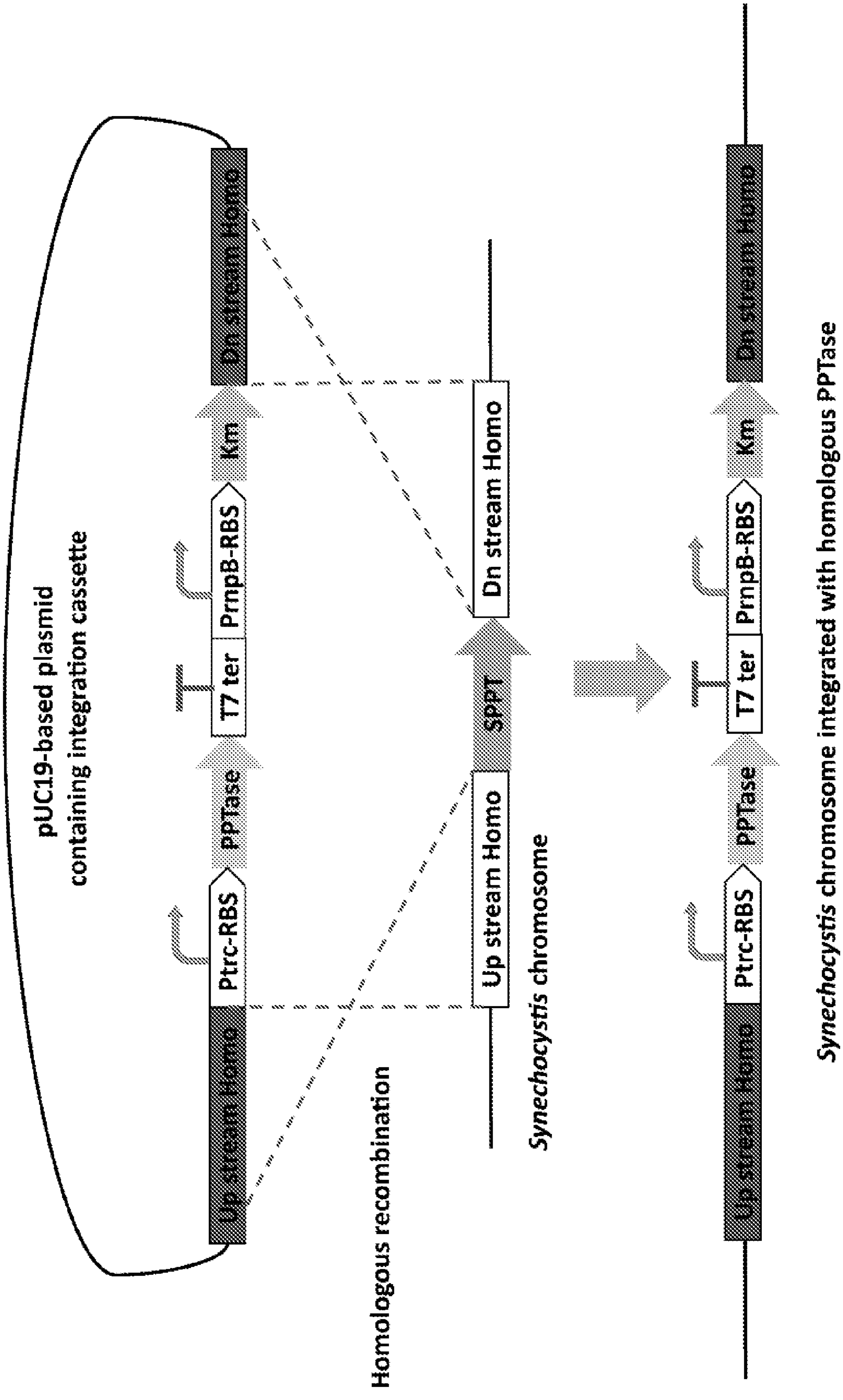
FIG. 18. Schematic representation of homologous replacement of the SPPT gene with foreign PPTase genes in *Synechocystis* sp. PCC6803.

All oligonucleotide primers used in this work were listed in FIG. 12. The PPTase and CP genes were PCR amplified and cloned into pET28b (Novagen) to generate the expression plasmids. The inserts in the integration plasmids were sequentially constructed in the PCR reactions as shown in FIG. 18. The details were included in the supporting information. Briefly, a T7 terminator fragment was first introduced to the 3'-end of APPT, MPPT and Sfp genes by the PCR reactions. The resulted amplicons were fused to the 3'-end of Ptrc promoter-ribosomal binding site (Ptrc-RBS) in the overlapping PCR reaction. Next, a kanamycin resistance cassette amplified from pUC4K (Pharmacia) was fused to the 3'-end of the above amplicons to generate the final insert products. The final products were cloned into the integration vector pUC19int. To generate the pUC19int, the upstream and downstream regions (~1 kb) of the SPPT gene in *Synechocystis* were amplified and fused in the PCR reactions. The fusion product was then digested by HindIII and EcoRI and cloned into pUC19 to create pUC19int. All constructed plasmids were sequenced to eliminate potential errors in the inserts.

Protein Expression and Purification

Recombinant proteins with a His-tag were expressed in *E. coli* BL21-CodonPlus (DE3) RIPL. Cells were grown at 37° C. to an OD600=0.5-0.6, and then cooled to 18° C. prior to the addition of 0.1-0.5 mM isopropyl-β-D-galactopyranoside (IPTG). The cultures were grown at 18° C. for another 18-20 h before harvesting. *E. coli* cells were collected after centrifugation at 4° C., 4,000×g for 15 min, and frozen at −80° C. until the use. Pellets were thawed on ice, resuspended in a suitable volume of lysis buffer (50 mM Tris-HCl buffer, pH 8.0, 300 mM NaCl, 3 mM BME, 10 mM imidazole, 10% glycerol; wt/vol=1:4), and subjected to sonication on ice with 2-s pulses. The soluble fractions were collected after centrifugation at 4° C., 25,000×g for 30 min, and incubated with Ni-NTA agarose resin (Thermo Fisher) at 4° C. for 1 h. The resin was then washed successively with ~10 column volumes of the lysis buffer containing 30 mM imidazole. Recombinant proteins were eluted with 50-300 mM imidazole in the lysis buffer. After SDS-PAGE analysis, elution fractions containing the targeted proteins were combined. The purified proteins were then exchanged into a storage buffer (50 mM Tris-HCl buffer, pH 8, 100 mM NaCl, 10% glycerol) using PD-10 column according to the manufacture's protocol (GE), aliquoted and stored at −80° C. until the use. The concentrations of recombinant proteins were determined by Nanodrop and/or Bradford assay.

HPLC and LC-MS Analysis

A Shimadzu Prominence UHPLC system (Kyoto, Japan) fitted with a Vydac 218TP54-C18 (5 μm, 4.6 mm×250 mm) column was used for HPLC analysis. Solvent A was $H_2O$ with 0.1% TFA and solvent B was $CH_3CN$ with 0.1% TFA. The column was equilibrated with 10% solvent B for 2 min and then protein sample was eluted with a linear gradient of 10-70% in 30 min, followed by another linear gradient of 70-98% solvent B in 1 min. The column was further cleaned with 98% solvent B for 5 min and then re-equilibrated with 10% solvent B for 2 min. The flow rate was set as 0.8 mL/min, and the product was detected at 220 nm with a PDA detector. Apo- and holo-proteins were further analyzed in LC-MS analysis. MS spectra were acquired by using an API Qstar Pulsar i hybrid tandem mass spectrometer (Applied Biosystems) as previously described. An Agilent Eclipse Plus C18, (3.5 um, 2.1×100 mm) was used. In LC-MS analysis, solvent A was $H_2O$ with 0.1% FA and solvent B was $CH_3CN$ with 0.1% FA. The protein samples were eluted with a linear gradient of 10-90% in 15 min at a flow rate of 0.3 mL/min. HRMS data were obtained using a Thermo Fisher Q Exactive Focus mass spectrometer equipped with electrospray probe on Universal Ion Max API source. The LC conditions were the same as those for the LC-MS analysis.

Phylogenetic Analysis of Cyanobacterial PPTases

*E. coli* AcpS and Sfp were used as two queries to mine the current available cyanobacterial genomes in NCBI database (up to Nov. 1, 2016) in BLAST analysis. The output data of BLAST were carefully analyzed to identify the sequences with comparatively high similarity (with e-values $\leq 10^{-5}$) and to eliminate redundant sequences from taxonomically close species. The selected cyanobacterial PPTase sequences along with those from *Streptomyces rapamycinicus* NRRL5491, *Xenopus laevis* and *Homo sapiens* were aligned by Clustal Omega and then analyzed by MEGA7 to construct a phylogenetic tree.

Biochemical Characterization of PPTase Activity

The enzyme reaction solutions (100 μl) typically contained 50 mM Tris-Cl, pH 8.0, 12.5 mM $MgCl_2$, 0.5 mM coenzyme A, 5 mM dithiothreitol (DTT) and 50 μM CPs. The reactions were initiated by adding 0.3 μM (final concentration) of PPTases and incubated at 37° C. After 20 min, the reactions were terminated by mixing with 100 μl of 10% formic acid. To quantitatively determine the relative activity of the enzymes, the reactions may be incubated for up to 40 min before the quenching. The quenched solutions were centrifuged at 4° C., 16,000×g for 15 min and clear supernatants were collected and subjected to HPLC and LCMS analysis with details shown in the supporting information. All experiments were repeated in triplicate. For kinetic studies, the reactions were set up as described above except that the concentrations of CPs were varied from 1 to 100 μM. The reactions were performed at 37° C. for 5-10 min to ensure that ≤10% of substrates were converted. To determine the concentrations of holo-CPs, 0.2 to 50 μM of apo-proteins were fully converted in the enzyme reactions and then quantitated in HPLC analysis to establish standard curves of holo-CPs. The concentrations of existing holo-CPs in the substrate solutions were subtracted in the data analysis. Data were fit into the Michaelis-Menten equation to determine kinetic parameters using GraphPad Prism 4.0. All experiments were independently repeated three times.

Genetic Engineering of *Synechocystis*

*Synechocystis* cells (about $1\times10^8$ cells/ml) in the exponential phase were collected after centrifugation at 8,000 rpm for 15 min and resuspended in fresh BG11 medium at a density of $1\times10^9$ cells/ml. Integration constructs at a final concentration of 10 μg/ml were then incubated with the cell solution at room temperature. After 5 h, the mixtures were spread onto BG11 agar plates supplemented with 5 μg/ml kanamycin. The segregation of wild type with the desirable mutants was achieved by iteratively streaking the colonies onto plates with progressively increased kanamycin (up to 50 μg/ml). The final stable mutants were genotyped by the colony PCR using the primers listed in FIG. 12. Growth curves of the wild type and three mutant strains were determined by daily record of the $OD_{730}$ of the liquid cultures over the period of 13 days.

Quantitative RT-PCR Analysis of the Integrated Exogenous PPTase Genes

Total RNA samples were isolated from *Synechocystis* and its mutants using ZR Fungal/Bacterial RNA MiniPrep kit (Zymo Research). The quantity and quality of the isolated RNAs were determined using Nanodrop. Synthesis of cDNAs was performed with random primers following the manufacturer's protocol (Thermo Scientific). The synthesized cDNAs were used as templates for qPCR to detect the transcription of the integrated PPTase genes, while the isolated RNA samples themselves were used as the templates of PCR reactions to detect any residual genomic DNAs using primers listed in FIG. 12. The student's t-test analysis was applied to determine significance difference between the samples, and a P-value <0.05 was considered to be significant.

Preparation of Cell Lysates of *Synechocystis* Mutants for PPTase Activity Test Cells of the wild type and three *Synechocystis* mutants were harvested from 0.8 to 1.0 L culture after centrifugation at 4° C., 4,000×g for 15 min. Cell pellets were washed with fresh BG11 medium and then resuspended in 4 ml of lysis buffer (50 mM MES, pH 7.0, 10 mM $MgCl_2$, 5 mM $CaCl_2$, 1 mM phenylmethylsulfonyl fluoride and 10% glycerol). The solutions were frozen at −80° C. and thawed at room temperature once prior to the sonication on ice with 2-s pulses. Cell homogenates were centrifuged at 4° C., 25,000×g for 30 min to collect clear cell lysates. The enzyme reaction mixtures were set up as described above but contained 70 μl of cell lysates. The reactions were incubated at 37° C. for 16 h, and the holo-products were detected in LCMS analysis as described above. The reactions were performed in triplicate.

DNA Manipulation and Plasmid Construction for Cloning of Shinorine Gene Cluster Genomic DNA was extracted from *Synechocystis* using a modification of the method described by Murray and Thompson. In brief, a 2 ml aliquot of late-logarithmic-phase cells was pelleted by centrifugation at 15,000 rpm for 5 min, the medium was decanted, and the pellet was resuspended in 567 μl of TE. Cells were lysed by the addition of 30 μl of 10% (wt/vol) SDS and 3.0 μl of 20 mg of proteinase K per ml to give final concentrations of 100 μg of proteinase K per ml and 0.5% (wt/vol) SDS. The solution was mixed thoroughly and incubated at 60° C. for 4 h before the addition of 100 μl of 5M NaCl and 80 μl of 10% (wt/vol) CTAB in 0.7% (wt/vol) NaCl. The CTAB-NaCl solution was prepared by slow addition of CTAB (10 g) to 100 ml of 0.7 M NaCl while heating and stirring. Samples were mixed thoroughly and incubated at 65° C. for 10 min. CTAB complexes were extracted with 1 volume of chloroform-isoamyl alcohol (24:1 [vol/vol]) and centrifugation at 15,000 rpm for 5 min, and the supernatant was transferred to a fresh tube. Any CTAB complexes remaining in the supernatant were extracted with 1 volume of phenol-chloroform-isoamyl alcohol (25:24:1 [vol/vol/vol]) and centrifugation at 15,000 rpm for 5 min. The supernatant was transferred to a fresh tube, and nucleic acids were precipitated by the addition of 0.6 volume of isopropanol. After the contents of the tubes were mixed by gentle inversion, the nucleic acids were collected by spooling on a glass rod and washed successively in 50, 70, and 100% (vol/vol) ethanol. Spooled and washed DNA was transferred to a fresh tube, dried briefly in vacuo, and resuspended in deionized water.

Genomic DNA was extracted from *Fischerella* by using a modification of the method described by Fiore et al. In brief, an aliquot of cultured cells (5 ml) were harvested in mid to late exponential phase (10-25 days) by centrifugation (15,000 rpm for 5 min at 25° C.) in a sterile 1.5 ml microcentrifuge tube. Cells were resuspended in 500 μl TE Buffer (10 mM Tris, 1 mM EDTA, pH 8.0) and subjected to sonic shock for 10 min. This treatment allowed cell separation and filament breakage. Cells that still presented aggregated colonies were dispersed by repeated pipetting with a 1.0-ml micropipette prior to the final centrifugation. Pelleted cells were washed in 1.0 ml of a solution containing 50 mM Tris-HCl, pH 8.0, 5 mM EDTA and 50 mM NaCl to reduce extracellular polysaccharides. Cell pellets were resuspended in a 200 μl solution of 50 mM Tris-HCl, pH 8.0, and 50 mM EDTA. Subsequently, 600 μl of prewarmed (55° C.) extraction buffer (3%, w/v, CTAB, 20 mM EDTA, 1.4 M NaCl, 0.1 M Tris-HCl, pH 8.0, 1% v/v, 2-mercaptoethanol, freshly prepared) were added and incubated at 55° C. in a water bath for 30 min with mixing by gentle inversion every 5-10 min. The mixture was allowed to cool for 30 s before adding 800 μl of chloroform:isoamyl alcohol (24:1, v/v) and mixed by gentle inversion (30 times) until an emulsion was formed. After centrifugation (15,000 rpm for 5 min at 25° C.), the supernatant (500 μl) was transferred to a sterile microcentrifuge tube and gently mixed with 0.6 volume of isopropanol until DNA precipitated. The DNA pellets were recovered by centrifugation, (10 min, 4° C., 15,000 rpm) and washed with 1 ml of ice-cold 70% ethanol to remove any residual salt. After a final centrifugation (5 min, 4° C., 15,000 rpm), the supernatant was discarded, and the pellets were dried before being resuspended in 100 μl TE Buffer (10 mM Tris, 1 mM EDTA, pH 8.0). The samples were treated with 1 μl of RNAse (10 mg/ml) for 1 h at 37° C.

For genomic DNA extraction from *Anabaena* 7120, cells were resuspended into 0.5 ml of 0.15 M NaCl and 0.1 M EDTA, and poured into 2 ml cryogenic vials. Three freeze-thawing cycles, alternating freezing in liquid nitrogen and thawing at 37° C. in a water bath, were used to damage the cell walls and render the cells more susceptible to further enzymatic lysis. The cells were then collected by centrifugation (10 min, 8000 rpm), resuspended in 0.5 ml TE Buffer (10 mM Tris, 1 mM EDTA, pH 8.0) and transferred to fresh 2 ml tubes for enzymatic cell wall lysis with 100 μl of 50 mg/ml lysozyme for 30 min at 37° C. Subsequently, proteins were degraded with 5 μl of 50 mg/ml proteinase K and in 2% SDS final concentration, for 1 h at 37° C. Polysaccharides, proteins and cell wall debris were thereafter removed by selective precipitation with CTAB in presence of NaCl: 150 μl of 5 M NaCl was added to the tubes, followed by 0.1 volume of a 10% CTAB stock solution. The samples were gently mixed by inversion, then further incubated at 65° C. for 10 min to optimize the formation of CTAB-protein and -polysaccharides complexes. Nucleic acids purification was achieved by extraction in 1 volume of chloroform:isoamyl alcohol (24:1). The tubes were placed on ice for 30 min to allow precipitation of CTAB complexes, before being centrifuged (10 min, 8000 rpm). The supernatant was transferred to a fresh tube, gently mixed with 0.6 volume of isopropanol until DNA precipitated. The DNA pellets were recovered by centrifugation, (10 min, 4° C., 15,000 rpm) and washed with 1 ml of ice-cold 70% ethanol to remove any residual salt. After a final centrifugation (5 min, 4° C., 15,000 rpm), the supernatant was discarded, and the pellets were dried before being resuspended in 100 μl TE Buffer (10 mM Tris, 1 mM EDTA, pH 8.0). The samples were treated with 1 μl of RNAse (10 mg/ml) for 1 h at 37° C.

PCR amplification of shinorine gene cluster was carried out by using the primers shown in table 1. The PCR-amplified products were subjected to the assembly of plasmid pSL1211-shinorine by enzyme digestion and ligation method. After sequencing confirmation of the correct construction of pSL1211-shinorine, shinorine gene cluster with the Ptrc promoter was amplified again and inserted into pRL1383a vector to construct plasmid pRL1383-Ptrc-shi. On the other hand, the *Fischerella* PPTase (Fppt) and *Anabaena* PPTase (Appt) were amplified from *Fischerella* and *Anabaena* genomic DNA, respectively. Also, the promoter PrnpB was amplified from *Synechocystis* genomic DNA. PCR fusion was performed to link PrnpB and Fppt/Appt. The fused genes were cloned into pRL1383-Ptrc-shi to construct the shinorine expression plasmids pRL1383-Ptrc-shi-PrnpB-Fppt and pRL1383-Ptrc-shi-PrnpB-Appt.

Conjugation Transfer of Shinorine Gene Cluster Containing Plasmid Into *Synechocystis*

Triparental mating was used to transfer the expression plasmid pRL1383-shinorine. In brief, both conjugal and cargo *E. coli* strains were grown in LB medium plus the appropriate antibiotics overnight at 37° C. For spot matings, 0.75 ml of each culture was transferred to 1.5 ml Eppendorf tube and centrifuged to collect the cells. Cell pellet was washed once with LB medium and resuspended in 0.75 ml LB medium without antibiotics. Two tubes of cells were then mixed and centrifuged again to collect cells. Cell pellet was then resuspended into 60 μl of fresh LB medium without antibiotics. On the other hand, 1 ml *Synechocystis* culture was centrifuged and cell pellet was washed once with fresh BG11 medium. The cell pellet was resuspended into 100 μl of BG11 medium. Following 5 μl of mixed *E. coli* culture and 5 μl of *Synechocystis* culture were mixed and 2 μl of the mixture was transferred on to a BG11-agar plate containing no antibiotics. The conjugation was conducted under normal growth conditions for *Synechocystis* for 24 h. Then, cells from the spot were spread on a BG11 plate with 20 μl/ml gentamycin. After single colonies are developed and visible, colonies were selected and transferred to tube and bottle culture.

Extraction of Shinorine from *Synechocystis*

The *Synechocystis* transformants were grown in the 300 ml BG11 medium at 26° C. with air bubbling. After incubation at 26° C. for 14 days with air bubbling the whole culture was mixed with an equal volume of methanol and the mixture was subjected to a vigorous vortex procedure. The supernatant was collected by centrifugation at 3,000 rpm for 10 min, and a 20 μl portion of the supernatant was directly analyzed by high-performance liquid chromatography (HPLC). On the other hand, the supernatant was evaporated to remove methanol and redissolved in 1 ml water for HPLC analysis. Authentic samples of shinorine were prepared from Helioguard 365.

Results and Discussion

Phylogenetic analysis of cyanobacterial Sfp-like PPTases. To gain an understanding of the evolutionary relationship of cyanobacterial PPTases, we mined all cyanobacterial genomes available in NCBI database using *E. coli* AcpS and Sfp as queries. We then selected and retrieved 39 sequences from strains covering all five subsections of cyanobacteria (FIG. 9). These sequences were phylogenetically analyzed along with AcpS, Sfp and enzymes from *Streptomyces rapamycinicus* NRRL5491, *Xenopus laevis* and *Homo sapiens* as outgroups. The constructed phylogenetic tree comprised an AcpS-like clade with AcpS and eight cyanobacterial PPTases and a Sfp-like clade containing all other enzymes (FIG. 1). Three outgroups along with Sfp were separated from cyanobacterial Sfp-like PPTases in the Sfp-like clade. This analysis further revealed that the PPTases from the heterocystous cyanobacteria (subsections IV and V) formed a separate sub-clade. The relationship of enzymes from the sections I-III was not obvious. For example, the PPTase from the subsection I *Gloeocapsa* sp. PCC73106 was in the same group as the one from *Spirulina subsalsa* (subsection III) (FIG. 1). These results indicate that cyanobacterial Sfp-like PPTases share a common ancestor and have acquired different traits over the course of evolution.

Selection of cyanobacterial Sfp-like PPTases and CP substrates. To biochemically characterize cyanobacterial Sfp-like PPTases, we next selected representative enzymes based on the result of phylogenetic analysis (FIG. 1) and predicted biosynthetic potential of cyanobacterial strains. The subsection V heterocystous cyanobacterium *Fischerella* sp. PCC9339 (referred to as *Fischerella*) possesses >10 NRP and/or PK gene clusters and its PPTase (FPPT) was therefore included in this work due to its potential substrate promiscuity. With the same rationale, we selected the PPTases from the subsection IV *Anabaena* sp. PCC7120 (hereafter referred to as *Anabaena*, APPT) and its close species *A. variabilis* ATCC29413 (AvPPT). In the constructed phylogenetic tree, FPPT and APPT/AvPPT belong to two distantly related groups in the same subclade and can potentially represent the enzymes from a variety of heterocystous cyanobacteria (FIG. 1). We also selected the PPTase from the subsection I *Microcystis aeruginosa* NIES843 (MPPT) that carries >10 NRP and/or PK gene clusters. On the other hand, although *Synechococcus elongatus* PCC7942 encodes no NRP or PK cluster, its PPTase (SePPT) becomes a separate leaf in the phylogenetic tree (FIG. 1) and was thus selected. Furthermore, we included SPPT as a control in this work due to its demonstrated incompetency in activating noncognate cyanobacterial CPs. Finally, the paucity of biochemical characterization of Sfp in activating cyanobacterial CPs led to its selection. These six selected cyanobacterial PPTases and Sfp contain the featured W/KEA motif (FIG. 14) and together cover the broad space of the constructed phylogenetic tree (FIG. 1).

We further chose 11 CPs from multiple biosynthetic pathways of different species for biochemical characterization of the selected PPTases (FIG. 10 and FIG. 15). They included two ACPs of FASs from *Synechocystis* (SFACP) and *Anabaena* (AFACP), the ACP of the glycolipid PKS in *Anabaena* (APACP), the ACP of the apratoxin (PK/NRP) gene cluster in *Lyngbya* sp. (AprACP), and the PCP of the shinorine gene cluster from *Fischerella*. In addition, we included three CPs of uncharacterized gene clusters from *Fischerella* (FNPCP, an NRP pathway), *Anabaena* (APNPCP, an NRP/PK pathway) and *M. aeruginosa* NIES843 (MACP, an NRP/PK pathway) and one homolog of previously characterized $ArCP_{Np}$ from *Fischerella* (FNsACP). To thoroughly examine the versatility of selected PPTases, we also included the ACP of a putative concanamycin gene cluster from *Streptomyces coelicolor* A(3)2 (ScACP) and the PCP of a thaxtomin cluster from plant pathogen *S. scabiei* 87.22 (SsPCP).

Figures 2A, 2B:
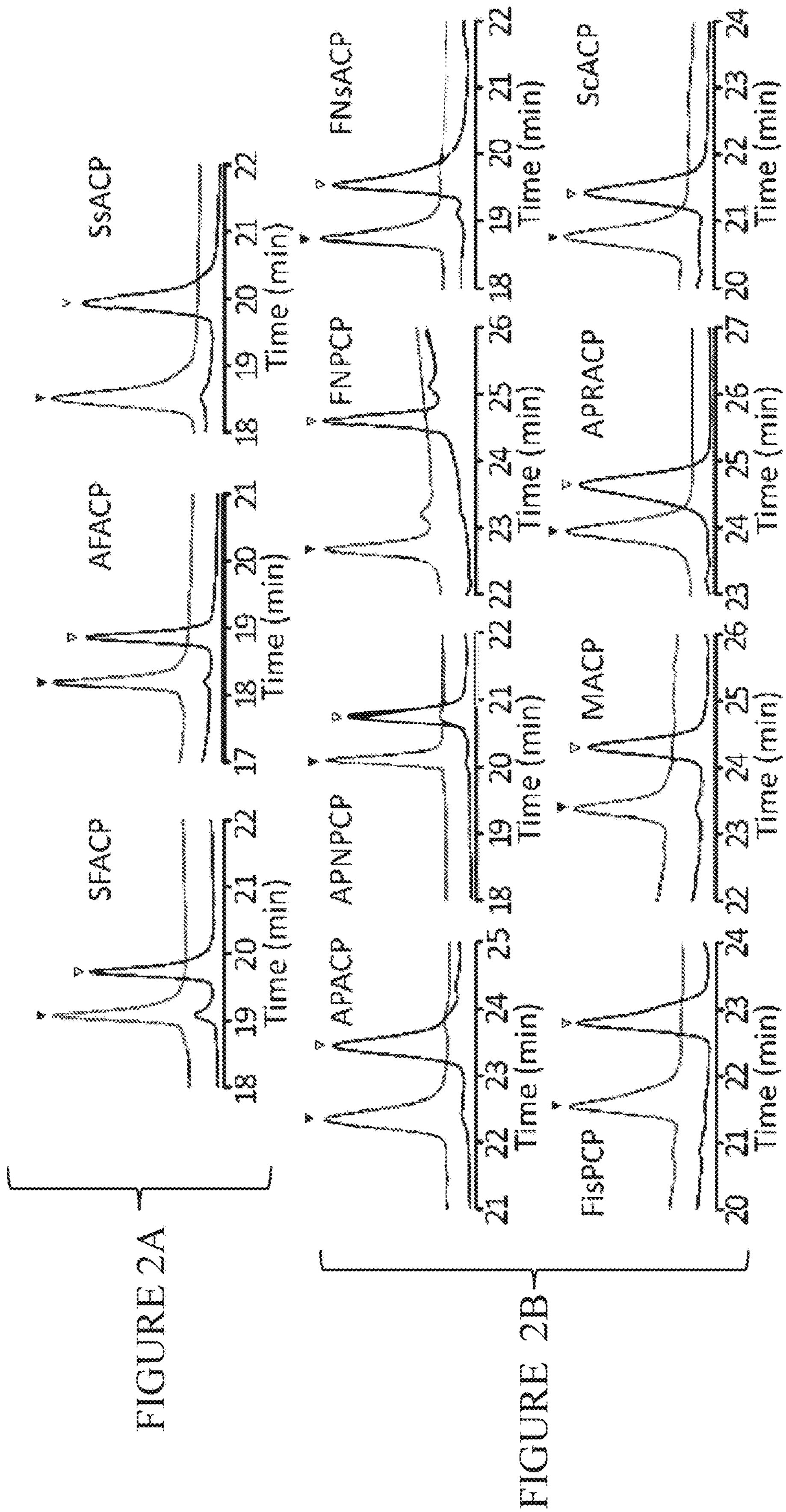
FIGS. 2A-2B. HPLC traces of selected PPTase reactions. (A) SFACP, AFACP and SsPCP substrates were partially phosphopantetheinylated over the course of overexpression in *E. coli*. They were fully-converted in some of PPTase reactions. (B) All other CPs were completely functionalized by some PPTases. Red traces represent the enzyme reactions and black ones show the substrates. ▼ indicates the holo-CP, while ∇ represents the apo-CPs. The minor peaks in APACP, APNPCP, and MACP substrates showed similar retention times to the corresponding holo-proteins but had different molecular weights in the MS analysis.
Figure 16A:
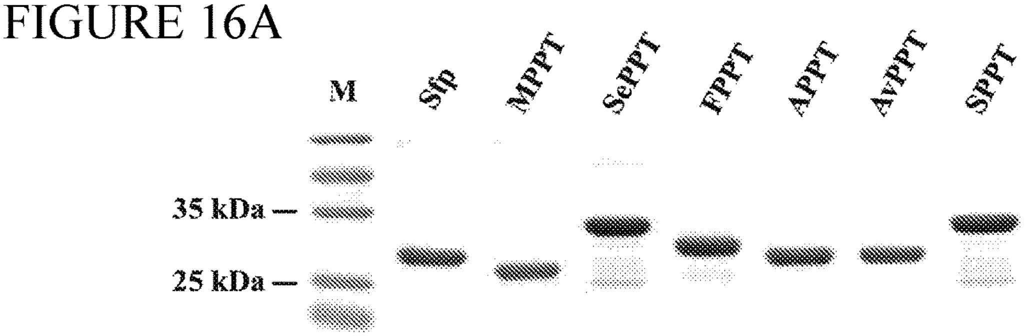
FIGS. 16A-16B. SDS-PAGE analysis of the purified PPTases and CP proteins. All proteins showed expected molecular weights and CPs were validated in LC-MS analysis.
Figure 16B:
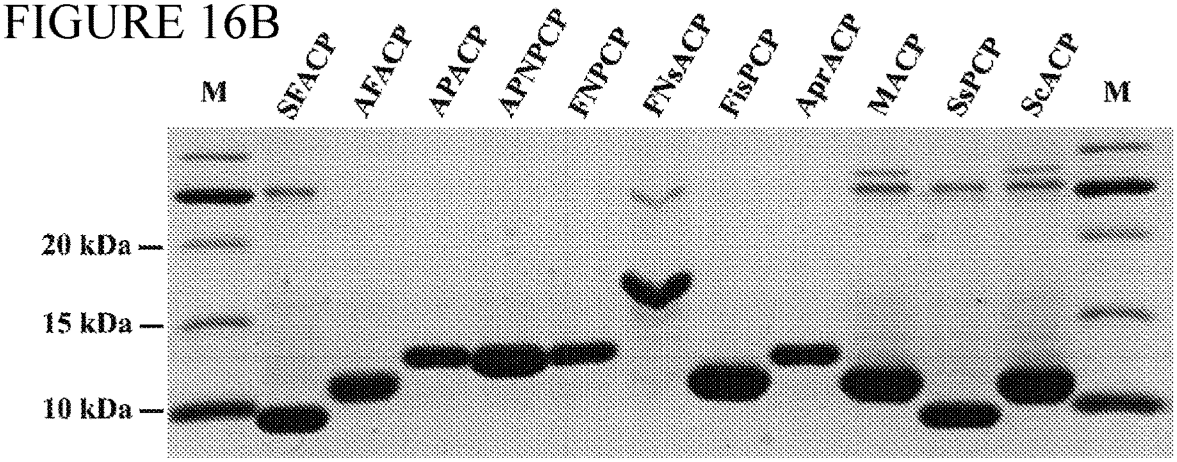
Figure 17:
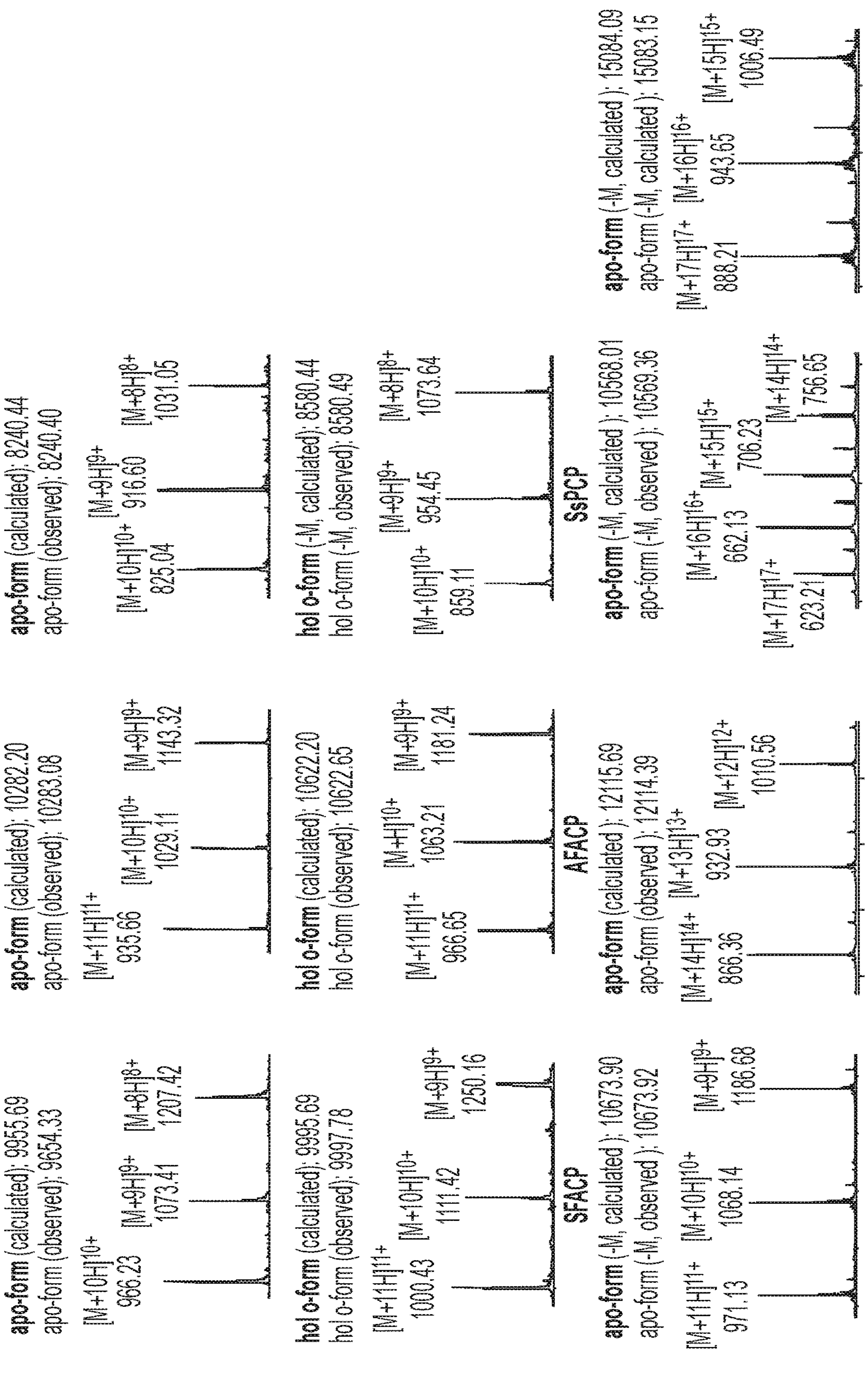
FIG. 17. HR-MS spectra of apo- and holo-CPs. The charge status, m/z value, and calculated and observed molecular weights of CPs were shown.
Figure 17:
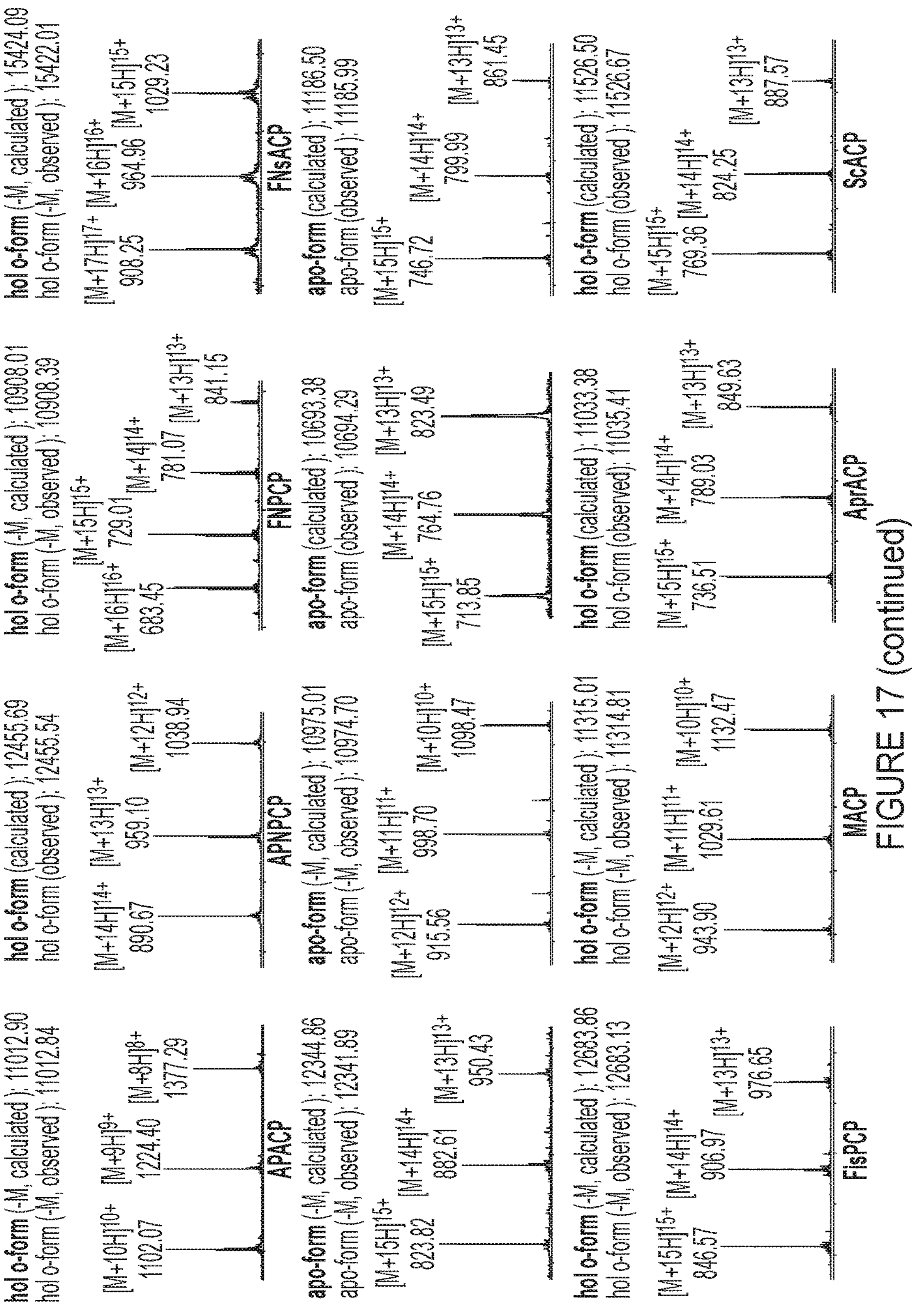

In vitro phosphopantetheinylation of cognate and noncognate CPs by selected PPTases. All selected genes were amplified from bacterial genomic DNAs or commercially synthesized (FIG. 15) and then expressed in *E. coli* BL21-CodonPlus (DE3) RIPL. Recombinant proteins were purified by a single step Ni-NTA affinity chromatography to achieve the high purity (FIG. 15). All purified proteins showed expected molecular weights in SDS-PAGE analysis (FIGS. 16A and 16B) and were further confirmed via LC-MS. SFACP, AFACP and SsPCP gave rise to two peaks in their HPLC traces (FIG. 2A). The MS analysis revealed the smaller peaks as the halo-proteins and the major peaks as the apo substrates (FIG. 10 and FIG. 17). The remaining eight CP substrates adapted the apo-form (FIG. 2B). This result suggests that *E. coli* AcpS activates noncognate ACPs of FASs to a low level and shows a limited promiscuity toward CPs of NPRSs and PKSs.

We next examined the catalytic activity of each PPTase toward all 11 recombinant CPs. The LC-MS analysis revealed the full conversion of the substrates to the holo-products in 69 out of 77 reactions (FIG. 2 and FIG. 3). In particular, APPT, AvPPT, MPPT and Sfp functionalized all substrates (FIG. 3 and FIG. 10). Unexpectedly, SPPT also phosphopantetheinylated all CP substrates except ScACP (FIG. 3 and FIG. 11), a strikingly different outcome compared with its narrow substrate specificity in an early report. On the other hand, we observed the relatively narrow substrate scope of SePPT and FPPT (FIG. 3 and FIG. 11). SePPT showed no activity toward APNPCP, MACP, ScACP, and SsPCP, while FPPT shared the same substrate scope as SePPT with the exception of its low activity toward SsPCP.

To quantitate the enzyme performance, we performed the reactions to phosphopantetheinylate <95% of a CP substrate. The activity of the most active enzyme was set as 100% to normalize the activities of the other PPTases toward the same substrate (FIG. 3 and FIG. 11). This analysis further confirmed the versatility and activity of APPT, AvPPT, MPPT, and SPPT. APPT showed the highest conversion rate toward seven cyanobacterial CPs from the fatty acid, PK, NRP, and PK/NRP biosynthetic pathways (FIG. 3 and FIG. 11). It also activated ScACP and SsPCP from *Streptomyces* species to a modest-to-significant extent. In line with this result, APPT functionalized the ACP of microalgal polyunsaturated fatty acid synthase in canola and allowed the heterologous production of lyngbyatoxin A in *Anabaena*. AvPPT possessed a similar substrate scope and comparable activities to the majority of substrates as APPT (FIG. 3 and FIG. 11). Addition to the two enzymes from the subsection IV, MPPT showed >84% relative activity toward all nine cyanobacterial CPs including the highest activity on MACP (FIG. 3 and FIG. 11). This enzyme also displayed a modest relative activity toward ScACP and SsPCP. Similarly, SPPT promoted >71% relative conversion of eight cyanobacterial CPs (FIG. 3 and FIG. 11). Despite the low or no activity toward MACP, SsPCP and ScACP, these data clearly highlighted the significant catalytic activity of SPPT in functionalizing noncognate cyanobacterial CPs of both primary and secondary metabolism. By contrast, both SePPT and FPPT showed a relatively narrow substrate scope (FIG. 3 and FIG. 11). SePPT demonstrated strong activity toward two ACPs of FASs but no others, while FPPT was not competent to activate SsPCP, APACP, APNPCP, MACP, and ScACP. We also quantitated the in vitro catalytic activity of Sfp. This enzyme functionalized seven cyanobacterial CPs to comparable levels of APPT and activated APNPCP and FisPCP to a modest-to-good level (FIG. 3 and FIG. 11). Among all PPTases, Sfp showed the highest relative activity toward ScACP and SsPCP. Collectively, these results provide the first comprehensive evaluation of cyanobacterial PPTases in terms of enzymatic activity and substrate scope, and suggest the potential applications of APPT, AvPPT, MPPT, SPPT and Sfp in synthesizing cyanobacterial natural products.

Kinetics analysis of APPT, MPPT, SPPT and Sfp. To further assess the catalytic performance of selected PPTases, we kinetically analyzed APPT, MPPT, SPPT and Sfp in activating all 11 substrates. This analysis determined the highest catalytic efficiency at $2.1\pm0.2\ \mu M^{-1}\ min^{-1}$ when Sfp converted SsPCP into the holo form (Table 1). Sfp also demonstrated a high $k_{cat}/K_m$ value in activating ScACP ($1.8\pm0.1\ \mu M^{-1}\ min^{-1}$), consistent with its overall kinetic performance toward CPs of actinomycetes. We further observed the varied catalytic efficiencies of Sfp toward cyanobacterial CPs (Table 1). Among them, APACP was the best substrate of Sfp ($k_{cat}/K_m=1.5\pm0.3\ \mu M^{-1}\ min^{-1}$), while the FisPCP was the least ($0.1\pm0.02\ \mu M^{-1}\ min^{-1}$). To our knowledge, AnaD, a standalone PCP, from *Oscillatoria* PCC6506 was the only cyanobacterial CP that has been kinetically evaluated in the studies of Sfp. This work adds new, useful information about this versatile enzyme and suggests its broad use in cyanobacterial natural products research.

Among all selected enzymes, APPT demonstrated the highest catalytic efficiencies toward AprACP, AFACP and APACP (1. 6 to 1.8 $\mu M^{-1}\ min^{-1}$) (Table 1). These three substrates were also favored by MPPT and SPPT ($k_{cat}/K_m\geq1.0\ \mu M^{-1}\ min^{-1}$) (Table 1). By contrast, neither FisPCP nor FNsACP were kinetically preferred by the selected cyanobacterial PPTases ($k_{cat}/K_m=0.3\ \mu M^{-1}\ min^{-1}$) and Sfp (Table 1). The $k_{cat}/K_m$ values of APPT, MPPT and SPPT toward four other cyanobacterial CP substrates varied from $0.1\pm0.02$ to $1.4\pm0.2\ \mu M^{-1}\ min^{-1}$. None of the selected PPTases showed a preference to substrates from any specific pathways or sources. Interestingly, the kinetic studies revealed overall high catalytic efficiency of cognate CP/PPTase pairs ($k_{cat}/K_m\geq0.9\ \mu M^{-1}\ min^{-1}$, e.g., MACP/MPPT, SFACP/SPPT and APNPCP/APPT), indicating the potential co-evolution of biosynthetic enzymes.

The $K_m$ values of four PPTases toward 11 CPs were in the μM range (Table 1). SFACP showed relatively tight interactions with all PPTases ($K_m$=1.5±0.2 to 3.2±0.2 μM), while overall relatively weak interactions were observed between all PPTases and APACP ($K_m$=10.0±0.9 μM to 26.5±5.2 μM). Conversely, these PPTases showed high activity toward APACP ($k_{cat}$≥14.6±1.3 $min^{-1}$) and low activity toward SFACP ($k_{cat}$≤2.2±0.1 $min^{-1}$). Furthermore, CP substrates demonstrated the lowest $K_m$ values with their cognate PPTases in comparison with other enzymes (Table 1), potentially indicating co-evolution. In this regard, SPPT showed higher $K_m$ values toward the majority of noncognate CPs in comparison with APPT and MPPT (Table 1), presumably because of the lack of any PK or NRP cluster in *Synechocystis*. Similarly, the relatively weak interactions of Sfp with the majority of cyanobacterial CPs may also support the biosynthetic co-evolution.

Figure 4A:
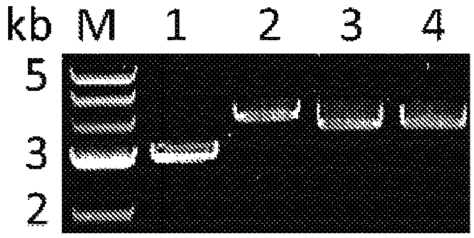
FIGS. 4A-4D. The in vivo activity of APPT, MPPT and Sfp in *Synechocystis*. (A) The APPT, MPPT and Sfp genes chromosomally replaced the SPPT gene in *Synechocystis* mutants. The PCR diagnosis detected the SPPT in the wild type (lane 1) but not in three mutants (lanes 2 to 4). The APPT, MPPT and Sfp genes were found in three mutants, respectively (lanes 2 to 4). (B) RT-PCR analysis of the transcription of SPPT, APPT, MPPT and Sfp genes in wild type *Synechocystis* and mutants (lanes 2 to 5). The rnpB gene encoding the RNA subunit of RNase P was used as a positive control (lane 1). (C) Quantitative analysis of transcriptional levels of SPPT, APPT, MPPT and Sfp genes. The signals were normalized with that of rnpB gene. The asterisk (*) indicates significance of the changes (≥95%). (D) Growth curve of wild type *Synechocystis* and mutants. $OD_{730}$ was continuously monitored for 13 days.
Figure 4B:
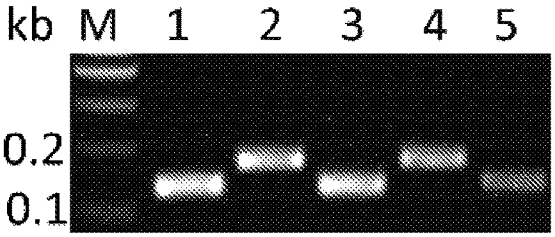
Figure 4C:
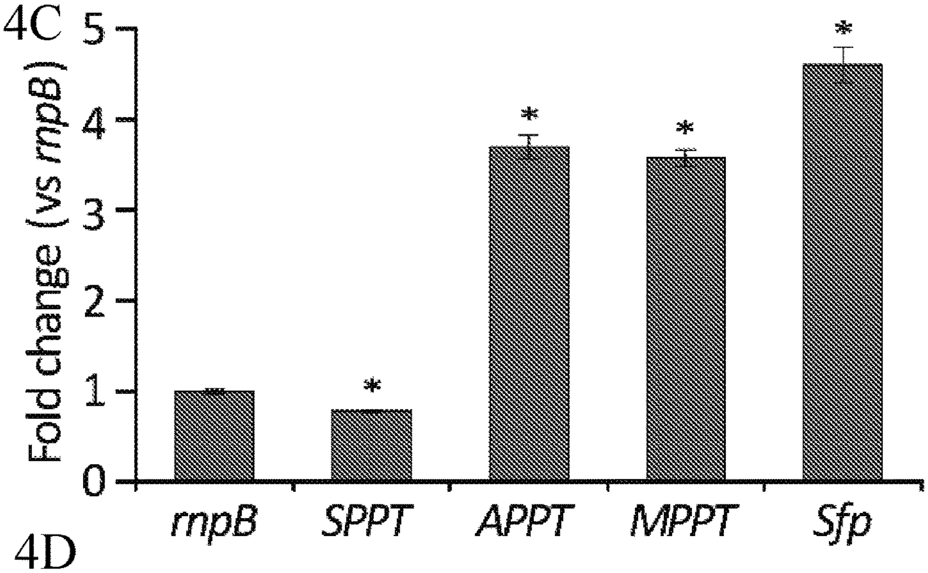
Figure 4D:
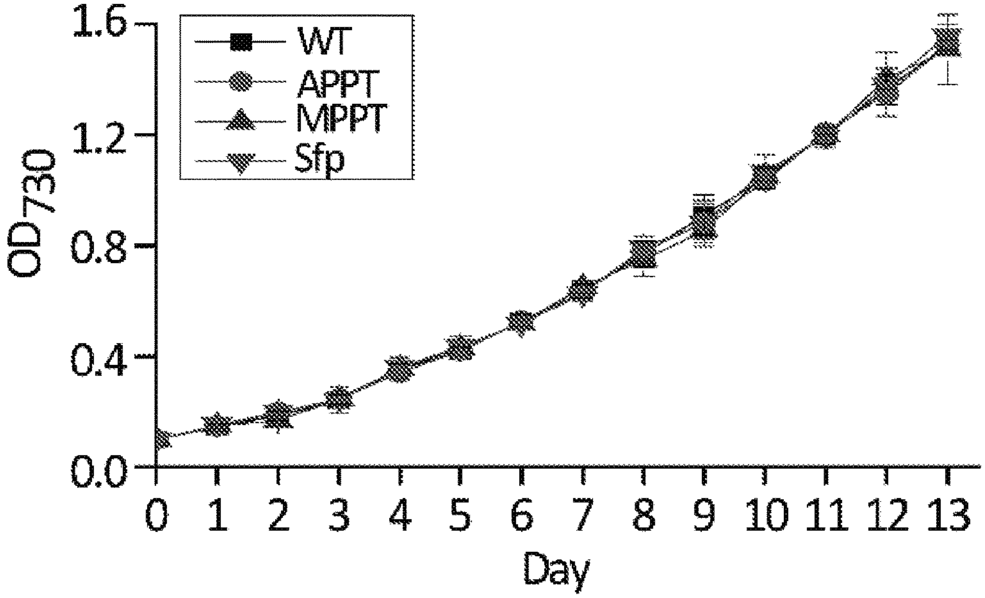
Figure 5:
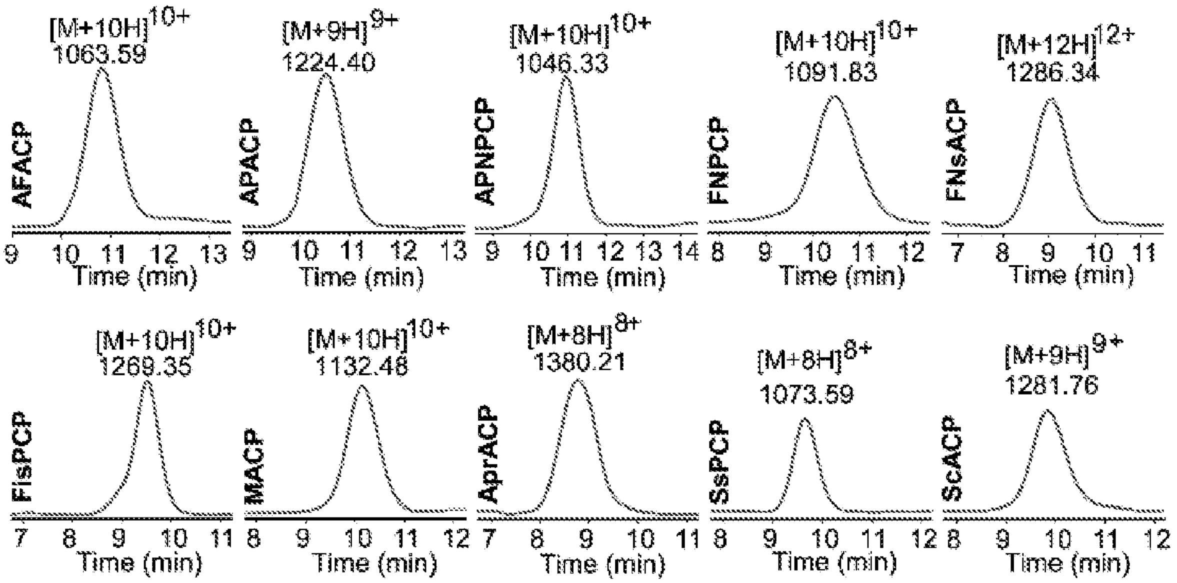
FIG. 5. Extracted ion chromatograms of holo-form of 10 CPs produced in the reactions of cell lysate of *Synechocystis* APPT mutant. The products showed the expected molecular weights. The similar traces were observed in the reactions of cell lysates of two other mutants.

In vivo and in vitro activity of transiently expressed APPT, MPPT and Sfp in *Synechocystis*. To further explore the in vivo catalytic performance of APPT, MPPT and Sfp, we chromosomally integrated their genes to replace the essential SPPT gene of *Synechocystis* (FIG. 4A and FIG. 18). The expression of the integrated PPTase genes was controlled by a constitutive strong promoter Ptrc. After homologous recombination and multiple rounds of segregation, three stable *Synechocystis* mutants were confirmed as the loss of the SPPT gene and the presence of foreign PPTase gene in the PCR diagnosis (FIG. 4A). The transcription levels of these PPTase genes in the mutants were five to six times higher than that of SPPT in the wild type in the quantitative reverse transcription PCR (RT-PCR) analysis (FIGS. 4B and 4C). Importantly, the growth curve of the three mutant strains closely resembled the wild type over the entire 13-day culturing period (FIG. 4D). This data suggested the successful expression of APPT, MPPT and Sfp in *Synechocystis* and demonstrated their in vivo function as activating SFACP for the synthesis of essential fatty acids. To evaluate the catalytic performance of these enzymes toward additional substrates, we prepared and employed the soluble cell lysates of three *Synechocystis* mutants to functionalize the selected 10 CPs except SFACP. LC-MS analysis detected holo-products from all 30 reactions after the incubation for 16 hours (FIG. 5), revealing the broad substrate scope of the transiently expressed APPT, MPPT, and Sfp in *Synechocystis*. The relatively long reaction time is likely caused by the low concentrations of recombinant proteins in the cyanobacterial expression system. A high-copy self-replicating vector can potentially alleviate this issue. The three *Synechocystis* mutants can find broad applications in the heterologous production of cyanobacterial PKs, NRPB, and their hybrids.

Figure 6:
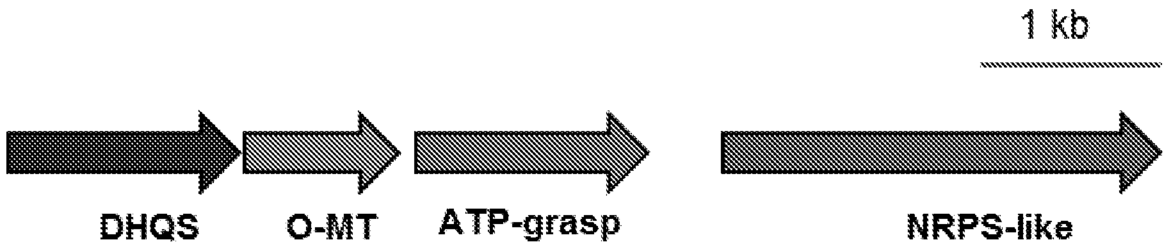
FIG. 6. *Fischerella* shinorine biosynthesis gene cluster.

Bioinformatics analysis of shinorine gene cluster in *Fischerella*. A homology search for a gene cluster for shinorine biosynthesis of *A. variabilis* ATCC29413 against public databases identified a similar gene cluster in the cyanobacterium *Fischerella*. The biosynthetic gene cluster in *Fischerella* is composed of four genes encoding putative dimethyl 4-deoxygadusol (DDG) synthase, O-methyltransferase (O-MT), ATP-grasp family protein and a NRPS-like protein (FIG. 6). The putative protein sequences encoded by these genes shared high similarity to the proteins encoded by Ava_3858-Ava_3855 of *A. variabilis* ATCC29413 (Table 2).

Figure 7A:
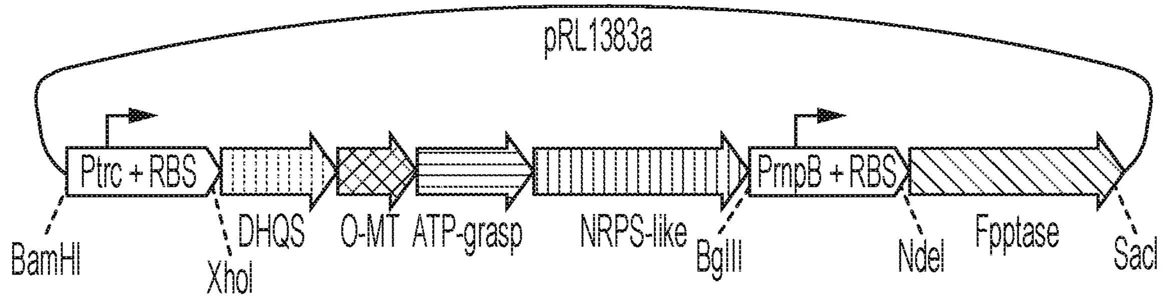
FIGS. 7A-7B. Plasmids for the expression of shinorine in *Synechocystis*. A and B. plasmids for *Synechocystis* expression of shinorine.
Figure 7B:
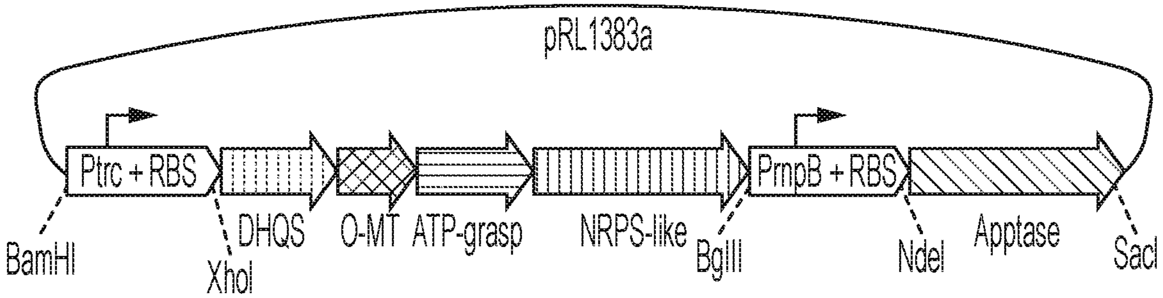

Cloning of shinorine gene cluster. PCR amplifications of shinorine gene cluster from *Fischerella* result into a 6.6 kb DNA fragments. Shinorine gene cluster amplified by using the primers pair Shino-BamHI-Fw and Shina-Xba-Xho-Rv was digested with BamHI and XhoI restriction enzymes and cloned into pET28b which was previously digested with the same pair of enzymes to construct the *E. coli* expression plasmid pET28b-shinorine (FIG. 7A). To facilitate the *Synechocystis* expression of shinorine, pRL1383a vector was used as backbone to clone the gene cluster (FIG. 7B). In this construct, Ptrc promoter was cloned in the upstream of the gene cluster to drive the expression of the genes. As a proper functional phosphopantetheinyl transferase (PPTase) is needed for cross-species modification of carrier proteins embedded in NRPS modules in the NRPS-like protein in the gene cluster, we cloned the PPTase from *Fischerella* or *Anabaena* into the plasmid. The transcription of PPTases in the plasmid will be driven by the inserted PrnpB promoter in the upstream of the PPTases (FIGS. 7A and 7B).

Figure 8:
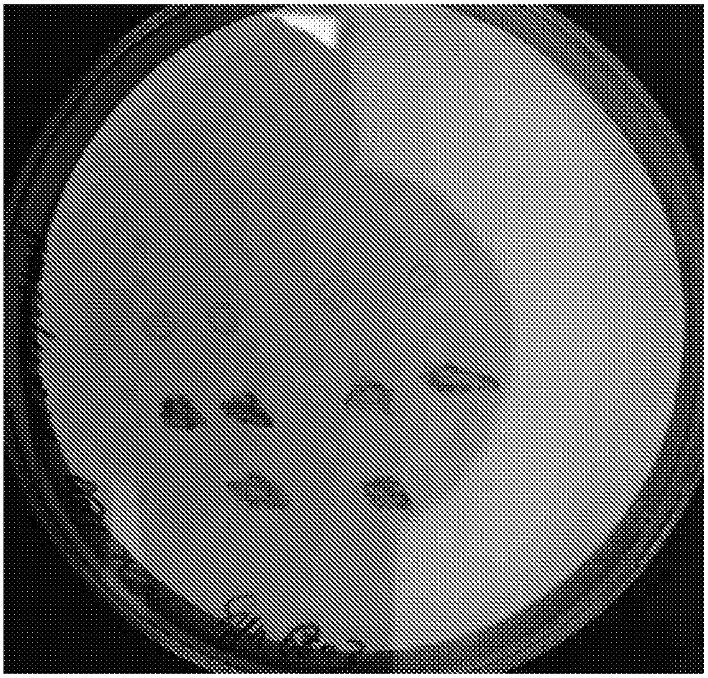
FIG. 8. Triparental mating conjugal transfer of shinorine expression plasmids into *Synechocystis*.
Figure 13:
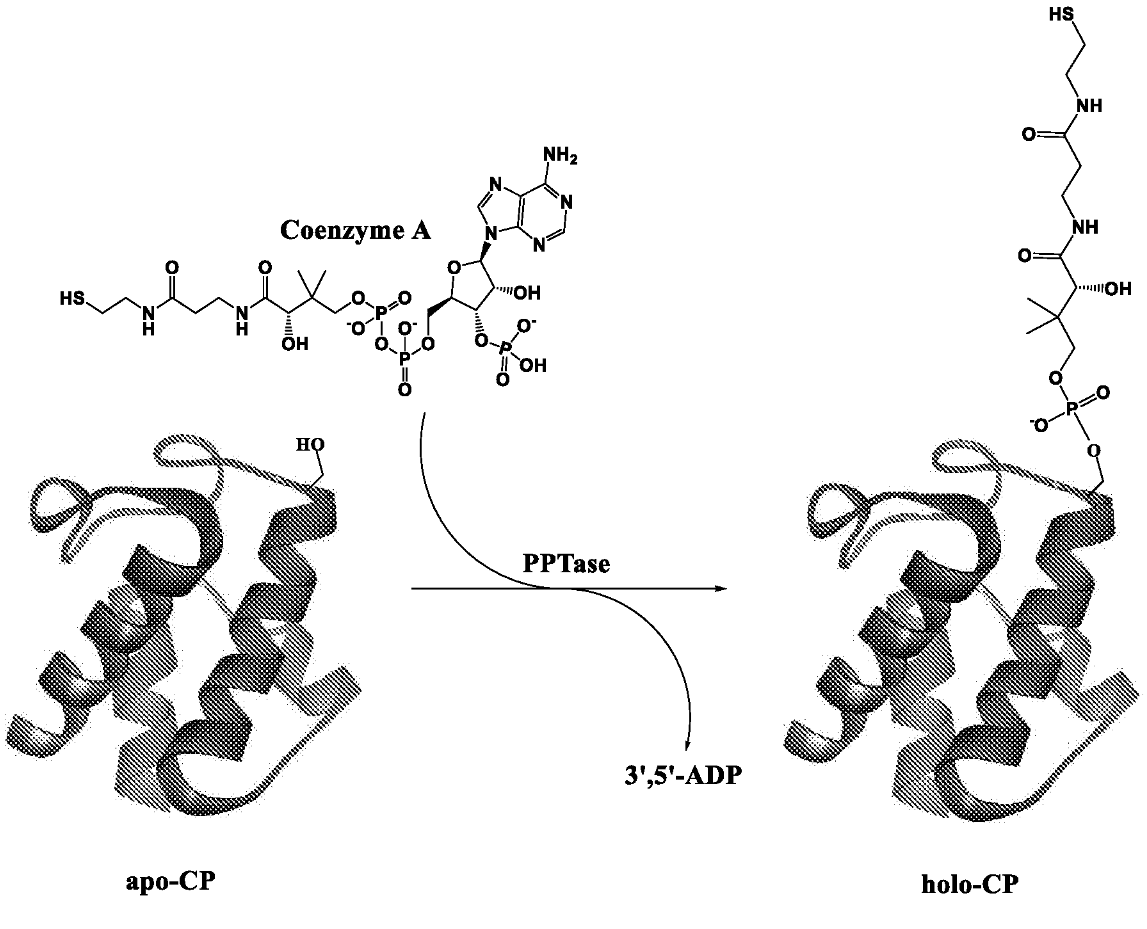
FIG. 13. Schematic representation of post-translational phosphopantetheinylation of a CP domain by a PPTase. The modification leads to a mass increase of 340 Dalton.

Triparental mating of *Synechocystis* for conjugal transfer of 1383a-SHI-APPT and 1383a-SHI-FPPT. For the *Synechocystis* expression of shinorine, the constructed plasmids 1383a-SHI-APPT and 1383a-SHI-FPPT were transferred into *Synechocystis* by using triparental mating method. As shown in FIG. 8, the conjugated *Synechocystis* showed growth on BG11-Agar plates with antibiotics. The colonies will be subjected to the following liquid culture and shinorine expression test.

HPLC and LCMS analysis of shinorine produced by *Fischerella* and *Synechocystis*. To investigate the production of shinorine in *Fischerella* and *Synechocystis*, these strains cultured in liquid BG11 medium were subjected to a natural product isolation approach described below. HPLC and LCMS analysis of the cell extract indicated the presence of a tiny amount of MAA-like compound from *Fischerella* and about 10-fold amount of MA that exhibited absorbance spectra characteristic for MAAs and whose retention time was identical to that of shinorine standard. The amount of MAA-like compound extracted from *Synechocystis* was about 10-fold to that from *Fischerella*.

Conclusions

PPTases are essential enzymes of all three domains of life as they functionalize CPs of FASs, PKSs, and NRPSs. The past two decades have witnessed significant advances of PPTase research, particularly about structure-function-relationship, the development of enzyme inhibitors, and biotechnological and biomedical applications. Here, we analyzed the phylogenetic relationships of cyanobacterial PPTases and rationally selected six cyanobacterial enzymes along with Sfp to characterize their substrate scope and catalytic activity toward 11 CPs of FASs, PKSs, and NRPSs from cyanobacteria and *Streptomyces* strains. Compared with Sfp, APPT and MPPT demonstrated higher or similar catalytic activity and kinetic performance toward the majority of cyanobacterial CPs. They can be useful plug-and-play tools to produce primary and secondary metabolites of cyanobacteria and potentially of strains from other phyla. In this regard, the validated in vivo and in vitro functions of transiently expressed APPT, MPPT and Sfp in the *Synechocystis* mutants indicate the availability of the novel, capable cyanobacterial synthetic biology chassis. Further studies will include the expression and optimization of selected cyanobacterial gene clusters in these chassis and develop additional cyanobacterial synthetic biology tools.

We have further identified the shinorine gene cluster in *Fischerella*. The gene cluster was cloned into different plasmid for *Synechocystis* expression of shinorine. With the HPLC and LC-MS results, we understand that the engineered *Synechosytis* strain produces shinorine with about 10-fold higher in yield compared with that produced by the native producer *Fischerella*.

TABLE 1

Kinetics parameters of four selected PPTases toward 11 CPs[a]

| Substrate | APPT $K_m$[b] | APPT $k_{cat}$[b] | APPT $k_{cat}/K_m$[b] | MPPT $K_m$ | MPPT $k_{cat}$ | MPPT $k_{cat}/K_m$ |
|---|---|---|---|---|---|---|
| SFACP | 2.8 ± 0.2 | 1.6 ± 0.09 | 0.6 ± 0.07 | 3.2 ± 0.2 | 1.2 ± 0.1 | 0.4 ± 0.07 |
| AFACP | 6.8 ± 0.5 | 11.7 ± 0.5 | 1.7 ± 0.2 | 6.9 ± 0.4 | 8.4 ± 0.2 | 1.2 ± 0.1 |
| APACP | 10.0 ± 0.9 | 17.0 ± 0.6 | 1.6 ± 0.2 | 23.1 ± 4.1 | 21.2 ± 1.6 | 0.9 ± 0.2 |
| ScACP | 14.1 ± 1.6 | 5.4 ± 0.3 | 0.4 ± 0.07 | 12.4 ± 1.5 | 2.6 ± 0.1 | 0.2 ± 0.04 |
| SsPCP | 7.4 ± 0.5 | 7.6 ± 0.2 | 1.0 ± 0.09 | 9.1 ± 0.3 | 7.1 ± 0.1 | 0.7 ± 0.04 |
| FNPCP | 12.1 ± 0.5 | 12.2 ± 0.3 | 1.0 ± 0.07 | 7.2 ± 0.7 | 9.6 ± 0.4 | 1.3 ± 0.2 |
| FisPCP | 7.1 ± 0.5 | 2.3 ± 0.06 | 0.3 ± 0.03 | 7.2 ± 0.3 | 1.9 ± 0.03 | 0.3 ± 0.02 |
| MACP | 7.9 ± 0.9 | 3.7 ± 0.2 | 0.5 ± 0.08 | 4.9 ± 0.3 | 4.2 ± 0.1 | 0.9 ± 0.07 |
| APNPCP | 1.6 ± 0.1 | 1.0 ± 0.05 | 0.6 ± 0.09 | 9.5 ± 0.4 | 1.9 ± 0.1 | 0.2 ± 0.02 |
| FNsACP | 8.4 ± 0.8 | 2.2 ± 0.08 | 0.3 ± 0.03 | 8.3 ± 0.8 | 2.1 ± 0.4 | 0.3 ± 0.07 |
| AprACP | 7.8 ± 0.8 | 14.3 ± 0.8 | 1.8 ± 0.3 | 9.1 ± 1.4 | 10.4 ± 0.8 | 1.1 ± 0.3 |

| Substrate | SPPT $K_m$ | SPPT $k_{cat}$ | SPPT $k_{cat}/K_m$ | Sfp $K_m$ | Sfp $k_{cat}$ | Sfp $k_{cat}/K_m$ |
|---|---|---|---|---|---|---|
| SFACP | 1.5 ± 0.2 | 1.4 ± 0.1 | 0.39 ± 0.2 | 2.5 ± 0.3 | 2.2 ± 0.1 | 0.9 ± 0.2 |
| AFACP | 13.3 ± 1.6 | 14.7 ± 1.1 | 1.1 ± 0.2 | 11.6 ± 0.6 | 9.8 ± 0.3 | 0.8 ± 0.07 |
| APACP | 26.5 ± 5.2 | 14.6 ± 1.3 | 0.5 ± 0.1 | 15.3 ± 2.1 | 22.1 ± 1.4 | 1.5 ± 0.3 |
| ScACP | N/A[c] | N/A[c] | N/A[c] | 8.3 ± 0.5 | 15.2 ± 0.5 | 1.8 ± 0.1 |
| SsPCP | 14.3 ± 1.1 | 1.0 ± 0.04 | 0.06 ± 0.008 | 7.9 ± 0.7 | 16.7 ± 0.7 | 2.1 ± 0.2 |
| FNPCP | 7.0 ± 0.6 | 10.1 ± 0.4 | 1.4 ± 0.2 | 11.7 ± 0.8 | 14.5 ± 0.6 | 1.2 ± 0.1 |
| FisPCP | 10.0 ± 0.5 | 2.5 ± 0.05 | 0.3 ± 0.02 | 14.0 ± 1.2 | 1.7 ± 0.07 | 0.1 ± 0.02 |
| MACP | 22.0 ± 1.6 | 4.3 ± 1.1 | 0.2 ± 0.06 | 6.7 ± 0.7 | 5.1 ± 0.2 | 0.8 ± 0.1 |
| APNPCP | 17.0 ± 1.3 | 2.3 ± 0.2 | 0.1 ± 0.02 | 12.0 ± 0.9 | 2.2 ± 0.2 | 0.2 ± 0.02 |
| FNsACP | 14.1 ± 1.4 | 1.5 ± 0.07 | 0.1 ± 0.02 | 10.9 ± 0.5 | 2.4 ± 0.05 | 0.2 ± 0.01 |
| AprACP | 12.9 ± 2.1 | 13.1 ± 1.2 | 1.0 ± 0.2 | 9.0 ± 1.0 | 2.9 ± 0.1 | 0.3 ± 0.05 |

[a]The data represent mean ± SD of three independent experiments;
[b]Units of $K_m$, $k_{cat}$, and $k_{cat}/K_m$ are μM, $min^{-1}$, $\mu M^{-1}$ $min^{-1}$, respectively;
[c]No detectable activity.

TABLE 2

Deduced functions of ORFs in the biosynthetic gene cluster for shinorine of *Anabaena variabilis* ATCC 29413 and *Fischerella* PCC 9339

| *Anabaena variabilis* ATCC 29413 ORF | aaa | *Fischerella* 9339 ORF | aaa | Identity/ similarity (%) | Predicted function |
|---|---|---|---|---|---|
| ava_3858 | 410 | PCC9339_ RS0123055 | 409 | 72/85 | Dimethyl 4-deoxygadusol (DDG) synthase |
| ava_3857 | 279 | PCC9339_ RS0123056 | 276 | 64/77 | O-Methyltransferase O-MT) |
| ava_3856 | 458 | PCC9339_ RS0123057 | 459 | 75/84 | ATP-grasp family protein |
| ava_3855 | 888 | PCC9339_ RS0123058 | 913 | 68/81 | NRPS-like protein |

Example 2

Mycosporine-like amino acids (MAAs) are water-soluble secondary metabolites produced by a variety of marine organisms including cyanobacteria and macroalgae. These compounds have strong ultraviolet (UV) absorption maxima between 310 and 362 nm and are biological sunscreens for counteracting the damaging effects of UV radiation. Shinorine is one MAA analog and is the key active ingredient of sunscreen creams. Commercially used shinorine is isolated from a red algae that is harvested from the wild. *Synechocystis* sp. PCC6803 as a novel host for the heterologous production of shinorine is described. A shinorine gene cluster was mined from the filamentous cyanobacterium *Fischerella* sp. PCC 9339. When expressing the cluster in *Synechocystis* sp. PCC6803, LC-MS analysis detected the production of shinorine but its productivity was three times lower than the native producer. Integrated transcriptional and metabolic profiling identified multiple rate-limiting steps in the heterologous production of shinorine. The use of multiple promoters led to a 10-fold increase of shinorine yield to 2.37±0.21 mg/g dry biomass weight, comparable to commercially used shinorine producer. The UV protection of shinorine was further confirmed using the engineered *Synechocystis* sp. PCC6803. As such, photosynthetic overproduction of MAA is demonstrated. These results suggest that *Synechocystis* sp. PCC6803 can have broad applications as the synthetic biology chassis to produce other cyanobacterial natural products, expediting the translation of genomes into chemicals.

Both ultraviolet (UV)-A (315-400 nm) and UV-B (280-315 nm) can induce DNA damages and generate reactive oxygen species, being harmful to humans. Recent depletion of stratospheric ozone layer has resulted in the increase of UV intensity reaching on earth. Sunscreens comprising different types of synthetic organic and/or inorganic compounds filter a broad spectrum of solar UV rays and prevent the UV-induced damages to humans when applied to the skin. However, multiple negative effects of these manmade UV radiation filters on aquatic ecosystems have become increasingly apparent and gradually shifted the trends of customers toward the use of more environmentally compatible products.

Mycosporine-like amino acids (MAAs) are a family of over 30 known water-soluble secondary metabolites produced by a variety of taxonomically diverse aquatic organisms (e.g., cyanobacteria and macroalgae) that are frequently exposed to high levels of UV radiation. These compounds share a 4-deoxygadusol (4-DG) core and possess various decorations, e.g., C1-oxo or imino group and C3-glycine, that influence their maximal absorbance wavelengths between 310 and 362 nm (ε=28,100-50,000 $M^{-1}$ $cm^{-1}$) (FIG. 20). MAAs promptly convert the absorbed energy to heat without the formation of free oxygen species (FIG. 20), making them biodegradable sunscreens. Indeed, shinorine (1), one MAA commonly produced by marine cyanobacteria and algae, is an important active ingredient of two commercial sunscreen products (Helioguard 365 and Helionori®). The commercially used shinorine is isolated from the red alga *Porphyra umbilicalis* with a yield of 3.27 mg/g dry biomass weight (DW). *P. umbilicalis* is often harvested from the wild and its MAA contents can seasonally and geographically vary. On the other hand, cultivation of *P. umbilicalis* is less economical because of its long doubling time even under the optimal culture conditions.

The biosynthesis of MAAs has been elucidated well in many organisms. 4-Deoxygadusol (4-DG) is the first key biosynthetic intermediate that is produced from the shikimate pathway by a dehydroquinate synthase (DHQS) (FIG. 21). Next, an ATP-grasp ligase conjugates glycine to the C3 of 4-DG to produce mycosporine-glycine (MG) that is then converted to shinorine (1) and other MAAs by a nonribosomal peptide synthetase (NRPS) or a d-Ala-d-Ala ligase-like protein (FIG. 21). Recently, an alternative route to 4-DG was discovered in cyanobacterial species, and requires both demethyl 4-deoxygadusol synthase (DDGS) and O-methyltransferase (O-MT) to produce 4-DG from sedoheptulose-7-phosphate (SH-7P) of the pentose phosphate pathway (FIG. 21). This four-gene cluster of shinorine is conserved among a number of cyanobacterial species, e.g., ava_3855 to ava_3858 in the filamentous cyanobacterium *Anabaena variabilis* ATCC29413.

Heterologous expression has proven to be a useful strategy for the production of natural products of diverse origins. Commonly used hosts in these studies include *Escherichia coli, Streptomyces* strains and yeast. However, these hosts have demonstrated limited successes in heterologous production of cyanobacterial natural products. Thus far, only several families of ribosomally synthesized and post-translationally modified peptides, lyngbyatoxin and microcystins have achieved successful production in *E. coli*, while 4-O-demethylbarbamide is the only cyanobacterial secondary metabolite produced in *Streptomyces* species (<1 μg/L). Shinorine (1) was also produced in *E. coli* expressing the cluster from *Anabaena* but its low yield of 145 μg/L and the significant accumulation of 4-DG indicate the inefficient and unbalanced production. Indeed, genetic backgrounds between cyanobacteria and *E. coli* are notably different (e.g., GC content and transcriptional elements), which might result in the no-to-low production of expressed cyanobacterial natural products. On the other hand, filamentous cyanobacterium *Anabaena* sp. PCC7120 was used to produce lyngbyatoxin A with the highest yield of 2.3 μg/g DW (Videau et al.). Videau et al. demonstrated the potential of cyanobacterial chassis in producing cyanobacterial natural products. However, the five NRPS/polyketide synthase (PKS) gene clusters in *Anabaena* sp. PCC7120 could compete with the expression of foreign clusters and complicate the identification and isolation of expressed natural products.

The unicellular cyanobacterium *Synechocystis* sp. PCC6803 has been used to produce biofuels, commodity chemicals and biomaterials. *Synechocystis* can be a suitable host for photosynthetically producing cyanobacterial natural products because (1) it has a short doubling time (5 to 10 h) compared with other cyanobacteria; (2) it is amenable to genetic modifications with a variety of available tools; and (3) it contains no NRPS/PKS cluster, avoiding inherent competition of biosynthetic building blocks and simplifying the isolation and identification of expressed products. The use of *Synechocystis* is provided as a heterologous host to express a shinorine gene cluster from the filamentous cyanobacterium *Fischerella* sp. PCC9339 (hereafter *Fischerella*). Combining transcriptional and metabolic profiling, the gene cluster was engineered to improve the productivity of shinorine close to the commercially used red algae and avoid the accumulation of biosynthetic intermediates. Furthermore, the UV protection effect of shinorine expressed in *Synechocystis* was confirmed. This Example provides *Synechocystis* in expressing the secondary metabolite gene cluster and suggests the broad uses of this new synthetic biology chassis to produce multiple families of cyanobacterial natural products.

The Shinorine Biosynthesis in *Fischerella*

Cyanobacteria can be classified into five subsections, and the subsection V strains are particularly rich of structurally diverse natural products in their genomes. When mining the genomes of all 18 subsection V cyanobacteria available in the NCBI Genbank database (as of July 2017), the MAA gene cluster from 10 strains (Table 3) were identified.

TABLE 3

Putative MAA gene clusters in *Anabaena* and subsection *V cyanobacteria.*

| Cyanobacterial strain/ Genome accession code | Genes involved in the biosynthesis of MAAs* DDGS homologue | O-Methyl-transferase | ATP-grasp homologue | NRP synthetase |
|---|---|---|---|---|
| *Anabaena variabilis* ATCC 29413/ NC_007413.1 | ava_3858 | ava_3857 | ava_3856 | ava_3855 |
| *Fischerella* sp. PCC 9339/ NZ_ALVS00000000.1 | PCC9339_RS0129530 (84.7%) | PCC9339_RS0129525 (77.1%) | PCC9339_RS0129520 (85.0%) | PCC9339_RS0129515 (77.8%) |
| *Fischerella* sp. PCC 9431/NZ_ALVS00000000.1 | FIS9431_RS0125705 (84.7%) | FIS9431_RS0125700 (77.8%) | FIS9431_RS0125700 (85.2%) | FIS9431_RS0125695 (79.2%) |
| *Fischerella muscicola* SAG 1427-1/ NZ_ALVX00000000.1 | UYG_RS0121930 (84.9%) | UYG_RS0121925 (77.4%) | UYG_RS0121920 (85.2%) | UYG_RS0121915 (77.1%) |
| *Mastigocoleus testarum* BC008/ | BC008_38355 | BC008_38350 | BC008_38345 | BC008_38340 |

TABLE 3-continued

Putative MAA gene clusters in *Anabaena* and subsection *V cyanobacteria*.

| Cyanobacterial strain/ Genome accession code | Genes involved in the biosynthesis of MAAs* DDGS homologue | O-Methyl-transferase | ATP-grasp homologue | NRP synthetase |
|---|---|---|---|---|
| NZ_AJLJ00000000.1 | (89.1%) | (77.4%) | (83.5%) | (53.6%) |
| *Chlorogloeopsis* PCC | UYE_RS0123135 | UYE_R50123130 | UYE_RS0123125 | UYE_RS0123120 |
| 9212/NZ AJLM00000000.1 | (91.3%) | (83.5%) | (86.5%) | (57.1%) |
| *Chlorogloeopsis fritschii* PCC | UYC_RS0133575 | UYC_RS0133570 | UYC_RS0133565 | UYC_RS0133560 |
| 6912/NZ AJLM00000000.1 | (91.3%) | (83.5%) | (86.5%) | (57.1%) |
| *Hapalosiphon* sp. | AMR41_RS24135 | AMR41_RS24130 | AMR41_RS24125 | AMR41_RS25775 |
| MRB220/NZ AJLN00000000.1 | (84.7%) | (77.8%) | (85.8%) | (77.6%) |
| *Mastigocladus laminosus* | SP67_25945 | SP67_25950 | SP67_25955 | SP67_25960 |
| UU774/NZ JXLI00000000.1 | (48.0%) | (35.1%) | (85.2%) | (75.4%) |
| *Westiella intricata* UH HT-29-1**/Reference 4 | + | + | + | + |
| *Hapalosiphon welwitschii* UH IC-52-3**/Reference 4 | + | + | + | + |

*The NCBI accession numbers of the genes are shown. The numbers in the parentheses indicate the percentage similarities of the genes compared to their homologs in Anabaena variabilis ATCC 29413.
**Genomes of Westiella intricata UH HT-29-1 and Hapalosiphon welwitschii UH IC-52-3 are not publically available, but the MAA biosynthetic gene clusters have been described in the reference Micallef et at.

Figure 22:
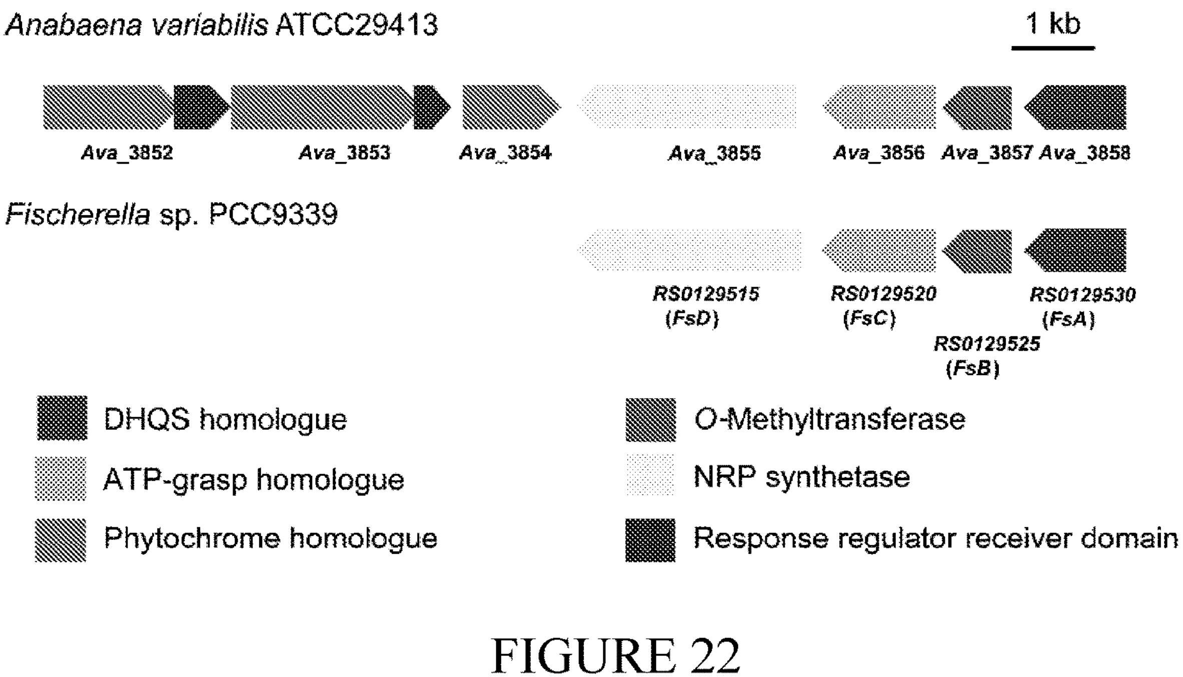
FIG. 22. The shinorine gene clusters in *Anabaena* and *Fischerella* share over 77% amino acid similarities. The shinorine gene cluster in *Anabaena* is flanked by five genes/domains encoding phytochrome-like sensor kinases and response regulators. These regulatory factors are not found in the surrounding regions of the gene cluster in *Fischerella*.
Figure 23:
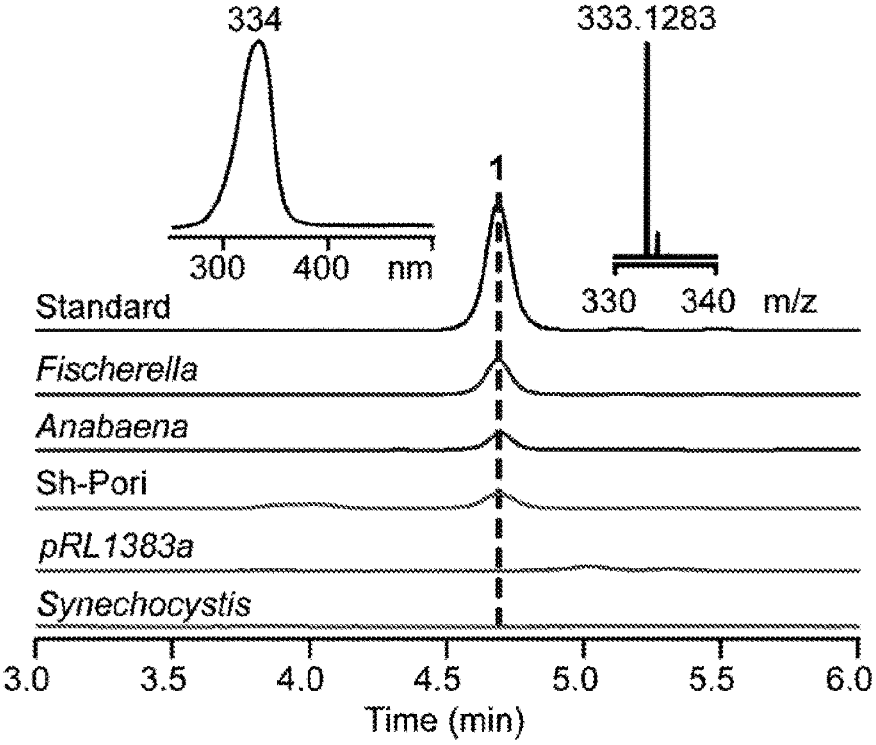
FIG. 23. HPLC and LC-MS analyses revealed the production of shinorine (1) by *Fischerella, Anabaena*, and Sh-Pori. Shinorine in the methanolic extracts of cyanobacterial cell biomass had the identical retention time as the standard, possessed the featured absorption spectrum (left-top) and showed the expected m/z value of its molecular ion (right-top). Wild type (WT) *Synechocystis* and the strain containing pRL1383a did not produce shinorine.
Figure 24:
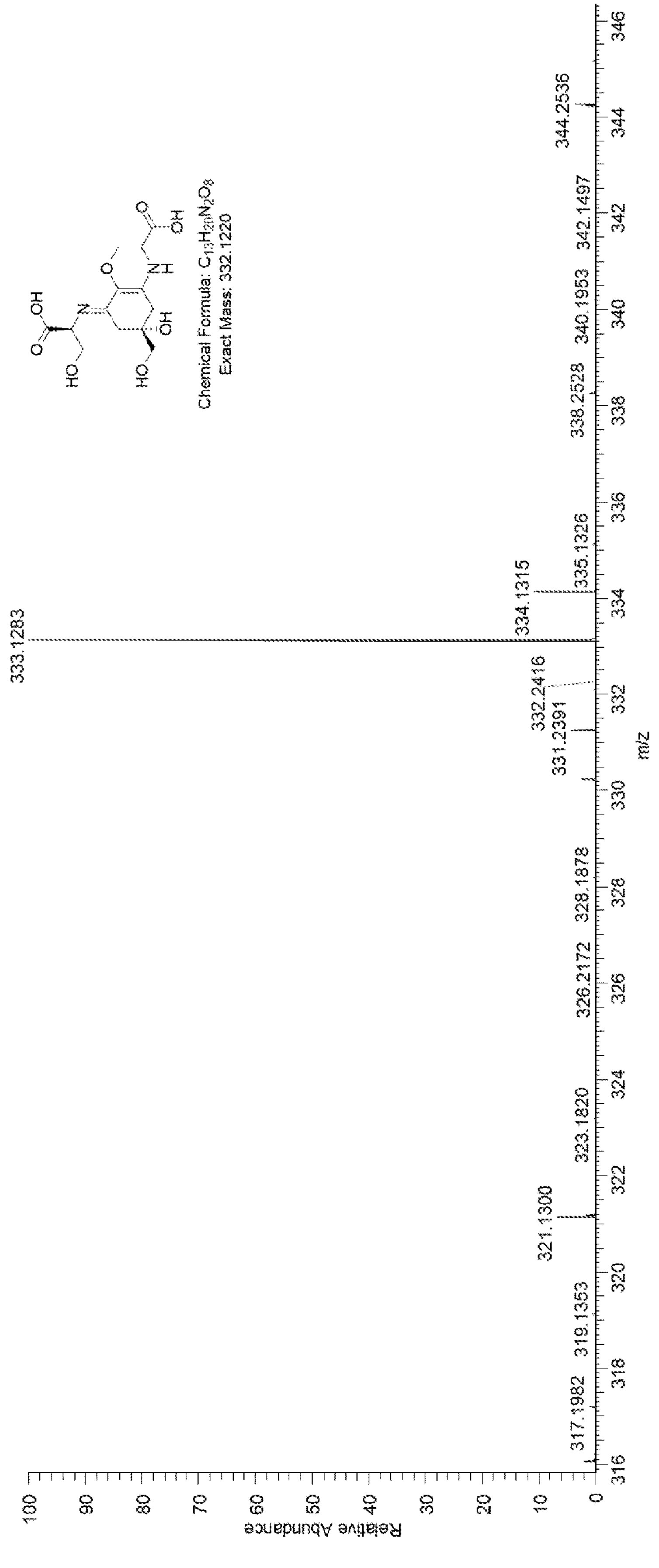
FIG. 24. HR-MS (top) and MS/MS (bottom) spectra of expressed shinorine in *Synechosystis*.
Figure 24:
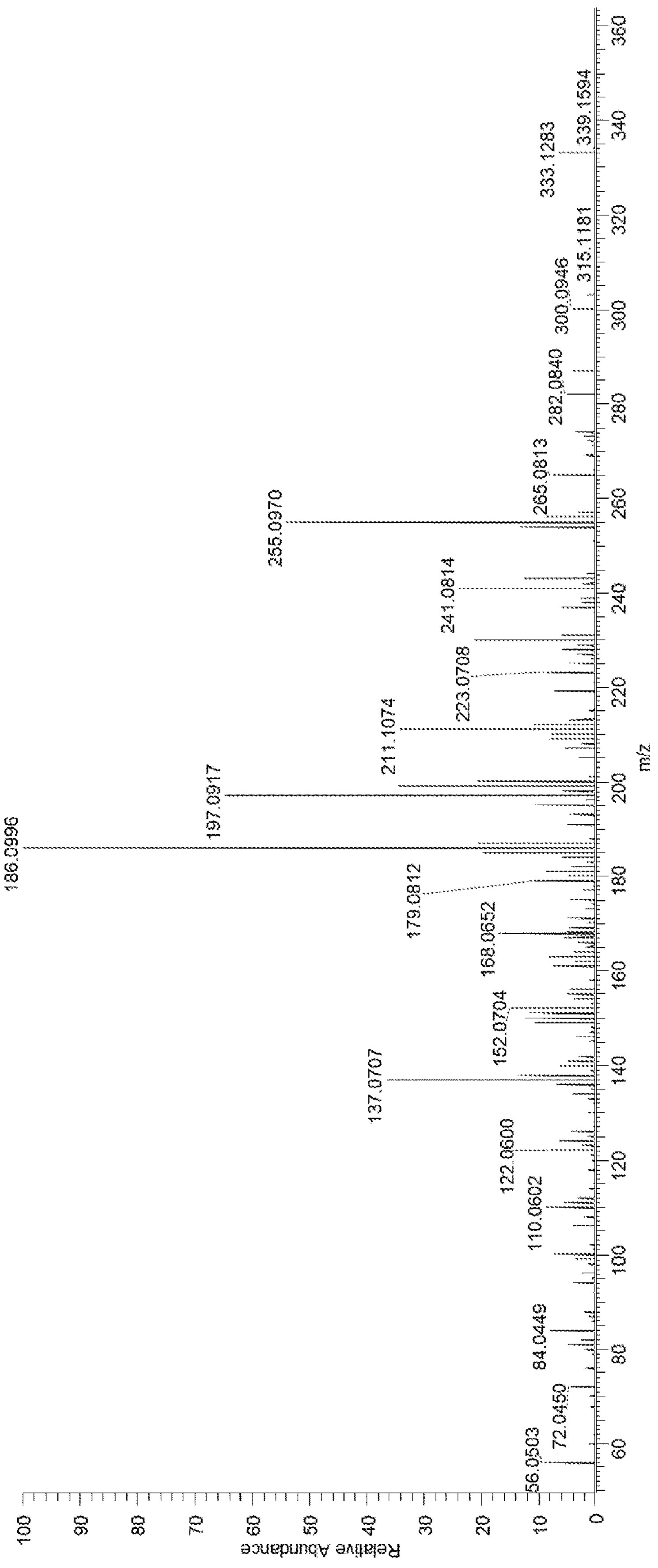

The *Fischerella* genome contains 40 natural product gene clusters including a putative shinorine cluster (NCBI Genbank: PCC9339 RS0129515-PCC9339 RS0129530, named as FsD-A) that shows over 77% amino acid similarities to the one in *Anabaena* (FIG. 22). To probe the function of this cluster, *Fischerella* and *Anabaena* were cultured in BG-11 medium at 26° C. for 21 days. HPLC analysis of methanolic extracts of pelleted *Fischerella* and *Anabaena* cells identified a peak with the diagnostic maximal absorbance wavelength at 334 nm and the identical retention time (4.7 min) to the shinorine standard (FIG. 23). The peak content showed an expected m/z value of 333.1283 (calculated $[M+H]^+$: 333.1220) in the high resolution (HR) MS analysis (FIG. 23). Furthermore, its fragmentation pattern agreed with the previous report (FIG. 24). Collectively, these results suggested a functional shinorine cluster in *Fischerella*. Indeed, *Fischerella* produced 2.5-fold more shinorine (1) than *Anabaena* under the same culture conditions (0.76±0.05 mg/g DW vs. 0.32±0.03 mg/g DW, Table 4). In this regard, *Fischerella* produced a comparable amount of shinorine (1) to other known cyanobacterial producers, such as *Aulosira fertilissima* (0.5 mg/g DW) and *Anabaena variabilis* PCC7937 (0.97 mg/g DW), although it is four times lower than the commercially used red algae *P. umbilicalis* (3.27 mg/g DW).

TABLE 4

Titers of shinorine in *Anabaena, Fischerella* and engineered *Synechocystis* strains.

| Strain | Shinorine (mg/g DW)* |
|---|---|
| *Anabaena* | 0.32 ± 0.03 |
| *Fischerella* | 0.76 ± 0.05 |
| Sh-Pori | 0.23 ± 0.08 |
| Sh-PrnpB | 0.82 ± 0.04 |
| Sh-Ptrc | 1.12 ± 0.05 |
| Sh-P560 | 1.67 ± 0.06 |
| Sh-DP560 | 1.93 ± 0.09 |
| Sh-TP560 | 2.37 ± 0.21 |
| Sh-TP560/Ser | 2.28 ± 0.27 |
| Sh-TP560/UV-A | 2.21 ± 0.37 |
| Sh-TP560/UV-B | 2.15 ± 0.34 |

*Data represent mean ± standard deviation (n = 3).

Heterologous Production of Shinorine in *Synechocystis*

Figure 25A:
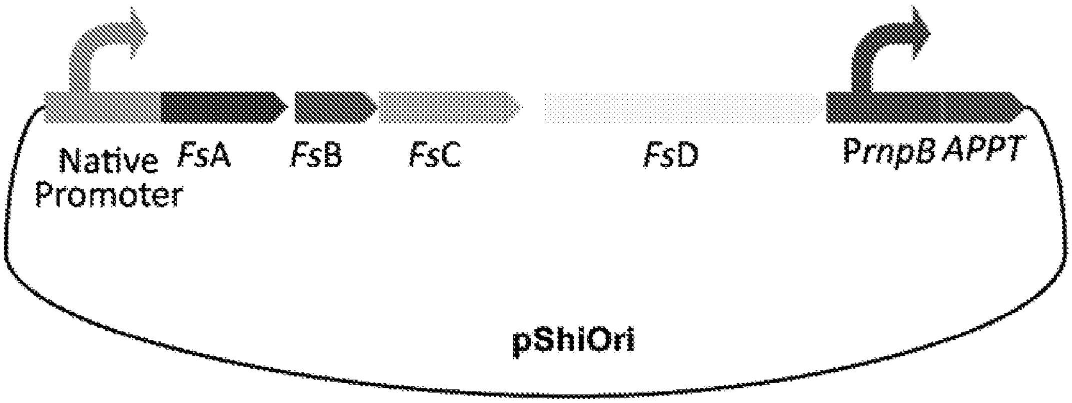
FIGS. 25A-25B. (A). Schematic representation of the construction of pShiOri (SEQ ID NO: 83). (B) Triparental mating of *Synechocystis* for the conjugation of the shinorine expression plasmid.
Figure 25B:
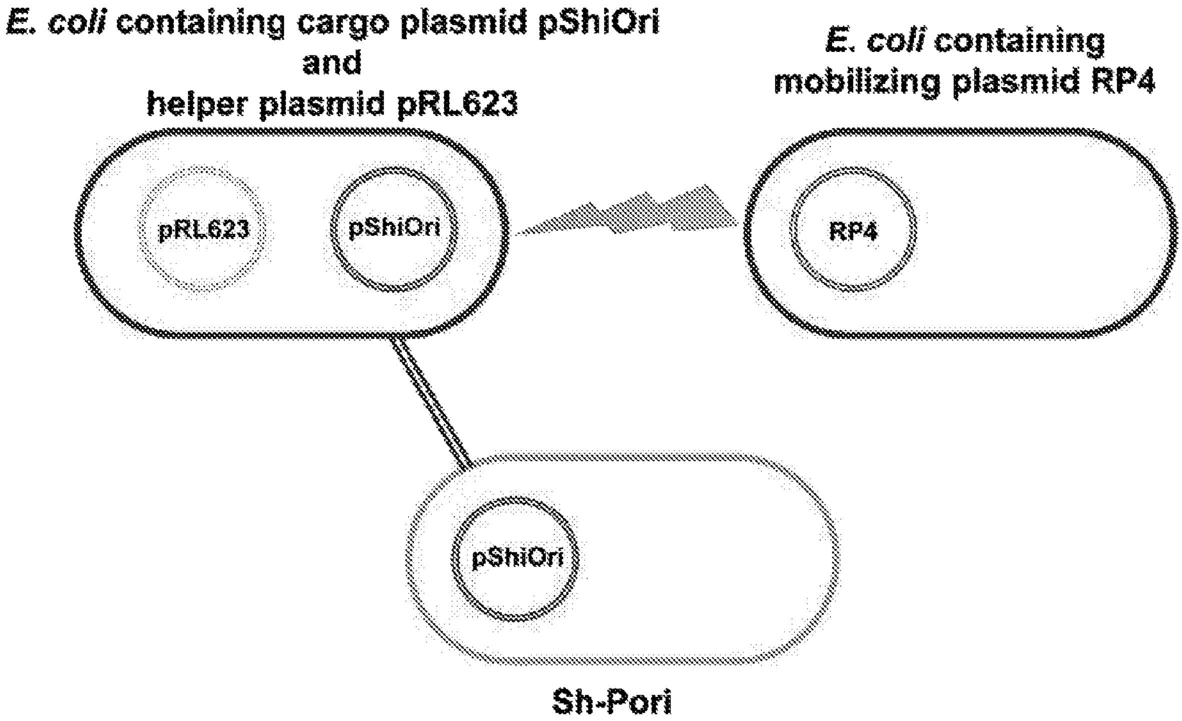
Figure 26A:
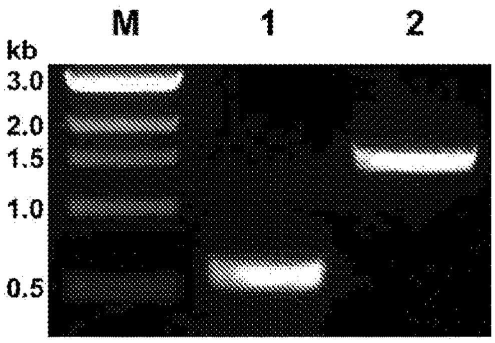
FIGS. 26A-26B. PCR analysis of the shinorine gene cluster in Sh-Pori. (A) Colony PCR diagnosis of Sh-Pori. M: NEB 1 kb DNA Ladder, lane 1: PCR amplicons by using primers Pori-FsA-F and Pori-FsA-R, lane 2: PCR amplicons by using primers FsD-APPT-F and FsD-APPT-R. (B) Reverse transcription PCR (RT-PCR) analysis detected the proper transcription of each cluster gene in Sh-Pori. M: NEB 100 bp DNA Ladder, lane 1-4: RT-PCR amplicons of FsA-D, respectively.
Figure 26B:
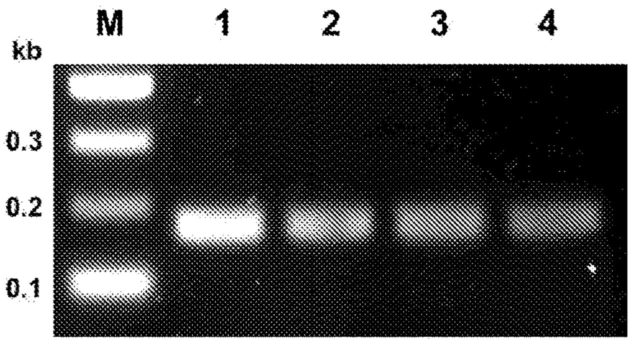

The red algae *P. umbilicalis* is used to commercially supply shinorine but has a long generation time that varies from 2 to 6 days under optimized laboratory conditions to at least 64 days in the wild. To access shinorine in a fast and reliable manner, its cluster from *Fischerella* in *Synechocystis* were heterologously expressed. As shown in FIG. 21, the final step of shinorine biosynthesis is catalyzed by the pathway-specific NRPS enzyme FsD. The proper function of FsD requires a posttranslational modification on its peptidyl carrier protein (PCP) domain, which is promoted by a phosphopantetheinyl transferase (PPT). *Synechocystis* carries one PPT gene (SPPT) but an early report indicated the catalytic incompetence of SPPT in activating foreign carrier protein domains including PCPs. By contrast, SPPT successfully modified multiple cyanobacterial carrier protein domains, including the one of FsD. Its in vitro catalytic efficiency ($k_{cat}/K_m$=0.3±0.02 $\mu M^{-1}$ $min^{-1}$) toward this substrate is three times higher than the canonical PPT Sfp from *Bacillus subtilis* and is at the same level as the PPT from *Anabaena* sp. PCC7120 (APPT), although APPT possesses a broader substrate scope. To ensure the successful production of shinorine, a self-replicative vector pRL1383a was used to co-express the APPT gene and the shinorine gene cluster including its native promoters (FIG. 25). The expression of APPT was under the control of PrnpB, a strong constitutive promoter of *Synechocysti*. The resultant construct was conjugated into *Synechocystis* via triparental mating to generate the production strain Sh-Pori. PCR-based diagnosis validated the presence of the shinorine cluster in Sh-Pori cells, and the proper transcription of each gene was observed by the reverse transcription PCR (RT-PCR) analysis (FIG. 26). Sh-Pori along with wild type (WT) *Synechocystis* and the engineered strain carrying pRL1383a (*Synechocystis*-pRL1383a) as two controls were cultured in BG-11 medium for 13 days. HPLC analysis of the methanolic extract of Sh-Pori biomass identified a new peak that was missing in the extracts of two controls (FIG. 23). The peak content was determined as shinorine by comparing its retention time with the authentic standard and analyzing its MS and MS/MS spectra (FIG. 24). The titer of shinorine was further determined to be 0.23±0.08 mg/g DW, about three times lower than its native producer *Fischerella* cultured for 21 days (Table 4). This study represents the first heterologous production of any MAA in a photosynthetic host. Heterologous expression of the shinorine cluster in *E. coli* leads to a low yield (~0.1 mg/L) and a high amount of 4-DG byproduct. In contrast, *Synechocystis* achieves a complete conversion of all biosynthetic intermediates, and is thus a superior host for expression of shinorine. *Synechocystis* does not encode any shinorine biosynthetic gene.

Production Improvement of Shinorine Using Different Promoters

Figure 27A:
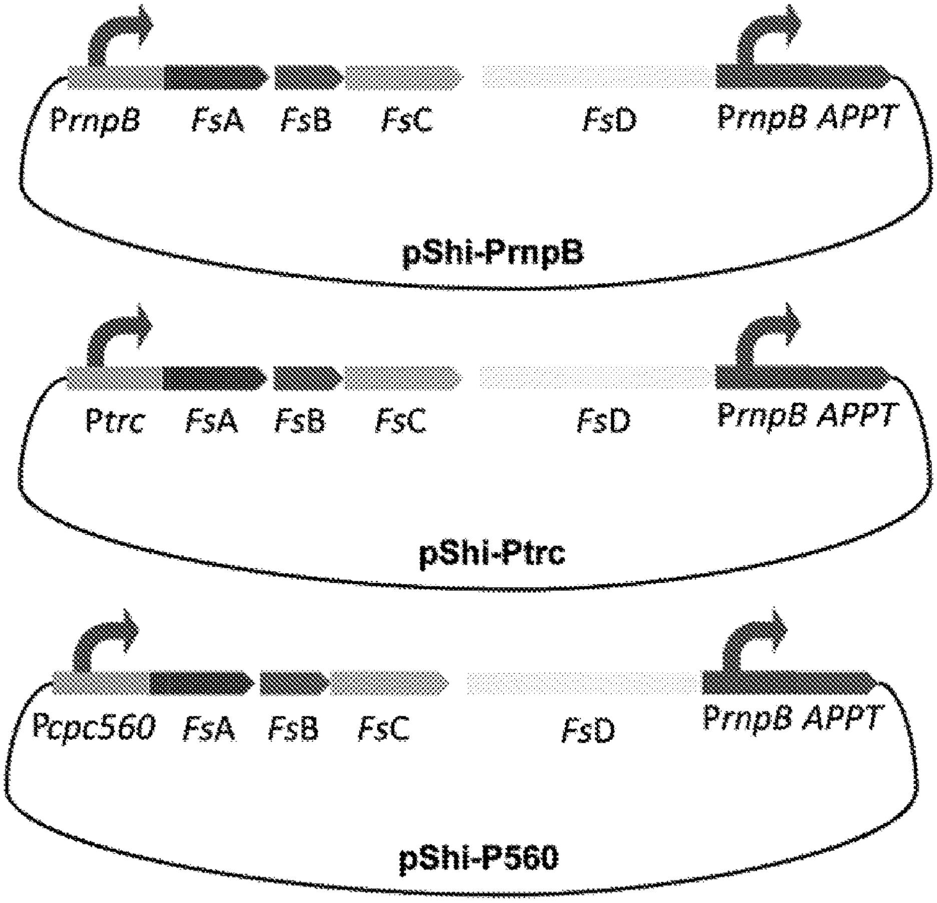
FIGS. 27A-27B. Expression of the shinorine gene clusters under the control of different promoters. (A) Schematic representation of the plasmids containing the shinorine gene cluster under the control of PrnpB (SEQ ID NO: 80), Ptrc (SEQ ID NO: 81) and Pcpc560 (SEQ ID NO: 82) promoters. (B) Colony PCR analysis of Sh-PrnpB, Sh-Ptrc and Sh-P560. M: NEB 1 kb DNA Ladder, lane 1-3: PCR amplicons of the shinorine gene cluster in Sh-PrnpB (containing plasmid pSh-PrnpB (SEQ ID NO: 84)), Sh-Ptrc (containing plasmid pSh-Ptrc (SEQ ID NO: 85) and Sh-P560 (containing plasmid pSh-P560 SEQ ID NO: 86), respectively.
Figure 27B:
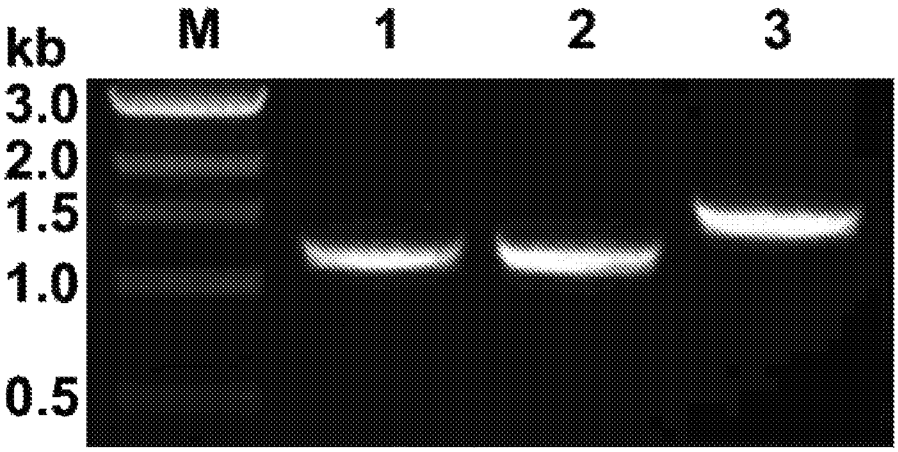
Figure 28A:
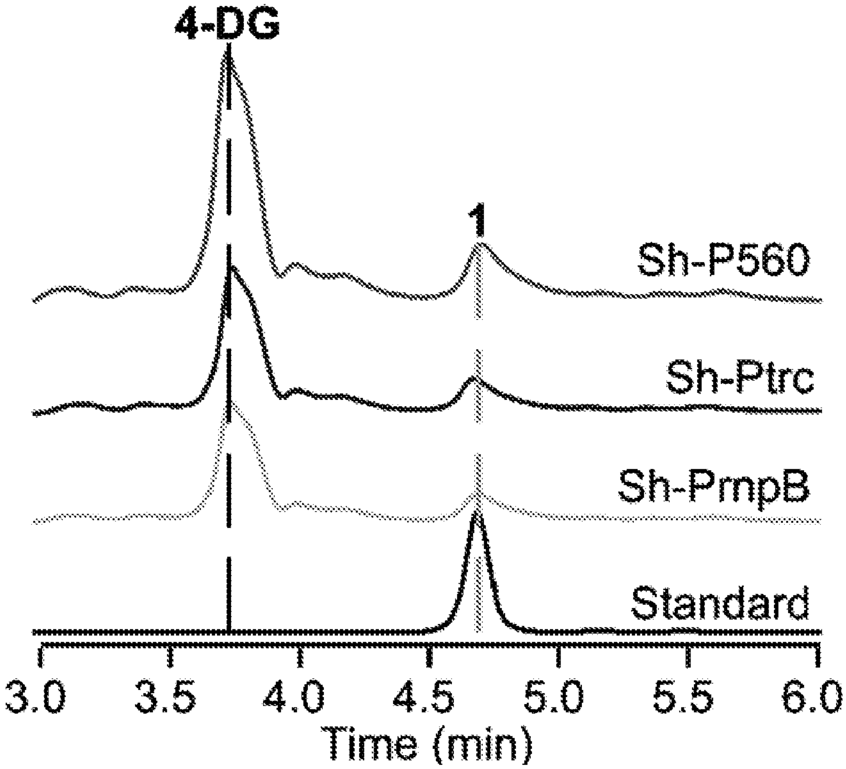
FIGS. 28A-28B. Enhanced production of shinorine in *Synechocystis* using different promoters. (A) HPLC analysis identified shinorine (1) and 4-DG in the extracts of Sh-Ptrc, Sh-PrnpB and Sh-P560. Biosynthetic intermediate 4-DG was the dominant product. (B) qRT-PCR analysis revealed that different promoters affected the transcription of shinorine biosynthetic genes to varying degrees. The rnpB gene was included as the positive control, and its transcription level was used to normalize the signals of the biosynthetic genes of the same strain. Data represent mean±standard deviation (n=3). * indicates statistically significant difference ($P<0.05$, Student's t-test) of the transcription levels of the same gene in two different strains.
Figure 29:
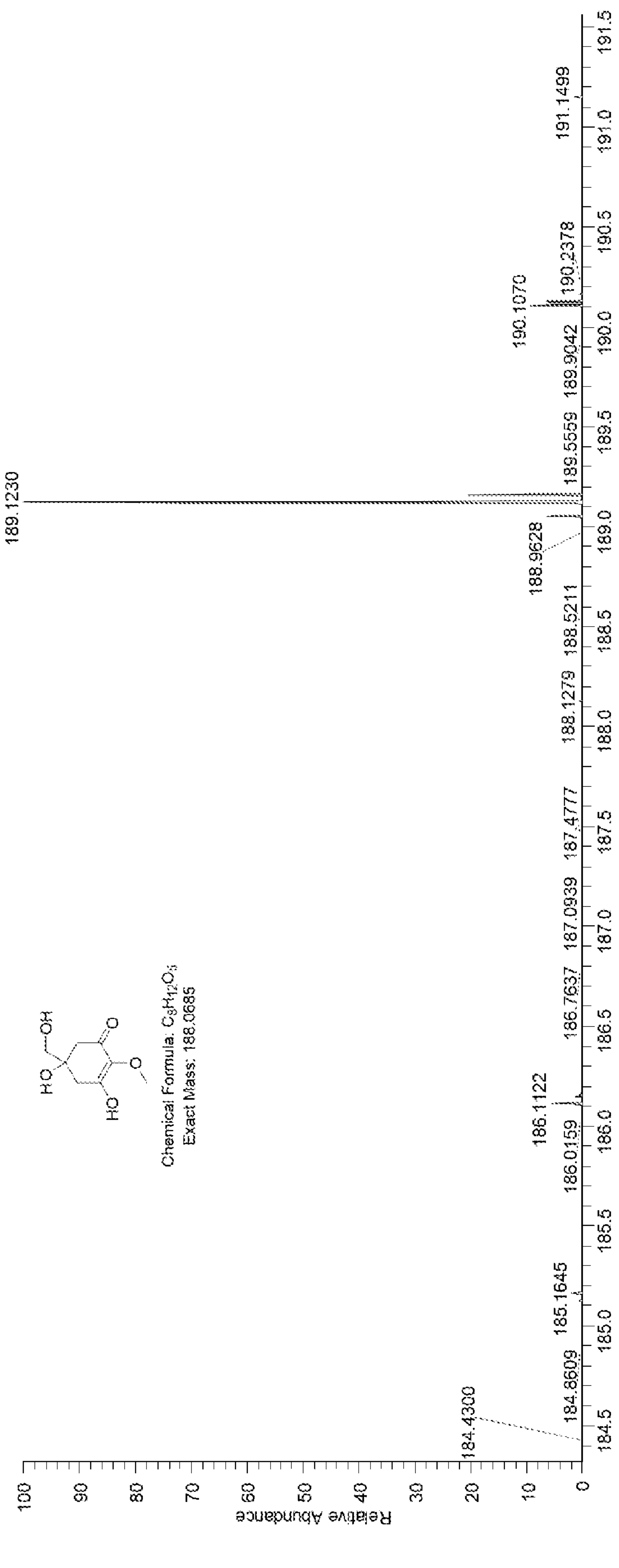
FIG. 29. The absorption (top), HRMS (middle) and MS/MS (bottom) spectra of expressed 4-DG in *Synechosystis.*
Figure 29:
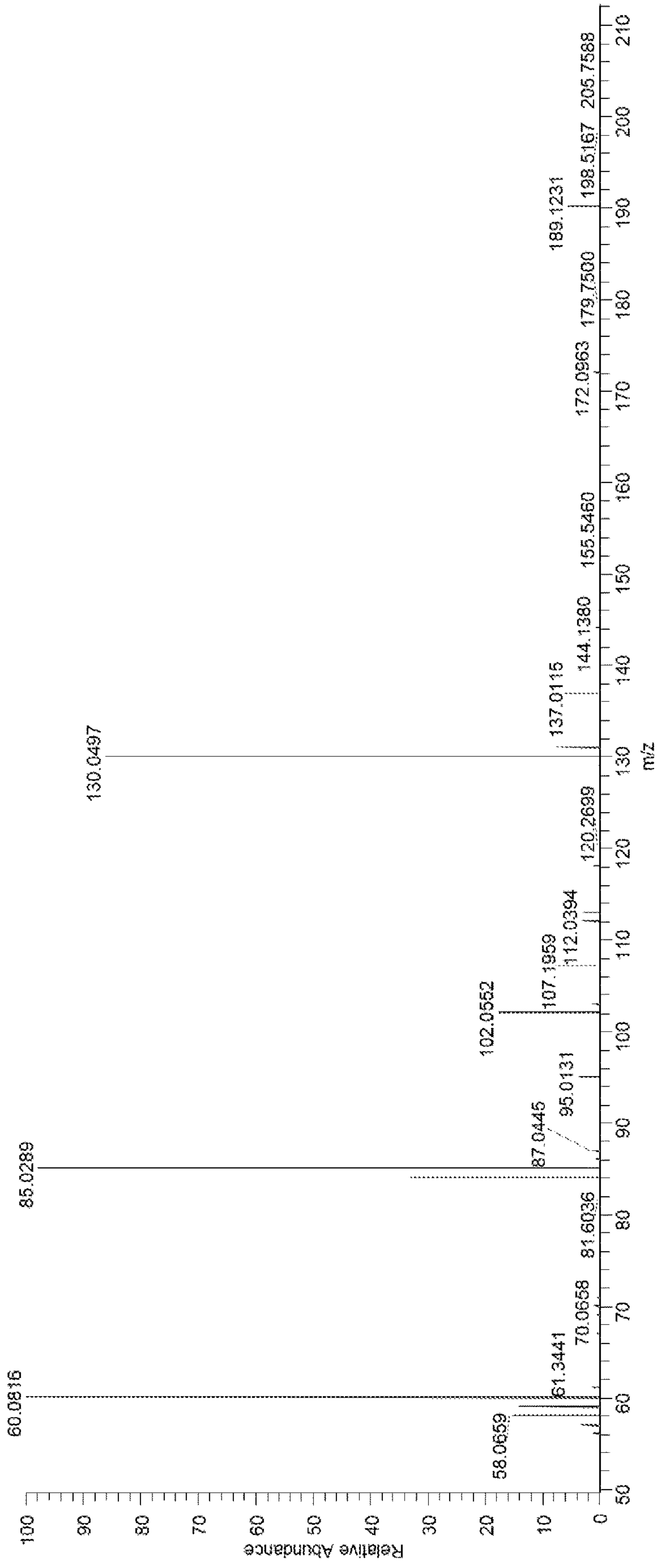
Figure 30A:
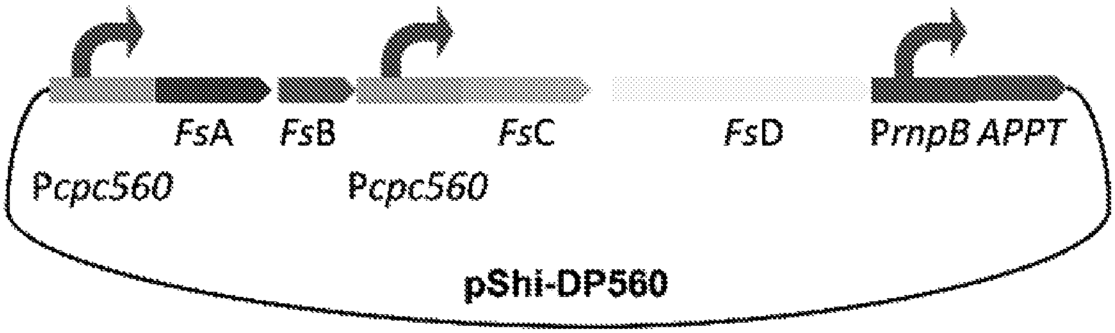
FIGS. 30A-30C. Expression of the shinorine gene clusters under the control of two Pcpc560 promoters. (A) Schematic representation of the plasmid containing the shinorine gene cluster under the control of two Pcpc560 promoters. (B) Colony PCR analysis of strain Sh-DP560 (containing plasmid pSh-DP560 having the sequence of SEQ ID NO: 87). M: NEB 1 kb DNA Ladder, lane 1: PCR amplicons using primers P560-FsA-F and FsA-R, lane 2: PCR amplicons using primers DP560-FsC-F and DP560-FsC-R. Expected sizes were found. (C) RT-PCR analysis demonstrated the proper transcription of the individual genes in Sh-DP560. M: NEB 100 bp DNA Ladder, lane 1-4: RT-PCR amplicons of FsA-D, respectively.
Figure 30B:
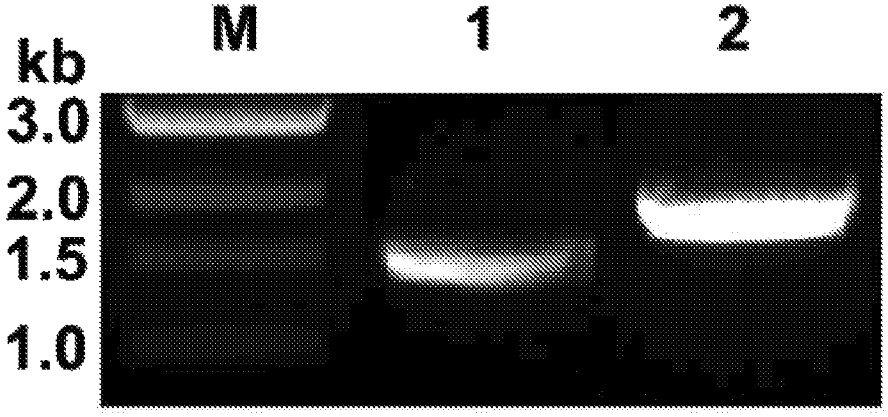
Figure 30C:
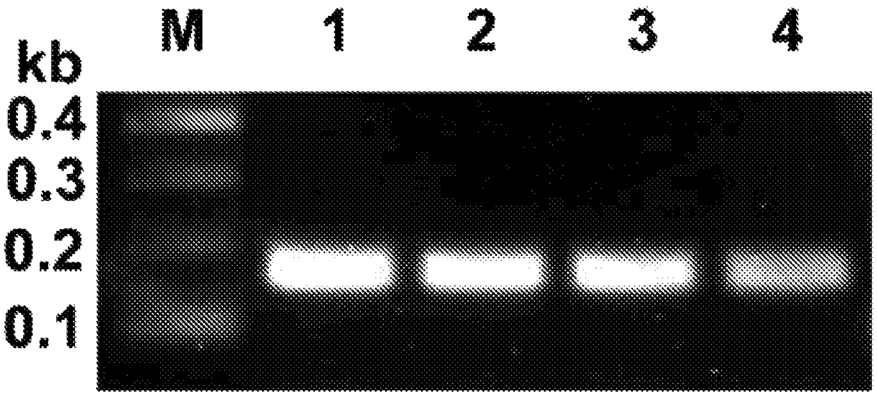

Transcriptional elements are known to control the productivity of expressed compounds in *Synechocystis*, but their functions vary among different cyanobacterial hosts. To overproduce shinorine in *Synechocystis*, the expression of its cluster was optimized using three promoters with varied strengths, including one synthetic promoter Ptrc and two promoters of *Synechocystis* PrnpB and Pcpc560. All three promoters have previously been used in *Synechocystis*. Since FsA-D have the same gene orientation, the replacement of the original promoter in the upstream of FsA with these new promoters can influence the expression of all four genes (FIG. 27A). Three new expression vectors were thus constructed and transformed into *Synechocystis* to create the production strains Sh-Ptrc, Sh-PrnpB, and Sh-P560, which were further validated in the PCR diagnosis (FIG. 27B). The yield of shinorine was quantitated in the strains that were cultured under the same conditions as Sh-Pori. Remarkably, the promoter engineering improved the titers of shinorine in Sh-PrnpB (0.82±0.04 mg/g DW), Sh-Ptrc (1.12±0.05 mg/g DW) and Sh-P560 (1.67±0.06 mg/g DW) by about 4, 5, and 8 times, respectively, compared with Sh-Pori (FIG. 28A, Table 4). Of note, both Sh-Ptrc and Sh-P560 produced more shinorine than any known cyanobacterial species. In addition to shinorine, these new strains produced a new compound that was shown as a dominant peak in the HPLC traces and was missing in the extract of Sh-Pori (FIG. 23, FIG. 28A). The peak content was determined to be 4-DG based on its absorbance maximum at 294 nm and its HRMS and MS/MS spectra (FIG. 29), which agreed well with the reported data of 4-DG. Among three strains, Sh-P560 accumulated the highest amount of 4-DG, while Sh-PrnpB had the least (FIG. 28A).

Figure 28B:
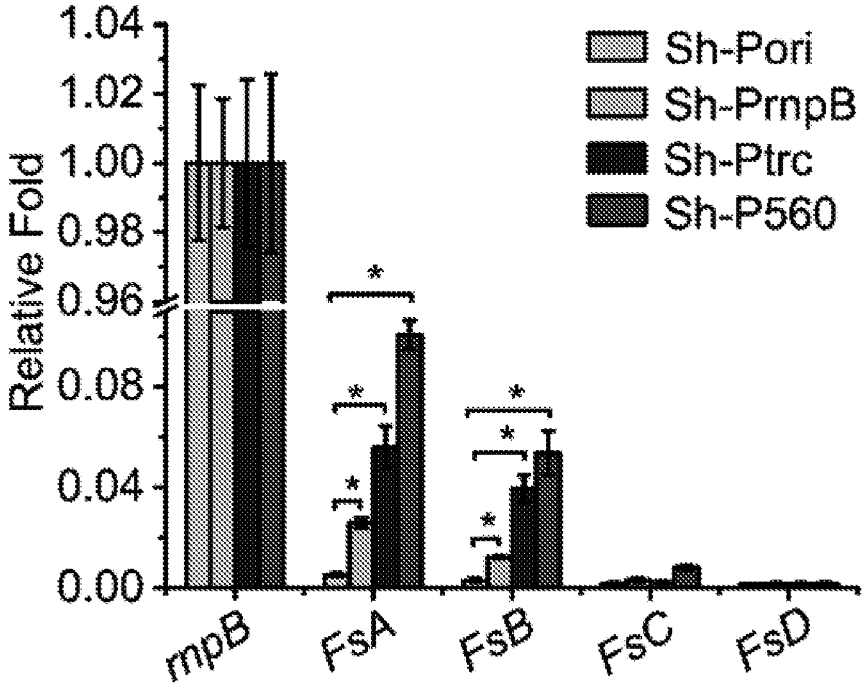

The accumulation of 4-DG likely indicated the imbalanced expression of shinorine biosynthetic genes in three new strains. To quantitate the effects of these promoters on the transcription of shinorine cluster, quantitative RT-PCR (qRT-PCR) analysis was performed. The transcription level of the conserved gene rnpB in each strain was set as 1 and then used to normalize other signals. This analysis revealed that the transcription level of FsA in Sh-Pori was about 2, 3, and 3 times higher than FsB, FsC, and FsD, respectively (FIG. 28B, Table 5). Compared with the original promoter, Ptrc, PrnpB and Pcpc560 statistically significantly enhanced the transcription levels of FsA and FsB by about 10, 5 and 19 folds, respectively, agreeing with the improved production of shinorine in the three new strains (FIG. 28A). By contrast, the transcription levels of FsC were enhanced to a modest extent, while the new promoters did not upregulate the expression of FsD (FIG. 28B, Table 5). Therefore, the transcriptional analysis indicated that the accumulation of 4-DG is caused by the relatively low expression of FsC whose encoded enzyme converts 4-DG into MG (FIG. 22). In line with this observation, the transcription level of FsC in Sh-P560 was 2-4 folds higher than Sh-Ptrc and Sh-PrnpB, likely leading to 1.5-2 times more shinorine in Sh-P560 (FIG. 28B, Table 4).

TABLE 5 qRT-PCR analysis of the shinorine biosynthetic genes in *Synechocystis* mutants.

| | *Synechocystis* mutants | | | | | |
|---|---|---|---|---|---|---|
| Gene | Sh-Pori | Sh-PrnpB | Sh-Ptrc | Sh-P560 | Sh-DP560 | Sh-TP560 |
| rnpB | 1 ± 0.0224 | 1 ± 0.0186 | 1 ± 0.0241 | 1 ± 0.0258 | 1 ± 0.0128 | 1 ± 0.0163 |
| FsA | 0.0053 ± 0.0007 | 0.0259 ± 0.0021 | 0.0558 ± 0.0085 | 0.1006 ± 0.0057 | 0.1042 ± 0.0120 | 0.1037 ± 0.0186 |
| FsB | 0.0031 ± 0.0008 | 0.0123 ± 0.0005 | 0.0393 ± 0.0055 | 0.0537 ± 0.0087 | 0.0576 ± 0.0108 | 0.0556 ± 0.0080 |
| FsC | 0.0018 ± 0.0005 | 0.0032 ± 0.0006 | 0.0022 ± 0.0007 | 0.0082 ± 0.0007 | 0.0349 ± 0.0008 | 0.0361 ± 0.0018 |
| FsD | 0.0016 ± 0.0004 | 0.0019 ± 0.0002 | 0.0018 ± 0.0003 | 0.0019 ± 0.0004 | 0.0154 ± 0.0029 | 0.0683 ± 0.0109 |

Overproduction of Shinorine by Tuning the Expression of Individual Genes

Figure 31:
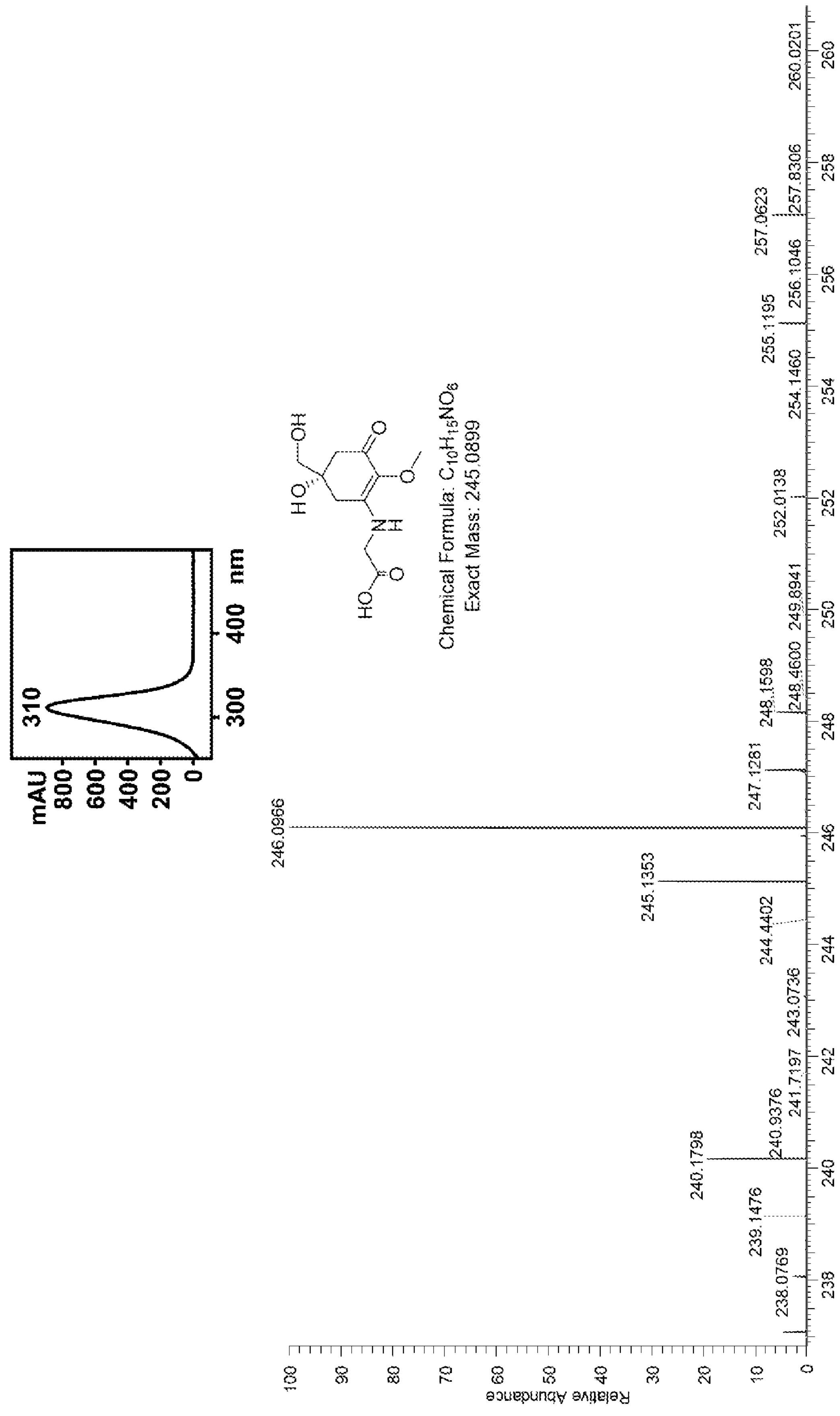
FIG. 31. The absorption (top), HRMS (middle) and MS/MS (bottom) spectra of expressed MG in Sh-DP560.
Figure 31:
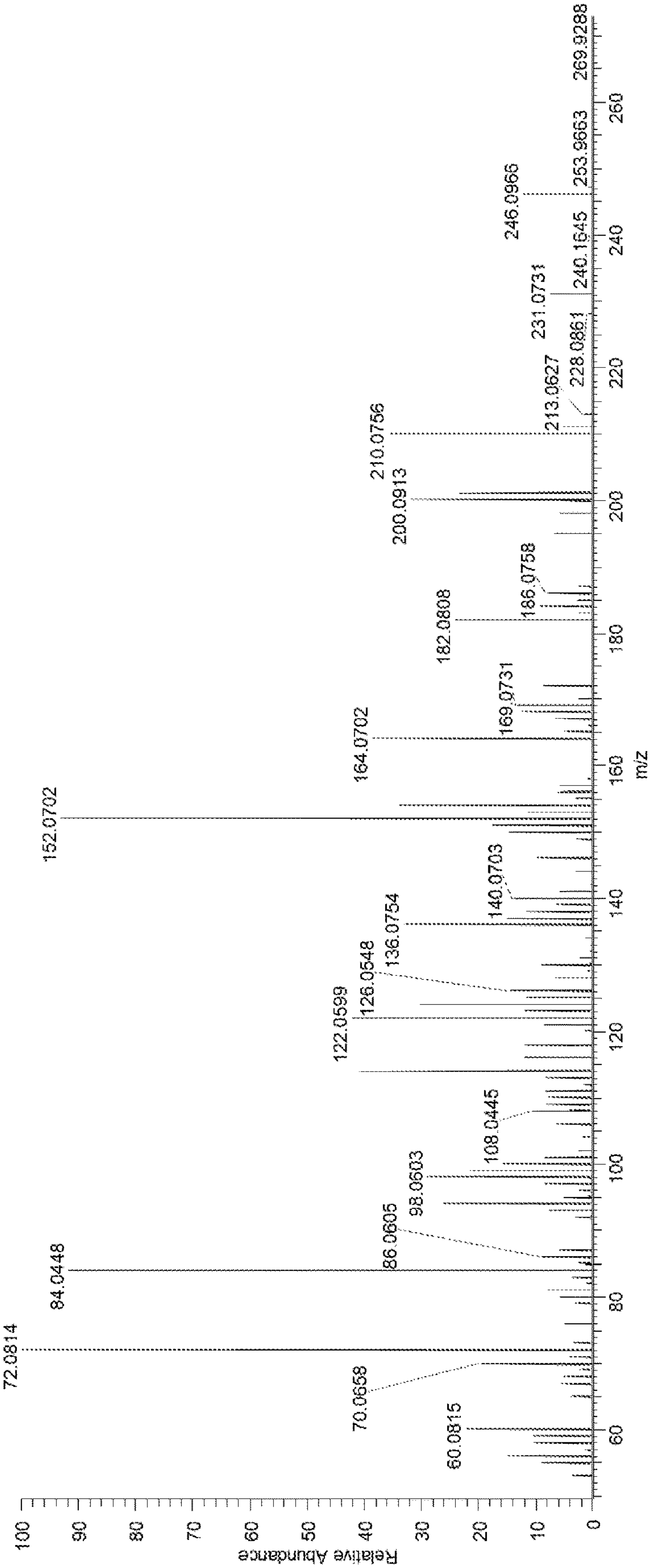
Figure 32A:
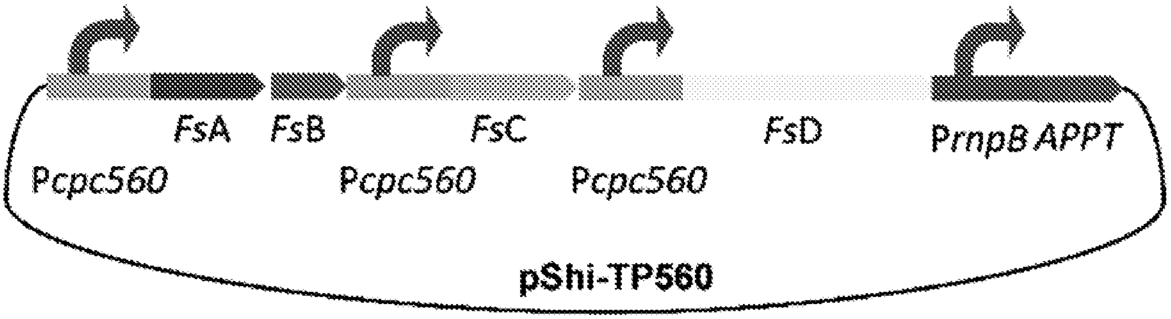
FIGS. 32A-32C. Expression of the shinorine gene clusters under the control of three Pcpc560 promoters (containing plasmid pSh-TP560 having the sequence of SEQ ID NO: 88). (A) Schematic representation of the plasmid containing the shinorine gene cluster under the control of three Pcpc560 promoters. (B) Colony PCR analysis of Sh-TP560. M: NEB 1 kb DNA Ladder, lane 1: PCR amplicons using primers P560-FsA-F and FsA-R, lane 2: PCR amplicons using primers DP560-FsC-F and DP560-FsC-R, lane 3: PCR amplicons using primers TP560-FsD-F and TP560-FsD-R. Expected sizes were found. (C) RT-PCR analysis demonstrated the proper transcription of the individual genes in Sh-TP560. M: NEB 100 bp DNA Ladder, lane 1-4: RT-PCR amplicons of FsA-D, respectively.
Figure 32B:
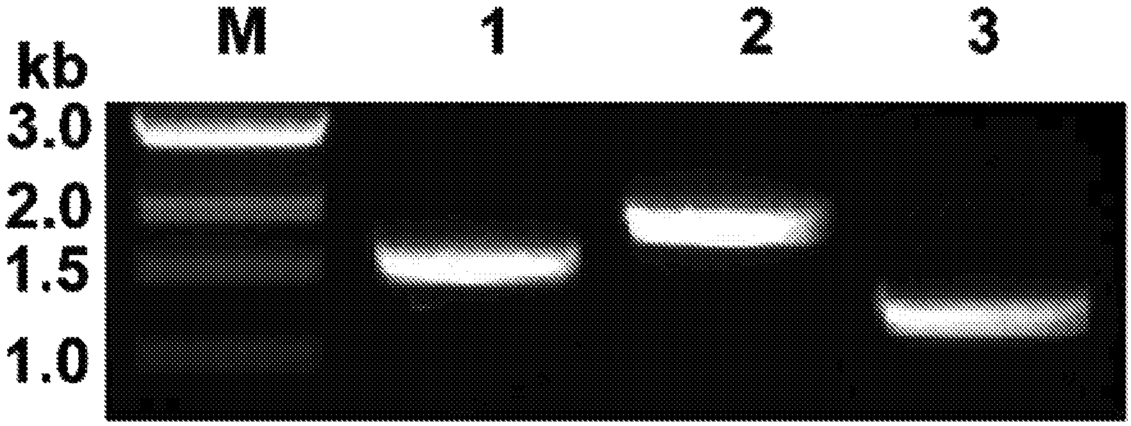
Figure 32C:
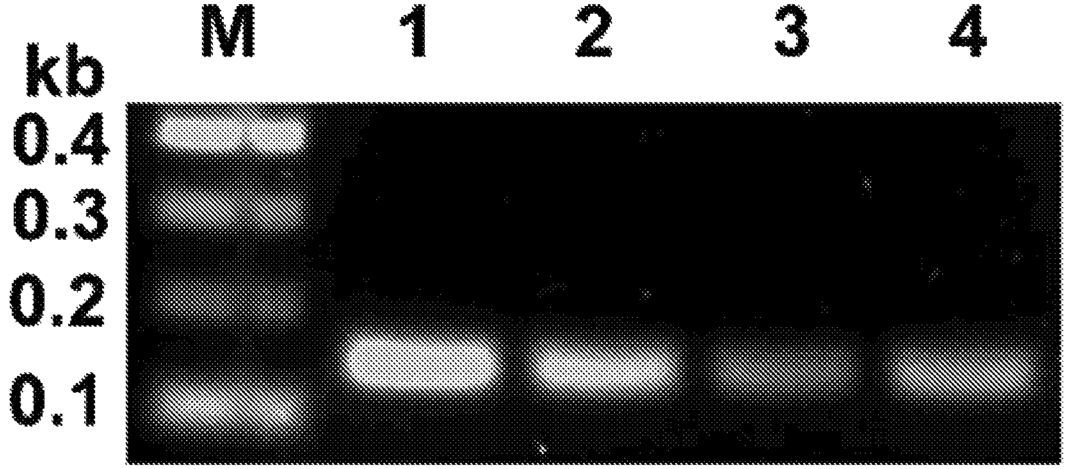
Figure 33A:
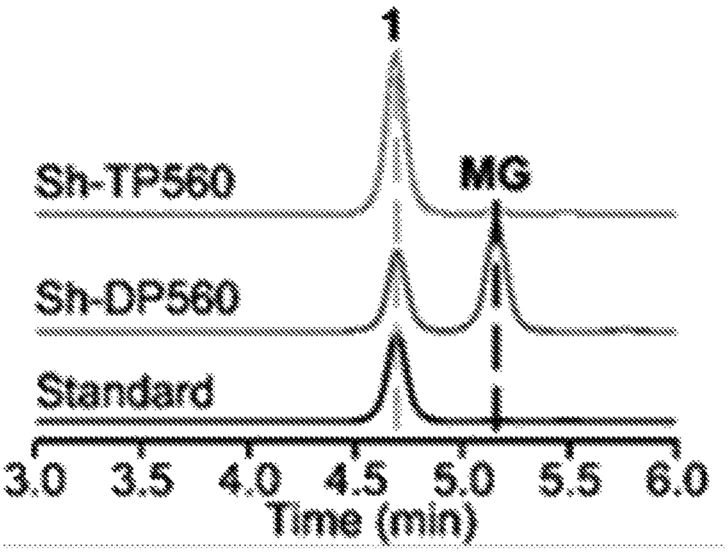
FIGS. 33A-33B. Overproduction of shinorine in *Synechocystis* by tuning the expression of individual genes. (A) HPLC analysis of the metabolic profiles of Sh-DP560 and Sh-Tp560. MG was produced in Sh-DP560 and completely converted into shinorine (1) in Sh-TP560. (B) qRT-PCR analysis of the transcription levels of FsC and FsD in Sh-P560, Sh-DP560 and Sh-TP560. The transcription level of rnpB gene in each strain was quantitated for normalizing the signals of these genes in the same strain. Data represent mean±standard deviation (n=3). * indicates statistically significant difference ($p<0.05$, Student's t-test).
Figure 33B:
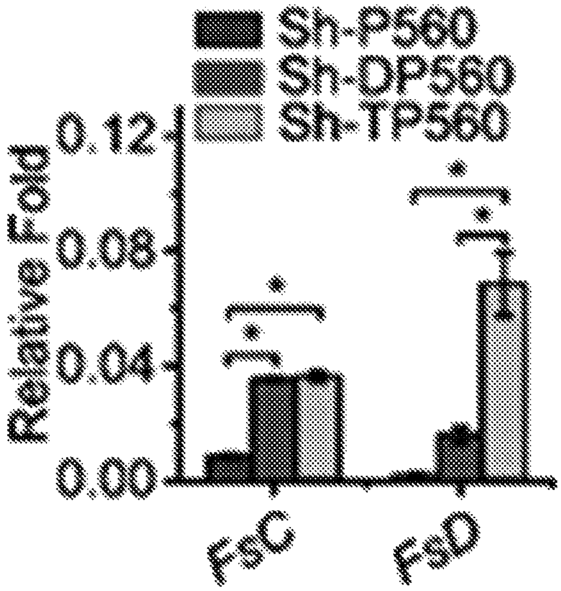
Figure 34:
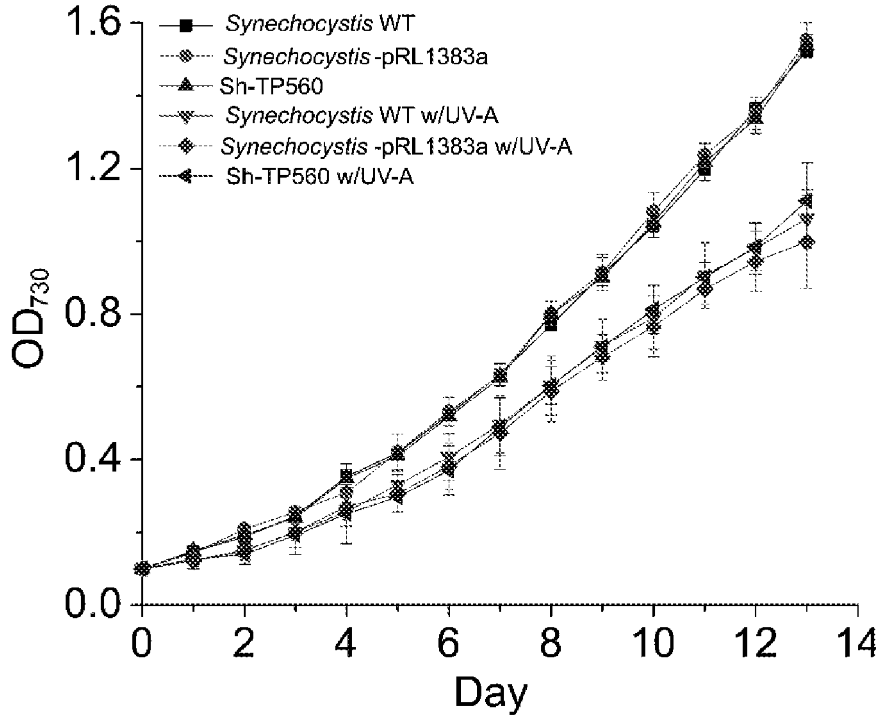
FIG. 34. Growth curves of wild type and engineered *Synechocystis* strains exposed to UV-A and white light. Data represent mean±standard deviation (n=3).

To further improve the shinorine productivity, the expression of FsC in Sh-P560 was enhanced, which can lead to the complete conversion of otherwise-accumulated 4-DG. Given its strongest strength among the tested promoters (FIGS. 28A-28B), Pcpc560 was selected and inserted upstream of FsC gene of the shinorine cluster in Sh-P560 (FIG. 32A). The new construct was then used to generate Sh-DP560 that was further validated by PCR and RT-PCR analysis (FIGS. 32B-32C). 4-DG disappeared from the methanolic extract of Sh-DP560 and the yield of shinorine was improved to 1.93±0.09 mg/g DW (FIG. 33A, Table 4). However, Sh-DP560 produced one new dominant compound along with shinorine, which had a retention time of 5.2 min in the HPLC analysis and was missing from Sh-Pori and Sh-P560 (FIGS. 28A and 33A). This compound was determined as MG based on its absorbance maximum at 310 nm and its expected molecular weight (FIG. 31). The disappeared 4-DG in Sh-DP560 indicated the improved expression of FsC by the newly inserted Pcpc560 but the accumulated MG suggested the relatively low transcription of FsD and/or the insufficient catalytic efficiency of its encoded NRPS. Indeed, the second Pcpc560 improved the transcription levels of FsC and FsD by 4 and 8 times, respectively, compared with Sh-P560 (FIG. 33B, Table 5). However, the level of FsD remained the lowest among all genes and was over 2 times lower than FsC. Improving the expression of FsD can likely divert more MG for the synthesis of shinorine. Accordingly, the third Pcpc560 promoter was inserted into the intergenic region of FsC and FsD and the production strain Sh-TP560 (FIGS. 32A-32C) was created. The qRT-PCR analysis revealed a 5-fold increase of FsD transcription in Sh-TP560, making it 2 times higher than FsC (FIG. 33B). Remarkably, all MG was converted to the final product in Sh-TP560 and the titer of shinorine was improved to 2.37±0.21 mg/g DW (FIG. 33A, Table 4). Importantly, the overproduction of shinorine had no effect on the growth of Sh-TP560 (FIG. 34). Compared with the commercially used red algae *P. umbilicalis*, Sh-TP560 possesses about 73% of its shinorine productivity but requires a significantly shorter growth period, suggesting the potential of Sh-TP560 to supply shinorine for commercial use. In addition, lack of any accumulation of any biosynthetic intermediate in Sh-TP560 makes it superior to other microbial hosts for the production of shinorine.

The Effect of Extracellular Serine on the Production of Shinorine in Sh-TP560

Figure 21A:
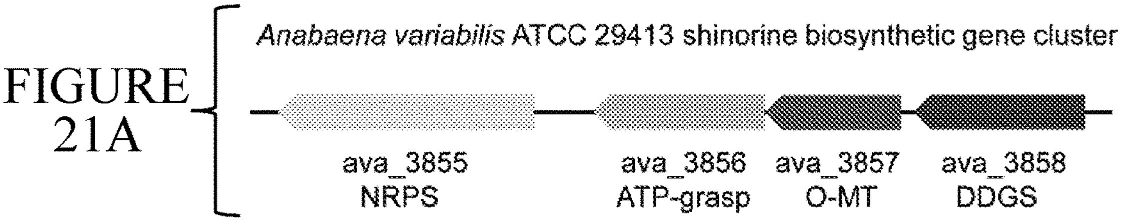
FIGS. 21A-21B. Biosynthesis pathway of shinorine. (A) The shinorine gene cluster in *Anabaena* consists of four genes encoding demethyl 4-deoxygadusol synthase, O-methyltransferase, ATP-grasp ligase, nonribosomal peptide synthetase (NRPS), respectively; (B) The biosynthesis of shinorine in *Anabeana* and other organisms. Two routes to 4-DG are known.
Figure 21B:
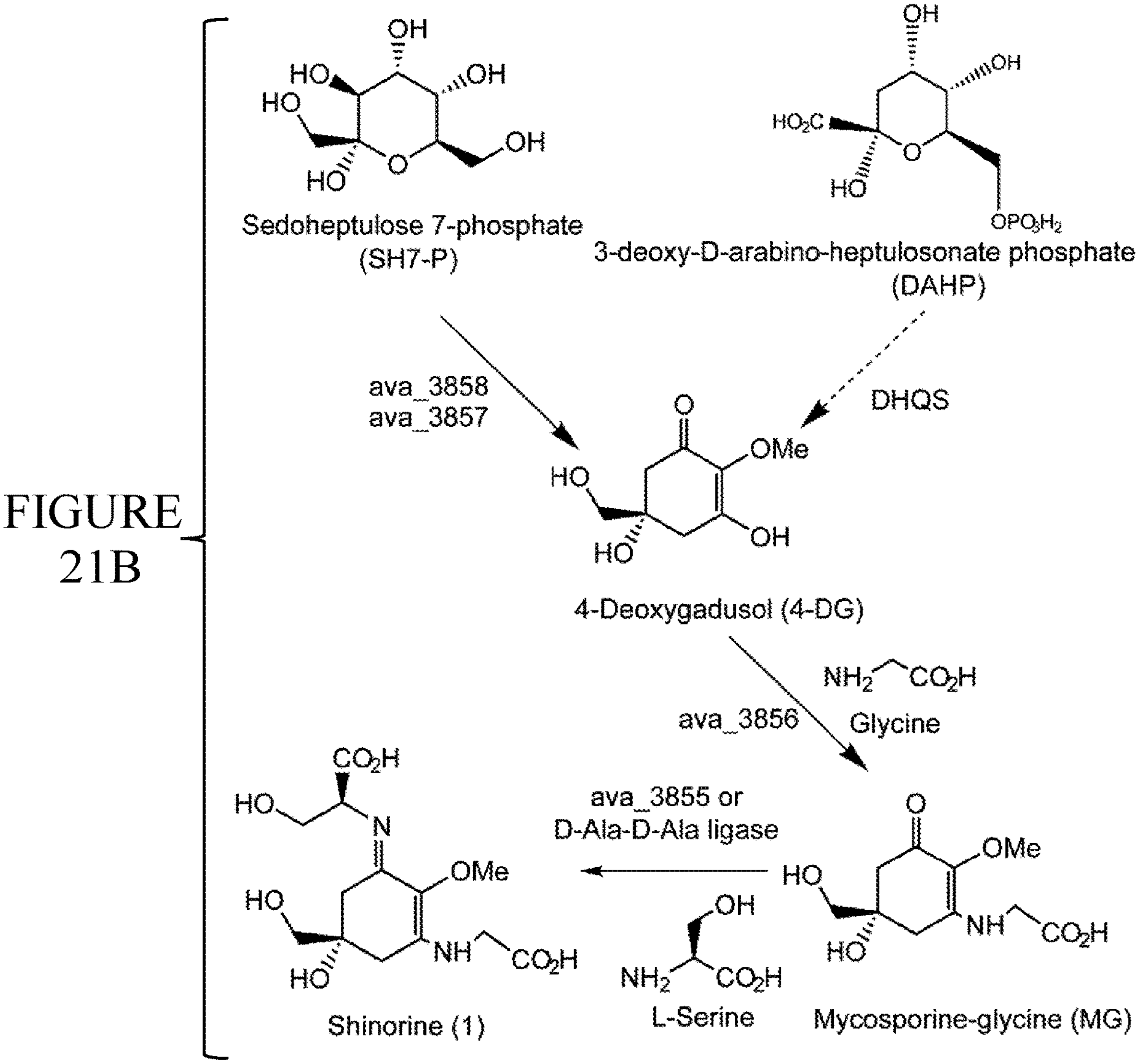

Increased precursor supply can improve the productivity of natural products in heterologous hosts. The shinorine biosynthesis requires SH-7P, glycine and serine as building blocks (FIGS. 21A-21B). The complete conversion of 4-DG into MG in Sh-DP560 and SH-TP560 suggested that shinorine biosynthesis is not limited by the cellular availability of glycine. On the other hand, the higher transcription level of FsD than FsC along with lack of any accumulation of MG in Sh-TP560 (FIG. 33B) led the examination of whether the availability of 1-serine might constrain the shinorine production. Therefore 1-serine was included at a final concentration of 0.5 mM in BG-11 medium to culture Sh-TP560 for 13 days. The same titers of shinorine were observed in serine-treated and serine-untreated Sh-TP560 (Table 4), suggesting 1-serine not to be a limiting factor of the shinorine production in Sh-TP560. When its concentration in BG-11 was higher than 0.5 mM, 1-serine inhibited the strain growth in a dose-dependent manner. Further improvement of shinorine production may be achieved by using stronger promoters, incorporating catalytically more active enzymes, and/or diverting additional metabolic flux toward the shinorine biosynthesis.

Protection of Sh-TP560 from UV Rays by the Expressed Shinorine

Figure 35:
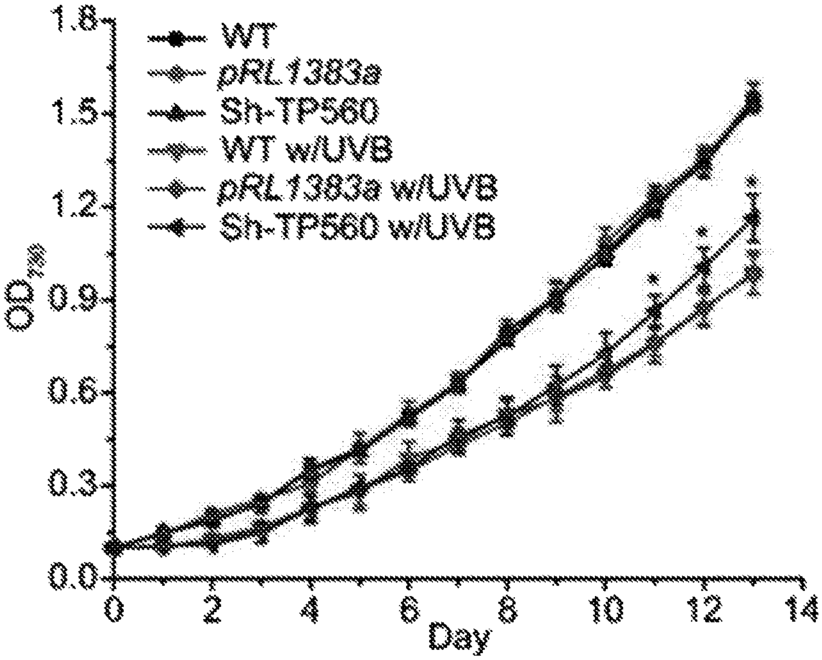
FIG. 35. Growth curves of WT and engineered *Synechocystis* strains under the treatment of UV rays and white lights for 13 days. Data represent mean±standard deviation (n=3). * indicates statistically significant difference ($p<0.05$, Student's t-test) of growth rates between Sh-TP560 and the two controls after UV-B exposure.

The primary biological function of MAAs is believed to protect organisms from the damages of UV radiation. To assess the photoprotective effect of shinorine on the growth of Sh-TP560, WT, *Synechocystis*-pRL1383a and Sh-TP560 were exposed to UV rays of 312 nm (UV-B) and 365 nm (UV-A) and white light for 5 hours per day for a total of 13 days. Compared with white light, UV rays reduced the growth of all strains (FIGS. 34 and 35). Remarkably, when exposed to UV-B, the cell densities ($OD_{730}$) of Sh-TP560 were similar to the two control strains within the first 10 days but were significantly higher from day 11 to 13 (FIG. 35). In contrast, no growth differences were observed when these strains were treated by UV-A (FIG. 34). Interestingly, UV rays had a minor effect on the production of shinorine in Sh-TP560 (Table 4). These results demonstrate that shinorine can protect its producer from the harmful effects of UV-B radiation.

As such, the current invention demonstrates the use of *Synechocystis* as the heterologous host to overproduce cyanobacterial natural product shinorine, a commercially valuable MAA. A useful strategy for improving the titer of shinorine in *Synechocystis* is provided, which integrated transcriptional and metabolic profiling with the transcriptional manipulation of biosynthetic genes. Sh-TP560 strain has shinorine productivity of 2.37±0.21 mg/g DW, marking it as a promising alternative of the red algae *P. umbilicalis* for the commercial supply of shinorine. Previous attempts to express cyanobacterial natural products, particularly polyketides and nonribosomal peptides, in *E. coli* or *Streptomyces* strains have resulted in limited success. These results indicate that *Synechocystis* is a new enabling host for probing the chemical potential of cyanobacterial species and producing cyanobacterial natural products and thereof. The photosynthetic nature of *Synechocystis* further makes the production of expressed compounds to be environmentally friendly and cost-effective. Also, the invention characterizes the photoprotective effects of shinorine in a heterologous host.

Materials and Methods

Extraction of Shinorine from Cyanobacterial Biomass

*Anabaena, Fischerella*, and wild type and engineered *Synechocystis* strains were grown in 600 ml of BG-11 medium at 26° C. with air bubbling. The culture media were centrifuged (4° C., 5,000 rpm for 10 min) to collect cell pellets after 13 days for *Synechocystis* strains and 21 days for filamentous strains. The pellets were then resuspended in 10 ml cooled methanol and lysed by sonication on ice with 2-s pulses. After centrifugation (4° C., 5,000 rpm for 30 min, the clear supernatants of lysates were collected and evaporated under reduced pressure. The dried residues were resuspended in water (1 ml) for HPLC and LC-MS analysis. Authentic shinorine was isolated from Helioguard 365 (Mibelle Biochemistry, USA) following the previous protocol.

Quantitative RT-PCR Analysis of Shinorine Biosynthetic Genes

Total RNA samples were isolated from engineered *Synechocystis* strains using ZR Fungal/Bacterial RNA MiniPrep kit (Zymo Research). The quantity and quality of the isolated RNAs were determined using Nanodrop. Synthesis of cDNAs was performed with random primers following the manufacturer's protocol (Thermo Scientific). The synthesized cDNAs were used as templates for qPCR to detect the transcription levels of shinorine biosynthetic genes and rnpB, while the isolated RNA samples themselves were used as the templates of PCR reactions to detect any residual genomic DNAs using primers listed in Table 6. The student's t-test analysis was applied to determine the difference between the samples, and a P-value <0.05 was considered to be statistically significant.

Reagents, Strains and Culture Conditions

Restriction enzymes, recombinant Taq DNA polymerase and Phusion DNA polymerase were purchased from Fisher Scientific or New England Labs. Spectinomycin and chloramphenicol were purchased from RPI Corp (USA). All other chemicals were from Fisher or Sigma-Aldrich. The GeneJET Plasmid Miniprep Kit, PCR Purification Kit and Gel Extraction Kit (Thermo Scientific) were used for molecular biology studies. All oligonucleotide primers used in this example were synthesized by Sigma-Aldrich and were listed in Table 6.

TABLE 6

Oligonucleotides used in Example 2.

| Primers | Sequence 5' to 3' | Function |
|---|---|---|
| Shi-Ori-F | CGTACGTACTACTTAATTGACAAATA (SEQ ID NO: 32) | Amplification of original gene cluster |
| Shi-Ori-R | GAGCTCCCCGACTTCTCAAAGGATAC (SEQ ID NO: 33) | |
| Shi-1211-F | CTCGAGGACGTCATGGGTACACCTCACG CTAC (SEQ ID NO: 34) | Cloning of gene cluster into pSL1211 |
| Shi-1211-R | CATATGCCCGACTTCTCAAAGGATAC (SEQ ID NO: 35) | |
| Ptrc-shi-F | CGTACGATTCTGAAATGAGCTGTTGACA A (SEQ ID NO: 36) | Amplification of Ptrc-shinorine gene cluster |
| Ptrc-shi-R | GAGCTCCCCGACTTCTCAAAGGATAC (SEQ ID NO: 37) | |
| PrnpB-AP-F | CTGCAGTTCAATGCGGTCCAATAC (SEQ ID NO: 38) | Amplification of PrnpB and fusion with APPT |
| PrnpB-AP-R | AGCCAAGTATGCTGCAACATTTTTTCTAG TGTGCCATTG (SEQ ID NO: 39) | |
| Pr-APPT-F | CAATGGCACACTAGAAAAAATGTTGCAG CATACTTGGCT (SEQ ID NO: 40) | Amplification of APPT and fusion with PrnpB |
| Pr-APPT-R | GCATGCTCAATAATGCCAGAATTTTG (SEQ ID NO: 41) | |
| PrnpB-F | CGTACGTTCAATGCGGTCCAATAC (SEQ ID NO: 42) | Amplification of PrnpB for the construction of pShi-PrnpB |
| PrnpB-R | ACGTCTTTTTCTAGTGTGCCATTG (SEQ ID NO: 43) | |
| P560-F | CGTACGCATTGAATTAATCTCCTAC (SEQ ID NO: 44) | Amplification of Pcpc560 for the construction of pShi-P560 |
| P560-R | GACGTCCACCTGTAGAGAAGAGTC (SEQ ID NO: 45) | |
| P560-FmysAB-F | CGTACGCATTGAATTAATCTC (SEQ ID NO: 46) | Amplification of Pcpc560-FsAB |
| P560-FmysAB-R | GAGCTCCTACAACCGCCGAATTAAAG (SEQ ID NO: 47) | |
| P560-CD-F | GAGCTCCATTGAATTAATCTCCTAC (SEQ ID NO: 48) | Amplification of Pcpc560 for fusion of P560-FsCD |
| P560-CD-R | CAGAAATAGATTGTGTCATCACCTGTAG AGAAGAGTC (SEQ ID NO: 49) | |
| P5-FmysCD-F | GACTCTTCTCTACAGGTGATGACACAATC TATTTCTG (SEQ ID NO: 50) | Amplification of FsCD for fusion of P560-FsCD |
| P5-FmysCD-R | CCGCTCGAGAGATTGTTCTTCCAATTCTT C (SEQ ID NO: 51) | |
| P560-C-F | GAGCTCCATTGAATTAATCTCCTAC (SEQ ID NO: 52) | Amplification of Pcpc560 for fusion of P560-FsC |
| P560-C-R | CAGAAATAGATTGTGTCATCACCTGTAG AGAAGAGTC (SEQ ID NO: 53) | |
| P5-FmysC-F | GACTCTTCTCTACAGGTGATGACACAATC TATTTCTG (SEQ ID NO: 54) | Amplification of FsC for fusion of P560-FsC |
| P5-FmysC-R | GGTACCCTAATCGCCACCAAACTC (SEQ ID NO: 55) | |
| P560-D-F | GTACCCATTGAATTAATCTCCTAC (SEQ ID NO: 56) | Amplification of Pcpc560 for fusion of P560-FsD |
| P560-D-R | CTAAAAAGTTTATTATTTCCATCACCTGT AGAGAAGAGTC (SEQ ID NO: 57) | |
| P5-FmysD-F | GACTCTTCTCTACAGGTGATGGAAATAAT AAACTTTTTAG (SEQ ID NO: 58) | Amplification of FsD for fusion of P560-FsD |
| P5-FmysD-R | GTCGACCCCGACTTCTCAAAGGATAC (SEQ ID NO: 59) | |
| Pori-FmysA-F | TGTGAATTAGTTGTAATG (SEQ ID NO: 60) | Colony PCR Pori-FsA |
| Pori-FmysA-R | CTACTTTAATCGCAATTC (SEQ ID NO: 61) | |

TABLE 6-continued

Oligonucleotides used in Example 2.

| Primers | Sequence 5' to 3' | Function |
|---|---|---|
| FmysD-APPT-F | CAATTCACCCATAGTAGC (SEQ ID NO: 62) | Colony PCR FsD-APPT |
| FmysD-APPT-R | TAATCAAATTTAACTTGC (SEQ ID NO: 63) | |
| Ptrc-FmysA-F | CGTACGATTCTGAAATGAGCTGTTGACAA (SEQ ID NO: 64) | Colony PCR Ptrc-FsA |
| PrnpB-FmysA-F | CGTACGTTCAATGCGGTCCAATAC (SEQ ID NO: 65) | Colony PCR PrnpB-FsA |
| P560-FmysA-F | CGTACGCATTGAATTAATCTCCTAC (SEQ ID NO: 66) | Colony PCR Pcpc560-FsA |
| FmysA-R primer | GCTCATGCAGGTTTGGAG (SEQ ID NO: 67) | Colony PCR Fs A reverse |
| DP560-FmysC-F | GAGCTCCATTGAATTAATCTCCTAC (SEQ ID NO: 68) | Colony PCR Pcpc560-FsC |
| DP560-FmysC-R | GTAAGCCTACCTACTGGA (SEQ ID NO: 69) | |
| TP560-FmysD-F | GGTACCCATTGAATTAATCTCCTAC (SEQ ID NO: 70) | Colony PCR Pcpc560-FsD |
| TP560-FmysD-R | GAGCGATGAATACCCATC (SEQ ID NO: 71) | |
| RT-FmysA-F | AGTAGTTGATGCGTTTGC (SEQ ID NO: 72) | RT-PCR FsA |
| RT-FmysA-R | CTACTTTAATCGCAATTC (SEQ ID NO: 73) | |
| RT-FmysB-F | GTGAACACACCACTACTG (SEQ ID NO: 74) | RT-PCR FsB |
| RT-FmysB-R | ACACTCTTGGCTTTAGTC (SEQ ID NO: 75) | |
| RT-FmysC-F | CAAGATGGCACAATCTAC (SEQ ID NO: 76) | RT-PCR FsC |
| RT-FmysC-R | TCCAGTAGGTAGGCTTAC (SEQ ID NO: 77) | |
| RT-FmysD-F | AACATGTCCAACCCATAC (SEQ ID NO: 78) | RT-PCR FsD |
| RT-FmysD-R | GAGCGATGAATACCCATC (SEQ ID NO: 79) | |

*E. coli* DH5a and *E. coli* HB101 were used for routine molecular biology studies and triparental-mating conjugation, respectively. Both strains were maintained in LB medium supplemented with 50 μg/ml spectinomycin or 25 μg/ml chloramphenicol. *Synechocystis, Fischerella*, and *Anabaena* were purchased from UTEX and *Anabaena* sp. PCC 7120 was received. All cyanobacteria strains were grown in media bottles containing 300-600 ml BG-11 medium. Spectinomycin was added in a final concentration of 50 μg/ml to the cultures of engineered *Synechocystis* strains. All cultures were incubated at 26° C. with continuous air bubbling and under 16 h/8 h light/dark lighting cycle with illumination of 2000-2500 lux during lighting period. For plate growth, BG-11 medium was supplemented with 1.0% (wt/vol) agar and 0.3% (wt/vol) sodium thiosulfate. To determine the growth curves, *Synechocystis* strains were inoculated to 300 mL of BG-11 to reach an initial $OD_{730}$ of 0.1 and then grew under the above conditions. Measurements were taken daily by detecting the $OD_{730}$ on a Shimadzu UV-2700 UV-Vis spectrophotometer.

To test the effects of serine on the shinorine production, Sh-TP560 cells were first grown under the above conditions for 5 days to reach an optical density ($OD_{730}$) of 0.4. Then, 0.5 mM L-serine was added into the cultures and shinorine was extracted from cell pellets after 8 days.

For UV radiation experiments, liquid cultures were grown in sterile plastic petri dishes (90 mm×15 mm) and exposed to UV and white lights for 5 hours per day. Light illumination was achieved through Spectronics ENB-260C 6W UV Lamp with the wavelength of 312 nm (UV-B) or 365 nm (UV-A) and LED lamp for the white light. The light intensity was 1.2 and 1.3 $W/m^{-2}$ for UV-B and UV-A, respectively. All cultures were shaken several times during the light exposure to avoid self-shading.

Bioinformatics Analysis of Shinorine Biosynthetic Gene Clusters in Cyanobacteria The protein sequences encoded by the shinorine biosynthetic genes in *Anabaena* (ava_3855-ava_3858) were used as queries to mine the genomes of subsection V cyanobacterial strains currently available in NCBI database (up to July, 2017) using BLAST program. Multiple sequence alignments and similarity scores were generated using Clustal Omega (see Worldwide Web site: ebi.ac.uk/Tools/msa/clustalo/). PromoterHunter program (see Worldwide Website: phisite.org/main/index.php?nav=tools&nav_sel=hunter) was used to analyze the upstream and the intergenic regions of the shinorine biosynthetic gene cluster in *Fischerella.*

DNA Manipulation and Plasmid Construction gDNA was isolated according to methods described in Example 1.

PCR amplification of the shinorine gene cluster in *Fischerella* was carried out using the primers shown in Table 6. The cluster was cloned into pRL1383a vector to create pRL1383-Pori-Shi. The APPT gene was amplified from *Anabaena* sp. PCC7120 gDNA. The PrnpB promoter was amplified from *Synechocystis* gDNA. PrnpB and APPT were fused in the PCR reaction and then cloned into pRL1383-Pori-Shi to generate the pShiOri (FIG. 25A). Following the similar strategy, other shinorine expression constructs were prepared.

HPLC and LC-MS Analysis of Extracted Shinorine

HPLC and LC-MS analysis of extracted shinorine were conducted according to the methods described in Example 1.

REFERENCES

1. Balskus, E. P., and Walsh, C. T. (2010) The genetic and molecular basis for sunscreen biosynthesis in cyanobacteria, Science 329, 1653-1656.
2. Baran, P. S., Maimone, T. J., and Richter, J. M. (2007) Total synthesis of marine natural products without using protecting groups, Nature 446, 404-408.
3. Barry, S. M., Kers, J. A., Johnson, E. G., Song, L., Aston, P. R., Patel, B., Krasnoff, S. B., Crane, B. R., Gibson, D. M., and Loria, R. (2012) Cytochrome P450-catalyzed L-tryptophan nitration in thaxtomin phytotoxin biosynthesis, Nature chemical biology 8, 814-816.
4. Baumann, H. I., Keller, S., Wolter, F. E., Nicholson, G. J., Jung, G., Süssmuth, R. D., and Jüttner, F. (2007) Planktocyclin, a cyclooctapeptide protease inhibitor produced by the freshwater cyanobacterium Planktothrix rubescens, Journal of natural products 70, 1611-1615.
5. Beck, C., Knoop, H., Axmann, I. M., and Steuer, R. (2012) The diversity of cyanobacterial metabolism: genome analysis of multiple phototrophic microorganisms, BMC Genomics 13, 56.
6. Becker, K., Hartmann, A., Ganzera, M., Fuchs, D., and Gostner, J. M. (2016) Immunomodulatory Effects of the Mycosporine-Like Amino Acids Shinorine and Porphyra-334, Marine drugs 14, 119.
7. Beld, J., Sonnenschein, E. C., Vickery, C. R., Noel, J. P., and Burkart, M. D. (2014) The phosphopantetheinyl transferases: catalysis of a post-translational modification crucial for life, Natural product reports 31, 61-108.
8. Berla, B. M., Saha, R., Immethun, C. M., Maranas, C. D., Moon, T. S., and Pakrasi, H. (2013) Synthetic biology of cyanobacteria: unique challenges and opportunities, Frontiers in microbiology 4, 246.
9. Burja, A. M., Banaigs, B., Abou-Mansour, E., Burgess, J. G., and Wright, P. C. (2001) Marine cyanobacteria—a prolific source of natural products, Tetrahedron 57, 9347-9377.
10. Campbell, E. L., Cohen, M. F., and Meeks, J. C. (1997) A polyketide-synthase-like gene is involved in the synthesis of heterocyst glycolipids in Nostoc punctiforme strain ATCC 29133, Archives of microbiology 167, 251-258.
11. Carreto, J. I., and Carignan, M. O. (2011) Mycosporine-like amino acids: relevant secondary metabolites. Chemical and ecological aspects, Marine drugs 9, 387-446.
12. Conde, F. R., Churio, M. S., and Previtali, C. M. (2004) The deactivation pathways of the excited-states of the mycosporine-like amino acids shinorine and porphyra-334 in aqueous solution, Photochemical & Photobiological Sciences 3, 960-967.
13. Copp, J. N., and Neilan, B. A. (2006) The phosphopantetheinyl transferase superfamily: phylogenetic analysis and functional implications in cyanobacteria, Applied and environmental microbiology 72, 2298-2305.
14. Copp, J., Roberts, A., Marahiel, M., and Neilan, B. (2007) Characterization of PPTNs, a cyanobacterial phosphopantetheinyl transferase from Nodularia spumigena NSOR10, Journal of bacteriology 189, 3133-3139.
15. D'Agostino, P. M., Javalkote, V. S., Mazmouz, R., Pickford, R., Puranik, P. R., and
Neilan, B. A. (2016) Comparative profiling and discovery of novel glycosylated mycosporine-like amino acids in two strains of the cyanobacterium *Scytonema* cf. crispum, Applied and environmental microbiology 82, 5951-5959.
16. De la Coba, F., Aguilera, J., De Galvez, M., Alvarez, M., Gallego, E., Figueroa, F., and Herrera, E. (2009) Prevention of the ultraviolet effects on clinical and histopathological changes, as well as the heat shock protein-70 expression in mouse skin by topical application of algal UV-absorbing compounds, Journal of dermatological science 55, 161-169.
17. Ding, Y., Rath, C. M., Bolduc, K. L., Hakansson, K., and Sherman, D. H. (2011) Chemoenzymatic synthesis of cryptophycin anticancer agents by an ester bond-forming non-ribosomal peptide synthetase module, J Am Chem Soc 133, 14492-14495.
18. Dittmann, E., Gugger, M., Sivonen, K., and Fewer, D. P. (2015) Natural product biosynthetic diversity and comparative genomics of the cyanobacteria, Trends in microbiology 23, 642-652.
19. Elhai, J., and Wolk, C. P. (1988) [83] Conjugal transfer of DNA to cyanobacteria, Methods in enzymology 167, 747-754.
20. Elovson, J., and Vagelos, P. R. (1968) Acyl carrier protein. X. Acyl carrier protein synthetase, The Journal of biological chemistry 243, 3603-3611.
21. Englund, E., Liang, F., and Lindberg, P. (2016) Evaluation of promoters and ribosome binding sites for biotechnological applications in the unicellular cyanobacterium *Synechocystis* sp. PCC 6803, Scientific reports 6, 36640.
22. Favre-Bonvin, J., Bernillon, J., Salin, N., and Arpin, N. (1987) Biosynthesis of mycosporines: mycosporine glutaminol in Trichothecium roseum, Phytochemistry 26, 2509-2514.
23. Gago-Ferrero, P., Diaz-Cruz, M. S., and Barcelo, D. (2012) An overview of UV-absorbing compounds (organic UV filters) in aquatic biota, Analytical and bioanalytical chemistry 404, 2597-2610.
24. Gao, Q., and Garcia-Pichel, F. (2011) An ATP-grasp ligase involved in the last biosynthetic step of the iminomycosporine shinorine in Nostoc punctiforme ATCC 29133, Journal of bacteriology 193, 5923-5928.
25. Garcia-Pichel, F., Wingard, C. E., and Castenholz, R. W. (1993) Evidence regarding the UV sunscreen role of a mycosporine-like compound in the cyanobacterium *Gloeocapsa* sp, Applied and Environmental Microbiology 59, 170-176.
26. George, N., Pick, H., Vogel, H., Johnsson, N., and Johnsson, K. (2004) Specific labeling of cell surface proteins with chemically diverse compounds, J Am Chem Soc 126, 8896-8897.

27. Gu, L., Wang, B., Kulkarni, A., Geders, T. W., Grindberg, R. V., Gerwick, L., Häkansson, K., Wipf, P., Smith, J. L., and Gerwick, W. H. (2009) Metamorphic enzyme assembly in polyketide diversification, Nature 459, 731-735.

28. Guerrero, F., Carbonell, V., Cossu, M., Correddu, D., and Jones, P. R. (2012) Ethylene synthesis and regulated expression of recombinant protein in *Synechocystis* sp. PCC 6803, PLoS One 7.

29. Hader, D.-P., Helbling, E., Williamson, C., and Worrest, R. (2011) Effects of UV radiation on aquatic ecosystems and interactions with climate change, Photochemical & Photobiological Sciences 10, 242-260.

30. Hartmann, A., Murauer, A., and Ganzera, M. (2017) Quantitative analysis of mycosporine-like amino acids in marine algae by capillary electrophoresis with diode-array detection, Journal of pharmaceutical and biomedical analysis 138, 153-157.

31. Hayashi, O., KATOH, T., and OKUWAKI, Y. (1994) Enhancement of antibody production in mice by dietary *Spirulina platensis*, Journal of nutritional science and vitaminology 40, 431-441.

32. Hopwood, D. A. (2009) Complex enzymes in microbial natural product biosynthesis, Part A: overview articles and peptides, Vol. 458, Academic Press.

33. Huang, H.-H., Camsund, D., Lindblad, P., and Heidorn, T. (2010) Design and characterization of molecular tools for a Synthetic Biology approach towards developing cyanobacterial biotechnology, Nucleic acids research 38, 2577-2593.

34. Jaki, B., Orjala, J., and Sticher, O. (1999) A novel extracellular diterpenoid with antibacterial activity from the cyanobacterium Nostoc commune, Journal of natural products 62, 502-503.

35. Jones, A. C., Ottilie, S., Eustáquio, A. S., Edwards, D. J., Gerwick, L., Moore, B. S., and Gerwick, W. H. (2012) Evaluation of *Streptomyces coelicolor* A3 (2) as a heterologous expression host for the cyanobacterial protein kinase C activator lyngbyatoxin A, FEBS Journal 279, 1243-1251.

36. Kanekiyo, K., Lee, J.-B., Hayashi, K., Takenaka, H., Hayakawa, Y., Endo, S., and Hayashi, T. (2005) Isolation of an Antiviral Polysaccharide, Nostoflan, from a Terrestrial Cyanobacterium, Nostoc f lagelliforme, Journal of natural products 68, 1037-1041.

37. Karentz, S., Cleaver, J. E., and Mitchell, D. L. (1991) DNA damage in the Antarctic, Nature 350, 28.

38. Katoch, M., Mazmouz, R., Chau, R., Pearson, L. A., Pickford, R., and Neilan, B. A. (2016) Heterologous Production of Cyanobacterial Mycosporine-Like Amino Acids Mycosporine-Ornithine and Mycosporine-Lysine in *Escherichia coli*, Applied and environmental microbiology 82, 6167-6173.

39. Kim, E. J., Lee, J. H., Choi, H., Pereira, A. R., Ban, Y. H., Yoo, Y. J., Kim, E., Park, J. W., Sherman, D. H., and Gerwick, W. H. (2012) Heterologous production of 4-O-demethylbarbamide, a marine cyanobacterial natural product, Organic letters 14, 5824-5827.

40. Koehn, F. E., and Carter, G. T. (2005) The evolving role of natural products in drug discovery, Nature reviews Drug discovery 4, 206-220.

41. Kumar, S., Stecher, G., and Tamura, K. (2016) MEGA7: Molecular Evolutionary Genetics Analysis version 7.0 for bigger datasets, Molecular biology and evolution, msw054.

42. Lai, M. C., and Lan, E. I. (2015) Advances in metabolic engineering of cyanobacteria for photosynthetic biochemical production, Metabolites 5, 636-658.

43. Lambalot, R. H., and Walsh, C. T. (1997) [27] Holo-[acyl-carrier-protein] synthase of *Escherichia coli*, Methods in enzymology 279, 254-262.

44. Lambalot, R. H., Gehring, A. M., Flugel, R. S., Zuber, P., LaCelle, M., Marahiel, M. A., Reid, R., Khosla, C., and Walsh, C. T. (1996) A new enzyme superfamily—the phosphopantetheinyl transferases, Chemistry & Biology 3, 923-936.

45. Lawrence, K. P., Long, P. F., and Young, A. R. (2017) Mycosporine-like Amino Acids for Skin Photoprotection, Current medicinal chemistry.

46. Leao, T., Castelão, G., Korobeynikov, A., Monroe, E. A., Podell, S., Glukhov, E., Allen, E. E., Gerwick, W. H., and Gerwick, L. (2017) Comparative genomics uncovers the prolific and distinctive metabolic potential of the cyanobacterial genus Moorea, Proceedings of the National Academy of Sciences 114, 3198-3203.

47. Li, B., Sher, D., Kelly, L., Shi, Y., Huang, K., Knerr, P. J., Joewono, I., Rusch, D., Chisholm, S. W., and Van Der Donk, W. A. (2010) Catalytic promiscuity in the biosynthesis of cyclic peptide secondary metabolites in planktonic marine cyanobacteria, Proceedings of the National Academy of Sciences 107, 10430-10435.

48. Lindberg, P., Park, S., and Melis, A. (2010) Engineering a platform for photosynthetic isoprene production in cyanobacteria, using *Synechocystis* as the model organism, Metabolic engineering 12, 70-79.

49. Liu, T., Mazmouz, R., Ongley, S. E., Chau, R., Pickford, R., Woodhouse, J. N., and Neilan, B. A. (2017) Directing the Heterologous Production of Specific Cyanobacterial Toxin Variants, 12, 2021-2029.

50. Llewellyn, C. A., and Airs, R. L. (2010) Distribution and abundance of MAAs in 33 species of microalgae across 13 classes, Mar Drugs 8, 1273-1291.

51. Luesch, H., Harrigan, G., Goetz, G., and Horgen, F. (2002) The cyanobacterial origin of potent anticancer agents originally isolated from sea hares, Current medicinal chemistry 9, 1791-1806.

52. Lüning, K., Titlyanov, E., and Titlyanova, T. (1997) Diurnal and circadian periodicity of mitosis and growth in marine macroalgae. III. The red alga *Porphyra umbilicalis*, European Journal of Phycology 32, 167-173.

53. Luo, Y., Enghiad, B., and Zhao, H. (2016) New tools for reconstruction and heterologous expression of natural product biosynthetic gene clusters, Natural product reports 33, 174-182.

54. Markley, A. L., Begemann, M. B., Clarke, R. E., Gordon, G. C., and Pfleger, B. F. (2014) Synthetic biology toolbox for controlling gene expression in the cyanobacterium *Synechococcus* sp. strain PCC 7002, ACS synthetic biology 4, 595-603.

55. Martins, A., Vieira, H., Gaspar, H., and Santos, S. (2014) Marketed marine natural products in the pharmaceutical and cosmeceutical industries: Tips for success, Marine drugs 12, 1066-1101.

56. Méjean, A., Mann, S., Vassiliadis, G. l., Lombard, B. r. r., Loew, D., and Ploux, O. (2009) In vitro reconstitution of the first steps of anatoxin-a biosynthesis in Oscillatoria PCC 6506: from free L-proline to acyl carrier protein bound dehydroproline, Biochemistry 49, 103-113.

57. Micallef, M. L., D'Agostino, P. M., Sharma, D., Viswanathan, R., and Moffitt, M. C. (2015) Genome mining for natural product biosynthetic gene clusters in the Subsection V cyanobacteria, BMC genomics 16, 669.

58. Miranda, L. N., Hutchison, K., Grossman, A. R., and Brawley, S. H. (2013) Diversity and abundance of the bacterial community of the red macroalga *Porphyra umbilicalis*: did bacterial farmers produce macroalgae?, PLoS One 8, e58269.

59. Miyamoto, K. T., Komatsu, M., and Ikeda, H. (2014) Discovery of gene cluster for mycosporine-like amino acid biosynthesis from Actinomycetales microorganisms and production of a novel mycosporine-like amino acid by heterologous expression, Applied and environmental microbiology 80, 5028-5036.

60. Mo, S., Krunic, A., Chlipala, G., and Orjala, J. (2009) Antimicrobial ambiguine isonitriles from the cyanobacterium *Fischerella ambigua*, Journal of natural products 72, 894.

61. Mootz, H. D., Finking, R., and Marahiel, M. A. (2001) 4'-Phosphopantetheine transfer in primary and secondary metabolism of *Bacillus subtilis*, Journal of Biological Chemistry 276, 37289-37298.

62. Mushir, S., and Fatma, T. (2011) Ultraviolet radiation-absorbing mycosporine-like amino acids in Cyanobacterium *Aulosira fertilissima*: environmental perspective and characterization, Curr Res J Biol Sci 3, 165-171.

63. Ongley, S. E., Bian, X., Neilan, B. A., and Muller, R. (2013) Recent advances in the heterologous expression of microbial natural product biosynthetic pathways, Natural product reports 30, 1121-1138.

64. Ongley, S. E., Bian, X., Zhang, Y., Chau, R., Gerwick, W. H., Muller, R., and Neilan, B. A. (2013) High-titer heterologous production in *E. coli* of lyngbyatoxin, a protein kinase C activator from an uncultured marine cyanobacterium, ACS chemical biology 8, 1888-1893.

65. Oren, A., and Gunde-Cimerman, N. (2007) Mycosporines and mycosporine-like amino acids: UV protectants or multipurpose secondary metabolites?, FEMS Microbiology Letters 269, 1-10.

66. Pfeifer, B. A., Admiraal, S. J., Gramajo, H., Cane, D. E., and Khosla, C. (2001) Biosynthesis of complex polyketides in a metabolically engineered strain of *E. coli*, Science 291, 1790-1792.

67. Quadri, L. E. N., Weinreb, P. H., Lei, M., Nakano, M. M., Zuber, P., and Walsh, C. T. (1998) Characterization of Sfp, a *Bacillus subtilis* Phosphopantetheinyl Transferase for Peptidyl Carrier Protein Domains in Peptide Synthetases, Biochemistry 37, 1585-1595.

68. Rastogi, R. P., Sinha, R. P., Singh, S. P., and Häder, D.-P. (2010) Photoprotective compounds from marine organisms, Journal of industrial microbiology & biotechnology 37, 537-558.

69. Rippka, R., Deruelles, J., Waterbury, J. B., Herdman, M., and Stanier, R. Y. (1979) Generic assignments, strain histories and properties of pure cultures of cyanobacteria, Microbiology 111, 1-61.

70. Roberts, A. A., Copp, J. N., Marahiel, M. A., and Neilan, B. A. (2009) The *Synechocystis* sp. PCC6803 Sfp-Type Phosphopantetheinyl Transferase Does Not Possess Characteristic Broad-Range Activity, ChemBioChem 10, 1869-1877.

71. Sanchez-Quiles, D., and Tovar-Sanchez, A. (2014) Sunscreens as a source of hydrogen peroxide production in coastal waters, Environmental science & technology 48, 9037-9042.

72. Schmidt, E. W., Nelson, J. T., Rasko, D. A., Sudek, S., Eisen, J. A., Haygood, M. G., and Ravel, J. (2005) Patellamide A and C biosynthesis by a microcin-like pathway in *Prochloron didemni*, the cyanobacterial symbiont of Lissoclinum patella, Proc Natl Acad Sci USA 102, 7315-7320.

73. Schneider, G. J., Tumer, N. E., Richaud, C., Borbely, G., and Haselkorn, R. (1987) Purification and characterization of RNA polymerase from the cyanobacterium *Anabaena* 7120, The Journal of biological chemistry 262, 14633-14639.

74. Shi, Y., Yang, X., Garg, N., and van der Donk, W. A. (2011) Production of lantipeptides in *Escherichia coli*, J Am Chem Soc 133, 2338-2341.

75. Shih, P. M., Wu, D., Latifi, A., Axen, S. D., Fewer, D. P., Talla, E., Calteau, A., Cai, F., Tandeau de Marsac, N., Rippka, R., Herdman, M., Sivonen, K., Coursin, T., Laurent, T., Goodwin, L., Nolan, M., Davenport, K. W., Han, C. S., Rubin, E. M., Eisen, J. A., Woyke, T., Gugger, M., and Kerfeld, C. A. (2013) Improving the coverage of the cyanobacterial phylum using diversity-driven genome sequencing, Proc Natl Acad Sci USA 110, 1053-1058.

76. Shinzato, C., Shoguchi, E., Kawashima, T., Hamada, M., Hisata, K., Tanaka, M., Fujie, M., Fujiwara, M., Koyanagi, R., Ikuta, T., Fujiyama, A., Miller, D. J., and Satoh, N. (2011) Using the *Acropora digitifera* genome to understand coral responses to environmental change, Nature 476, 320-323.

77. Singh, R. K., Tiwari, S. P., Rai, A. K., and Mohapatra, T. M. (2011) Cyanobacteria: an emerging source for drug discovery, The Journal of antibiotics 64, 401-412.

78. Singh, S. P., Klisch, M., Hader, D.-P., and Sinha, R. P. (2008) Role of various growth media on shinorine (mycosporine-like amino acid) concentration and photosynthetic yield in *Anabaena variabilis* PCC 7937, World Journal of Microbiology and Biotechnology 24, 3111.

79. Singh, S. P., Klisch, M., Sinha, R. P., and Hader, D.-P. (2010) Genome mining of mycosporine-like amino acid (MAA) synthesizing and non-synthesizing cyanobacteria: a bioinformatics study, Genomics 95, 120-128.

80. Tan, L. T. (2007) Bioactive natural products from marine cyanobacteria for drug discovery, Phytochemistry 68, 954-979.

81. Tang, Y., Frewert, S., Harmrolfs, K., Herrmann, J., Karmann, L., Kazmaier, U., Xia, L., Zhang, Y., and Muller, R. (2015) Heterologous expression of an orphan NRPS gene cluster from *Paenibacillus larvae* in *Escherichia coli* revealed production of sevadicin, Journal of biotechnology 194, 112-114.

82. Tianero, M. D. B., Donia, M. S., Young, T. S., Schultz, P. G., and Schmidt, E. W. (2011) Ribosomal route to small-molecule diversity, Journal of the American Chemical Society 134, 418-425.

83. Varman, A. M., Xiao, Y., Pakrasi, H. B., and Tang, Y. J. (2013) Metabolic engineering of *Synechocystis* sp. strain PCC 6803 for isobutanol production, Applied and environmental microbiology 79, 908-914.

84. Veetil, V. P., Angermayr, S. A., and Hellingwerf, K. J. (2017) Ethylene production with engineered *Synechocystis* sp PCC 6803 strains, Microbial cell factories 16, 34.

85. Videau, P., Wells, K. N., Singh, A. J., Gerwick, W. H., and Philmus, B. (2016) Assessment of *Anabaena* sp. strain PCC 7120 as a heterologous expression host for cyanobacterial natural products: production of lyngbyatoxin a, ACS synthetic biology 5, 978-988.

86. Walsh, T. A., Bevan, S. A., Gachotte, D. J., Larsen, C. M., Moskal, W. A., Merlo, P. A., Sidorenko, L. V., Hampton, R. E., Stoltz, V., Pareddy, D., Anthony, G. I., Bhaskar, P. B., Marri, P. R., Clark, L. M., Chen, W., Adu-Peasah, P. S., Wensing, S. T., Zirkle, R., and Metz, J.

G. (2016) Canola engineered with a microalgal polyketide synthase-like system produces oil enriched in docosahexaenoic acid, Nat Biotechnol 34, 881-887.
87. Wang, W., Liu, X., and Lu, X. (2013) Engineering cyanobacteria to improve photosynthetic production of alka (e) nes, Biotechnology for biofuels 6, 1.
88. Wang, Y., Sun, T., Gao, X., Shi, M., Wu, L., Chen, L., and Zhang, W. (2016) Biosynthesis of platform chemical 3-hydroxypropionic acid (3-HP) directly from CO 2 in cyanobacterium *Synechocystis* sp. PCC 6803, Metabolic engineering 34, 60-70.
89. Weber, T., Blin, K., Duddela, S., Krug, D., Kim, H. U., Bruccoleri, R., Lee, S. Y., Fischbach, M. A., Müller, R., and Wohlleben, W. (2015) antiSMASH 3.0—a comprehensive resource for the genome mining of biosynthetic gene clusters, Nucleic acids research 43, W237-W243.
90. Whitehead, K., and Hedges, J. I. (2003) Electrospray ionization tandem mass spectrometric and electron impact mass spectrometric characterization of mycosporine-like amino acids, Rapid Commun Mass Spectrom 17, 2133-2138.
91. Xue, Y., Zhang, Y., Cheng, D., Daddy, S., and He, Q. (2014) Genetically engineering *Synechocystis* sp. Pasteur Culture Collection 6803 for the sustainable production of the plant secondary metabolite p-coumaric acid, Proceedings of the National Academy of Sciences 111, 9449-9454.
92. Yan, C., and Xu, X. (2008) Bifunctional enzyme FBPase/SBPase is essential for photoautotrophic growth in cyanobacterium *Synechocystis* sp. PCC 6803, Progress in Natural Science 18, 149-153.
93. Yang, G., Zhang, Y., Lee, N. K., Cozad, M. A., Kearney, S. E., Luesch, H., and Ding, Y. (2017) Cyanobacterial Sfp-type phosphopantetheinyl transferases functionalize carrier proteins of diverse biosynthetic pathways, Sci Rep 7, 11888.
94. Young, A. R., Claveau, J., and Rossi, A. B. (2017) Ultraviolet radiation and the skin: Photobiology and sunscreen photoprotection, Journal of the American Academy of Dermatology 76, S100-s109.
95. Yu, Y., You, L., Liu, D., Hollinshead, W., Tang, Y., and Zhang, F. (2013) Development of *Synechocystis* sp. PCC 6803 as a Phototrophic Cell Factory, Marine Drugs 11, 2894.
96. Zhang, H., Boghigian, B. A., Armando, J., and Pfeifer, B. A. (2011) Methods and options for the heterologous production of complex natural products, Natural product reports 28, 125-151.
97. Zhang, L., Li, L., and Wu, Q. (2007) Protective effects of mycosporine-like amino acids of *Synechocystis* sp. PCC 6803 and their partial characterization, Journal of photochemistry and photobiology. B, Biology 86, 240-245.
98. Zhou, J., Zhang, H., Meng, H., Zhu, Y., Bao, G., Zhang, Y., Li, Y., and Ma, Y. (2014) Discovery of a super-strong promoter enables efficient production of heterologous proteins in cyanobacteria, Scientific reports 4.
99. Ziemert, N., Ishida, K., Liaimer, A., Hertweck, C., and Dittmann, E. (2008) Ribosomal synthesis of tricyclic depsipeptides in bloom-forming cyanobacteria, Angew Chem Int Ed Engl 47, 7756-7759. Murray, M. G., and Thompson, W. F. (1980) Rapid isolation of high molecular weight plant DNA, Nucleic Acids Res 8, 4321-4326.
100. Fiore, M. F., Moon, D. H., Tsai, S. M., Lee, H., and Trevors, J. T. (2000) Miniprep DNA isolation from unicellular and filamentous cyanobacteria, J Microbiol Methods 39, 159-169.
101. Roberts, A. A., Copp, J. N., Marahiel, M. A., and Neilan, B. A. (2009) The *Synechocystis* sp. PCC6803 Sfptype phosphopantetheinyl transferase does not possess characteristic broad-range activity, ChemBioChem 10, 1869-1877.
102. Micallef, M. L., D'Agostino, P. M., Sharma, D., Viswanathan, R., and Moffitt, M. C. (2015) Genome mining for natural product biosynthetic gene clusters in the subsection V cyanobacteria, BMC Genomics 16, 669.

We claim:

1. A recombinant cyanobacterial cell comprising (i) at least one nucleic acid construct encoding a heterologous phosphopantetheinyl transferase (PPTase) and (ii) at least one genetic modification that alters the expression of an endogenous PPTase.

2. The recombinant cyanobacterial cell according to claim 1, said recombinant cyanobacterial cell further comprising at least one nucleic acid construct encoding an exogenous carrier protein (CP).

3. The recombinant cyanobacterial cell according to claim 1, said recombinant cyanobacterial cell further comprising at least one genetic modification that alters expression of an endogenous CP.

4. The recombinant cyanobacterial cell according to claim 1, wherein the genetic modification that alters the expression of the endogenous PPTase comprises the integration and operable linkage of a heterologous constitutive or inducible promoter to the endogenous PPTase and the nucleic acid constructs encoding the heterologous PPTase comprise a constitutive or inducible promoter operably linked to a nucleotide sequence encoding said heterologous PPTase.

5. The recombinant cyanobacterial cell according to claim 1, said recombinant cyanobacterial cell further comprising a nucleic acid construct encoding a compound of interest.

6. The recombinant cyanobacterial cell according to claim 1, wherein said heterologous PPTase is selected from SEQ ID NO: 1, 2, 3, 4, 5, 6 or 7 and said heterologous CP is selected from SEQ ID NO: 9, 11, 13, 15, 17, 19, 21, 23, 25, 27 or 29.

7. The recombinant cyanobacterial cell according to claim 1, wherein the genetic modification comprises a heterologous nucleic acid sequence encoding a knockdown component that reduces or eliminates the expression of an endogenous PPTase and/or an endogenous CP.

8. The recombinant cyanobacterial cell according to claim 1, wherein the genetic modification comprises at least partial disruption or complete removal of an endogenous PPTase and/or an endogenous CP.

9. The recombinant cyanobacterial cell according to claim 1, wherein the nucleic acid construct is integrated into the chromosome of the cyanobacterial cell or is present in a self-replicating plasmids or modules.

10. A method for producing a chemical compound of interest with the recombinant cyanobacterial cell of claim 1, comprising a) culturing the recombinant cyanobacterial cell of claim 1 under conditions permitting the production of said chemical compound of interest, and b) isolating or recovering said compound of interest.

11. The method of claim 10, wherein the chemical compound of interest is an analog of cyanobacterial secondary metabolites, polyketides, non-ribosomal peptides or hybrids of non-ribosomal peptides.

12. The recombinant cyanobacterial cell according to claim 1, said recombinant cyanobacterial cells further comprising at least one nucleic acid construct encoding a heterologous shinorine gene cluster.

13. The recombinant cyanobacterial cell of claim 12, wherein the cell belongs to the genus *Synechocystis* and the heterologous shinorine gene cluster is obtained from a *Fischerella* sp.

14. The recombinant cyanobacterial cell of claim 12, wherein the cell belongs to the genus *Synechocystis* and the cell comprises:

i) the heterologous shinorine gene cluster obtained from a *Fischerella* sp. under the control of the promoter Pcpc560, and ii) the nucleic acid encoding the heterologous PPTase obtained from the *Anabaena* sp.

* * * * *

SEQUENCE LISTING

```
<160> NUMBER OF SEQ ID NOS: 179

<210> SEQ ID NO 1
<211> LENGTH: 237
<212> TYPE: PRT
<213> ORGANISM: Unknown
<220> FEATURE:
<223> OTHER INFORMATION: Nostoc sp. PCC7120

<400> SEQUENCE: 1

Met Leu Gln His Thr Trp Leu Pro Lys Pro Pro Asn Leu Thr Leu Leu
1               5                   10                  15

Ser Asp Glu Val His Leu Trp Arg Ile Pro Leu Asp Gln Pro Glu Ser
            20                  25                  30

Gln Leu Gln Asp Leu Ala Ala Thr Leu Ser Ser Asp Glu Leu Ala Arg
        35                  40                  45

Ala Asn Arg Phe Tyr Phe Pro Glu His Arg Arg Arg Phe Thr Ala Gly
    50                  55                  60

Arg Gly Ile Leu Arg Ser Ile Leu Gly Gly Tyr Leu Gly Val Glu Pro
65                  70                  75                  80

Gly Gln Val Lys Phe Asp Tyr Glu Ser Arg Gly Lys Pro Ile Leu Gly
                85                  90                  95

Asp Arg Phe Ala Glu Ser Gly Leu Leu Phe Asn Leu Ser His Ser Gln
```

```
            100                 105                 110

Asn Leu Ala Leu Cys Ala Val Asn Tyr Thr Arg Gln Ile Gly Ile Asp
        115                 120                 125

Leu Glu Tyr Leu Arg Pro Thr Ser Asp Leu Glu Ser Leu Ala Lys Arg
    130                 135                 140

Phe Phe Leu Pro Arg Glu Tyr Glu Leu Leu Arg Ser Leu Pro Asp Glu
145                 150                 155                 160

Gln Lys Gln Lys Ile Phe Phe Arg Tyr Trp Thr Cys Lys Glu Ala Tyr
                165                 170                 175

Leu Lys Ala Thr Gly Asp Gly Ile Ala Lys Leu Glu Glu Ile Glu Ile
            180                 185                 190

Ala Leu Thr Pro Thr Glu Pro Ala Lys Leu Gln Thr Ala Pro Ala Trp
        195                 200                 205

Ser Leu Leu Glu Leu Val Pro Asp Asp Asn Cys Val Ala Ala Val Ala
    210                 215                 220

Val Ala Gly Phe Gly Trp Gln Pro Lys Phe Trp His Tyr
225                 230                 235


<210> SEQ ID NO 2
<211> LENGTH: 237
<212> TYPE: PRT
<213> ORGANISM: Anabaena variabilis

<400> SEQUENCE: 2

Met Leu Gln His Thr Trp Leu Pro Lys Pro Pro Asn Leu Thr Leu Leu
1               5                   10                  15

Ser Asp Glu Val His Leu Trp Arg Ile Pro Leu Asp Arg Pro Glu Ser
            20                  25                  30

Gln Leu Gln His Leu Ala Ala Thr Leu Ser Ser Asp Glu Leu Ala Arg
        35                  40                  45

Ala Asn Arg Phe Tyr Phe Pro Glu His Arg Gln Arg Phe Thr Ala Gly
    50                  55                  60

Arg Gly Ile Leu Arg Ser Ile Leu Gly Leu Tyr Leu Gly Val Glu Pro
65                  70                  75                  80

Lys Gln Val Lys Phe Glu Tyr Glu Ser Arg Gly Lys Pro Val Leu Gly
                85                  90                  95

Asp Arg Phe Ala Asp Ser Gly Leu Leu Phe Asn Leu Ser His Ser Gln
            100                 105                 110

Asn Leu Gly Leu Cys Ala Val Asn Tyr Thr Arg Gln Ile Gly Ile Asp
        115                 120                 125

Leu Glu Tyr Leu Arg Pro Thr Ser Asp Leu Glu Ser Leu Ala Lys Arg
    130                 135                 140

Phe Phe Leu Pro Arg Glu Tyr Glu Leu Leu Arg Ser Leu Pro Asp Glu
145                 150                 155                 160

Gln Lys Gln Lys Ile Phe Phe Arg Tyr Trp Thr Cys Lys Glu Ala Tyr
                165                 170                 175

Leu Lys Ala Thr Gly Asp Gly Ile Ala Lys Leu Glu Glu Ile Glu Ile
            180                 185                 190

Ala Leu Thr Pro Thr Glu Pro Ala Lys Leu Gln Thr Thr Pro Ala Trp
        195                 200                 205

Ser Leu Leu Glu Leu Val Pro Asp Asp Asn Cys Val Ala Ala Val Ala
    210                 215                 220

Val Ala Gly Phe Gly Trp Gln Pro Lys Phe Trp Gln Tyr
225                 230                 235
```

<210> SEQ ID NO 3
<211> LENGTH: 220
<212> TYPE: PRT
<213> ORGANISM: Microcystis aeruginosa

<400> SEQUENCE: 3

```
Met Phe Ile Ser Thr Asp Glu Val His Leu Tyr Phe Ile Ser Leu Asp
1               5                   10                  15

Pro Ser Gly Asp Arg Leu Glu Thr Leu Ala Ser Leu Leu Ser Glu Asp
            20                  25                  30

Glu Ile Ile Arg Ala Asn Arg Tyr His Phe Pro Glu His Lys Arg Arg
        35                  40                  45

Phe Leu Val Ala Arg Gly Cys Leu Arg Glu Ile Leu Gly Ser Tyr Leu
    50                  55                  60

Ala Ile Ser Pro Glu Lys Ile Glu Phe Ile Tyr Ser Glu Arg Gly Lys
65                  70                  75                  80

Pro Ser Ile Asn Tyr Gln Leu Gln Phe Asn Leu Ser His Ser Glu Glu
                85                  90                  95

Met Ala Ile Cys Gly Leu Thr Leu Thr Ala Arg Ile Gly Val Asp Leu
            100                 105                 110

Glu Lys Met Arg Gln Met Lys Asp Leu Asp Ser Leu Thr Lys Arg Phe
        115                 120                 125

Phe Cys Ala Arg Glu His Glu Leu Val Glu Lys Ser Ala Glu Lys Glu
    130                 135                 140

Lys Leu Phe Phe Gln Leu Trp Thr Ala Lys Glu Ala Tyr Leu Lys Ala
145                 150                 155                 160

Val Gly Thr Gly Ile Ser Gly Gly Leu Asp Arg Val Glu Val Gly Leu
                165                 170                 175

Asn Pro Leu Lys Leu Asp Asn Val Ala Gly Glu Trp Gln Leu Trp Thr
            180                 185                 190

Ala Ala Ile Gly Asp Asn Tyr Arg Ala Thr Val Val Ile Glu Gly Ser
        195                 200                 205

Asp Arg Val Ile Lys Thr Phe Gly Leu Ser Asp Leu
    210                 215                 220
```

<210> SEQ ID NO 4
<211> LENGTH: 240
<212> TYPE: PRT
<213> ORGANISM: Unknown
<220> FEATURE:
<223> OTHER INFORMATION: Fischerella

<400> SEQUENCE: 4

```
Met Gly Ser Glu Thr Asn His Leu Trp Leu Thr Ala Pro Thr Asn Leu
1               5                   10                  15

Thr Leu Leu Pro Asp Asp Val His Val Trp Arg Ile Ser Leu Asp Arg
            20                  25                  30

Pro Glu Ser Glu Leu Gln Ala Leu Gln Thr Thr Leu Ser Ser Asp Glu
        35                  40                  45

Ile Ala Arg Ala Gln Arg Phe Tyr Phe Glu Gln His Arg Gln Arg Phe
    50                  55                  60

Val Ala Gly Arg Gly Ile Leu Arg Thr Ile Leu Gly Arg Tyr Leu Gly
65                  70                  75                  80

Val Glu Pro Gln Ala Val Glu Phe Thr Tyr Glu Leu Arg Gly Lys Pro
                85                  90                  95

Leu Leu Ala Asp Arg Phe Ala Asp Ser Gly Val Ser Phe Asn Leu Ser
```

```
            100                 105                 110

His Ser Gln Asp Leu Ala Leu Cys Gly Val Ser Arg Asn Arg Lys Ile
        115                 120                 125

Gly Ile Asp Val Glu Tyr Met Arg Ser Val Ser Asp Val Glu Ala Leu
    130                 135                 140

Ala Glu Arg Phe Phe Ala Pro Arg Glu Tyr Glu Val Val Arg Ser Leu
145                 150                 155                 160

Pro Ser Asn Gln Gln Gln Gln Val Phe Phe Arg Tyr Trp Thr Cys Lys
                165                 170                 175

Glu Ala Tyr Leu Lys Ala Ile Gly Val Gly Ile Val Gln Leu Glu Lys
            180                 185                 190

Val Glu Ile Ser Leu Thr Leu Glu Gln Pro Ala Lys Leu Ile Thr Asp
        195                 200                 205

Glu Glu Trp Ser Leu Ile Glu Leu Val Pro Gly Asp His Tyr Leu Gly
    210                 215                 220

Ala Val Ala Ile Ala Gly Gln Asn Leu Asp Leu Lys Tyr Trp Gln Tyr
225                 230                 235                 240


<210> SEQ ID NO 5
<211> LENGTH: 259
<212> TYPE: PRT
<213> ORGANISM: Synechococcus elongatus

<400> SEQUENCE: 5

Met Gln Arg Pro Asn Pro Ser Asp Ala Val Pro Val Pro Ser Ile Pro
1               5                   10                  15

Ser Cys Asp Arg Gly Pro Ile Pro Asn Pro Val Thr Trp Arg Thr Ser
            20                  25                  30

Pro Glu Pro Leu Phe Leu Ser Ala Gln Thr Val His Leu Trp Arg Cys
        35                  40                  45

Ser Leu Thr Arg Ser Leu Ser Ser Ala Glu Gln Ala Ile Val Ala Ala
    50                  55                  60

Asp Cys Asp Arg Ala Gln Ala Tyr Gly Ser Asn Arg Arg His Gln Phe
65                  70                  75                  80

Leu Cys Gly Arg Trp Trp Leu Arg Gln Leu Leu Ser Leu Tyr Leu Pro
                85                  90                  95

Glu Glu Pro Ala Asp Phe Arg Phe Gln Leu Ser Pro Thr Gly Lys Pro
            100                 105                 110

Glu Leu Pro Gln Ser Asn Leu Cys Phe Asn Leu Ser His Ser Gly Ser
        115                 120                 125

Thr Leu Leu Ile Ala Ile Ala Trp Gln Pro Val Gly Val Asp Val Glu
    130                 135                 140

Gln Pro Arg Ser Arg Ser Trp Leu Ala Leu Ala Arg Arg Tyr Phe Pro
145                 150                 155                 160

Ser Ala Glu Leu Ala Ala Met Gln Gln Ser Thr Asp Cys Asp Arg Trp
                165                 170                 175

Gly Leu Ala Ser Trp Val Cys Lys Glu Ala Trp Ile Lys Ala Gln Gly
            180                 185                 190

Arg Thr Leu Ala Asn Ser Leu Arg His Leu Gln Cys Ala Trp Thr Ala
        195                 200                 205

Asn Gly Gln Pro Arg Leu Ser Gly Leu Gly Ser Glu Glu Ser Gln Val
    210                 215                 220

Gln Leu Leu Gln Val Asp Pro Gln Glu Gln Leu Trp Ala Ala Ile Ala
225                 230                 235                 240
```

```
Met Pro Ala Gly Trp Asn Tyr Gln Thr Trp Thr Ala Ala Ile Ile Arg
                245                 250                 255

Lys Asn His


<210> SEQ ID NO 6
<211> LENGTH: 246
<212> TYPE: PRT
<213> ORGANISM: Unknown
<220> FEATURE:
<223> OTHER INFORMATION: Synechocystis

<400> SEQUENCE: 6

Met Leu Pro Gln Pro Gln Ile Trp Leu Cys Pro Thr Asp Arg Pro Leu
1               5                   10                  15

Ile Pro Gly Tyr Gln Ala Leu Leu Ser Ser Glu Glu Met Ala Arg Gly
            20                  25                  30

Glu Arg Tyr Gln Arg Pro Gln Asp Lys Gln Arg Phe Leu Thr Met Arg
        35                  40                  45

Leu Ala Leu Arg Ile Leu Leu Ala Arg Gln Leu Asp Cys Leu Pro Gln
    50                  55                  60

Gln Leu Gln Phe Thr Tyr Gly Pro Gln Gly Lys Pro Glu Leu Val Asp
65                  70                  75                  80

Arg Glu Arg Arg Ser Pro Trp Phe Asn Val Ala His Ser Gly Asn Tyr
                85                  90                  95

Gly Leu Ile Gly Leu Ser Thr Glu Gly Glu Ile Gly Val Asp Leu Gln
            100                 105                 110

Ile Met Leu Pro Lys Pro His Tyr Leu Lys Leu Ala Lys Arg Phe Phe
        115                 120                 125

Ala Pro Gln Glu Val Gln Gln Leu Glu Ser Leu Glu Gly Glu Lys Arg
    130                 135                 140

Thr Lys Leu Phe Tyr Gln Leu Trp Thr Ala Lys Glu Ala Phe Leu Lys
145                 150                 155                 160

Ala Thr Gly Lys Gly Ile Ser Gly Gly Leu Asn Gln Val Ile Pro Asp
                165                 170                 175

Glu Asn Leu Ala Lys Tyr Gln Tyr Leu Pro Asp Ser Gly Asp Thr Asn
            180                 185                 190

His Trp Arg Leu Ser Ser Gln Pro Leu Leu Ala Asp Gln Gly Ser Asn
        195                 200                 205

Asp Asn Tyr Trp Met Ala Ile Ala Trp Cys Thr Asn Glu Val Asn Gln
    210                 215                 220

Val Glu Ser Asn Tyr Leu Pro Asn Ile Gln Pro Phe Gln Trp Pro Arg
225                 230                 235                 240

Asn Leu Asp Ser Leu Pro
                245


<210> SEQ ID NO 7
<211> LENGTH: 224
<212> TYPE: PRT
<213> ORGANISM: Bacillus subtilis

<400> SEQUENCE: 7

Met Lys Ile Tyr Gly Ile Tyr Met Asp Arg Pro Leu Ser Gln Glu Glu
1               5                   10                  15

Asn Glu Arg Phe Met Thr Phe Ile Ser Pro Glu Lys Arg Glu Lys Cys
            20                  25                  30

Arg Arg Phe Tyr His Lys Glu Asp Ala His Arg Thr Leu Leu Gly Asp
        35                  40                  45
```

```
Val Leu Val Arg Ser Val Ile Ser Arg Gln Tyr Gln Leu Asp Lys Ser
    50                  55                  60

Asp Ile Arg Phe Ser Thr Gln Glu Tyr Gly Lys Pro Cys Ile Pro Asp
65                  70                  75                  80

Leu Pro Asp Ala His Phe Asn Ile Ser His Ser Gly Arg Trp Val Ile
                85                  90                  95

Gly Ala Phe Asp Ser Gln Pro Ile Gly Ile Asp Ile Glu Lys Thr Lys
            100                 105                 110

Pro Ile Ser Leu Glu Ile Ala Lys Arg Phe Phe Ser Lys Thr Glu Tyr
        115                 120                 125

Ser Asp Leu Leu Ala Lys Asp Lys Asp Glu Gln Thr Asp Tyr Phe Tyr
    130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175

Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
        195                 200                 205

Pro Asp Phe Pro Glu Asp Ile Thr Met Val Ser Tyr Glu Glu Leu Leu
    210                 215                 220


<210> SEQ ID NO 8
<211> LENGTH: 231
<212> TYPE: DNA
<213> ORGANISM: Unknown
<220> FEATURE:
<223> OTHER INFORMATION: Synechocystis
<220> FEATURE:
<221> NAME/KEY: CDS
<222> LOCATION: (1)..(231)

<400> SEQUENCE: 8

atg gat cag gaa att ttt gaa aaa gta aaa aaa atc gtc gtg gaa cag       48
Met Asp Gln Glu Ile Phe Glu Lys Val Lys Lys Ile Val Val Glu Gln
1               5                   10                  15

ttg gaa gtg gat cct gac aaa gtg acc ccc gat gcc acc ttt gcc gaa       96
Leu Glu Val Asp Pro Asp Lys Val Thr Pro Asp Ala Thr Phe Ala Glu
            20                  25                  30

gat tta ggg gct gat tcc ctc gat aca gtg gaa ttg gtc atg gcc ctg      144
Asp Leu Gly Ala Asp Ser Leu Asp Thr Val Glu Leu Val Met Ala Leu
        35                  40                  45

gaa gaa gag ttt gat att gaa att ccc gat gaa gtg gcg gaa acc att      192
Glu Glu Glu Phe Asp Ile Glu Ile Pro Asp Glu Val Ala Glu Thr Ile
    50                  55                  60

gat acc gtg ggc aaa gcc gtt gag cat atc gaa agt aaa                  231
Asp Thr Val Gly Lys Ala Val Glu His Ile Glu Ser Lys
65                  70                  75


<210> SEQ ID NO 9
<211> LENGTH: 77
<212> TYPE: PRT
<213> ORGANISM: Unknown
<220> FEATURE:
<223> OTHER INFORMATION: Synthetic Construct

<400> SEQUENCE: 9

Met Asp Gln Glu Ile Phe Glu Lys Val Lys Lys Ile Val Val Glu Gln
1               5                   10                  15
```

```
Leu Glu Val Asp Pro Asp Lys Val Thr Pro Asp Ala Thr Phe Ala Glu
            20                  25                  30

Asp Leu Gly Ala Asp Ser Leu Asp Thr Val Glu Leu Val Met Ala Leu
        35                  40                  45

Glu Glu Glu Phe Asp Ile Glu Ile Pro Asp Glu Val Ala Glu Thr Ile
    50                  55                  60

Asp Thr Val Gly Lys Ala Val Glu His Ile Glu Ser Lys
65                  70                  75


<210> SEQ ID NO 10
<211> LENGTH: 252
<212> TYPE: DNA
<213> ORGANISM: Unknown
<220> FEATURE:
<223> OTHER INFORMATION: Anabaena
<220> FEATURE:
<221> NAME/KEY: CDS
<222> LOCATION: (1)..(252)

<400> SEQUENCE: 10

atg ggc caa tca gaa act ttt gaa aaa gtc aaa aaa att gtt atc gaa       48
Met Gly Gln Ser Glu Thr Phe Glu Lys Val Lys Lys Ile Val Ile Glu
1               5                   10                  15

caa cta agt gtg gag aac cct gac aca gta act cca gaa gct agt ttt       96
Gln Leu Ser Val Glu Asn Pro Asp Thr Val Thr Pro Glu Ala Ser Phe
            20                  25                  30

gcc aac gat tta cag gct gat tcc ctc gat aca gta gaa cta gta atg      144
Ala Asn Asp Leu Gln Ala Asp Ser Leu Asp Thr Val Glu Leu Val Met
        35                  40                  45

gct ttg gaa gaa gaa ttt gat atc gaa att ccc gat gaa gcc gca gag      192
Ala Leu Glu Glu Glu Phe Asp Ile Glu Ile Pro Asp Glu Ala Ala Glu
    50                  55                  60

aaa att acc act gtt caa gaa gcg gtg gat tac atc aat aac caa gtt      240
Lys Ile Thr Thr Val Gln Glu Ala Val Asp Tyr Ile Asn Asn Gln Val
65                  70                  75                  80

gcc gca tca gct                                                      252
Ala Ala Ser Ala


<210> SEQ ID NO 11
<211> LENGTH: 84
<212> TYPE: PRT
<213> ORGANISM: Unknown
<220> FEATURE:
<223> OTHER INFORMATION: Synthetic Construct

<400> SEQUENCE: 11

Met Gly Gln Ser Glu Thr Phe Glu Lys Val Lys Lys Ile Val Ile Glu
1               5                   10                  15

Gln Leu Ser Val Glu Asn Pro Asp Thr Val Thr Pro Glu Ala Ser Phe
            20                  25                  30

Ala Asn Asp Leu Gln Ala Asp Ser Leu Asp Thr Val Glu Leu Val Met
        35                  40                  45

Ala Leu Glu Glu Glu Phe Asp Ile Glu Ile Pro Asp Glu Ala Ala Glu
    50                  55                  60

Lys Ile Thr Thr Val Gln Glu Ala Val Asp Tyr Ile Asn Asn Gln Val
65                  70                  75                  80

Ala Ala Ser Ala


<210> SEQ ID NO 12
<211> LENGTH: 264
```

<212> TYPE: DNA
<213> ORGANISM: Unknown
<220> FEATURE:
<223> OTHER INFORMATION: Anabaena
<220> FEATURE:
<221> NAME/KEY: CDS
<222> LOCATION: (1)..(264)

<400> SEQUENCE: 12

```
atg ggt cta aaa caa aat tat agt gca gca gat att caa gct tgg atg       48
Met Gly Leu Lys Gln Asn Tyr Ser Ala Ala Asp Ile Gln Ala Trp Met
1               5                   10                  15

ata tct aat cta gct gaa ttg ttg gga gta gat ggt gat gaa atc gat       96
Ile Ser Asn Leu Ala Glu Leu Leu Gly Val Asp Gly Asp Glu Ile Asp
            20                  25                  30

gct act gtc aat tta gaa agc tat ggt ttg gat tcg gca cag gca atg      144
Ala Thr Val Asn Leu Glu Ser Tyr Gly Leu Asp Ser Ala Gln Ala Met
        35                  40                  45

gta cta gtt agt aaa cta gag caa ttg ttg gga ttt caa cca tca cct      192
Val Leu Val Ser Lys Leu Glu Gln Leu Leu Gly Phe Gln Pro Ser Pro
    50                  55                  60

ttg ttg ttg tgg cat tac ccc act att gaa tcg ttg tct gaa cgt tta      240
Leu Leu Leu Trp His Tyr Pro Thr Ile Glu Ser Leu Ser Glu Arg Leu
65                  70                  75                  80

gct gaa gaa ttg gaa gaa caa tct                                      264
Ala Glu Glu Leu Glu Glu Gln Ser
                85
```

<210> SEQ ID NO 13
<211> LENGTH: 88
<212> TYPE: PRT
<213> ORGANISM: Unknown
<220> FEATURE:
<223> OTHER INFORMATION: Synthetic Construct

<400> SEQUENCE: 13

```
Met Gly Leu Lys Gln Asn Tyr Ser Ala Ala Asp Ile Gln Ala Trp Met
1               5                   10                  15

Ile Ser Asn Leu Ala Glu Leu Leu Gly Val Asp Gly Asp Glu Ile Asp
            20                  25                  30

Ala Thr Val Asn Leu Glu Ser Tyr Gly Leu Asp Ser Ala Gln Ala Met
        35                  40                  45

Val Leu Val Ser Lys Leu Glu Gln Leu Leu Gly Phe Gln Pro Ser Pro
    50                  55                  60

Leu Leu Leu Trp His Tyr Pro Thr Ile Glu Ser Leu Ser Glu Arg Leu
65                  70                  75                  80

Ala Glu Glu Leu Glu Glu Gln Ser
                85
```

<210> SEQ ID NO 14
<211> LENGTH: 300
<212> TYPE: DNA
<213> ORGANISM: Unknown
<220> FEATURE:
<223> OTHER INFORMATION: Anabaena
<220> FEATURE:
<221> NAME/KEY: CDS
<222> LOCATION: (1)..(300)

<400> SEQUENCE: 14

```
atg gaa caa tct aca act aat cac gcc cgc ccc caa att acc gct acc       48
Met Glu Gln Ser Thr Thr Asn His Ala Arg Pro Gln Ile Thr Ala Thr
1               5                   10                  15
```

```
tac ctt ccc ccc agc aat gaa att gaa gcc aga gtc acc caa gta atg       96
Tyr Leu Pro Pro Ser Asn Glu Ile Glu Ala Arg Val Thr Gln Val Met
            20                  25                  30

gag agt tta ttg gga atc gct cct att ggg gtt aat gat aac ttc ttt      144
Glu Ser Leu Leu Gly Ile Ala Pro Ile Gly Val Asn Asp Asn Phe Phe
        35                  40                  45

gag tta gga gga cat tcc ctg tta gca att caa gca gtt tca cag cta      192
Glu Leu Gly Gly His Ser Leu Leu Ala Ile Gln Ala Val Ser Gln Leu
    50                  55                  60

cgg gaa gaa ttt caa gta gaa tta ccc atg cga caa ttt tta ttt gag      240
Arg Glu Glu Phe Gln Val Glu Leu Pro Met Arg Gln Phe Leu Phe Glu
65                  70                  75                  80

tca ccc aca att ggg ggg ata gcc aaa att atc att gaa aat caa tcg      288
Ser Pro Thr Ile Gly Gly Ile Ala Lys Ile Ile Ile Glu Asn Gln Ser
                85                  90                  95

cct att act gat                                                      300
Pro Ile Thr Asp
            100


<210> SEQ ID NO 15
<211> LENGTH: 100
<212> TYPE: PRT
<213> ORGANISM: Unknown
<220> FEATURE:
<223> OTHER INFORMATION: Synthetic Construct

<400> SEQUENCE: 15

Met Glu Gln Ser Thr Thr Asn His Ala Arg Pro Gln Ile Thr Ala Thr
1               5                   10                  15

Tyr Leu Pro Pro Ser Asn Glu Ile Glu Ala Arg Val Thr Gln Val Met
            20                  25                  30

Glu Ser Leu Leu Gly Ile Ala Pro Ile Gly Val Asn Asp Asn Phe Phe
        35                  40                  45

Glu Leu Gly Gly His Ser Leu Leu Ala Ile Gln Ala Val Ser Gln Leu
    50                  55                  60

Arg Glu Glu Phe Gln Val Glu Leu Pro Met Arg Gln Phe Leu Phe Glu
65                  70                  75                  80

Ser Pro Thr Ile Gly Gly Ile Ala Lys Ile Ile Ile Glu Asn Gln Ser
                85                  90                  95

Pro Ile Thr Asp
            100


<210> SEQ ID NO 16
<211> LENGTH: 255
<212> TYPE: DNA
<213> ORGANISM: Unknown
<220> FEATURE:
<223> OTHER INFORMATION: Fischerella
<220> FEATURE:
<221> NAME/KEY: CDS
<222> LOCATION: (1)..(255)

<400> SEQUENCE: 16

atg gcc caa cgc cct atc att atc cct cgt aca aat act gaa cag cga       48
Met Ala Gln Arg Pro Ile Ile Ile Pro Arg Thr Asn Thr Glu Gln Arg
1               5                   10                  15

ata ggc gag att tgg aag aag gcg atg aag tgg gat tct gtc tcg ata       96
Ile Gly Glu Ile Trp Lys Lys Ala Met Lys Trp Asp Ser Val Ser Ile
            20                  25                  30

tgt gat gat ttc ttt gaa tct ggc gga aat tca ctt att gct gtg aga      144
Cys Asp Asp Phe Phe Glu Ser Gly Gly Asn Ser Leu Ile Ala Val Arg
        35                  40                  45
```

```
ata atc aac gct atc aac aaa gaa ttt cat tgt gcc ttg cct tta cat      192
Ile Ile Asn Ala Ile Asn Lys Glu Phe His Cys Ala Leu Pro Leu His
    50                  55                  60

gct ctt ttt gaa gct cca agc att gaa aag ctc gct cat aag gtt gat      240
Ala Leu Phe Glu Ala Pro Ser Ile Glu Lys Leu Ala His Lys Val Asp
65                  70                  75                  80

agt gat gaa gtt gaa                                                  255
Ser Asp Glu Val Glu
                85


<210> SEQ ID NO 17
<211> LENGTH: 85
<212> TYPE: PRT
<213> ORGANISM: Unknown
<220> FEATURE:
<223> OTHER INFORMATION: Synthetic Construct

<400> SEQUENCE: 17

Met Ala Gln Arg Pro Ile Ile Ile Pro Arg Thr Asn Thr Glu Gln Arg
1               5                   10                  15

Ile Gly Glu Ile Trp Lys Lys Ala Met Lys Trp Asp Ser Val Ser Ile
            20                  25                  30

Cys Asp Asp Phe Phe Glu Ser Gly Gly Asn Ser Leu Ile Ala Val Arg
        35                  40                  45

Ile Ile Asn Ala Ile Asn Lys Glu Phe His Cys Ala Leu Pro Leu His
    50                  55                  60

Ala Leu Phe Glu Ala Pro Ser Ile Glu Lys Leu Ala His Lys Val Asp
65                  70                  75                  80

Ser Asp Glu Val Glu
                85


<210> SEQ ID NO 18
<211> LENGTH: 372
<212> TYPE: DNA
<213> ORGANISM: Unknown
<220> FEATURE:
<223> OTHER INFORMATION: Fischerella
<220> FEATURE:
<221> NAME/KEY: CDS
<222> LOCATION: (1)..(372)

<400> SEQUENCE: 18

atg gct ttt cta gaa gat gtc cct cca aca gaa cgt cga gaa cac tta       48
Met Ala Phe Leu Glu Asp Val Pro Pro Thr Glu Arg Arg Glu His Leu
1               5                   10                  15

tta gaa tat ctt gga aaa gaa gta gca aaa atc tta gga ata aaa cat       96
Leu Glu Tyr Leu Gly Lys Glu Val Ala Lys Ile Leu Gly Ile Lys His
            20                  25                  30

ata ccc gac cca gaa caa gga ttt ata gaa atg gga att gac tct ttg      144
Ile Pro Asp Pro Glu Gln Gly Phe Ile Glu Met Gly Ile Asp Ser Leu
        35                  40                  45

ctt tcc att gaa ttc aaa aat cgt tta gaa aaa gga tta gaa att gct      192
Leu Ser Ile Glu Phe Lys Asn Arg Leu Glu Lys Gly Leu Glu Ile Ala
    50                  55                  60

tta cca tct act tta ata ttt gat ttt ccg aat att agc aaa tta aat      240
Leu Pro Ser Thr Leu Ile Phe Asp Phe Pro Asn Ile Ser Lys Leu Asn
65                  70                  75                  80

aat tat cta ttt gag caa att tat ggt tgg gaa gta aat act acc gtg      288
Asn Tyr Leu Phe Glu Gln Ile Tyr Gly Trp Glu Val Asn Thr Thr Val
                85                  90                  95

gag aca act gtt gat att gta gaa gtt aat gaa gat tta att ttg caa      336
```

```
Glu Thr Thr Val Asp Ile Val Glu Val Asn Glu Asp Leu Ile Leu Gln
            100                 105                 110

gaa ctg gca gat tta gaa gct ttt cta ggt aat tcc                    372
Glu Leu Ala Asp Leu Glu Ala Phe Leu Gly Asn Ser
        115                 120


<210> SEQ ID NO 19
<211> LENGTH: 124
<212> TYPE: PRT
<213> ORGANISM: Unknown
<220> FEATURE:
<223> OTHER INFORMATION: Synthetic Construct

<400> SEQUENCE: 19

Met Ala Phe Leu Glu Asp Val Pro Pro Thr Glu Arg Arg Glu His Leu
1               5                   10                  15

Leu Glu Tyr Leu Gly Lys Glu Val Ala Lys Ile Leu Gly Ile Lys His
            20                  25                  30

Ile Pro Asp Pro Glu Gln Gly Phe Ile Glu Met Gly Ile Asp Ser Leu
        35                  40                  45

Leu Ser Ile Glu Phe Lys Asn Arg Leu Glu Lys Gly Leu Glu Ile Ala
    50                  55                  60

Leu Pro Ser Thr Leu Ile Phe Asp Phe Pro Asn Ile Ser Lys Leu Asn
65                  70                  75                  80

Asn Tyr Leu Phe Glu Gln Ile Tyr Gly Trp Glu Val Asn Thr Thr Val
                85                  90                  95

Glu Thr Thr Val Asp Ile Val Glu Val Asn Glu Asp Leu Ile Leu Gln
            100                 105                 110

Glu Leu Ala Asp Leu Glu Ala Phe Leu Gly Asn Ser
        115                 120


<210> SEQ ID NO 20
<211> LENGTH: 303
<212> TYPE: DNA
<213> ORGANISM: Unknown
<220> FEATURE:
<223> OTHER INFORMATION: Fischerella
<220> FEATURE:
<221> NAME/KEY: CDS
<222> LOCATION: (1)..(303)

<400> SEQUENCE: 20

atg gga tcg ctt ccc aaa cct gat ttt tct aac tta atc act cat gaa      48
Met Gly Ser Leu Pro Lys Pro Asp Phe Ser Asn Leu Ile Thr His Glu
1               5                   10                  15

gat ttt acg cct gca cgc aat gat tta gag aga aaa atc gcg cag att      96
Asp Phe Thr Pro Ala Arg Asn Asp Leu Glu Arg Lys Ile Ala Gln Ile
            20                  25                  30

tgg tca gaa att tta cag att tcg gaa att gat att aga gat aac ttt     144
Trp Ser Glu Ile Leu Gln Ile Ser Glu Ile Asp Ile Arg Asp Asn Phe
        35                  40                  45

ttt gaa gtt ggt ggt aat tcc ctt tta gca tta cat tta atg aat gcc     192
Phe Glu Val Gly Gly Asn Ser Leu Leu Ala Leu His Leu Met Asn Ala
    50                  55                  60

atc gaa caa aaa ttt ggt cga gag tta gca ctg tca act tta ctt act     240
Ile Glu Gln Lys Phe Gly Arg Glu Leu Ala Leu Ser Thr Leu Leu Thr
65                  70                  75                  80

aat aac tca att gaa aaa cta gca gaa att ctg caa aac ccc aca gat     288
Asn Asn Ser Ile Glu Lys Leu Ala Glu Ile Leu Gln Asn Pro Thr Asp
                85                  90                  95

gtt ttt ccc aat tca                                                 303
```

Val Phe Pro Asn Ser
100

<210> SEQ ID NO 21
<211> LENGTH: 101
<212> TYPE: PRT
<213> ORGANISM: Unknown
<220> FEATURE:
<223> OTHER INFORMATION: Synthetic Construct

<400> SEQUENCE: 21

Met Gly Ser Leu Pro Lys Pro Asp Phe Ser Asn Leu Ile Thr His Glu
1 5 10 15

Asp Phe Thr Pro Ala Arg Asn Asp Leu Glu Arg Lys Ile Ala Gln Ile
20 25 30

Trp Ser Glu Ile Leu Gln Ile Ser Glu Ile Asp Ile Arg Asp Asn Phe
35 40 45

Phe Glu Val Gly Gly Asn Ser Leu Leu Ala Leu His Leu Met Asn Ala
50 55 60

Ile Glu Gln Lys Phe Gly Arg Glu Leu Ala Leu Ser Thr Leu Leu Thr
65 70 75 80

Asn Asn Ser Ile Glu Lys Leu Ala Glu Ile Leu Gln Asn Pro Thr Asp
85 90 95

Val Phe Pro Asn Ser
100

<210> SEQ ID NO 22
<211> LENGTH: 246
<212> TYPE: DNA
<213> ORGANISM: Lyngbya sp
<220> FEATURE:
<221> NAME/KEY: CDS
<222> LOCATION: (1)..(246)

<400> SEQUENCE: 22 atg gaa att ttt gaa cag gaa tgt cga aaa tta tta aaa tct cta ctg 48
Met Glu Ile Phe Glu Gln Glu Cys Arg Lys Leu Leu Lys Ser Leu Leu
1 5 10 15 ggt gtt caa cgt atg gag aga ttg cct ggt gac aca cca cta atg gag 96
Gly Val Gln Arg Met Glu Arg Leu Pro Gly Asp Thr Pro Leu Met Glu
20 25 30 tca gga atg gat tca ctg gag ttg tta gaa ttt cgt gct ctt ata gaa 144
Ser Gly Met Asp Ser Leu Glu Leu Leu Glu Phe Arg Ala Leu Ile Glu
35 40 45 aga aag ttt ggg att aag tta aag tct acc ttc ttt ttt agt tac aaa 192
Arg Lys Phe Gly Ile Lys Leu Lys Ser Thr Phe Phe Phe Ser Tyr Lys
50 55 60 act ctt ata gcg gta gca gag tat ctt tca gaa cgg gaa gat att aat 240
Thr Leu Ile Ala Val Ala Glu Tyr Leu Ser Glu Arg Glu Asp Ile Asn
65 70 75 80 ttt agt 246
Phe Ser

<210> SEQ ID NO 23
<211> LENGTH: 82
<212> TYPE: PRT
<213> ORGANISM: Lyngbya sp

<400> SEQUENCE: 23

Met Glu Ile Phe Glu Gln Glu Cys Arg Lys Leu Leu Lys Ser Leu Leu
1 5 10 15

```
Gly Val Gln Arg Met Glu Arg Leu Pro Gly Asp Thr Pro Leu Met Glu
            20                  25                  30

Ser Gly Met Asp Ser Leu Glu Leu Leu Glu Phe Arg Ala Leu Ile Glu
        35                  40                  45

Arg Lys Phe Gly Ile Lys Leu Lys Ser Thr Phe Phe Phe Ser Tyr Lys
    50                  55                  60

Thr Leu Ile Ala Val Ala Glu Tyr Leu Ser Glu Arg Glu Asp Ile Asn
65                  70                  75                  80

Phe Ser


<210> SEQ ID NO 24
<211> LENGTH: 261
<212> TYPE: DNA
<213> ORGANISM: Unknown
<220> FEATURE:
<223> OTHER INFORMATION: M. aeruginosa NIES843
<220> FEATURE:
<221> NAME/KEY: CDS
<222> LOCATION: (1)..(261)

<400> SEQUENCE: 24

atg gtg aca act gtt caa tct cct tgt acc gtt gaa gac att caa aac       48
Met Val Thr Thr Val Gln Ser Pro Cys Thr Val Glu Asp Ile Gln Asn
1               5                   10                  15

tgg ctc gtt gat cag ttt gct caa caa ctc gat gtt gac ctt gat gac       96
Trp Leu Val Asp Gln Phe Ala Gln Gln Leu Asp Val Asp Leu Asp Asp
            20                  25                  30

att gat att gaa gaa cct ttt gat aat tat gaa ctc gac tca cga aaa      144
Ile Asp Ile Glu Glu Pro Phe Asp Asn Tyr Glu Leu Asp Ser Arg Lys
        35                  40                  45

gcg tta gtt tta tta gga cgc tta gaa aaa tgg ctc gga aag gaa tta      192
Ala Leu Val Leu Leu Gly Arg Leu Glu Lys Trp Leu Gly Lys Glu Leu
    50                  55                  60

aat cct gtg gtc att ttt aac tat ccc acc att gct gaa tta gca acc      240
Asn Pro Val Val Ile Phe Asn Tyr Pro Thr Ile Ala Glu Leu Ala Thr
65                  70                  75                  80

cga tta ggg gaa tta tat ctt                                          261
Arg Leu Gly Glu Leu Tyr Leu
                85


<210> SEQ ID NO 25
<211> LENGTH: 87
<212> TYPE: PRT
<213> ORGANISM: Unknown
<220> FEATURE:
<223> OTHER INFORMATION: Synthetic Construct

<400> SEQUENCE: 25

Met Val Thr Thr Val Gln Ser Pro Cys Thr Val Glu Asp Ile Gln Asn
1               5                   10                  15

Trp Leu Val Asp Gln Phe Ala Gln Gln Leu Asp Val Asp Leu Asp Asp
            20                  25                  30

Ile Asp Ile Glu Glu Pro Phe Asp Asn Tyr Glu Leu Asp Ser Arg Lys
        35                  40                  45

Ala Leu Val Leu Leu Gly Arg Leu Glu Lys Trp Leu Gly Lys Glu Leu
    50                  55                  60

Asn Pro Val Val Ile Phe Asn Tyr Pro Thr Ile Ala Glu Leu Ala Thr
65                  70                  75                  80

Arg Leu Gly Glu Leu Tyr Leu
                85
```

<210> SEQ ID NO 26
<211> LENGTH: 285
<212> TYPE: DNA
<213> ORGANISM: Streptomyces coelicolor
<220> FEATURE:
<221> NAME/KEY: CDS
<222> LOCATION: (1)..(285)

<400> SEQUENCE: 26

```
atg gag cag cgg ctg gct ccg ctg tcc gcg gcc gag cgc gag cgg gca       48
Met Glu Gln Arg Leu Ala Pro Leu Ser Ala Ala Glu Arg Glu Arg Ala
1               5                   10                  15

ctc acg gat ctc gtg cgc gtc cag gtc gcg gcg gtg ctc ggg cac tct       96
Leu Thr Asp Leu Val Arg Val Gln Val Ala Ala Val Leu Gly His Ser
            20                  25                  30

gac ccc ggc gcg atc gag tcc ggc cgg gcc ttc cag gag ctg ggc ttc      144
Asp Pro Gly Ala Ile Glu Ser Gly Arg Ala Phe Gln Glu Leu Gly Phe
        35                  40                  45

gac tca ctg aca gcc gtc gaa ctt cgc aac cag ctg agc acc gcg agc      192
Asp Ser Leu Thr Ala Val Glu Leu Arg Asn Gln Leu Ser Thr Ala Ser
    50                  55                  60

gga ctg cgc ctg ccc acc acc ctc gtc ttc gac cac ccc tcc ccc gcc      240
Gly Leu Arg Leu Pro Thr Thr Leu Val Phe Asp His Pro Ser Pro Ala
65                  70                  75                  80

gct ctc gcc gcc cac ctc tcg gcg gag ctg ttc ggc gag cag gag          285
Ala Leu Ala Ala His Leu Ser Ala Glu Leu Phe Gly Glu Gln Glu
                85                  90                  95
```

<210> SEQ ID NO 27
<211> LENGTH: 95
<212> TYPE: PRT
<213> ORGANISM: Streptomyces coelicolor

<400> SEQUENCE: 27

```
Met Glu Gln Arg Leu Ala Pro Leu Ser Ala Ala Glu Arg Glu Arg Ala
1               5                   10                  15

Leu Thr Asp Leu Val Arg Val Gln Val Ala Ala Val Leu Gly His Ser
            20                  25                  30

Asp Pro Gly Ala Ile Glu Ser Gly Arg Ala Phe Gln Glu Leu Gly Phe
        35                  40                  45

Asp Ser Leu Thr Ala Val Glu Leu Arg Asn Gln Leu Ser Thr Ala Ser
    50                  55                  60

Gly Leu Arg Leu Pro Thr Thr Leu Val Phe Asp His Pro Ser Pro Ala
65                  70                  75                  80

Ala Leu Ala Ala His Leu Ser Ala Glu Leu Phe Gly Glu Gln Glu
                85                  90                  95
```

<210> SEQ ID NO 28
<211> LENGTH: 294
<212> TYPE: DNA
<213> ORGANISM: Streptomyces scabiei
<220> FEATURE:
<221> NAME/KEY: CDS
<222> LOCATION: (1)..(294)

<400> SEQUENCE: 28

```
atg gcc cgc cgg ctc gaa ccg ttg gac gaa ccc gcg cga cgc cgt ctg       48
Met Ala Arg Arg Leu Glu Pro Leu Asp Glu Pro Ala Arg Arg Arg Leu
1               5                   10                  15

ctg ctc gac ctg gtg tgc gac cac gcg gcc gcg gtc ctc ggc cac acc       96
Leu Leu Asp Leu Val Cys Asp His Ala Ala Ala Val Leu Gly His Thr
            20                  25                  30
```

```
ggc cgc cag gcc gtc ccg gcc gac cag gcg ttc tcc gcc gtc ggg ttc      144
Gly Arg Gln Ala Val Pro Ala Asp Gln Ala Phe Ser Ala Val Gly Phe
        35                  40                  45

gac tcg atg ctc gcc gtg tcc ttc cgt aac cgg ctg cgc acc gcg acc      192
Asp Ser Met Leu Ala Val Ser Phe Arg Asn Arg Leu Arg Thr Ala Thr
    50                  55                  60

ggc gtc ccc gtc gcc gcg acg gtg gtg ttc gac cat ccc acc ccc gcc      240
Gly Val Pro Val Ala Ala Thr Val Val Phe Asp His Pro Thr Pro Ala
65                  70                  75                  80

gcc ctc gcc gac cac ctg tac gac ggg ttg agc gcc cgt ccc gga ccg      288
Ala Leu Ala Asp His Leu Tyr Asp Gly Leu Ser Ala Arg Pro Gly Pro
                85                  90                  95

gcc gtt                                                              294
Ala Val


<210> SEQ ID NO 29
<211> LENGTH: 98
<212> TYPE: PRT
<213> ORGANISM: Streptomyces scabiei

<400> SEQUENCE: 29

Met Ala Arg Arg Leu Glu Pro Leu Asp Glu Pro Ala Arg Arg Arg Leu
1               5                   10                  15

Leu Leu Asp Leu Val Cys Asp His Ala Ala Ala Val Leu Gly His Thr
            20                  25                  30

Gly Arg Gln Ala Val Pro Ala Asp Gln Ala Phe Ser Ala Val Gly Phe
        35                  40                  45

Asp Ser Met Leu Ala Val Ser Phe Arg Asn Arg Leu Arg Thr Ala Thr
    50                  55                  60

Gly Val Pro Val Ala Ala Thr Val Val Phe Asp His Pro Thr Pro Ala
65                  70                  75                  80

Ala Leu Ala Asp His Leu Tyr Asp Gly Leu Ser Ala Arg Pro Gly Pro
                85                  90                  95

Ala Val


<210> SEQ ID NO 30
<211> LENGTH: 675
<212> TYPE: DNA
<213> ORGANISM: Bacillus subtilis
<220> FEATURE:
<221> NAME/KEY: CDS
<222> LOCATION: (1)..(675)

<400> SEQUENCE: 30

atg aaa att tat ggg att tac atg gat aga ccc ctg agc caa gaa gaa       48
Met Lys Ile Tyr Gly Ile Tyr Met Asp Arg Pro Leu Ser Gln Glu Glu
1               5                   10                  15

aac gaa cgc ttt atg acc ttt att agc cct gaa aaa cgg gaa aaa tgt       96
Asn Glu Arg Phe Met Thr Phe Ile Ser Pro Glu Lys Arg Glu Lys Cys
            20                  25                  30

cgc cgt ttt tat cat aaa gaa gat gcc cat cgt acc tta ttg ggt gat      144
Arg Arg Phe Tyr His Lys Glu Asp Ala His Arg Thr Leu Leu Gly Asp
        35                  40                  45

gtg ttg gtt cgg agt gtg att tct cgc caa tac caa ttg gat aaa agt      192
Val Leu Val Arg Ser Val Ile Ser Arg Gln Tyr Gln Leu Asp Lys Ser
    50                  55                  60

gat att cgg ttt tct act caa gaa tat ggt aaa ccc tgt att ccc gat      240
Asp Ile Arg Phe Ser Thr Gln Glu Tyr Gly Lys Pro Cys Ile Pro Asp
65                  70                  75                  80
```

-continued

```
ttg ccc gat gcc cat ttt aat att agt cat tct ggt cgc tgg gtt att      288
Leu Pro Asp Ala His Phe Asn Ile Ser His Ser Gly Arg Trp Val Ile
                85                  90                  95

ggt gct ttt gat agt caa ccc att ggt att gat att gaa aaa acc aaa      336
Gly Ala Phe Asp Ser Gln Pro Ile Gly Ile Asp Ile Glu Lys Thr Lys
            100                 105                 110

ccc att tct ttg gaa att gcc aaa cgc ttt ttc agt aaa acc gaa tac      384
Pro Ile Ser Leu Glu Ile Ala Lys Arg Phe Phe Ser Lys Thr Glu Tyr
        115                 120                 125

tct gat tta ttg gct aaa gat aaa gat gaa caa act gat tac ttt tac      432
Ser Asp Leu Leu Ala Lys Asp Lys Asp Glu Gln Thr Asp Tyr Phe Tyr
    130                 135                 140

cat ttg tgg agt atg aaa gaa tct ttt att aaa caa gaa ggt aaa ggt      480
His Leu Trp Ser Met Lys Glu Ser Phe Ile Lys Gln Glu Gly Lys Gly
145                 150                 155                 160

tta agt ttg ccc tta gat agt ttt tct gtg cgg ttg cat caa gat ggt      528
Leu Ser Leu Pro Leu Asp Ser Phe Ser Val Arg Leu His Gln Asp Gly
                165                 170                 175

caa gtt agt att gaa tta ccc gat agt cat tct ccc tgt tac att aaa      576
Gln Val Ser Ile Glu Leu Pro Asp Ser His Ser Pro Cys Tyr Ile Lys
            180                 185                 190

act tat gaa gtt gat ccc ggt tat aaa atg gct gtt tgt gca gca cac      624
Thr Tyr Glu Val Asp Pro Gly Tyr Lys Met Ala Val Cys Ala Ala His
        195                 200                 205

ccc gat ttt cca gaa gat att act atg gtt tcc tat gaa gaa ctg ttg      672
Pro Asp Phe Pro Glu Asp Ile Thr Met Val Ser Tyr Glu Glu Leu Leu
    210                 215                 220

tag                                                                  675


<210> SEQ ID NO 31
<211> LENGTH: 224
<212> TYPE: PRT
<213> ORGANISM: Bacillus subtilis

<400> SEQUENCE: 31

Met Lys Ile Tyr Gly Ile Tyr Met Asp Arg Pro Leu Ser Gln Glu Glu
1               5                   10                  15

Asn Glu Arg Phe Met Thr Phe Ile Ser Pro Glu Lys Arg Glu Lys Cys
            20                  25                  30

Arg Arg Phe Tyr His Lys Glu Asp Ala His Arg Thr Leu Leu Gly Asp
        35                  40                  45

Val Leu Val Arg Ser Val Ile Ser Arg Gln Tyr Gln Leu Asp Lys Ser
    50                  55                  60

Asp Ile Arg Phe Ser Thr Gln Glu Tyr Gly Lys Pro Cys Ile Pro Asp
65                  70                  75                  80

Leu Pro Asp Ala His Phe Asn Ile Ser His Ser Gly Arg Trp Val Ile
                85                  90                  95

Gly Ala Phe Asp Ser Gln Pro Ile Gly Ile Asp Ile Glu Lys Thr Lys
            100                 105                 110

Pro Ile Ser Leu Glu Ile Ala Lys Arg Phe Phe Ser Lys Thr Glu Tyr
        115                 120                 125

Ser Asp Leu Leu Ala Lys Asp Lys Asp Glu Gln Thr Asp Tyr Phe Tyr
    130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
                165                 170                 175
```

```
Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
        195                 200                 205

Pro Asp Phe Pro Glu Asp Ile Thr Met Val Ser Tyr Glu Glu Leu Leu
    210                 215                 220
```

<210> SEQ ID NO 32
<211> LENGTH: 26
<212> TYPE: DNA
<213> ORGANISM: Artificial Sequence
<220> FEATURE:
<223> OTHER INFORMATION: primer

<400> SEQUENCE: 32
cgtacgtact acttaattga caaata 26

<210> SEQ ID NO 33
<211> LENGTH: 26
<212> TYPE: DNA
<213> ORGANISM: Artificial Sequence
<220> FEATURE:
<223> OTHER INFORMATION: primer

<400> SEQUENCE: 33
gagctccccg acttctcaaa ggatac 26

<210> SEQ ID NO 34
<211> LENGTH: 32
<212> TYPE: DNA
<213> ORGANISM: Artificial Sequence
<220> FEATURE:
<223> OTHER INFORMATION: primer

<400> SEQUENCE: 34
ctcgaggacg tcatgggtac acctcacgct ac 32

<210> SEQ ID NO 35
<211> LENGTH: 26
<212> TYPE: DNA
<213> ORGANISM: Artificial Sequence
<220> FEATURE:
<223> OTHER INFORMATION: primer

<400> SEQUENCE: 35
catatgcccg acttctcaaa ggatac 26

<210> SEQ ID NO 36
<211> LENGTH: 29
<212> TYPE: DNA
<213> ORGANISM: Artificial Sequence
<220> FEATURE:
<223> OTHER INFORMATION: primer

<400> SEQUENCE: 36
cgtacgattc tgaaatgagc tgttgacaa 29

<210> SEQ ID NO 37
<211> LENGTH: 26
<212> TYPE: DNA
<213> ORGANISM: Artificial Sequence
<220> FEATURE:
<223> OTHER INFORMATION: primer

<400> SEQUENCE: 37
gagctccccg acttctcaaa ggatac 26

<210> SEQ ID NO 38
<211> LENGTH: 24
<212> TYPE: DNA
<213> ORGANISM: Artificial Sequence
<220> FEATURE:
<223> OTHER INFORMATION: primer

<400> SEQUENCE: 38
ctgcagttca atgcggtcca atac 24

<210> SEQ ID NO 39
<211> LENGTH: 39
<212> TYPE: DNA
<213> ORGANISM: Artificial Sequence
<220> FEATURE:
<223> OTHER INFORMATION: primer

<400> SEQUENCE: 39
agccaagtat gctgcaacat tttttctagt gtgccattg 39

<210> SEQ ID NO 40
<211> LENGTH: 39
<212> TYPE: DNA
<213> ORGANISM: Artificial Sequence
<220> FEATURE:
<223> OTHER INFORMATION: primer

<400> SEQUENCE: 40
caatggcaca ctagaaaaaa tgttgcagca tacttggct 39

<210> SEQ ID NO 41
<211> LENGTH: 26
<212> TYPE: DNA
<213> ORGANISM: Artificial Sequence
<220> FEATURE:
<223> OTHER INFORMATION: primer

<400> SEQUENCE: 41
gcatgctcaa taatgccaga attttg 26

<210> SEQ ID NO 42
<211> LENGTH: 24
<212> TYPE: DNA
<213> ORGANISM: Artificial Sequence
<220> FEATURE:
<223> OTHER INFORMATION: primer

<400> SEQUENCE: 42
cgtacgttca atgcggtcca atac 24

<210> SEQ ID NO 43
<211> LENGTH: 24
<212> TYPE: DNA
<213> ORGANISM: Artificial Sequence
<220> FEATURE:
<223> OTHER INFORMATION: primer

<400> SEQUENCE: 43
acgtcttttt ctagtgtgcc attg 24

<210> SEQ ID NO 44
<211> LENGTH: 25
<212> TYPE: DNA
<213> ORGANISM: Artificial Sequence
<220> FEATURE:
<223> OTHER INFORMATION: primer

<400> SEQUENCE: 44
cgtacgcatt gaattaatct cctac 25

<210> SEQ ID NO 45
<211> LENGTH: 24
<212> TYPE: DNA
<213> ORGANISM: Artificial Sequence
<220> FEATURE:
<223> OTHER INFORMATION: primer

<400> SEQUENCE: 45
gacgtccacc tgtagagaag agtc 24

<210> SEQ ID NO 46
<211> LENGTH: 21
<212> TYPE: DNA
<213> ORGANISM: Artificial Sequence
<220> FEATURE:
<223> OTHER INFORMATION: primer

<400> SEQUENCE: 46
cgtacgcatt gaattaatct c 21

<210> SEQ ID NO 47
<211> LENGTH: 26
<212> TYPE: DNA
<213> ORGANISM: Artificial Sequence
<220> FEATURE:
<223> OTHER INFORMATION: primer

<400> SEQUENCE: 47
gagctcctac aaccgccgaa ttaaag 26

<210> SEQ ID NO 48
<211> LENGTH: 25
<212> TYPE: DNA
<213> ORGANISM: Artificial Sequence
<220> FEATURE:
<223> OTHER INFORMATION: primer

<400> SEQUENCE: 48
gagctccatt gaattaatct cctac 25

<210> SEQ ID NO 49
<211> LENGTH: 37
<212> TYPE: DNA
<213> ORGANISM: Artificial Sequence
<220> FEATURE:
<223> OTHER INFORMATION: primer

<400> SEQUENCE: 49
cagaaataga ttgtgtcatc acctgtagag aagagtc 37

<210> SEQ ID NO 50
<211> LENGTH: 37
<212> TYPE: DNA
<213> ORGANISM: Artificial Sequence
<220> FEATURE:
<223> OTHER INFORMATION: primer

<400> SEQUENCE: 50
gactcttctc tacaggtgat gacacaatct atttctg 37

<210> SEQ ID NO 51
<211> LENGTH: 30
<212> TYPE: DNA
<213> ORGANISM: Artificial Sequence
<220> FEATURE:
<223> OTHER INFORMATION: primer

<400> SEQUENCE: 51
ccgctcgaga gattgttctt ccaattcttc 30

<210> SEQ ID NO 52
<211> LENGTH: 25
<212> TYPE: DNA
<213> ORGANISM: Artificial Sequence
<220> FEATURE:
<223> OTHER INFORMATION: primer

<400> SEQUENCE: 52
gagctccatt gaattaatct cctac 25

<210> SEQ ID NO 53
<211> LENGTH: 37
<212> TYPE: DNA
<213> ORGANISM: Artificial Sequence
<220> FEATURE:
<223> OTHER INFORMATION: primer

<400> SEQUENCE: 53
cagaaataga ttgtgtcatc acctgtagag aagagtc 37

<210> SEQ ID NO 54
<211> LENGTH: 37
<212> TYPE: DNA
<213> ORGANISM: Artificial Sequence
<220> FEATURE:
<223> OTHER INFORMATION: primer

<400> SEQUENCE: 54
gactcttctc tacaggtgat gacacaatct atttctg 37

<210> SEQ ID NO 55
<211> LENGTH: 24
<212> TYPE: DNA
<213> ORGANISM: Artificial Sequence
<220> FEATURE:
<223> OTHER INFORMATION: primer

<400> SEQUENCE: 55
ggtaccctaa tcgccaccaa actc 24

<210> SEQ ID NO 56
<211> LENGTH: 24
<212> TYPE: DNA
<213> ORGANISM: Artificial Sequence
<220> FEATURE:
<223> OTHER INFORMATION: primer

<400> SEQUENCE: 56
gtacccattg aattaatctc ctac 24

<210> SEQ ID NO 57
<211> LENGTH: 40
<212> TYPE: DNA
<213> ORGANISM: Artificial Sequence
<220> FEATURE:
<223> OTHER INFORMATION: primer

<400> SEQUENCE: 57
ctaaaaagtt tattatttcc atcacctgta gagaagagtc 40

<210> SEQ ID NO 58
<211> LENGTH: 40
<212> TYPE: DNA
<213> ORGANISM: Artificial Sequence
<220> FEATURE:
<223> OTHER INFORMATION: primer

<400> SEQUENCE: 58
gactcttctc tacaggtgat ggaaataata aactttttag 40

<210> SEQ ID NO 59
<211> LENGTH: 26
<212> TYPE: DNA
<213> ORGANISM: Artificial Sequence
<220> FEATURE:
<223> OTHER INFORMATION: primer

<400> SEQUENCE: 59
gtcgaccccg acttctcaaa ggatac 26

<210> SEQ ID NO 60
<211> LENGTH: 18
<212> TYPE: DNA
<213> ORGANISM: Artificial Sequence
<220> FEATURE:
<223> OTHER INFORMATION: primer

<400> SEQUENCE: 60
tgtgaattag ttgtaatg 18

<210> SEQ ID NO 61
<211> LENGTH: 18
<212> TYPE: DNA
<213> ORGANISM: Artificial Sequence
<220> FEATURE:
<223> OTHER INFORMATION: primer

<400> SEQUENCE: 61
ctactttaat cgcaattc 18

<210> SEQ ID NO 62
<211> LENGTH: 18
<212> TYPE: DNA
<213> ORGANISM: Artificial Sequence
<220> FEATURE:
<223> OTHER INFORMATION: primer

<400> SEQUENCE: 62
caattcaccc atagtagc 18

<210> SEQ ID NO 63
<211> LENGTH: 18
<212> TYPE: DNA
<213> ORGANISM: Artificial Sequence
<220> FEATURE:
<223> OTHER INFORMATION: primer

<400> SEQUENCE: 63
taatcaaatt taacttgc 18

<210> SEQ ID NO 64

<211> LENGTH: 29
<212> TYPE: DNA
<213> ORGANISM: Artificial Sequence
<220> FEATURE:
<223> OTHER INFORMATION: primer

<400> SEQUENCE: 64
cgtacgattc tgaaatgagc tgttgacaa 29

<210> SEQ ID NO 65
<211> LENGTH: 24
<212> TYPE: DNA
<213> ORGANISM: Artificial Sequence
<220> FEATURE:
<223> OTHER INFORMATION: primer

<400> SEQUENCE: 65
cgtacgttca atgcggtcca atac 24

<210> SEQ ID NO 66
<211> LENGTH: 25
<212> TYPE: DNA
<213> ORGANISM: Artificial Sequence
<220> FEATURE:
<223> OTHER INFORMATION: primer

<400> SEQUENCE: 66
cgtacgcatt gaattaatct cctac 25

<210> SEQ ID NO 67
<211> LENGTH: 18
<212> TYPE: DNA
<213> ORGANISM: Artificial Sequence
<220> FEATURE:
<223> OTHER INFORMATION: primer

<400> SEQUENCE: 67
gctcatgcag gtttggag 18

<210> SEQ ID NO 68
<211> LENGTH: 25
<212> TYPE: DNA
<213> ORGANISM: Artificial Sequence
<220> FEATURE:
<223> OTHER INFORMATION: primer

<400> SEQUENCE: 68
gagctccatt gaattaatct cctac 25

<210> SEQ ID NO 69
<211> LENGTH: 18
<212> TYPE: DNA
<213> ORGANISM: Artificial Sequence
<220> FEATURE:
<223> OTHER INFORMATION: primer

<400> SEQUENCE: 69
gtaagcctac ctactgga 18

<210> SEQ ID NO 70
<211> LENGTH: 25
<212> TYPE: DNA
<213> ORGANISM: Artificial Sequence
<220> FEATURE:
<223> OTHER INFORMATION: primer

<400> SEQUENCE: 70
ggtacccatt gaattaatct cctac 25

<210> SEQ ID NO 71
<211> LENGTH: 18
<212> TYPE: DNA
<213> ORGANISM: Artificial Sequence
<220> FEATURE:
<223> OTHER INFORMATION: primer

<400> SEQUENCE: 71
gagcgatgaa tacccatc 18

<210> SEQ ID NO 72
<211> LENGTH: 18
<212> TYPE: DNA
<213> ORGANISM: Artificial Sequence
<220> FEATURE:
<223> OTHER INFORMATION: primer

<400> SEQUENCE: 72
agtagttgat gcgtttgc 18

<210> SEQ ID NO 73
<211> LENGTH: 18
<212> TYPE: DNA
<213> ORGANISM: Artificial Sequence
<220> FEATURE:
<223> OTHER INFORMATION: primer

<400> SEQUENCE: 73
ctactttaat cgcaattc 18

<210> SEQ ID NO 74
<211> LENGTH: 18
<212> TYPE: DNA
<213> ORGANISM: Artificial Sequence
<220> FEATURE:
<223> OTHER INFORMATION: primer

<400> SEQUENCE: 74
gtgaacacac cactactg 18

<210> SEQ ID NO 75
<211> LENGTH: 18
<212> TYPE: DNA
<213> ORGANISM: Artificial Sequence
<220> FEATURE:
<223> OTHER INFORMATION: primer

<400> SEQUENCE: 75
acactcttgg ctttagtc 18

<210> SEQ ID NO 76
<211> LENGTH: 18
<212> TYPE: DNA
<213> ORGANISM: Artificial Sequence
<220> FEATURE:
<223> OTHER INFORMATION: primer

<400> SEQUENCE: 76
caagatggca caatctac 18

<210> SEQ ID NO 77
<211> LENGTH: 18
<212> TYPE: DNA

<213> ORGANISM: Artificial Sequence
<220> FEATURE:
<223> OTHER INFORMATION: primer

<400> SEQUENCE: 77
tccagtaggt aggcttac 18

<210> SEQ ID NO 78
<211> LENGTH: 18
<212> TYPE: DNA
<213> ORGANISM: Artificial Sequence
<220> FEATURE:
<223> OTHER INFORMATION: primer

<400> SEQUENCE: 78
aacatgtcca acccatac 18

<210> SEQ ID NO 79
<211> LENGTH: 18
<212> TYPE: DNA
<213> ORGANISM: Artificial Sequence
<220> FEATURE:
<223> OTHER INFORMATION: primer

<400> SEQUENCE: 79
gagcgatgaa tacccatc 18

<210> SEQ ID NO 80
<211> LENGTH: 208
<212> TYPE: DNA
<213> ORGANISM: Unknown
<220> FEATURE:
<223> OTHER INFORMATION: Synechocystis PCC6803

<400> SEQUENCE: 80
ttcaatgcgg tccaatacct cccctgccca actgggtaag ctcgcggctc cactgagtaa 60
tacagacaag gctaaacagg caaatttttt cattggtcaa ctcctagcac caatttccca 120
agactacgga gggggcaatg aagtttcaat taattggggt cacaaaccac agcggcctat 180
ggctctaatc aatggcacac tagaaaaa 208

<210> SEQ ID NO 81
<211> LENGTH: 30
<212> TYPE: DNA
<213> ORGANISM: Artificial Sequence
<220> FEATURE:
<223> OTHER INFORMATION: hybrid promoter

<400> SEQUENCE: 81
ttgacaatta atcatccggc tcgtataatg 30

<210> SEQ ID NO 82
<211> LENGTH: 560
<212> TYPE: DNA
<213> ORGANISM: Unknown
<220> FEATURE:
<223> OTHER INFORMATION: Synechocystis PCC6803

<400> SEQUENCE: 82
ttgaattaat ctcctacttg actttatgag ttgggatttt cttaaacaca attccccccgg 60 ataaactgag ggagtccaaa gtaatgaccc tagagttatt gttactgatc tccattaact 120
ttcgttaact acccggggat ttatgagaga tattacctaa ataaatccag ggagaaacac 180
ggaggcagcg acaagggcca ccgggatgct caaacagctc agcgcctagg cttgaatgct 240
tttgcaatcc cacagttaac tttatacaac ggtgatggga cttatgtctg ttacatcttg 300
ttaattttat tcctgctttt ttgttaagta atgttgcagg ggattctcag attgtcctgg 360
attgggaagg gaagacaacc agtttcgttc agcttatgtt ttagggctaa aattatgcaa 420
ttgatgttcg gtgcgaactt ttctcgtttt tttagtttcc agtggggtag ggaagactgt 480
tgcctaggga accacagcct actttccttt ttgagctttt tatcccacca ttttgatatt 540
cagggactct tctctacagg 560

<210> SEQ ID NO 83
<211> LENGTH: 17733
<212> TYPE: DNA
<213> ORGANISM: Artificial Sequence
<220> FEATURE:
<223> OTHER INFORMATION: sequence of plasmid Sh-Pori

<400> SEQUENCE: 83
ctcgcgagaa ttaattcaga taaaaaaaat ccttagcttt cgctaaggat gatttctagc 60
gatgaccctg ctgattggtt cgctgaccat ttccgggtgc gggacggcgt taccagaaac 120
tcagaaggtt cgtccaacca aaccgactct gacggcagtt tacgagagag atgatagggt 180
ctgcttcagt aagccagatg ctacacaatt aggcttgtac gggtactcga cctgcatccc 240
ttaacttact tattaaataa tttatagcta ttgaaaagag ataagaattg ttcaaagcta 300
atattgttta aatcgtcaat tcctgcatgt tttaaggaat tgttaaattg atttttttgta 360 aatattttct tgtattcttt gttaaaataa aaaaggggac ctctagggtc cccaattaat 420
tagtaatata atctattaaa ggtcattcaa aaggtcatcc accggatcag cttagtaaag 480
ccctcgctag attttaatgc ggatgttgcg attacttcgc caactattgc gataacaaga 540
aaaagccagc ctttcatgat atatctccca atttgtgtag ggcttattat gcacgcttaa 600
aaataataaa agcagacttg acctgatagt ttggctgtga gcaattatgt gcttagtgca 660
tctaacgctt gagttaagcc gcgccgcgaa gcggcgtcgg cttgaacgaa ttgttagaca 720
ttatttgccg actaccttgg tgatctcgcc tttcacgtag tggacaaatt cttccaactg 780
atctgcgcgc gaggccaagc gatcttcttc ttgtccaaga taagcctgtc tagcttcaag 840
tatgacgggc tgatactggg ccggcaggcg ctccattgcc cagtcggcag cgacatcctt 900
cggcgcgatt ttgccggtta ctgcgctgta ccaaatgcgg gacaacgtaa gcactacatt 960
tcgctcatcg ccagcccagt cgggcggcga gttccatagc gttaaggttt catttagcgc 1020
ctcaaataga tcctgttcag gaaccggatc aaagagttcc tccgccgctg gacctaccaa 1080
ggcaacgcta tgttctcttg cttttgtcag caagatagcc agatcaatgt cgatcgtggc 1140
tggctcgaag atacctgcaa gaatgtcatt gcgctgccat tctccaaatt gcagttcgcg 1200
cttagctgga taacgccacg gaatgatgtc gtcgtgcaca acaatggtga cttctacagc 1260
gcggagaatc tcgctctctc caggggaagc cgaagtttcc aaaaggtcgt tgatcaaagc 1320
tcgccgcgtt gtttcatcaa gccttacggt caccgtaacc agcaaatcaa tatcactgtg 1380
tggcttcagg ccgccatcca ctgcggagcc gtacaaatgt acggccagca acgtcggttc 1440
gagatggcgc tcgatgacgc caactacctc tgatagttga gtcgatactt cggcgatcac 1500
cgcttccctc atgatgttta actttgtttt agggcgactg ccctgctgcg taacatcgtt 1560
gctgctccat aacatcaaac atcgacccac ggcgtaacgc gcttgctgct tggatgcccg 1620
aggcatagac tgtaccccaa aaaaacagtc ataacaagcc atgaaaaccg ccactgcgcc 1680

-continued

```
gttaccaccg ctgcgttcgg tcaaggttct ggaccagttg cgtgagcgca tacgctactt   1740
gcattacagc ttacgaaccg aacaggctta tgtccactgg gttcgtgcct tcatccgttt   1800
ccacggtgtg cgtcacccgg caaccttggg cagcagcgaa gtcgaggcat ttctgtcctg   1860
gctggcgaac gagcgcaagg tttcggtctc cacgcatcgt caggcattgg cggccttgct   1920
gttcttctac ggcaaggtgc tgtgcacgga tctgccctgg cttcaggaga tcggaagacc   1980
tcggccgtcg cggcgcttgc cggtggtgct gaccccggat gaagtggttc gcatcctcgg   2040
ttttctggaa ggcgagcatc gtttgttcgc ccagcttctg tatggaacgg gcggatcagt   2100
gagggtttgc aactgcgggt caaggatctg gatttcgatc acggcacgat catcgtgcgg   2160
gagggcaagg gctccaagga tcgggccttg atgttacccg agagcttggc acccagcctg   2220
cgcgagcagg ggaattgatc cggtggatga ccttttgaat gacctttaat agattatatt   2280
actaattaat tggggaccct agaggtcccc tttttattt tctgaacggt ctggttatag   2340
gtacattgag caactgactg aaatgcctca aaatgttctt tacgatgcca ttgggatata   2400
tcaacggtgg tatatccagt gatttttttc tccattttag cttccttagc tcctgaaaat   2460
ctcgataact caaaaaatac gcccggtagt gatcttattt cattatggtg aaagttggaa   2520
cctcttacga gcggccgcat acgatttagg tgacactata ggatccctgc cggccggtcc   2580
ggcgcgcccg ggctcgagtg cacgtacgta ctacttaatt gacaaatatg catcacacca   2640
tagacatata gttcccgtat ttctcagaa aataacaata ttcagtaatt aaaaattcta   2700
aacagcaaat ccagagatat tttggctcta tcgatatttt ttcgtcagaa cttgtctgat   2760
ctgcaaaatt ttttaggggt tcacatatca tatttagtac attgagaaat catatcttat   2820
ttttatttaa tttttttctta gtaataaatt atcctaatat atattttggt agatattttc   2880
tctattagag ttaagctaaa ttttgttaag gatactcatt aattaatttg tgttccacag   2940
agttaagtta aacacttatc tcttgatgtt gctttgaaaa ctgacaaagt aactgcgatt   3000
gatttggctt tcagcttgaa taacatttcc agccttttta ggtatggcag agtatcactt   3060
ttgacacaaa tataaggttc tagataaatg ttaaaaaaca gcgaactgaa tatcaatcag   3120
ggctgtaatc ttcagtggaa gctaggagac aagcagagaa agttttccac actaaaagtc   3180
ctgcaaatca tagcagttga agatcagcta taatcgcaaa agttaataat tttcattgcc   3240
attaacatca gttgaatctt ggtatcttgt taccttcaaa tattgcatgt atactaaaaa   3300
cggcttagag atttacttgt tttgaagagt tcaaatcttt tttaggcaat gtttataact   3360
aatttaggtg aaactccggc tattagtcgt tcatagtata gactaacaat gcatcgttgt   3420
cagaaacaga tgttgttttt tagtggtctt tatttgattg taattaggta ttgaatcaag   3480
ttttcgaggc tatcttatga ttcgtttatg tatagtagaa acctaaaaga tagcttgaaa   3540
atagtgaatt ttcattgttg attaatatcc aacaccaact aggatgagat agtagtttat   3600
ctacttattc ttgtttgtga attagttgta atgtggagta aaaaagcaat caacattcaa   3660
cgtggatatt gttcagatcc attccccgca ttcatacgta aaggacaaaa ataatgggta   3720
cacctcacgc tacttttgca gctactgaga cagcatttca tgtgacgggc tacgaaaaga   3780
tagattttag cctggtttat gtgaatggtg tattcaacat caaaaacaca gaaattgctg   3840
atagttatca gaagtttgga cgctgcttga ctgttgttga tcataatgtc taccgtttgt   3900
atggagacca aattaagtca tattttcgtt actacgacat agacttaact gtgtttccaa   3960
ttactattac tgaacctggc aaaaccatgt caacttttga acaagtagtt gatgcgtttg   4020
ccgattttgg cttaattcgt aaagaaccag ttttagtagt tggtggtggt ttagttactg   4080
```

-continued atgttgtagg ttttgcttgt gcagcttatc gtcgcagtac taactatatt cgcattccca 4140
cgactttgat tggtttgata gatgctggaa ttgcgattaa agtagcagtc aatcataaaa 4200
agctgaaaaa tcgcttgggt gcttaccatg caccgcagaa agtcattcta gacttttcct 4260
ttctcaagac actaccaaca gcccaagtcc ggaatggaat ggcggagtta gtgaaaattg 4320
ctgtggtagc aaatgcagaa gtttttaatt ggctgtatga gtacggagaa gatttactgc 4380
atacacactt tggctatctc aacggtacag aggaactgca agaaattgct cacaaagtta 4440
actacgaagc aattaaaacc atgctggagt tagaaactcc aaacctgcat gagctagact 4500
tagatcgcgt cattgcttat ggtcacactt ggagtccgac actagaatta gcaccgcggg 4560
ttcctctgta tcatggtcat gctgtcaaca tcgatatggc gctatcagca actattgctg 4620
aacgacgggg atatattact gtagcagaac gcgatcgcat tcttggattg atgagtcgtc 4680
taggtttagc ccttgatcat ccccttctag atagcgattt gttatggtac gctacccagt 4740
ctatcaccca gacaagagac gggaaacaac gcgccgccat gccaaaacct attggtgagt 4800
gtttctttgt caatgaccta acccgtgaag aattgcatca agctttgatt gcacacaagg 4860
atgtatgtgc aacatatccc cgtggtggag atgggattga agcctatatc agtgcagaac 4920
aatctgagat ggtaggagtt tagaatcgtg actagcattg ttgaaaagaa cacagctaga 4980
cccgtaactc cccacggtat cttggttgaa cagctacaaa aaactctggc tttggcagaa 5040
tcaggaaata cacctgaaac tgttgtgact gcactacgac aggcgtatca attagcggcg 5100
ggtttagaac cttatattag tgaacacacc actactgaat ctgacgcctt agcagcactg 5160
gtacaaaaaa ctaccaaaga agactggaca aaacgtttca ctgatggtga aacagtgcgt 5220
caactagaac aggaaatgct ttctggacac gtcgagggac aaaccctgaa aatgtttgtt 5280
cacatgacta aagccaagag tgttttggaa gtaggaatgt tcaccgggta ttctgctttg 5340
gcaatggcag aggcattacc tgatgatgga cgagtggtag catgtgaagt agactcttat 5400
gttgctagct ttgctcaaac ttgtttccaa aactcgcccc acggtcataa aattactgtg 5460
gaagttgcac cagccttgga aactctgcaa aaacttgcag cagcaggtga atcatttgat 5520
ttgatattca tcgatgctga caagaaagag tatgtgcagt atttccagat catcttggat 5580
aataatctac ttgcatctaa cggcattatt tgtgtagata acactttaat gcagggacag 5640
gtttatctgc caccagaaca acgtacagct aatggtgaag cgatcgctca atttaaccaa 5700
atcattaccc aagatccgcg tgtagaacaa gttatactac cgcttcgtga tggtgtgact 5760
ttaattcggc ggttgtagaa ggatggggtt tgggtggtac tgatgggttt tttttgaggg 5820
cgaattatat gacacaatct atttctgtgg cttctgttgg acaaacaact cagtcggtga 5880
gcctgggact tcgcatatct gcgttgtgga aaagtttagc tacacttgca ctgctgttgt 5940
tagtattgcc aatcaatgct gcgattgtgt tggtatcgct gttattgggt agtcaatcgc 6000
aagcgatcgc caccgaaccc aaaaacatct tgattagtgg cggtaaaatg actaaggcgt 6060
tacaattagc ccgtagtttt cacgccgccg gacatcgagt ggttttagta gaaactcaca 6120
aatactggtt aacgggacac cgattttcca aagcagtaag tcgtttctac actctaccaa 6180
cgccccaatc tgatcctgaa gcatacaccc aagccctatt agatattgtt caaaaagaaa 6240
atatcgatgt ctatgtaccc gtgtgcagtc cggttgctag ttactacgac tctttagcta 6300
aacccgtact gtcgaagtac tgcgaggttt ttcactgtga cgcagatgtc acccaaatgt 6360
tggatgataa atacgctttt gctgagaaag cgcggagttt ggggttatct gttcccaagt 6420

-continued

```
ctttcaaaat tactgacccg gaacaggtga gcaactttga tttttctcaa gaaaagcgta   6480
aatacatcct caaaagcatt ccttatgact ctgttcgtcg cttagattta accaaacttc   6540
cttgtgagac tcccgaagca acagcagatt ttgtcaacag cttacccatc agttcccaaa   6600
agccatggat tatgcaagaa ttcattcctg gaaaagaatt ttgcacccac agcactgtcc   6660
gcaatgggga gttgagaatg cattgctgtt gtgaatcttc ggcatttcaa gttaactatg   6720
agaatgtcga tcatccccaa attttggaat gggtgcgaca ctttgtcaaa gcattaggta   6780
tcactggaca ggtatctttt gattttatcg aagcacaaga tggcacaatc tacgccattg   6840
aatgtaatcc gcgtacccat tctgccatca ctatgttcta caatcatccg gatgtggcaa   6900
atgcttattt gagtgaaatt ccacaagtag aaccaattca acctctgatt aatagtaagc   6960
ctacctactg gacttatcac gaaatttggc gattgacagg aattcgttct ttctcacagt   7020
tgcaaacttg gttgaaaaac ttttttggtg gaaaagatgc gatttacagt ttgagtgatc   7080
ctctaccttt tttaacagtt catcactggc aaattccttt attattgcta caaaatttgc   7140
aacagctaaa aggttggatc aggatagatt ttaatattgg gaaattggtt gagtttggtg   7200
gcgattagat tcagttatca gttatcagtt atcagttagt agctgttcac tgataattta   7260
tagatattga atatatataa gactcatatt tgatttctga aatacacgta gggtgcgtga   7320
tagctacgcc ataacacacc ctactggcgc gtcaagccta aaatgttgca ataaatctct   7380
gattctatct ctgtgttctc tctcttgaaa agctttgatc ggaggaaacc tccgctcaaa   7440
cttttcgctg cttcctctgc ggtttattaa tgcactattt taaggctgtc gcgccctttg   7500
ttaaagtcaa atttttttat caaaccgcag aggcgcagag gaatcagaga gaaggaaata   7560
attcttaatt gaattgtatt aagttataaa tcactatatt ttatcaaaga tggaaataat   7620
aaacttttta gatgattctc tggaaattga agaacagaag aaaaattggg aaagacaggt   7680
aggagatatt tctgatcttt ctctgctgag tttagaagaa cagcaaaaaa tattatttat   7740
atggaatcag acagaaagta attatgattt gtcgatttgt ctacatgagt tatttgcagc   7800
acaggtagag aaaacaccag atgcaaaagc tctcaagttt gctgatcaag aattgagtta   7860
tcatcagtta aattgtcggg cgaatcaact cgctcactat ttgcaatctt tgggaattgt   7920
aactgaagat ttagttggga tttgtgtgga acgttcccta gaaatggttg tggggttatt   7980
gggtattttg aaagcgggtg cggcttatgt tccaattgat cctggatatc cccaagaacg   8040
tttaggatat atgttggcgg attcccaggt gtcggtgttg ttgactcaaa gtcatttagt   8100
cgatagttta ccaacatgtc caacccatac tatttgcttg gatactgact gggatctgat   8160
ttctcaatat agcgatcgca atctccaaaa tacaacgaca ccagaaaatc tcgcttatgt   8220
aatttacact tctggttcta ctggtaaacc taaaggagcg atgaataccc atcgcggtat   8280
ttgcaatcgt ctgttatgga tgcaagatgc ttatcaactc actcaacaag atcgggttct   8340
gcaaaaaact ccctttagtt ttgatgtctc tgtctgggaa ttcttttggc cgttgattac   8400
cggggcgcgg ctgattatag cacaaccagg tggacacaag gatagttctt atctaattaa   8460
tacaattatc caagaagaaa ttaccacatt acattttgtt ccttcgatgt tgcaggtatt   8520
tttgcaagct aaaggagtgg aaaattgtca gtcattaaaa cgggtaatta ctagtggtga   8580
agctttacct gtgagtctgc aagaacggtt ttttgaacgt ttgggatgtg aactgcacaa   8640
tctttatggt cctacagaag cagcgatcga tgttacgttt tggcagtgtc aacctcaaag   8700
tcaatatcaa acagtaccga ttggtcgtcc catcgctaat actcaaatat atatattaga   8760
tcaacatttg caacctgtgc ctgtgggtgt tgtgggtgaa ctttatattg gtggtgtggg   8820
```

```
agttgccaga ggttactggc gtcgtccaga attaactaca gaaagatttg tatctaatcc   8880
ctttgcaacg ggacaaatgt ataaaactgg tgacttggcg cgctatttac ctgatggtaa   8940
tatcgagtat gttggcagaa ttgacgatca agttaaaatt cgcggttttc ggattgagtt   9000
gggagaaatt gagagtacgc tgacgcaaca ttcccagatt agtcaagctg tggttgtcgc   9060
ccagacagat aatttgaata ataagcattt aattgcttat attgttcccc agggagaacc   9120
acccacacca acccaactgc ggaatttcct tcagggtaag ctacctgaat tcatggttcc   9180
ctcagctttt gtctgcttaa attcctttcc tctcactcct agtggaaaaa tagacaggcg   9240
atcgcttccc aaacctgatt tttctaactt aatcactcat gaagatttta cgcctgcacg   9300
caatgattta gagagaaaaa tcgcgcagat ttggtcagaa attttacaga tttcggaaat   9360
tgatattaga gataactttt ttgaagttgg tggtaattcc cttttagcat tacatttaat   9420
gaatgccatc gaacaaaaat ttggtcgaga gttagcactg tcaactttac ttactaataa   9480
ctcaattgaa aaactagcag aaattctgca aaaccccaca gatgttttc ccaattcacc   9540
catagtagca attcagccca aaggtacaaa acgtcctttt ttctgcatcc atccagccgg   9600
cggacatgta ctttgctatt ttagtttggc gcattattta ggcactgacc agccatttta   9660
cggtttacaa gcacagggtt tttatggtga agaagaacca ctaactacag ttgtagaaat   9720
ggctaggctt tatgctcaag ctatacaaac aattcaaccc acagggccat atcaaattgg   9780
tggttggtcg tttggtggtg tagttgccta tgaaacggct caacaactac accaacaagg   9840
aaaagaagtt tcattactag caattttaga ttcctacgtg ccaattctgt tagataaaaa   9900
taaaaaaatt gatgatgttt atttagttgg tgtactatcc cgtgtatttg gcggaatgtt   9960
tggtcaagat aatctgattt cactagcgga aatcgaaaat ttaagtgtgg aagaaagttt  10020
aaattacatc atcgaaaaag cacgccaagc caaaattttt ccgccaggag tggaacgtca  10080
caacaatcgc cgcattttag atgttttagt cggaacttta aaagccactt attcttatga  10140
acgttgtccc tatcctggca aagttactat ttttagagcc agagaaaaac atatcatggc  10200
tcctgatcct actttagttt gggtagaatt attttcagtt ttggctgcgg aggaaattga  10260
aattcataat gtccccggta atcactattc atttgtttta gaacctcacg tccaagcttt  10320
ggctgaaagt ttgcagaaat gtttgtgctg atacaagatc cccgacttct ttgaggatgc  10380
agctggcgaa tagggggtca aacccctcgt gcgcccacaa attggttgta gagacgcgcc  10440
atggcgcgtc tctacatctg gtggaatgac gaaaaatctc ggtgaggggt gtcacccctg  10500
attcgccagc tgtatccttt gagaagtcgg ggagctcggt accoctagag tcgacctgca  10560
gttcaatgcg gtccaatacc tcccctgccc aactgggtaa gctcgcggct ccactgagta  10620
atacagacaa ggctaaacag gcaaattttt tcattggtca actcctagca ccaatttccc  10680
aagactacgg agggggcaat gaagtttcaa ttaattgggg tcacaaacca cagcggccta  10740
tggctctaat caatggcaca ctagaaaaaa tgttgcagca tacttggcta ccaaaacccc  10800
caaatttaac cttattgtca gatgaagttc atctctggcg cattcccctt gaccaaccag  10860
aatcacagct acaggattta gccgctacct tatctagtga cgaattagcc cgtgcaaaca  10920
gattttattt tcccgaacat cgccggcgtt ttactgctgg tcgtggtatt ctccgcagta  10980
tcttgggggg ctatttgggt gtggaaccag ggcaagttaa atttgattat gaatcccgtg  11040
gtaaaccaat attaggcgat cgctttgccg agagtggttt attatttaac ttgtcacact  11100
cccagaactt ggccttgtgt gcagtcaatt acacgcgcca aatcggcatc gatttagaat  11160
```

atctccgccc cacatctgat ttagaatccc ttgccaaaag gttcttttta ccgcgagaat 11220
atgaattatt gcgatcgcta cccgatgagc aaaaacaaaa aattttcttt cgttactgga 11280
cttgtaaaga ggcttatctt aaagcaacgg gtgacggcat cgctaaatta gaggaaattg 11340
aaatagcact aactcccaca gaaccagcta agttacagac agctccagcg tggagtctcc 11400
tagagctagt gccagatgat aattgtgttg ctgctgttgc cgtggcgggt tttggctggc 11460
agccaaaatt ctggcattat tgagcatgca agcttctccc tatagtgagt cgtattagcg 11520
gccgcatcga atataacttc gtataatgta tgctatacga agttattagc gatgaggaca 11580
tgaggttgcc ccgtattcag tgtcgctgat ttgtattgtc tgaagttgtt tttacgttaa 11640
gttgatgcag atcaattaat acgatacctg cgtcataatt gattatttga cgtggtttga 11700
tggcctccac gcacgttgtg atatgtagat gataatcatt atcactttac gggtcctttc 11760
cggtgatccg acaggttacg gggcggcgac ctcgcgggtt ttcgctattt atgaaaattt 11820
tccggtttaa ggcgtttccg ttcttcttcg tcataactta atgtttttat ttaaaatacc 11880
ctctgaaaag aaaggaaacg acaggtgctg aaagcgaggc tttttggcct ctgtcgtttc 11940
ctttctctgt ttttgtccgt ggaatgaaca atggaagtcc tcgtctcgcc ctcgaattag 12000
cccgcctaat gagcgggctt tttttgaatt aattctcgcg agctggcacg acaggtttcc 12060
cgactggaaa gcgggcagtg agcgcaacgc aattaatgta agttagcgcg aattgcaagc 12120
tggccgacgc gctgggctac gtcttgctgg cgttcgggag cagaagagca tacatctgga 12180
agcaaagcca ggaaagcggc ctatggagct gtgcggcagc gctcagtagg caatttttca 12240
aaatattgtt aagccttttc tgagcatggt atttttcatg gtattaccaa ttagcaggaa 12300
aataagccat tgaatataaa agataaaaat gtcttgttta caatagagtg gggggggtca 12360
gcctgccgcc ttgggccggg tgatgtcgta cttgcccgcc gcgaactcgg ttaccgtcca 12420
gcccagcgcg accagctccg gcaacgcctc gcgcacccgc ttgcggcgct tgcgcatggt 12480
cgaaccactg gcctctgacg gccagacata gccgcacaag gtatctatgg aagccttgcc 12540
ggttttgccg gggtcgatcc agccacacag ccgctggtgc agcaggcggg cggtttcgct 12600
gtccagcgcc cgcacctcgt ccatgctgat gcgcacatgc tggccgccac ccatgacggc 12660
ctgcgcgatc aaggggttca gggccacgta caggcgcccg tccgcctcgt cgctggcgta 12720
ctccgacagc agccgaaacc cctgccgctt gcggccattc tgggcgatga tggatacctt 12780
ccaaaggcgc tcgatgcagt cctgtatgtg cttgagcgcc ccaccactat cgacctctgc 12840
cccgatttcc tttgccagcg cccgatagct acctttgacc acatggcatt cagcggtgac 12900
ggcctcccac ttgggttcca ggaacagccg gagctgccgt ccgccttcgg tcttgggttc 12960
cgggccaagc actaggccat taggcccagc catggccacc agcccttgca ggatgcgcag 13020
atcatcagcg cccagcggct ccgggccgct gaactcgatc cgcttgccgt cgccgtagtc 13080
atacgtcacg tccagcttgc tgcgcttgcg ctcgccccgc ttgagggcac ggaacaggcc 13140
gggggccaga cagtgcgccg ggtcgtgccg gacgtggctg aggctgtgct tgttcttagg 13200
cttcaccacg gggcaccccc ttgctcttgc gctgcctctc cagcacggcg ggcttgagca 13260
ccccgccgtc atgccgcctg aaccaccgat cagcgaacgg tgcgccatag ttggccttgc 13320
tcacaccgaa gcggacgaag aaccggcgct ggtcgtcgtc cacaccccat tcctcggcct 13380
cggcgctggt catgctcgac aggtaggact gccagcggat gttatcgacc agtaccgagc 13440
tgccccggct ggcctgctgc tggtcgcctg cgcccatcat ggccgcgccc ttgctggcat 13500
ggtgcaggaa cacgatagag cacccggtat cggcggcgat ggcctccatg cgaccgatga 13560
cctgggccat ggggccgctg gcgttttctt cctcgatgtg gaaccggcgc agcgtgtcca 13620
gcaccatcag gcggcggccc tcggcggcgc gcttgaggcc gtcgaaccac tccggggcca 13680
tgatgttggg caggctgccg atcagcggct ggatcagcag gccgtcagcc acggcttgcc 13740
gttcctcggc gctgaggtgc gccccaaggg cgtgcaggcg gtgatgaatg gcggtgggcg 13800
ggtcttcggc gggcaggtag atcaccgggc cggtgggcag ttcgcccacc tccagcagat 13860
ccggcccgcc tgcaatctgt gcggccagtt gcagggccag catggattta ccggcaccac 13920
cgggcgacac cagcgccccg accgtaccgg ccaccatgtt gggcaaaacg tagtccagcg 13980
gtggcggcgc tgctgcgaac gcctccagaa tattgatagg cttatgggta gccattgatt 14040
gcctcctttg caggcagttg gtggttaggc gctggcgggg tcactacccc cgccctgcgc 14100
cgctctgagt tcttccaggc actcgcgcag cgcctcgtat tcgtcgtcgg tcagccagaa 14160
cttgcgctga cgcatccctt tggccttcat gcgctcggca tatcgcgctt ggcgtacagc 14220
gtcagggctg gccagcaggt cgccggtctg cttgtccttt tggtctttca tatcagtcac 14280
cgagaaactt gccggggccg aaaggcttgt cttcgcggaa caaggacaag gtgcagccgt 14340
caaggttaag gctggccata tcagcgactg aaaagcggcc agcctcggcc ttgtttgacg 14400
tataaccaaa gccaccgggc aaccaatagc ccttgtcact tttgatcagg tagaccgacc 14460
ctgaagcgct tttttcgtat tccataaaac cccccttctgt gcgtgagtac tcatagtata 14520
acaggcgtga gtaccaacgc aagcactaca tgctgaaatc tggcccgccc ctgtccatgc 14580
ctcgctggcg gggtgccggt gcccgtgcca gctcggcccg cgcaagctgg acgctgggca 14640
gacccatgac cttgctgacg gtgcgctcga tgtaatccgc ttcgtggccg ggcttgcgct 14700
ctgccagcgc tgggctggcc tcggccatgg ccttgccgat ttcctcggca ctgcggcccc 14760
ggctggccag cttctgcgcg gcgataaagt cgcacttgct gaggtcatga ccgaagcgct 14820
tgaccagccc ggccatctcg ctgcggtact cgtccagcgc cgtgcgccgg tggcggctaa 14880
gctgccgctc gggcagttcg aggctggcca gcctgcgggc cttctcctgc tgccgctggg 14940
cctgctcgat ctgctggcca gcctgctgca ccagcgccgg gccagcggtg gcggtcttgc 15000
ccttggattc acgcagcagc acccacggct gataaccggc gcgggtggtg tgcttgtcct 15060
tgcggttggt gaagcccgcc aagcggccat agtggcggct gtcggcgctg gccgggtcgg 15120
cgtcgtactc gctggccagc gtccgggcaa tctgcccccg aagttcaccg cctgcggcgt 15180
cggccacctt gacccatgcc tgatagttct tcgggctggt ttccactacc agggcaggct 15240
cccggccctc ggctttcatg tcatccaggt caaactcgct gaggtcgtcc accagcacca 15300
gaccatgccg ctcctgctcg gcgggcctga tatacacgtc attgccctgg gcattcatcc 15360
gcttgagcca tggcgtgttc tggagcactt cggcggctga ccattcccgg ttcatcatct 15420
ggccggtggg tgcgtccctg acgccgatat cgaagcgctc acagcccatg gccttgagct 15480
gtcggcctat ggcctgcaaa gtcctgtcgt tcttcatcgg gccaccaagc gcagccagat 15540
cgagccgtcc tcggttgtca gtggcgtcag gtcgagcaag agcaacgatg cgatcagcag 15600
caccaccgta ggcatcatgg aagccagcat cacggttagc catagcttcc agtgccaccc 15660
ccgcgacgcg ctccgggcgc tctgcgcggc gctgctcacc tcggcggcta cctcccgcaa 15720
ctctttggcc agctccaccc atgccgcccc tgtctggcgc tgggctttca gccactccgc 15780
cgcctgcgcc tcgctggcct gcttggtctg gctcatgacc tgccgggctt cgtcggccag 15840
tgtcgccatg ctctgggcca gcggttcgat ctgctccgct aactcgttga tgcctctgga 15900
tttcttcact ctgtcgattg cgttcatggt ctattgcctc ccggtattcc tgtaagtcga 15960
tgatctgggc gttggcggtg tcgatgttca gggccacgtc tgcccggtcg gtgcggatgc 16020
cccggccttc catctccacc acgttcggcc ccaggtgaac accgggcagg cgctcgatgc 16080
cctgcgcctc aagtgttctg tggtcaatgc gggcgtcgtg gccagcccgc tctaatgccc 16140
ggttggcatg gtcggcccat gcctcgcggg tctgctcaag ccatgccttg ggcttgagcg 16200
cttcggtctt ctgtgccccg cccttctccg gggtcttgcc gttgtaccgc ttgaaccact 16260
gagcggcggg ccgctcgatg ccgtcattga tccgctcgga gatcatcagg tggcagtgcg 16320
ggttctcgcc gccaccggca tggatggcca gcgtatacgg caggcgctcg gcaccggtca 16380
ggtgctgggc gaactcggac gccagcgcct tctgctggtc gagggtcagc tcgaccggca 16440
gggcaaattc gacctccttg aacagccgcc cattggcgcg ttcatacagg tcggcagcat 16500
cccagtagtc ggcgggccgc tcgacgaact ccggcatgtg cccggattcg gcgtgcaaga 16560
cttcatccat gtcgcgggca tacttgcctt cgcgctggat gtagtcggcc ttggccctgg 16620
ccgattggcc gcccgacctg ctgccggttt tcgccgtaag gtgataaatc gccatgctgc 16680
ctcgctgttg cttttgcttt tcggctccat gcaatggccc tcggagagcg caccgcccga 16740
agggtggccg ttaggccagt ttctcgaaga gaaaccggta agtgcgccct cccctacaaa 16800
gtagggtcgg gattgccgcc gctgtgcctc catgatagcc tacgagacag cacattaaca 16860
atggggtgtc aagatggtta aggggagcaa caaggcggcg gatcggctgg ccaagctcga 16920
agaacaacga gcgcgaatca atgccgaaat tcagcgggag cgggcaaggg aacagcagca 16980
agagcgcaag aacgaaacaa ggcgcaaggt gctggtgggg gccatgattt tggccaaggt 17040
gaacagcagc gagtggccgg aggatcggct catggcggca atggatgcgt accttgaacg 17100
cgaccacgac cgcgccttgt tcggtctgcc gccacgccag aaggatgagc cgggctgaat 17160
gatcgaccga gacaggccct gcggggctgc acacgcgccc ccacccttcg ggtaggggga 17220
aaggccgcta aagcggctaa aagcgctcca gcgtatttct gcggggtttg gtgtggggtt 17280
tagcgggctt tgcccgcctt tccccctgcc gcgcagcggt ggggcggtgt gtagcctagc 17340
gcagcgaata gaccagctat ccggcctctg gccgggcata ttgggcaagg gcagcagcgc 17400
cccacaaggg cgctgataac cgcgcctagt ggattattct tagataatca tggatggatt 17460
tttccaacac cccgccagcc cccgcccctg ctgggtttgc aggtttgggg gcgtgacagt 17520
tattgcaggg gttcgtgaca gttattgcag gggggcgtga cagttattgc aggggttcgt 17580
gacagttagt acgggagtga cgggcactgg ctggcaatgt ctagcaacgg caggcatttc 17640
ggctgagggt aaaagaactt tccgctaagc gatagactgt atgtaaacac agtattgcaa 17700
ggacgcggaa catgcctcat gtggcggcca gga 17733

<210> SEQ ID NO 84
<211> LENGTH: 16842
<212> TYPE: DNA
<213> ORGANISM: Artificial Sequence
<220> FEATURE:
<223> OTHER INFORMATION: sequence of plasmid Sh-PrnpB

<400> SEQUENCE: 84
ctcgcgagaa ttaattcaga taaaaaaaat ccttagcttt cgctaaggat gatttctagc 60
gatgaccctg ctgattggtt cgctgaccat ttccgggtgc gggacggcgt taccagaaac 120
tcagaaggtt cgtccaacca aaccgactct gacggcagtt tacgagagag atgataggt 180 ctgcttcagt aagccagatg ctacacaatt aggcttgtac gggtactcga cctgcatccc 240

```
ttaacttact tattaaataa tttatagcta ttgaaaagag ataagaattg ttcaaagcta    300
atattgttta aatcgtcaat tcctgcatgt tttaaggaat tgttaaattg attttttgta    360
aatattttct tgtattcttt gttaaaataa aaaaggggac ctctagggtc cccaattaat    420
tagtaatata atctattaaa ggtcattcaa aaggtcatcc accggatcag cttagtaaag    480
ccctcgctag attttaatgc ggatgttgcg attacttcgc caactattgc gataacaaga    540
aaaagccagc ctttcatgat atatctccca atttgtgtag ggcttattat gcacgcttaa    600
aaataataaa agcagacttg acctgatagt ttggctgtga gcaattatgt gcttagtgca    660
tctaacgctt gagttaagcc gcgccgcgaa gcggcgtcgg cttgaacgaa ttgttagaca    720
ttatttgccg actaccttgg tgatctcgcc tttcacgtag tggacaaatt cttccaactg    780
atctgcgcgc gaggccaagc gatcttcttc ttgtccaaga taagcctgtc tagcttcaag    840
tatgacgggc tgatactggg ccggcaggcg ctccattgcc cagtcggcag cgacatcctt    900
cggcgcgatt ttgccggtta ctgcgctgta ccaaatgcgg gacaacgtaa gcactacatt    960
tcgctcatcg ccagcccagt cgggcggcga gttccatagc gttaaggttt catttagcgc   1020
ctcaaataga tcctgttcag gaaccggatc aaagagttcc tccgccgctg gacctaccaa   1080
ggcaacgcta tgttctcttg cttttgtcag caagatagcc agatcaatgt cgatcgtggc   1140
tggctcgaag atacctgcaa gaatgtcatt gcgctgccat tctccaaatt gcagttcgcg   1200
cttagctgga taacgccacg gaatgatgtc gtcgtgcaca acaatggtga cttctacagc   1260
gcggagaatc tcgctctctc caggggaagc cgaagtttcc aaaaggtcgt tgatcaaagc   1320
tcgccgcgtt gtttcatcaa gccttacggt caccgtaacc agcaaatcaa tatcactgtg   1380
tggcttcagg ccgccatcca ctgcggagcc gtacaaatgt acggccagca acgtcggttc   1440
gagatggcgc tcgatgacgc caactacctc tgatagttga gtcgatactt cggcgatcac   1500
cgcttccctc atgatgttta actttgtttt agggcgactg ccctgctgcg taacatcgtt   1560
gctgctccat aacatcaaac atcgacccac ggcgtaacgc gcttgctgct tggatgcccg   1620
aggcatagac tgtaccccaa aaaaacagtc ataacaagcc atgaaaaccg ccactgcgcc   1680
gttaccaccg ctgcgttcgg tcaaggttct ggaccagttg cgtgagcgca tacgctactt   1740
gcattacagc ttacgaaccg aacaggctta tgtccactgg gttcgtgcct tcatccgttt   1800
ccacggtgtg cgtcacccgg caaccttggg cagcagcgaa gtcgaggcat ttctgtcctg   1860
gctggcgaac gagcgcaagg tttcggtctc cacgcatcgt caggcattgg cggccttgct   1920
gttcttctac ggcaaggtgc tgtgcacgga tctgccctgg cttcaggaga tcggaagacc   1980
tcggccgtcg cggcgcttgc cggtggtgct gaccccggat gaagtggttc gcatcctcgg   2040
ttttctggaa ggcgagcatc gtttgttcgc ccagcttctg tatggaacgg gcggatcagt   2100
gagggtttgc aactgcgggt caaggatctg gatttcgatc acggcacgat catcgtgcgg   2160
gagggcaagg gctccaagga tcgggccttg atgttacccg agagcttggc acccagcctg   2220
cgcgagcagg ggaattgatc cggtggatga ccttttgaat gacctttaat agattatatt   2280
actaattaat tggggaccct agaggtcccc tttttatttt tctgaacggt ctggttatag   2340
gtacattgag caactgactg aaatgcctca aaatgttctt tacgatgcca ttgggatata   2400
tcaacggtgg tatatccagt gatttttttc tccattttag cttccttagc tcctgaaaat   2460
ctcgataact caaaaaatac gcccggtagt gatcttattt cattatggtg aaagttggaa   2520
cctcttacga gcggccgcat acgatttagg tgacactata ggatccctgc cggccggtcc   2580
```

-continued

```
ggcgcgcccg ggctcgagtg cacgtacgtt caatgcggtc caatacctcc cctgcccaac   2640
tgggtaagct cgcggctcca ctgagtaata cagacaaggc taaacaggca aatttttca    2700
ttggtcaact cctagcacca atttcccaag actacggagg gggcaatgaa gtttcaatta   2760
attggggtca caaaccacag cggcctatgg ctctaatcaa tggcacacta gaaaaagacg   2820
tcatgggtac acctcacgct acttttgcag ctactgagac agcatttcat gtgacgggct   2880
acgaaaagat agattttagc ctggtttatg tgaatggtgt attcaacatc aaaaacacag   2940
aaattgctga tagttatcag aagtttggac gctgcttgac tgttgttgat cataatgtct   3000
accgtttgta tggagaccaa attaagtcat attttcgtta ctacgacata gacttaactg   3060
tgtttccaat tactattact gaacctggca aaaccatgtc aacttttgaa caagtagttg   3120
atgcgtttgc cgattttggc ttaattcgta aagaaccagt tttagtagtt ggtggtggtt   3180
tagttactga tgttgtaggt tttgcttgtg cagcttatcg tcgcagtact aactatattc   3240
gcattcccac gactttgatt ggtttgatag atgctggaat tgcgattaaa gtagcagtca   3300
atcataaaaa gctgaaaaat cgcttgggtg cttaccatgc accgcagaaa gtcattctag   3360
acttttcctt tctcaagaca ctaccaacag cccaagtccg gaatggaatg gcggagttag   3420
tgaaaattgc tgtggtagca aatgcagaag tttttaattg gctgtatgag tacggagaag   3480
atttactgca tacacacttt ggctatctca acggtacaga ggaactgcaa gaaattgctc   3540
acaaagttaa ctacgaagca attaaaacca tgctggagtt agaaactcca aacctgcatg   3600
agctagactt agatcgcgtc attgcttatg gtcacacttg gagtccgaca ctagaattag   3660
caccgcgggt tcctctgtat catggtcatg ctgtcaacat cgatatggcg ctatcagcaa   3720
ctattgctga acgacgggga tatattactg tagcagaacg cgatcgcatt cttggattga   3780
tgagtcgtct aggtttagcc cttgatcatc cccttctaga tagcgatttg ttatggtacg   3840
ctacccagtc tatcacccag acaagagacg ggaaacaacg cgccgccatg ccaaaaccta   3900
ttggtgagtg tttctttgtc aatgacctaa cccgtgaaga attgcatcaa gctttgattg   3960
cacacaagga tgtatgtgca acatatcccc gtggtggaga tgggattgaa gcctatatca   4020
gtgcagaaca atctgagatg gtaggagttt agaatcgtga ctagcattgt tgaaaagaac   4080
acagctagac ccgtaactcc ccacggtatc ttggttgaac agctacaaaa aactctggct   4140
ttggcagaat caggaaatac acctgaaact gttgtgactg cactacgaca ggcgtatcaa   4200
ttagcggcgg gtttagaacc ttatattagt gaacacacca ctactgaatc tgacgcctta   4260
gcagcactgg tacaaaaaac taccaaagaa gactggacaa aacgtttcac tgatggtgaa   4320
acagtgcgtc aactagaaca ggaaatgctt tctggacacg tcgagggaca aaccctgaaa   4380
atgtttgttc acatgactaa agccaagagt gttttggaag taggaatgtt caccgggtat   4440
tctgctttgg caatggcaga ggcattacct gatgatggac gagtggtagc atgtgaagta   4500
gactcttatg ttgctagctt tgctcaaact tgtttccaaa actcgcccca cggtcataaa   4560
attactgtgg aagttgcacc agccttggaa actctgcaaa aacttgcagc agcaggtgaa   4620
tcatttgatt tgatattcat cgatgctgac aagaaagagt atgtgcagta tttccagatc   4680
atcttggata ataatctact tgcatctaac ggcattattt gtgtagataa cactttaatg   4740
cagggacagg tttatctgcc accagaacaa cgtacagcta atggtgaagc gatcgctcaa   4800
tttaaccaaa tcattaccca agatccgcgt gtagaacaag ttatactacc gcttcgtgat   4860
ggtgtgactt taattcggcg gttgtagaag gatggggttt gggtggtact gatgggtttt   4920
ttttgagggc gaattatatg acacaatcta tttctgtggc ttctgttgga caaacaactc   4980
```

```
agtcggtgag cctgggactt cgcatatctg cgttgtggaa aagtttagct acacttgcac   5040
tgctgttgtt agtattgcca atcaatgctg cgattgtgtt ggtatcgctg ttattgggta   5100
gtcaatcgca agcgatcgcc accgaaccca aaaacatctt gattagtggc ggtaaaatga   5160
ctaaggcgtt acaattagcc cgtagttttc acgccgccgg acatcgagtg gttttagtag   5220
aaactcacaa atactggtta acgggacacc gattttccaa agcagtaagt cgtttctaca   5280
ctctaccaac gccccaatct gatcctgaag catacaccca agccctatta gatattgttc   5340
aaaaagaaaa tatcgatgtc tatgtacccg tgtgcagtcc ggttgctagt tactacgact   5400
ctttagctaa acccgtactg tcgaagtact gcgaggtttt tcactgtgac gcagatgtca   5460
cccaaatgtt ggatgataaa tacgcttttg ctgagaaagc gcggagtttg gggttatctg   5520
ttcccaagtc tttcaaaatt actgacccgg aacaggtgag caactttgat ttttctcaag   5580
aaaagcgtaa atacatcctc aaaagcattc cttatgactc tgttcgtcgc ttagatttaa   5640
ccaaacttcc ttgtgagact cccgaagcaa cagcagattt tgtcaacagc ttacccatca   5700
gttcccaaaa gccatggatt atgcaagaat tcattcctgg aaaagaattt tgcacccaca   5760
gcactgtccg caatggggag ttgagaatgc attgctgttg tgaatcttcg gcatttcaag   5820
ttaactatga gaatgtcgat catccccaaa ttttggaatg ggtgcgacac tttgtcaaag   5880
cattaggtat cactggacag gtatcttttg attttatcga agcacaagat ggcacaatct   5940
acgccattga atgtaatccg cgtacccatt ctgccatcac tatgttctac aatcatccgg   6000
atgtggcaaa tgcttatttg agtgaaattc cacaagtaga accaattcaa cctctgatta   6060
atagtaagcc tacctactgg acttatcacg aaatttggcg attgacagga attcgttctt   6120
tctcacagtt gcaaacttgg ttgaaaaact tttttggtgg aaaagatgcg atttacagtt   6180
tgagtgatcc tctacctttt ttaacagttc atcactggca aattccttta ttattgctac   6240
aaaatttgca acagctaaaa ggttggatca ggatagattt taatattggg aaattggttg   6300
agtttggtgg cgattagatt cagttatcag ttatcagtta tcagttagta gctgttcact   6360
gataatttat agatattgaa tatatataag actcatattt gatttctgaa atacacgtag   6420
ggtgcgtgat agctacgcca taacacaccc tactggcgcg tcaagcctaa aatgttgcaa   6480
taaatctctg attctatctc tgtgttctct ctcttgaaaa gctttgatcg gaggaaacct   6540
ccgctcaaac ttttcgctgc ttcctctgcg gtttattaat gcactatttt aaggctgtcg   6600
cgccctttgt taaagtcaaa ttttttatc aaaccgcaga ggcgcagagg aatcagagag   6660
aaggaaataa ttcttaattg aattgtatta agttataaat cactatattt tatcaaagat   6720
ggaaataata aactttttag atgattctct ggaaattgaa gaacagaaga aaaattggga   6780
aagacaggta ggagatattt ctgatctttc tctgctgagt ttagaagaac agcaaaaaat   6840
attatttata tggaatcaga cagaaagtaa ttatgatttg tcgatttgtc tacatgagtt   6900
atttgcagca caggtagaga aaacaccaga tgcaaaagct ctcaagtttg ctgatcaaga   6960
attgagttat catcagttaa attgtcgggc gaatcaactc gctcactatt tgcaatcttt   7020
gggaattgta actgaagatt tagttgggat ttgtgtggaa cgttccctag aaatggttgt   7080
ggggttattg ggtattttga aagcgggtgc ggcttatgtt ccaattgatc ctggatatcc   7140
ccaagaacgt ttaggatata tgttggcgga ttcccaggtg tcggtgttgt tgactcaaag   7200
tcatttagtc gatagtttac caacatgtcc aacccatact atttgcttgg atactgactg   7260
ggatctgatt tctcaatata gcgatcgcaa tctccaaaat acaacgacac cagaaaatct   7320
```

-continued

```
cgcttatgta atttacactt ctggttctac tggtaaacct aaaggagcga tgaataccca   7380
tcgcggtatt tgcaatcgtc tgttatggat gcaagatgct tatcaactca ctcaacaaga   7440
tcgggttctg caaaaaactc cctttagttt tgatgtctct gtctgggaat tcttttggcc   7500
gttgattacc ggggcgcggc tgattatagc acaaccaggt ggacacaagg atagttctta   7560
tctaattaat acaattatcc aagaagaaat taccacatta cattttgttc cttcgatgtt   7620
gcaggtattt ttgcaagcta aaggagtgga aaattgtcag tcattaaaac gggtaattac   7680
tagtggtgaa gctttacctg tgagtctgca agaacggttt tttgaacgtt tgggatgtga   7740
actgcacaat ctttatggtc ctacagaagc agcgatcgat gttacgtttt ggcagtgtca   7800
acctcaaagt caatatcaaa cagtaccgat tggtcgtccc atcgctaata ctcaaatata   7860
tatattagat caacatttgc aacctgtgcc tgtgggtgtt gtgggtgaac tttatattgg   7920
tggtgtggga gttgccagag gttactggcg tcgtccagaa ttaactacag aaagatttgt   7980
atctaatccc tttgcaacgg gacaaatgta taaaactggt gacttggcgc gctatttacc   8040
tgatggtaat atcgagtatg ttggcagaat tgacgatcaa gttaaaattc gcggttttcg   8100
gattgagttg ggagaaattg agagtacgct gacgcaacat tcccagatta gtcaagctgt   8160
ggttgtcgcc cagacagata atttgaataa taagcattta attgcttata ttgttcccca   8220
gggagaacca cccacaccaa cccaactgcg gaatttcctt cagggtaagc tacctgaatt   8280
catggttccc tcagcttttg tctgcttaaa ttcctttcct ctcactccta gtggaaaaat   8340
agacaggcga tcgcttccca aacctgattt ttctaactta atcactcatg aagattttac   8400
gcctgcacgc aatgatttag agagaaaaat cgcgcagatt tggtcagaaa ttttacagat   8460
ttcggaaatt gatattagag ataacttttt tgaagttggt ggtaattccc ttttagcatt   8520
acatttaatg aatgccatcg aacaaaaatt tggtcgagag ttagcactgt caactttact   8580
tactaataac tcaattgaaa aactagcaga aattctgcaa aaccccacag atgtttttcc   8640
caattcaccc atagtagcaa ttcagcccaa aggtacaaaa cgtccttttt tctgcatcca   8700
tccagccggc ggacatgtac tttgctattt tagtttggcg cattatttag gcactgacca   8760
gccattttac ggtttacaag cacagggttt ttatggtgaa gaagaaccac taactacagt   8820
tgtagaaatg gctaggcttt atgctcaagc tatacaaaca attcaaccca cagggccata   8880
tcaaattggt ggttggtcgt ttggtggtgt agttgcctat gaaacggctc aacaactaca   8940
ccaacaagga aaagaagttt cattactagc aattttagat tcctacgtgc caattctgtt   9000
agataaaaat aaaaaaattg atgatgttta tttagttggt gtactatccc gtgtatttgg   9060
cggaatgttt ggtcaagata atctgatttc actagcggaa atcgaaaatt taagtgtgga   9120
agaaagttta aattacatca tcgaaaaagc acgccaagcc aaaatttttc cgccaggagt   9180
ggaacgtcac aacaatcgcc gcattttaga tgttttagtc ggaactttaa aagccactta   9240
ttcttatgaa cgttgtccct atcctggcaa agttactatt tttagagcca gagaaaaaca   9300
tatcatggct cctgatccta ctttagtttg ggtagaatta ttttcagttt tggctgcgga   9360
ggaaattgaa attcataatg tccccggtaa tcactattca tttgttttag aacctcacgt   9420
ccaagctttg gctgaaagtt tgcagaaatg tttgtgctga tacaagatcc ccgacttctt   9480
tgaggatgca gctggcgaat agggggtcaa accccctcgtg cgcccacaaa ttggttgtag   9540
agacgcgcca tggcgcgtct ctacatctgg tggaatgacg aaaaatctcg gtgaggggtg   9600
tcacccctga ttcgccagct gtatcctttg agaagtcggg gagctcggta cccctagagt   9660
cgacctgcag ttcaatgcgg tccaatacct cccctgccca actgggtaag ctcgcggctc   9720
```

```
cactgagtaa tacagacaag gctaaacagg caaatttttt cattggtcaa ctcctagcac    9780
caatttccca agactacgga gggggcaatg aagtttcaat taattggggt cacaaaccac    9840
agcggcctat ggctctaatc aatggcacac tagaaaaaat gttgcagcat acttggctac    9900
caaaaccccc aaatttaacc ttattgtcag atgaagttca tctctggcgc attccccttg    9960
accaaccaga atcacagcta caggatttag ccgctacctt atctagtgac gaattagccc   10020
gtgcaaacag attttatttt cccgaacatc gccggcgttt tactgctggt cgtggtattc   10080
tccgcagtat cttgggggc tatttgggtg tggaaccagg gcaagttaaa tttgattatg    10140
aatcccgtgg taaaccaata ttaggcgatc gctttgccga gagtggttta ttatttaact   10200
tgtcacactc ccagaacttg gccttgtgtg cagtcaatta cacgcgccaa atcggcatcg   10260
atttagaata tctccgcccc acatctgatt tagaatccct tgccaaaagg ttctttttac   10320
cgcgagaata tgaattattg cgatcgctac ccgatgagca aaaacaaaaa atttctttc    10380
gttactggac ttgtaaagag gcttatctta aagcaacggg tgacggcatc gctaaattag   10440
aggaaattga aatagcacta actcccacag aaccagctaa gttacagaca gctccagcgt   10500
ggagtctcct agagctagtg ccagatgata attgtgttgc tgctgttgcc gtggcgggtt   10560
ttggctggca gccaaaattc tggcattatt gagcatgcaa gcttctccct atagtgagtc   10620
gtattagcgg ccgcatcgaa tataacttcg tataatgtat gctatacgaa gttattagcg   10680
atgaggacat gaggttgccc cgtattcagt gtcgctgatt tgtattgtct gaagttgttt   10740
ttacgttaag ttgatgcaga tcaattaata cgatacctgc gtcataattg attatttgac   10800
gtggtttgat ggcctccacg cacgttgtga tatgtagatg ataatcatta tcactttacg   10860
ggtcctttcc ggtgatccga caggttacgg ggcggcgacc tcgcgggttt tcgctattta   10920
tgaaaatttt ccggtttaag gcgtttccgt tcttcttcgt cataacttaa tgtttttatt   10980
taaaataccc tctgaaaaga aaggaaacga caggtgctga aagcgaggct ttttggcctc   11040
tgtcgtttcc tttctctgtt tttgtccgtg gaatgaacaa tggaagtcct cgtctcgccc   11100
tcgaattagc ccgcctaatg agcgggcttt ttttgaatta attctcgcga gctggcacga   11160
caggtttccc gactggaaag cgggcagtga gcgcaacgca attaatgtaa gttagcgcga   11220
attgcaagct ggccgacgcg ctgggctacg tcttgctggc gttcgggagc agaagagcat   11280
acatctggaa gcaaagccag gaaagcggcc tatggagctg tgcggcagcg ctcagtaggc   11340
aatttttcaa aatattgtta agcctttttct gagcatggta tttttcatgg tattaccaat  11400
tagcaggaaa ataagccatt gaatataaaa gataaaaatg tcttgtttac aatagagtgg   11460
ggggggtcag cctgccgcct tgggccgggt gatgtcgtac ttgcccgccg cgaactcggt   11520
taccgtccag cccagcgcga ccagctccgg caacgcctcg cgcacccgct tgcggcgctt   11580
gcgcatggtc gaaccactgg cctctgacgg ccagacatag ccgcacaagg tatctatgga   11640
agccttgccg gttttgccgg ggtcgatcca gccacacagc cgctggtgca gcaggcgggc   11700
ggtttcgctg tccagcgccc gcacctcgtc catgctgatg cgcacatgct ggccgccacc   11760
catgacggcc tgcgcgatca aggggttcag ggccacgtac aggcgcccgt ccgcctcgtc   11820
gctggcgtac tccgacagca gccgaaaccc ctgccgcttg cggccattct gggcgatgat   11880
ggataccttc caaaggcgct cgatgcagtc ctgtatgtgc ttgagcgccc caccactatc   11940
gacctctgcc ccgatttcct ttgccagcgc ccgatagcta cctttgacca catggcattc   12000
agcggtgacg gcctcccact tgggttccag gaacagccgg agctgccgtc cgccttcggt   12060
```

-continued

```
cttgggttcc gggccaagca ctaggccatt aggcccagcc atggccacca gcccttgcag  12120
gatgcgcaga tcatcagcgc ccagcggctc cgggccgctg aactcgatcc gcttgccgtc  12180
gccgtagtca tacgtcacgt ccagcttgct gcgcttgcgc tcgccccgct tgagggcacg  12240
gaacaggccg gggccagac agtgcgccgg gtcgtgccgg acgtggctga ggctgtgctt  12300
gttcttaggc ttcaccacgg ggcacccccct tgctcttgcg ctgcctctcc agcacggcgg  12360
gcttgagcac cccgccgtca tgccgcctga accaccgatc agcgaacggt gcgccatagt  12420
tggccttgct cacaccgaag cggacgaaga accggcgctg gtcgtcgtcc acaccccatt  12480
cctcggcctc ggcgctggtc atgctcgaca ggtaggactg ccagcggatg ttatcgacca  12540
gtaccgagct gccccggctg gcctgctgct ggtcgcctgc gcccatcatg gccgcgccct  12600
tgctggcatg gtgcaggaac acgatagagc acccggtatc ggcggcgatg gcctccatgc  12660
gaccgatgac ctgggccatg gggccgctgg cgttttcttc ctcgatgtgg aaccggcgca  12720
gcgtgtccag caccatcagg cggcggccct cggcggcgcg cttgaggccg tcgaaccact  12780
ccggggccat gatgttgggc aggctgccga tcagcggctg gatcagcagg ccgtcagcca  12840
cggcttgccg ttcctcggcg ctgaggtgcg ccccaagggc gtgcaggcgg tgatgaatgg  12900
cggtgggcgg gtcttcggcg ggcaggtaga tcaccgggcc ggtgggcagt tcgcccacct  12960
ccagcagatc cggcccgcct gcaatctgtg cggccagttg cagggccagc atggatttac  13020
cggcaccacc gggcgacacc agcgccccga ccgtaccggc caccatgttg ggcaaaacgt  13080
agtccagcgg tggcggcgct gctgcgaacg cctccagaat attgataggc ttatgggtag  13140
ccattgattg cctcctttgc aggcagttgg tggttaggcg ctggcggggt cactaccccc  13200
gccctgcgcc gctctgagtt cttccaggca ctcgcgcagc gcctcgtatt cgtcgtcggt  13260
cagccagaac ttgcgctgac gcatcccttt ggccttcatg cgctcggcat atcgcgcttg  13320
gcgtacagcg tcagggctgg ccagcaggtc gccggtctgc ttgtcctttt ggtctttcat  13380
atcagtcacc gagaaacttg ccggggccga aaggcttgtc ttcgcggaac aaggacaagg  13440
tgcagccgtc aaggttaagg ctggccatat cagcgactga aaagcggcca gcctcggcct  13500
tgtttgacgt ataaccaaag ccaccgggca accaatagcc cttgtcactt ttgatcaggt  13560
agaccgaccc tgaagcgctt ttttcgtatt ccataaaacc cccttctgtg cgtgagtact  13620
catagtataa caggcgtgag taccaacgca agcactacat gctgaaatct ggcccgcccc  13680
tgtccatgcc tcgctggcgg ggtgccggtg cccgtgccag ctcggcccgc gcaagctgga  13740
cgctgggcag acccatgacc ttgctgacgg tgcgctcgat gtaatccgct tcgtggccgg  13800
gcttgcgctc tgccagcgct gggctggcct cggccatggc cttgccgatt tcctcggcac  13860
tgcggccccg gctggccagc ttctgcgcgg cgataaagtc gcacttgctg aggtcatgac  13920
cgaagcgctt gaccagcccg gccatctcgc tgcggtactc gtccagcgcc gtgcgccggt  13980
ggcggctaag ctgccgctcg ggcagttcga ggctggccag cctgcgggcc ttctcctgct  14040
gccgctgggc ctgctcgatc tgctggccag cctgctgcac cagcgccggg ccagcggtgg  14100
cggtcttgcc cttggattca cgcagcagca cccacggctg ataaccggcg cgggtggtgt  14160
gcttgtcctt gcggttggtg aagcccgcca agcggccata gtggcggctg tcggcgctgg  14220
ccgggtcggc gtcgtactcg ctggccagcg tccgggcaat ctgcccccga agttcaccgc  14280
ctgcggcgtc ggccaccttg acccatgcct gatagttctt cgggctggtt tccactacca  14340
gggcaggctc ccggccctcg gctttcatgt catccaggtc aaactcgctg aggtcgtcca  14400
ccagcaccag accatgccgc tcctgctcgg cgggcctgat atacacgtca ttgccctggg  14460
```

cattcatccg cttgagccat ggcgtgttct ggagcacttc ggcggctgac cattcccggt 14520
tcatcatctg gccggtgggt gcgtccctga cgccgatatc gaagcgctca cagcccatgg 14580
ccttgagctg tcggcctatg gcctgcaaag tcctgtcgtt cttcatcggg ccaccaagcg 14640
cagccagatc gagccgtcct cggttgtcag tggcgtcagg tcgagcaaga gcaacgatgc 14700
gatcagcagc accaccgtag gcatcatgga agccagcatc acggttagcc atagcttcca 14760
gtgccacccc cgcgacgcgc tccgggcgct ctgcgcggcg ctgctcacct cggcggctac 14820
ctcccgcaac tctttggcca gctccaccca tgccgcccct gtctggcgct gggctttcag 14880
ccactccgcc gcctgcgcct cgctggcctg cttggtctgg ctcatgacct gccgggcttc 14940
gtcggccagt gtcgccatgc tctgggccag cggttcgatc tgctccgcta actcgttgat 15000
gcctctggat ttcttcactc tgtcgattgc gttcatggtc tattgcctcc cggtattcct 15060
gtaagtcgat gatctgggcg ttggcggtgt cgatgttcag ggccacgtct gcccggtcgg 15120
tgcggatgcc ccggccttcc atctccacca cgttcggccc caggtgaaca ccgggcaggc 15180
gctcgatgcc ctgcgcctca agtgttctgt ggtcaatgcg ggcgtcgtgg ccagcccgct 15240
ctaatgcccg gttggcatgg tcggcccatg cctcgcgggt ctgctcaagc catgccttgg 15300
gcttgagcgc ttcggtcttc tgtgccccgc ccttctccgg ggtcttgccg ttgtaccgct 15360
tgaaccactg agcggcgggc cgctcgatgc cgtcattgat ccgctcggag atcatcaggt 15420
ggcagtgcgg gttctcgccg ccaccggcat ggatggccag cgtatacggc aggcgctcgg 15480
caccggtcag gtgctgggcg aactcggacg ccagcgcctt ctgctggtcg agggtcagct 15540
cgaccggcag ggcaaattcg acctccttga acagccgccc attggcgcgt tcatacaggt 15600
cggcagcatc ccagtagtcg gcgggccgct cgacgaactc cggcatgtgc ccggattcgg 15660
cgtgcaagac ttcatccatg tcgcgggcat acttgccttc gcgctggatg tagtcggcct 15720
tggccctggc cgattggccg cccgacctgc tgccggtttt cgccgtaagg tgataaatcg 15780
ccatgctgcc tcgctgttgc ttttgctttt cggctccatg caatggccct cggagagcgc 15840
accgcccgaa gggtggccgt taggccagtt tctcgaagag aaaccggtaa gtgcgccctc 15900
ccctacaaag tagggtcggg attgccgccg ctgtgcctcc atgatagcct acgagacagc 15960
acattaacaa tggggtgtca agatggttaa ggggagcaac aaggcggcgg atcggctggc 16020
caagctcgaa gaacaacgag cgcgaatcaa tgccgaaatt cagcgggagc gggcaaggga 16080
acagcagcaa gagcgcaaga acgaaacaag gcgcaaggtg ctggtggggg ccatgatttt 16140
ggccaaggtg aacagcagcg agtggccgga ggatcggctc atggcggcaa tggatgcgta 16200
ccttgaacgc gaccacgacc gcgccttgtt cggtctgccg ccacgccaga aggatgagcc 16260
gggctgaatg atcgaccgag acaggccctg cggggctgca cacgcgcccc caccettcgg 16320 gtagggggaa aggccgctaa agcggctaaa agcgctccag cgtatttctg cggggtttgg 16380
tgtggggttt agcgggcttt gcccgccttt ccccctgccg cgcagcggtg gggcggtgtg 16440
tagcctagcg cagcgaatag accagctatc cggcctctgg ccgggcatat tgggcaaggg 16500
cagcagcgcc ccacaagggc gctgataacc gcgcctagtg gattattctt agataatcat 16560
ggatggattt ttccaacacc ccgccagccc ccgcccctgc tgggtttgca ggtttggggg 16620
cgtgacagtt attgcagggg ttcgtgacag ttattgcagg ggggcgtgac agttattgca 16680
ggggttcgtg acagttagta cgggagtgac gggcactggc tggcaatgtc tagcaacggc 16740
aggcatttcg gctgagggta aaagaacttt ccgctaagcg atagactgta tgtaaacaca 16800
gtattgcaag gacgcggaac atgcctcatg tggcggccag ga 16842

<210> SEQ ID NO 85
<211> LENGTH: 16985
<212> TYPE: DNA
<213> ORGANISM: Artificial Sequence
<220> FEATURE:
<223> OTHER INFORMATION: sequence of plasmid Sh-Ptrc

<400> SEQUENCE: 85
ctcgcgagaa ttaattcaga taaaaaaaat ccttagcttt cgctaaggat gatttctagc 60
gatgaccctg ctgattggtt cgctgaccat ttccgggtgc gggacggcgt taccagaaac 120
tcagaaggtt cgtccaacca aaccgactct gacggcagtt tacgagagag atgatagggt 180
ctgcttcagt aagccagatg ctacacaatt aggcttgtac gggtactcga cctgcatccc 240
ttaacttact tattaaataa tttatagcta ttgaaaagag ataagaattg ttcaaagcta 300
atattgttta aatcgtcaat tcctgcatgt tttaaggaat tgttaaattg atttttgta 360 aatattttct tgtattcttt gttaaaataa aaaaggggac ctctagggtc cccaattaat 420
tagtaatata atctattaaa ggtcattcaa aaggtcatcc accggatcag cttagtaaag 480
ccctcgctag attttaatgc ggatgttgcg attacttcgc caactattgc gataacaaga 540
aaaagccagc ctttcatgat atatctccca atttgtgtag ggcttattat gcacgcttaa 600
aaataataaa agcagacttg acctgatagt ttggctgtga gcaattatgt gcttagtgca 660
tctaacgctt gagttaagcc gcgccgcgaa gcggcgtcgg cttgaacgaa ttgttagaca 720
ttatttgccg actaccttgg tgatctcgcc tttcacgtag tggacaaatt cttccaactg 780
atctgcgcgc gaggccaagc gatcttcttc ttgtccaaga taagcctgtc tagcttcaag 840
tatgacgggc tgatactggg ccggcaggcg ctccattgcc cagtcggcag cgacatcctt 900
cggcgcgatt ttgccggtta ctgcgctgta ccaaatgcgg gacaacgtaa gcactacatt 960
tcgctcatcg ccagcccagt cgggcggcga gttccatagc gttaaggttt catttagcgc 1020
ctcaaataga tcctgttcag gaaccggatc aaagagttcc tccgccgctg gacctaccaa 1080
ggcaacgcta tgttctcttg cttttgtcag caagatagcc agatcaatgt cgatcgtggc 1140
tggctcgaag atacctgcaa gaatgtcatt gcgctgccat tctccaaatt gcagttcgcg 1200
cttagctgga taacgccacg gaatgatgtc gtcgtgcaca acaatggtga cttctacagc 1260
gcggagaatc tcgctctctc caggggaagc cgaagtttcc aaaaggtcgt tgatcaaagc 1320
tcgccgcgtt gtttcatcaa gccttacggt caccgtaacc agcaaatcaa tatcactgtg 1380
tggcttcagg ccgccatcca ctgcggagcc gtacaaatgt acggccagca acgtcggttc 1440
gagatggcgc tcgatgacgc caactacctc tgatagttga gtcgatactt cggcgatcac 1500
cgcttccctc atgatgttta actttgtttt agggcgactg ccctgctgcg taacatcgtt 1560
gctgctccat aacatcaaac atcgacccac ggcgtaacgc gcttgctgct tggatgcccg 1620
aggcatagac tgtaccccaa aaaaacagtc ataacaagcc atgaaaaccg ccactgcgcc 1680
gttaccaccg ctgcgttcgg tcaaggttct ggaccagttg cgtgagcgca tacgctactt 1740
gcattacagc ttacgaaccg aacaggctta tgtccactgg gttcgtgcct tcatccgttt 1800
ccacggtgtg cgtcacccgg caaccttggg cagcagcgaa gtcgaggcat ttctgtcctg 1860
gctggcgaac gagcgcaagg tttcggtctc cacgcatcgt caggcattgg cggccttgct 1920
gttcttctac ggcaaggtgc tgtgcacgga tctgccctgg cttcaggaga tcggaagacc 1980
tcggccgtcg cggcgcttgc cggtggtgct gaccccggat gaagtggttc gcatcctcgg 2040

```
ttttctggaa ggcgagcatc gtttgttcgc ccagcttctg tatggaacgg gcggatcagt   2100
gagggtttgc aactgcgggt caaggatctg gatttcgatc acggcacgat catcgtgcgg   2160
gagggcaagg gctccaagga tcgggccttg atgttacccg agagcttggc acccagcctg   2220
cgcgagcagg ggaattgatc cggtggatga ccttttgaat gacctttaat agattatatt   2280
actaattaat tggggaccct agaggtcccc tttttatttt tctgaacggt ctggttatag   2340
gtacattgag caactgactg aaatgcctca aaatgttctt tacgatgcca ttgggatata   2400
tcaacggtgg tatatccagt gatttttttc tccattttag cttccttagc tcctgaaaat   2460
ctcgataact caaaaaatac gcccggtagt gatcttattt cattatggtg aaagttggaa   2520
cctcttacga gcggccgcat acgatttagg tgacactata ggatccctgc cggccggtcc   2580
ggcgcgcccg ggctcgagtg cacgtacgat tctgaaatga gctgttgaca attaatcatc   2640
cggctcgtat aatgtgtgga attgtgagcg gataacaatt tcacacagga aacagcgccg   2700
ctgagaaaaa gcgaagcggc actgctcttt aacaatttat cagacaatct gtgtgggcac   2760
tcgaccggaa ttatcgatta actttattat taaaaattaa agaggtatat attaatgtat   2820
cgattaaata aggaggaata aaccatgggg ggttctcatc atcatcatca tcatggtatg   2880
gctagcatga ctggtggaca gcaaatgggt cgggatctgt acgacgatga cgataaggat   2940
cgatggatcc gacctcgagg acgtcatggg tacacctcac gctacttttg cagctactga   3000
gacagcattt catgtgacgg gctacgaaaa gatagatttt agcctggttt atgtgaatgg   3060
tgtattcaac atcaaaaaca cagaaattgc tgatagttat cagaagtttg gacgctgctt   3120
gactgttgtt gatcataatg tctaccgttt gtatggagac caaattaagt catattttcg   3180
ttactacgac atagacttaa ctgtgtttcc aattactatt actgaacctg gcaaaaccat   3240
gtcaactttt gaacaagtag ttgatgcgtt tgccgatttt ggcttaattc gtaaagaacc   3300
agttttagta gttggtggtg gtttagttac tgatgttgta ggttttgctt gtgcagctta   3360
tcgtcgcagt actaactata ttcgcattcc cacgactttg attggtttga tagatgctgg   3420
aattgcgatt aaagtagcag tcaatcataa aaagctgaaa aatcgcttgg gtgcttacca   3480
tgcaccgcag aaagtcattc tagacttttc ctttctcaag acactaccaa cagcccaagt   3540
ccggaatgga atggcggagt tagtgaaaat tgctgtggta gcaaatgcag aagtttttaa   3600
ttggctgtat gagtacggag aagatttact gcatacacac tttggctatc tcaacggtac   3660
agaggaactg caagaaattg ctcacaaagt taactacgaa gcaattaaaa ccatgctgga   3720
gttagaaact ccaaacctgc atgagctaga cttagatcgc gtcattgctt atggtcacac   3780
ttggagtccg acactagaat tagcaccgcg ggttcctctg tatcatggtc atgctgtcaa   3840
catcgatatg gcgctatcag caactattgc tgaacgacgg ggatatatta ctgtagcaga   3900
acgcgatcgc attcttggat tgatgagtcg tctaggttta gcccttgatc atccccttct   3960
agatagcgat ttgttatggt acgctaccca gtctatcacc cagacaagag acgggaaaca   4020
acgcgccgcc atgccaaaac ctattggtga gtgtttcttt gtcaatgacc taacccgtga   4080
agaattgcat caagctttga ttgcacacaa ggatgtatgt gcaacatatc cccgtggtgg   4140
agatgggatt gaagcctata tcagtgcaga acaatctgag atggtaggag tttagaatcg   4200
tgactagcat tgttgaaaag aacacagcta gacccgtaac tccccacggt atcttggttg   4260
aacagctaca aaaaactctg gctttggcag aatcaggaaa tacacctgaa actgttgtga   4320
ctgcactacg acaggcgtat caattagcgg cgggtttaga accttatatt agtgaacaca   4380
```

-continued

```
ccactactga atctgacgcc ttagcagcac tggtacaaaa aactaccaaa gaagactgga   4440
caaaacgttt cactgatggt gaaacagtgc gtcaactaga acaggaaatg ctttctggac   4500
acgtcgaggg acaaaccctg aaaatgtttg ttcacatgac taaagccaag agtgttttgg   4560
aagtaggaat gttcaccggg tattctgctt tggcaatggc agaggcatta cctgatgatg   4620
gacgagtggt agcatgtgaa gtagactctt atgttgctag ctttgctcaa acttgtttcc   4680
aaaactcgcc ccacggtcat aaaattactg tggaagttgc accagccttg gaaactctgc   4740
aaaaacttgc agcagcaggt gaatcatttg atttgatatt catcgatgct gacaagaaag   4800
agtatgtgca gtatttccag atcatcttgg ataataatct acttgcatct aacggcatta   4860
tttgtgtaga taacacttta atgcagggac aggtttatct gccaccagaa caacgtacag   4920
ctaatggtga agcgatcgct caatttaacc aaatcattac ccaagatccg cgtgtagaac   4980
aagttatact accgcttcgt gatggtgtga ctttaattcg gcggttgtag aaggatgggg   5040
tttgggtggt actgatgggt ttttttgag ggcgaattat atgacacaat ctatttctgt   5100
ggcttctgtt ggacaaacaa ctcagtcggt gagcctggga cttcgcatat ctgcgttgtg   5160
gaaaagttta gctacacttg cactgctgtt gttagtattg ccaatcaatg ctgcgattgt   5220
gttggtatcg ctgttattgg gtagtcaatc gcaagcgatc gccaccgaac ccaaaaacat   5280
cttgattagt ggcggtaaaa tgactaaggc gttacaatta gcccgtagtt ttcacgccgc   5340
cggacatcga gtggttttag tagaaactca caaatactgg ttaacgggac accgattttc   5400
caaagcagta agtcgtttct acactctacc aacgccccaa tctgatcctg aagcatacac   5460
ccaagcccta ttagatattg ttcaaaaaga aaatatcgat gtctatgtac ccgtgtgcag   5520
tccggttgct agttactacg actctttagc taaacccgta ctgtcgaagt actgcgaggt   5580
tttcactgt gacgcagatg tcacccaaat gttggatgat aaatacgctt ttgctgagaa   5640
agcgcggagt ttggggttat ctgttcccaa gtctttcaaa attactgacc cggaacaggt   5700
gagcaacttt gatttttctc aagaaaagcg taaatacatc ctcaaaagca ttccttatga   5760
ctctgttcgt cgcttagatt taaccaaact tccttgtgag actcccgaag caacagcaga   5820
ttttgtcaac agcttaccca tcagttccca aaagccatgg attatgcaag aattcattcc   5880
tggaaaagaa ttttgcaccc acagcactgt ccgcaatggg gagttgagaa tgcattgctg   5940
ttgtgaatct tcggcatttc aagttaacta tgagaatgtc gatcatcccc aaattttgga   6000
atgggtgcga cactttgtca aagcattagg tatcactgga caggtatctt ttgattttat   6060
cgaagcacaa gatggcacaa tctacgccat tgaatgtaat ccgcgtaccc attctgccat   6120
cactatgttc tacaatcatc cggatgtggc aaatgcttat ttgagtgaaa ttccacaagt   6180
agaaccaatt caacctctga ttaatagtaa gcctacctac tggacttatc acgaaatttg   6240
gcgattgaca ggaattcgtt ctttctcaca gttgcaaact tggttgaaaa actttttttgg   6300
tggaaaagat gcgatttaca gtttgagtga tcctctacct tttttaacag ttcatcactg   6360
gcaaattcct ttattattgc tacaaaattt gcaacagcta aaaggttgga tcaggataga   6420
ttttaatatt gggaaattgg ttgagtttgg tggcgattag attcagttat cagttatcag   6480
ttatcagtta gtagctgttc actgataatt tatagatatt gaatatatat aagactcata   6540
tttgatttct gaaatacacg tagggtgcgt gatagctacg ccataacaca ccctactggc   6600
gcgtcaagcc taaaatgttg caataaatct ctgattctat ctctgtgttc tctctcttga   6660
aaagctttga tcggaggaaa cctccgctca aacttttcgc tgcttcctct gcggtttatt   6720
aatgcactat tttaaggctg tcgcgccctt tgttaaagtc aaattttttt atcaaaccgc   6780
```

```
agaggcgcag aggaatcaga gagaaggaaa taattcttaa ttgaattgta ttaagttata   6840
aatcactata ttttatcaaa gatggaaata ataaactttt tagatgattc tctggaaatt   6900
gaagaacaga agaaaaattg ggaaagacag gtaggagata tttctgatct ttctctgctg   6960
agtttagaag aacagcaaaa aatattattt atatggaatc agacagaaag taattatgat   7020
ttgtcgattt gtctacatga gttatttgca gcacaggtag agaaaacacc agatgcaaaa   7080
gctctcaagt ttgctgatca agaattgagt tatcatcagt taaattgtcg ggcgaatcaa   7140
ctcgctcact atttgcaatc tttgggaatt gtaactgaag atttagttgg gatttgtgtg   7200
gaacgttccc tagaaatggt tgtggggtta ttgggtattt tgaaagcggg tgcggcttat   7260
gttccaattg atcctggata tccccaagaa cgtttaggat atatgttggc ggattcccag   7320
gtgtcggtgt tgttgactca aagtcattta gtcgatagtt taccaacatg tccaacccat   7380
actatttgct tggatactga ctgggatctg atttctcaat atagcgatcg caatctccaa   7440
aatacaacga caccagaaaa tctcgcttat gtaatttaca cttctggttc tactggtaaa   7500
cctaaaggag cgatgaatac ccatcgcggt atttgcaatc gtctgttatg gatgcaagat   7560
gcttatcaac tcactcaaca agatcgggtt ctgcaaaaaa ctccctttag ttttgatgtc   7620
tctgtctggg aattcttttg gccgttgatt accggggcgc ggctgattat agcacaacca   7680
ggtggacaca aggatagttc ttatctaatt aatacaatta tccaagaaga aattaccaca   7740
ttacattttg ttccttcgat gttgcaggta tttttgcaag ctaaaggagt ggaaaattgt   7800
cagtcattaa aacgggtaat tactagtggt gaagctttac ctgtgagtct gcaagaacgg   7860
tttttttgaac gtttgggatg tgaactgcac aatctttatg gtcctacaga agcagcgatc   7920
gatgttacgt tttggcagtg tcaacctcaa agtcaatatc aaacagtacc gattggtcgt   7980
cccatcgcta atactcaaat atatatatta gatcaacatt tgcaacctgt gcctgtgggt   8040
gttgtgggtg aactttatat tggtggtgtg ggagttgcca gaggttactg gcgtcgtcca   8100
gaattaacta cagaaagatt tgtatctaat ccctttgcaa cgggacaaat gtataaaact   8160
ggtgacttgg cgcgctattt acctgatggt aatatcgagt atgttggcag aattgacgat   8220
caagttaaaa ttcgcggttt tcggattgag ttgggagaaa ttgagagtac gctgacgcaa   8280
cattcccaga ttagtcaagc tgtggttgtc gcccagacag ataatttgaa taataagcat   8340
ttaattgctt atattgttcc ccagggagaa ccacccacac caacccaact gcggaatttc   8400
cttcagggta agctacctga attcatggtt ccctcagctt ttgtctgctt aaattccttt   8460
cctctcactc ctagtggaaa aatagacagg cgatcgcttc ccaaacctga tttttctaac   8520
ttaatcactc atgaagattt tacgcctgca cgcaatgatt tagagagaaa aatcgcgcag   8580
atttggtcag aaattttaca gatttcggaa attgatatta gagataactt ttttgaagtt   8640
ggtggtaatt ccccttttagc attacattta atgaatgcca tcgaacaaaa atttggtcga   8700
gagttagcac tgtcaacttt acttactaat aactcaattg aaaaactagc agaaattctg   8760
caaaaacccca cagatgtttt tcccaattca cccatagtag caattcagcc caaaggtaca   8820
aaacgtcctt ttttctgcat ccatccagcc ggcggacatg tactttgcta ttttagtttg   8880
gcgcattatt taggcactga ccagccattt tacggtttac aagcacaggg tttttatggt   8940
gaagaagaac cactaactac agttgtagaa atggctaggc tttatgctca agctatacaa   9000
acaattcaac ccacagggcc atatcaaatt ggtggttggt cgtttggtgg tgtagttgcc   9060
tatgaaacgg ctcaacaact acaccaacaa ggaaaagaag tttcattact agcaatttta   9120
```

gattcctacg tgccaattct gttagataaa aataaaaaaa ttgatgatgt ttatttagtt 9180
ggtgtactat cccgtgtatt tggcggaatg tttggtcaag ataatctgat ttcactagcg 9240
gaaatcgaaa atttaagtgt ggaagaaagt ttaaattaca tcatcgaaaa agcacgccaa 9300
gccaaaattt ttccgccagg agtggaacgt cacaacaatc gccgcatttt agatgtttta 9360
gtcggaactt taaaagccac ttattcttat gaacgttgtc cctatcctgg caaagttact 9420
atttttagag ccagagaaaa acatatcatg gctcctgatc ctactttagt ttgggtagaa 9480
ttattttcag ttttggctgc ggaggaaatt gaaattcata atgtccccgg taatcactat 9540
tcatttgttt tagaacctca cgtccaagct ttggctgaaa gtttgcagaa atgtttgtgc 9600
tgatacaaga tccccgactt ctttgaggat gcagctggcg aataggggggt caaacccctc 9660
gtgcgcccac aaattggttg tagagacgcg ccatggcgcg tctctacatc tggtggaatg 9720
acgaaaaatc tcggtgaggg gtgtcacccc tgattcgcca gctgtatcct ttgagaagtc 9780
ggggagctcg gtacccctag agtcgacctg cagttcaatg cggtccaata cctcccctgc 9840
ccaactgggt aagctcgcgg ctccactgag taatacagac aaggctaaac aggcaaattt 9900
tttcattggt caactcctag caccaatttc ccaagactac ggagggggca atgaagtttc 9960
aattaattgg ggtcacaaac cacagcggcc tatggctcta atcaatggca cactagaaaa 10020
aatgttgcag catacttggc taccaaaacc cccaaattta accttattgt cagatgaagt 10080
tcatctctgg cgcattcccc ttgaccaacc agaatcacag ctacaggatt tagccgctac 10140
cttatctagt gacgaattag cccgtgcaaa cagattttat tttcccgaac atcgccggcg 10200
ttttactgct ggtcgtggta ttctccgcag tatcttgggg ggctatttgg gtgtggaacc 10260
agggcaagtt aaatttgatt atgaatcccg tggtaaacca atattaggcg atcgctttgc 10320
cgagagtggt ttattattta acttgtcaca ctcccagaac ttggccttgt gtgcagtcaa 10380
ttacacgcgc caaatcggca tcgatttaga atatctccgc cccacatctg atttagaatc 10440
ccttgccaaa aggttctttt taccgcgaga atatgaatta ttgcgatcgc tacccgatga 10500
gcaaaaacaa aaaatttttct ttcgttactg gacttgtaaa gaggcttatc ttaaagcaac 10560
gggtgacggc atcgctaaat tagaggaaat tgaaatagca ctaactccca cagaaccagc 10620
taagttacag acagctccag cgtggagtct cctagagcta gtgccagatg ataattgtgt 10680
tgctgctgtt gccgtggcgg gttttggctg gcagccaaaa ttctggcatt attgagcatg 10740
caagcttctc cctatagtga gtcgtattag cggccgcatc gaatataact tcgtataatg 10800
tatgctatac gaagttatta gcgatgagga catgaggttg ccccgtattc agtgtcgctg 10860
atttgtattg tctgaagttg tttttacgtt aagttgatgc agatcaatta atacgatacc 10920
tgcgtcataa ttgattattt gacgtggttt gatggcctcc acgcacgttg tgatatgtag 10980
atgataatca ttatcacttt acgggtcctt tccggtgatc cgacaggtta cggggcggcg 11040
acctcgcggg ttttcgctat ttatgaaaat tttccggttt aaggcgtttc cgttcttctt 11100
cgtcataact taatgttttt atttaaaata ccctctgaaa agaaaggaaa cgacaggtgc 11160
tgaaagcgag gctttttggc ctctgtcgtt tcctttctct gtttttgtcc gtggaatgaa 11220
caatggaagt cctcgtctcg ccctcgaatt agcccgccta atgagcgggc ttttttttgaa 11280
ttaattctcg cgagctggca cgacaggttt cccgactgga aagcgggcag tgagcgcaac 11340
gcaattaatg taagttagcg cgaattgcaa gctggccgac gcgctgggct acgtcttgct 11400
ggcgttcggg agcagaagag catacatctg gaagcaaagc caggaaagcg gcctatggag 11460
ctgtgcggca gcgctcagta ggcaattttt caaaatattg ttaagccttt tctgagcatg 11520

```
gtatttttca tggtattacc aattagcagg aaaataagcc attgaatata aaagataaaa  11580
atgtcttgtt tacaatagag tgggggggt cagcctgccg ccttgggccg ggtgatgtcg  11640
tacttgcccg ccgcgaactc ggttaccgtc cagcccagcg cgaccagctc cggcaacgcc  11700
tcgcgcaccc gcttgcggcg cttgcgcatg gtcgaaccac tggcctctga cggccagaca  11760
tagccgcaca aggtatctat ggaagccttg ccggttttgc cggggtcgat ccagccacac  11820
agccgctggt gcagcaggcg ggcggtttcg ctgtccagcg cccgcacctc gtccatgctg  11880
atgcgcacat gctggccgcc acccatgacg gcctgcgcga tcaaggggtt cagggccacg  11940
tacaggcgcc cgtccgcctc gtcgctggcg tactccgaca gcagccgaaa cccctgccgc  12000
ttgcggccat tctgggcgat gatggatacc ttccaaaggc gctcgatgca gtcctgtatg  12060
tgcttgagcg ccccaccact atcgacctct gccccgattt cctttgccag cgcccgatag  12120
ctacctttga ccacatggca ttcagcggtg acggcctccc acttgggttc caggaacagc  12180
cggagctgcc gtccgccttc ggtcttgggt tccgggccaa gcactaggcc attaggccca  12240
gccatggcca ccagcccttg caggatgcgc agatcatcag cgcccagcgg ctccgggccg  12300
ctgaactcga tccgcttgcc gtcgccgtag tcatacgtca cgtccagctt gctgcgcttg  12360
cgctcgcccc gcttgagggc acggaacagg ccgggggcca gacagtgcgc cgggtcgtgc  12420
cggacgtggc tgaggctgtg cttgttctta ggcttcacca cggggcaccc ccttgctctt  12480
gcgctgcctc tccagcacgg cgggcttgag caccccgccg tcatgccgcc tgaaccaccg  12540
atcagcgaac ggtgcgccat agttggcctt gctcacaccg aagcggacga agaaccggcg  12600
ctggtcgtcg tccacacccc attcctcggc ctcggcgctg gtcatgctcg acaggtagga  12660
ctgccagcgg atgttatcga ccagtaccga gctgccccgg ctggcctgct gctggtcgcc  12720
tgcgcccatc atggccgcgc ccttgctggc atggtgcagg aacacgatag agcacccggt  12780
atcggcggcg atggcctcca tgcgaccgat gacctgggcc atggggccgc tggcgttttc  12840
ttcctcgatg tggaaccggc gcagcgtgtc cagcaccatc aggcggcggc cctcggcggc  12900
gcgcttgagg ccgtcgaacc actccggggc catgatgttg ggcaggctgc cgatcagcgg  12960
ctggatcagc aggccgtcag ccacggcttg ccgttcctcg gcgctgaggt gcgccccaag  13020
ggcgtgcagg cggtgatgaa tggcggtggg cgggtcttcg gcgggcaggt agatcaccgg  13080
gccggtgggc agttcgccca cctccagcag atccggcccg cctgcaatct gtgcggccag  13140
ttgcagggcc agcatggatt taccggcacc accgggcgac accagcgccc cgaccgtacc  13200
ggccaccatg ttgggcaaaa cgtagtccag cggtggcggc gctgctgcga acgcctccag  13260
aatattgata ggcttatggg tagccattga ttgcctcctt tgcaggcagt tggtggttag  13320
gcgctggcgg ggtcactacc cccgccctgc gccgctctga gttcttccag gcactcgcgc  13380
agcgcctcgt attcgtcgtc ggtcagccag aacttgcgct gacgcatccc tttggccttc  13440
atgcgctcgg catatcgcgc ttggcgtaca gcgtcagggc tggccagcag gtcgccggtc  13500
tgcttgtcct tttggtcttt catatcagtc accgagaaac ttgccggggc cgaaaggctt  13560
gtcttcgcgg aacaaggaca aggtgcagcc gtcaaggtta aggctggcca tatcagcgac  13620
tgaaaagcgg ccagcctcgg ccttgtttga cgtataacca aagccaccgg gcaaccaata  13680
gcccttgtca cttttgatca ggtagaccga ccctgaagcg cttttttcgt attccataaa  13740
accccccttct gtgcgtgagt actcatagta taacaggcgt gagtaccaac gcaagcacta  13800
catgctgaaa tctggcccgc ccctgtccat gcctcgctgg cggggtgccg gtgcccgtgc  13860
```

```
cagctcggcc cgcgcaagct ggacgctggg cagacccatg accttgctga cggtgcgctc  13920
gatgtaatcc gcttcgtggc cgggcttgcg ctctgccagc gctgggctgg cctcggccat  13980
ggccttgccg atttcctcgg cactgcggcc ccggctggcc agcttctgcg cggcgataaa  14040
gtcgcacttg ctgaggtcat gaccgaagcg cttgaccagc ccggccatct cgctgcggta  14100
ctcgtccagc gccgtgcgcc ggtggcggct aagctgccgc tcgggcagtt cgaggctggc  14160
cagcctgcgg gccttctcct gctgccgctg ggcctgctcg atctgctggc cagcctgctg  14220
caccagcgcc gggccagcgg tggcggtctt gcccttggat tcacgcagca gcacccacgg  14280
ctgataaccg gcgcgggtgg tgtgcttgtc cttgcggttg gtgaagcccg ccaagcggcc  14340
atagtggcgg ctgtcggcgc tggccgggtc ggcgtcgtac tcgctggcca gcgtccgggc  14400
aatctgcccc cgaagttcac cgcctgcggc gtcggccacc ttgacccatg cctgatagtt  14460
cttcgggctg gtttccacta ccagggcagg ctcccggccc tcggctttca tgtcatccag  14520
gtcaaactcg ctgaggtcgt ccaccagcac cagaccatgc cgctcctgct cggcgggcct  14580
gatatacacg tcattgccct gggcattcat ccgcttgagc catggcgtgt tctggagcac  14640
ttcggcggct gaccattccc ggttcatcat ctggccggtg ggtgcgtccc tgacgccgat  14700
atcgaagcgc tcacagccca tggccttgag ctgtcggcct atggcctgca aagtcctgtc  14760
gttcttcatc gggccaccaa gcgcagccag atcgagccgt cctcggttgt cagtggcgtc  14820
aggtcgagca agagcaacga tgcgatcagc agcaccaccg taggcatcat ggaagccagc  14880
atcacggtta gccatagctt ccagtgccac ccccgcgacg cgctccgggc gctctgcgcg  14940
gcgctgctca cctcggcggc tacctcccgc aactctttgg ccagctccac ccatgccgcc  15000
cctgtctggc gctgggcttt cagccactcc gccgcctgcg cctcgctggc ctgcttggtc  15060
tggctcatga cctgccgggc ttcgtcggcc agtgtcgcca tgctctgggc cagcggttcg  15120
atctgctccg ctaactcgtt gatgcctctg gatttcttca ctctgtcgat tgcgttcatg  15180
gtctattgcc tcccggtatt cctgtaagtc gatgatctgg gcgttggcgg tgtcgatgtt  15240
cagggccacg tctgcccggt cggtgcggat gccccggcct tccatctcca ccacgttcgg  15300
ccccaggtga acaccgggca ggcgctcgat gccctgcgcc tcaagtgttc tgtggtcaat  15360
gcgggcgtcg tggccagccc gctctaatgc ccggttggca tggtcggccc atgcctcgcg  15420
ggtctgctca agccatgcct tgggcttgag cgcttcggtc ttctgtgccc cgcccttctc  15480
cggggtcttg ccgttgtacc gcttgaacca ctgagcggcg ggccgctcga tgccgtcatt  15540
gatccgctcg gagatcatca ggtggcagtg cgggttctcg ccgccaccgg catggatggc  15600
cagcgtatac ggcaggcgct cggcaccggt caggtgctgg gcgaactcgg acgccagcgc  15660
cttctgctgg tcgagggtca gctcgaccgg cagggcaaat tcgacctcct tgaacagccg  15720
cccattggcg cgttcataca ggtcggcagc atcccagtag tcggcgggcc gctcgacgaa  15780
ctccggcatg tgcccggatt cggcgtgcaa gacttcatcc atgtcgcggg catacttgcc  15840
ttcgcgctgg atgtagtcgg ccttggccct ggccgattgg ccgcccgacc tgctgccggt  15900
tttcgccgta aggtgataaa tcgccatgct gcctcgctgt tgcttttgct tttcggctcc  15960
atgcaatggc cctcggagag cgcaccgccc gaagggtggc cgttaggcca gtttctcgaa  16020
gagaaaccgg taagtgcgcc ctcccctaca aagtagggtc gggattgccg ccgctgtgcc  16080
tccatgatag cctacgagac agcacattaa caatggggtg tcaagatggt taaggggagc  16140
aacaaggcgg cggatcggct ggccaagctc gaagaacaac gagcgcgaat caatgccgaa  16200
attcagcggg agcgggcaag ggaacagcag caagagcgca agaacgaaac aaggcgcaag  16260
```

-continued

```
gtgctggtgg gggccatgat tttggccaag gtgaacagca gcgagtggcc ggaggatcgg  16320

ctcatggcgg caatggatgc gtaccttgaa cgcgaccacg accgcgcctt gttcggtctg  16380

ccgccacgcc agaaggatga gccgggctga atgatcgacc gagacaggcc ctgcggggct  16440

gcacacgcgc ccccaccctt cgggtagggg gaaaggccgc taaagcggct aaaagcgctc  16500

cagcgtattt ctgcggggtt tggtgtgggg tttagcgggc tttgcccgcc tttccccctg  16560

ccgcgcagcg gtggggcggt gtgtagccta gcgcagcgaa tagaccagct atccggcctc  16620

tggccgggca tattgggcaa gggcagcagc gccccacaag ggcgctgata accgcgccta  16680

gtggattatt cttagataat catggatgga tttttccaac accccgccag cccccgcccc  16740

tgctgggttt gcaggtttgg gggcgtgaca gttattgcag gggttcgtga cagttattgc  16800

agggggggcgt gacagttatt gcaggggttc gtgacagtta gtacgggagt gacgggcact  16860

ggctggcaat gtctagcaac ggcaggcatt tcggctgagg gtaaaagaac tttccgctaa  16920

gcgatagact gtatgtaaac acagtattgc aaggacgcgg aacatgcctc atgtggcggc  16980

cagga                                                             16985
```

<210> SEQ ID NO 86
<211> LENGTH: 17198
<212> TYPE: DNA
<213> ORGANISM: Artificial Sequence
<220> FEATURE:
<223> OTHER INFORMATION: sequence of plasmid Sh-P560

<400> SEQUENCE: 86

```
ctcgcgagaa ttaattcaga taaaaaaaat ccttagcttt cgctaaggat gatttctagc     60

gatgaccctg ctgattggtt cgctgaccat ttccgggtgc gggacggcgt taccagaaac    120

tcagaaggtt cgtccaacca aaccgactct gacggcagtt tacgagagag atgatagggt    180

ctgcttcagt aagccagatg ctacacaatt aggcttgtac gggtactcga cctgcatccc    240

ttaacttact tattaaataa tttatagcta ttgaaaagag ataagaattg ttcaaagcta    300

atattgttta aatcgtcaat tcctgcatgt tttaaggaat tgttaaattg attttttgta    360

aatattttct tgtattcttt gttaaaataa aaaaggggac ctctagggtc cccaattaat    420

tagtaatata atctattaaa ggtcattcaa aaggtcatcc accggatcag cttagtaaag    480

ccctcgctag attttaatgc ggatgttgcg attacttcgc caactattgc gataacaaga    540

aaaagccagc ctttcatgat atatctccca atttgtgtag ggcttattat gcacgcttaa    600

aaataataaa agcagacttg acctgatagt ttggctgtga gcaattatgt gcttagtgca    660

tctaacgctt gagttaagcc gcgccgcgaa gcggcgtcgg cttgaacgaa ttgttagaca    720

ttatttgccg actaccttgg tgatctcgcc tttcacgtag tggacaaatt cttccaactg    780

atctgcgcgc gaggccaagc gatcttcttc ttgtccaaga taagcctgtc tagcttcaag    840

tatgacgggc tgatactggg ccggcaggcg ctccattgcc cagtcggcag cgacatcctt    900

cggcgcgatt ttgccggtta ctgcgctgta ccaaatgcgg gacaacgtaa gcactacatt    960

tcgctcatcg ccagcccagt cgggcggcga gttccatagc gttaaggttt catttagcgc   1020

ctcaaataga tcctgttcag gaaccggatc aaagagttcc tccgccgctg gacctaccaa   1080

ggcaacgcta tgttctcttg cttttgtcag caagatagcc agatcaatgt cgatcgtggc   1140

tggctcgaag atacctgcaa gaatgtcatt gcgctgccat tctccaaatt gcagttcgcg   1200

cttagctgga taacgccacg gaatgatgtc gtcgtgcaca acaatggtga cttctacagc   1260
```

-continued

```
gcggagaatc tcgctctctc caggggaagc cgaagtttcc aaaaggtcgt tgatcaaagc   1320
tcgccgcgtt gtttcatcaa gccttacggt caccgtaacc agcaaatcaa tatcactgtg   1380
tggcttcagg ccgccatcca ctgcggagcc gtacaaatgt acggccagca acgtcggttc   1440
gagatggcgc tcgatgacgc caactacctc tgatagttga gtcgatactt cggcgatcac   1500
cgcttccctc atgatgttta actttgtttt agggcgactg ccctgctgcg taacatcgtt   1560
gctgctccat aacatcaaac atcgacccac ggcgtaacgc gcttgctgct tggatgcccg   1620
aggcatagac tgtaccccaa aaaaacagtc ataacaagcc atgaaaaccg ccactgcgcc   1680
gttaccaccg ctgcgttcgg tcaaggttct ggaccagttg cgtgagcgca tacgctactt   1740
gcattacagc ttacgaaccg aacaggctta tgtccactgg gttcgtgcct tcatccgttt   1800
ccacggtgtg cgtcacccgg caaccttggg cagcagcgaa gtcgaggcat ttctgtcctg   1860
gctggcgaac gagcgcaagg tttcggtctc cacgcatcgt caggcattgg cggccttgct   1920
gttcttctac ggcaaggtgc tgtgcacgga tctgccctgg cttcaggaga tcggaagacc   1980
tcggccgtcg cggcgcttgc cggtggtgct gaccccggat gaagtggttc gcatcctcgg   2040
ttttctggaa ggcgagcatc gtttgttcgc ccagcttctg tatggaacgg gcggatcagt   2100
gagggtttgc aactgcgggt caaggatctg gatttcgatc acggcacgat catcgtgcgg   2160
gagggcaagg gctccaagga tcgggccttg atgttacccg agagcttggc acccagcctg   2220
cgcgagcagg ggaattgatc cggtggatga cctttgaat gacctttaat agattatatt   2280
actaattaat tggggaccct agaggtcccc ttttttattt tctgaacggt ctggttatag   2340
gtacattgag caactgactg aaatgcctca aaatgttctt tacgatgcca ttgggatata   2400
tcaacggtgg tatatccagt gattttttc tccattttag cttccttagc tcctgaaaat   2460
ctcgataact caaaaaatac gcccggtagt gatcttattt cattatggtg aaagttggaa   2520
cctcttacga gcggccgcat acgatttagg tgacactata ggatccctgc cggccggtcc   2580
ggcgcgcccg ggctcgagtg cacgtacgca ttgaattaat ctcctacttg actttatgag   2640
ttgggatttt cttaaacaca attcccccgg ataaactgag ggagtccaaa gtaatgaccc   2700
tagagttatt gttactgatc tccattaact ttcgttaact acccggggat ttatgagaga   2760
tattacctaa ataaatccag ggagaaacac ggaggcagcg acaagggcca ccgggatgct   2820
caaacagctc agcgcctagg cttgaatgct tttgcaatcc cacagttaac tttatacaac   2880
ggtgatggga cttatgtctg ttacatcttg ttaattttat tcctgctttt ttgttaagta   2940
atgttgcagg ggattctcag attgtcctgg attgggaagg gaagacaacc agtttcgttc   3000
agcttatgtt ttagggctaa aattatgcaa ttgatgttcg gtgcgaactt ttctcgtttt   3060
tttagtttcc agtggggtag ggaagactgt tgcctaggga accacagcct actttccttt   3120
ttgagctttt tatcccacca ttttgatatt cagggactct tctctacagg tggacgtcat   3180
gggtacacct cacgctactt ttgcagctac tgagacagca tttcatgtga cgggctacga   3240
aaagatagat tttagcctgg tttatgtgaa tggtgtattc aacatcaaaa acacagaaat   3300
tgctgatagt tatcagaagt ttggacgctg cttgactgtt gttgatcata atgtctaccg   3360
tttgtatgga gaccaaatta agtcatattt tcgttactac gacatagact taactgtgtt   3420
tccaattact attactgaac ctggcaaaac catgtcaact tttgaacaag tagttgatgc   3480
gtttgccgat tttggcttaa ttcgtaaaga accagtttta gtagttggtg gtggtttagt   3540
tactgatgtt gtaggttttg cttgtgcagc ttatcgtcgc agtactaact atattcgcat   3600
tcccacgact ttgattggtt tgatagatgc tggaattgcg attaaagtag cagtcaatca   3660
```

-continued

```
taaaaagctg aaaaatcgct tgggtgctta ccatgcaccg cagaaagtca ttctagactt   3720
ttcctttctc aagacactac caacagccca agtccggaat ggaatggcgg agttagtgaa   3780
aattgctgtg gtagcaaatg cagaagtttt taattggctg tatgagtacg gagaagattt   3840
actgcataca cactttggct atctcaacgg tacagaggaa ctgcaagaaa ttgctcacaa   3900
agttaactac gaagcaatta aaaccatgct ggagttagaa actccaaacc tgcatgagct   3960
agacttagat cgcgtcattg cttatggtca cacttggagt ccgacactag aattagcacc   4020
gcgggttcct ctgtatcatg gtcatgctgt caacatcgat atggcgctat cagcaactat   4080
tgctgaacga cggggatata ttactgtagc agaacgcgat cgcattcttg gattgatgag   4140
tcgtctaggt ttagcccttg atcatcccct tctagatagc gatttgttat ggtacgctac   4200
ccagtctatc acccagacaa gagacgggaa acaacgcgcc gccatgccaa aacctattgg   4260
tgagtgtttc tttgtcaatg acctaacccg tgaagaattg catcaagctt tgattgcaca   4320
caaggatgta tgtgcaacat atccccgtgg tggagatggg attgaagcct atatcagtgc   4380
agaacaatct gagatggtag gagtttagaa tcgtgactag cattgttgaa aagaacacag   4440
ctagacccgt aactccccac ggtatcttgg ttgaacagct acaaaaaact ctggctttgg   4500
cagaatcagg aaatacacct gaaactgttg tgactgcact acgacaggcg tatcaattag   4560
cggcgggttt agaaccttat attagtgaac acaccactac tgaatctgac gccttagcag   4620
cactggtaca aaaaactacc aaagaagact ggacaaaacg tttcactgat ggtgaaacag   4680
tgcgtcaact agaacaggaa atgctttctg gacacgtcga gggacaaacc ctgaaaatgt   4740
ttgttcacat gactaaagcc aagagtgttt tggaagtagg aatgttcacc gggtattctg   4800
ctttggcaat ggcagaggca ttacctgatg atggacgagt ggtagcatgt gaagtagact   4860
cttatgttgc tagctttgct caaacttgtt tccaaaactc gccccacggt cataaaatta   4920
ctgtggaagt tgcaccagcc ttggaaactc tgcaaaaact tgcagcagca ggtgaatcat   4980
ttgatttgat attcatcgat gctgacaaga aagagtatgt gcagtatttc cagatcatct   5040
tggataataa tctacttgca tctaacggca ttatttgtgt agataacact ttaatgcagg   5100
gacaggttta tctgccacca gaacaacgta cagctaatgg tgaagcgatc gctcaattta   5160
accaaatcat tacccaagat ccgcgtgtag aacaagttat actaccgctt cgtgatggtg   5220
tgactttaat tcggcggttg tagaaggatg gggtttgggt ggtactgatg ggtttttttt   5280
gagggcgaat tatatgacac aatctatttc tgtggcttct gttggacaaa caactcagtc   5340
ggtgagcctg ggacttcgca tatctgcgtt gtggaaaagt ttagctacac ttgcactgct   5400
gttgttagta ttgccaatca atgctgcgat tgtgttggta tcgctgttat tgggtagtca   5460
atcgcaagcg atcgccaccg aacccaaaaa catcttgatt agtggcggta aaatgactaa   5520
ggcgttacaa ttagcccgta gttttcacgc cgccggacat cgagtggttt tagtagaaac   5580
tcacaaatac tggttaacgg gacaccgatt ttccaaagca gtaagtcgtt tctacactct   5640
accaacgccc caatctgatc ctgaagcata cacccaagcc ctattagata ttgttcaaaa   5700
agaaaatatc gatgtctatg tacccgtgtg cagtccggtt gctagttact acgactcttt   5760
agctaaaccc gtactgtcga agtactgcga ggtttttcac tgtgacgcag atgtcaccca   5820
aatgttggat gataaatacg cttttgctga gaaagcgcgg agtttggggt tatctgttcc   5880
caagtctttc aaaattactg acccggaaca ggtgagcaac tttgattttt ctcaagaaaa   5940
gcgtaaatac atcctcaaaa gcattcctta tgactctgtt cgtcgcttag atttaaccaa   6000
```

-continued

```
acttccttgt gagactcccg aagcaacagc agattttgtc aacagcttac ccatcagttc   6060
ccaaaagcca tggattatgc aagaattcat tcctggaaaa gaattttgca cccacagcac   6120
tgtccgcaat ggggagttga gaatgcattg ctgttgtgaa tcttcggcat ttcaagttaa   6180
ctatgagaat gtcgatcatc cccaaatttt ggaatgggtg cgacactttg tcaaagcatt   6240
aggtatcact ggacaggtat cttttgattt tatcgaagca caagatggca caatctacgc   6300
cattgaatgt aatccgcgta cccattctgc catcactatg ttctacaatc atccggatgt   6360
ggcaaatgct tatttgagtg aaattccaca agtagaacca attcaacctc tgattaatag   6420
taagcctacc tactggactt atcacgaaat ttggcgattg acaggaattc gttctttctc   6480
acagttgcaa acttggttga aaaacttttt tggtggaaaa gatgcgattt acagtttgag   6540
tgatcctcta cctttttttaa cagttcatca ctggcaaatt cctttattat tgctacaaaa   6600
tttgcaacag ctaaaaggtt ggatcaggat agattttaat attgggaaat tggttgagtt   6660
tggtggcgat tagattcagt tatcagttat cagttatcag ttagtagctg ttcactgata   6720
atttatagat attgaatata tataagactc atatttgatt tctgaaatac acgtagggtg   6780
cgtgatagct acgccataac acaccctact ggcgcgtcaa gcctaaaatg ttgcaataaa   6840
tctctgattc tatctctgtg ttctctctct tgaaaagctt tgatcggagg aaacctccgc   6900
tcaaactttt cgctgcttcc tctgcggttt attaatgcac tattttaagg ctgtcgcgcc   6960
ctttgttaaa gtcaaatttt tttatcaaac cgcagaggcg cagaggaatc agagagaagg   7020
aaataattct taattgaatt gtattaagtt ataaatcact atattttatc aaagatggaa   7080
ataataaact ttttagatga ttctctggaa attgaagaac agaagaaaaa ttgggaaaga   7140
caggtaggag atatttctga tctttctctg ctgagtttag aagaacagca aaaaatatta   7200
tttatatgga atcagacaga aagtaattat gatttgtcga tttgtctaca tgagttattt   7260
gcagcacagg tagagaaaac accagatgca aaagctctca agtttgctga tcaagaattg   7320
agttatcatc agttaaattg tcgggcgaat caactcgctc actatttgca atctttggga   7380
attgtaactg aagatttagt tgggatttgt gtggaacgtt ccctagaaat ggttgtgggg   7440
ttattgggta ttttgaaagc gggtgcggct tatgttccaa ttgatcctgg atatccccaa   7500
gaacgtttag gatatatgtt ggcggattcc caggtgtcgg tgttgttgac tcaaagtcat   7560
ttagtcgata gtttaccaac atgtccaacc catactattt gcttggatac tgactgggat   7620
ctgatttctc aatatagcga tcgcaatctc caaaatacaa cgacaccaga aaatctcgct   7680
tatgtaattt acacttctgg ttctactggt aaacctaaag gagcgatgaa tacccatcgc   7740
ggtatttgca atcgtctgtt atggatgcaa gatgcttatc aactcactca acaagatcgg   7800
gttctgcaaa aaactccctt tagttttgat gtctctgtct gggaattctt ttggccgttg   7860
attaccgggg cgcggctgat tatagcacaa ccaggtggac acaaggatag ttcttatcta   7920
attaatacaa ttatccaaga agaaattacc acattacatt ttgttccttc gatgttgcag   7980
gtatttttgc aagctaaagg agtggaaaat tgtcagtcat taaaacgggt aattactagt   8040
ggtgaagctt tacctgtgag tctgcaagaa cggtttttttg aacgtttggg atgtgaactg   8100
cacaatcttt atggtcctac agaagcagcg atcgatgtta cgttttggca gtgtcaacct   8160
caaagtcaat atcaaacagt accgattggt cgtcccatcg ctaatactca aatatatata   8220
ttagatcaac atttgcaacc tgtgcctgtg ggtgttgtgg gtgaacttta tattggtggt   8280
gtgggagttg ccagaggtta ctggcgtcgt ccagaattaa ctacagaaag atttgtatct   8340
aatccctttg caacgggaca aatgtataaa actggtgact tggcgcgcta tttacctgat   8400
```

```
ggtaatatcg agtatgttgg cagaattgac gatcaagtta aaattcgcgg ttttcggatt   8460
gagttgggag aaattgagag tacgctgacg caacattccc agattagtca agctgtggtt   8520
gtcgcccaga cagataattt gaataataag catttaattg cttatattgt tccccaggga   8580
gaaccaccca caccaaccca actgcggaat ttccttcagg gtaagctacc tgaattcatg   8640
gttccctcag cttttgtctg cttaaattcc tttcctctca ctcctagtgg aaaaatagac   8700
aggcgatcgc ttcccaaacc tgatttttct aacttaatca ctcatgaaga ttttacgcct   8760
gcacgcaatg atttagagag aaaaatcgcg cagatttggt cagaaatttt acagatttcg   8820
gaaattgata ttagagataa ctttttgaa gttggtggta attccctttt agcattacat   8880
ttaatgaatg ccatcgaaca aaaatttggt cgagagttag cactgtcaac tttacttact   8940
aataactcaa ttgaaaaact agcagaaatt ctgcaaaacc ccacagatgt tttcccaat    9000
tcacccatag tagcaattca gcccaaaggt acaaaacgtc ctttttctg catccatcca    9060
gccggcggac atgtactttg ctattttagt ttggcgcatt atttaggcac tgaccagcca   9120
ttttacggtt tacaagcaca gggtttttat ggtgaagaag aaccactaac tacagttgta   9180
gaaatggcta ggctttatgc tcaagctata caaacaattc aacccacagg gccatatcaa   9240
attggtggtt ggtcgtttgg tggtgtagtt gcctatgaaa cggctcaaca actacaccaa   9300
caaggaaaag aagtttcatt actagcaatt ttagattcct acgtgccaat tctgttagat   9360
aaaaataaaa aaattgatga tgtttattta gttggtgtac tatcccgtgt atttggcgga   9420
atgtttggtc aagataatct gatttcacta gcggaaatcg aaaatttaag tgtggaagaa   9480
agtttaaatt acatcatcga aaaagcacgc caagccaaaa tttttccgcc aggagtggaa   9540
cgtcacaaca atcgccgcat tttagatgtt ttagtcggaa ctttaaaagc cacttattct   9600
tatgaacgtt gtccctatcc tggcaaagtt actattttta gagccagaga aaaacatatc   9660
atggctcctg atcctacttt agtttgggta gaattatttt cagttttggc tgcggaggaa   9720
attgaaattc ataatgtccc cggtaatcac tattcatttg ttttagaacc tcacgtccaa   9780
gctttggctg aaagtttgca gaaatgtttg tgctgataca agatccccga cttctttgag   9840
gatgcagctg gcgaataggg ggtcaaaccc ctcgtgcgcc cacaaattgg ttgtagagac   9900
gcgccatggc gcgtctctac atctggtgga atgacgaaaa atctcggtga ggggtgtcac   9960
ccctgattcg ccagctgtat cctttgagaa gtcggggagc tcggtacccc tagagtcgac  10020
ctgcagttca atgcggtcca atacctcccc tgcccaactg ggtaagctcg cggctccact  10080
gagtaataca gacaaggcta aacaggcaaa ttttttcatt ggtcaactcc tagcaccaat  10140
ttcccaagac tacggagggg gcaatgaagt ttcaattaat tggggtcaca aaccacagcg  10200
gcctatggct ctaatcaatg gcacactaga aaaaatgttg cagcatactt ggctaccaaa  10260
acccccaaat ttaaccttat tgtcagatga agttcatctc tggcgcattc cccttgacca  10320
accagaatca cagctacagg atttagccgc taccttatct agtgacgaat tagcccgtgc  10380
aaacagattt tattttcccg aacatcgccg gcgttttact gctggtcgtg gtattctccg  10440
cagtatcttg gggggctatt tgggtgtgga accagggcaa gttaaatttg attatgaatc  10500
ccgtggtaaa ccaatattag gcgatcgctt tgccgagagt ggtttattat ttaacttgtc  10560
acactcccag aacttggcct tgtgtgcagt caattacacg cgccaaatcg gcatcgattt  10620
agaatatctc cgccccacat ctgatttaga atcccttgcc aaaaggttct tttaccgcg   10680
agaatatgaa ttattgcgat cgctacccga tgagcaaaaa caaaaaattt tctttcgtta  10740
```

```
ctggacttgt aaagaggctt atcttaaagc aacgggtgac ggcatcgcta aattagagga  10800
aattgaaata gcactaactc ccacagaacc agctaagtta cagacagctc cagcgtggag  10860
tctcctagag ctagtgccag atgataattg tgttgctgct gttgccgtgg cgggttttgg  10920
ctggcagcca aaattctggc attattgagc atgcaagctt ctccctatag tgagtcgtat  10980
tagcggccgc atcgaatata acttcgtata atgtatgcta tacgaagtta ttagcgatga  11040
ggacatgagg ttgccccgta ttcagtgtcg ctgatttgta ttgtctgaag ttgtttttac  11100
gttaagttga tgcagatcaa ttaatacgat acctgcgtca taattgatta tttgacgtgg  11160
tttgatggcc tccacgcacg ttgtgatatg tagatgataa tcattatcac tttacgggtc  11220
ctttccggtg atccgacagg ttacggggcg gcgacctcgc gggttttcgc tatttatgaa  11280
aattttccgg tttaaggcgt ttccgttctt cttcgtcata acttaatgtt tttatttaaa  11340
ataccctctg aaaagaaagg aaacgacagg tgctgaaagc gaggcttttt ggcctctgtc  11400
gtttcctttc tctgtttttg tccgtggaat gaacaatgga agtcctcgtc tcgccctcga  11460
attagcccgc ctaatgagcg ggcttttttt gaattaattc tcgcgagctg gcacgacagg  11520
tttcccgact ggaaagcggg cagtgagcgc aacgcaatta atgtaagtta gcgcgaattg  11580
caagctggcc gacgcgctgg gctacgtctt gctggcgttc gggagcagaa gagcatacat  11640
ctggaagcaa agccaggaaa gcggcctatg gagctgtgcg gcagcgctca gtaggcaatt  11700
tttcaaaata ttgttaagcc ttttctgagc atggtatttt tcatggtatt accaattagc  11760
aggaaaataa gccattgaat ataaaagata aaaatgtctt gtttacaata gagtgggggg  11820
ggtcagcctg ccgccttggg ccgggtgatg tcgtacttgc ccgccgcgaa ctcggttacc  11880
gtccagccca gcgcgaccag ctccggcaac gcctcgcgca cccgcttgcg gcgcttgcgc  11940
atggtcgaac cactggcctc tgacggccag acatagccgc acaaggtatc tatggaagcc  12000
ttgccggttt tgccggggtc gatccagcca cacagccgct ggtgcagcag gcgggcggtt  12060
tcgctgtcca gcgcccgcac ctcgtccatg ctgatgcgca catgctggcc gccacccatg  12120
acggcctgcg cgatcaaggg gttcagggcc acgtacaggc gcccgtccgc ctcgtcgctg  12180
gcgtactccg acagcagccg aaacccctgc cgcttgcggc cattctgggc gatgatggat  12240
accttccaaa ggcgctcgat gcagtcctgt atgtgcttga gcgccccacc actatcgacc  12300
tctgccccga tttcctttgc cagcgcccga tagctacctt tgaccacatg gcattcagcg  12360
gtgacggcct cccacttggg ttccaggaac agccggagct gccgtccgcc ttcggtcttg  12420
ggttccgggc caagcactag gccattaggc ccagccatgg ccaccagccc ttgcaggatg  12480
cgcagatcat cagcgcccag cggctccggg ccgctgaact cgatccgctt gccgtcgccg  12540
tagtcatacg tcacgtccag cttgctgcgc ttgcgctcgc cccgcttgag ggcacggaac  12600
aggccggggg ccagacagtg cgccgggtcg tgccggacgt ggctgaggct gtgcttgttc  12660
ttaggcttca ccacggggca ccccccttgct cttgcgctgc ctctccagca cggcgggctt  12720
gagcaccccg ccgtcatgcc gcctgaacca ccgatcagcg aacggtgcgc catagttggc  12780
cttgctcaca ccgaagcgga cgaagaaccg gcgctggtcg tcgtccacac cccattcctc  12840
ggcctcggcg ctggtcatgc tcgacaggta ggactgccag cggatgttat cgaccagtac  12900
cgagctgccc cggctggcct gctgctggtc gcctgcgccc atcatggccg cgcccttgct  12960
ggcatggtgc aggaacacga tagagcaccc ggtatcggcg gcgatggcct ccatgcgacc  13020
gatgacctgg gccatggggc cgctggcgtt ttcttcctcg atgtggaacc ggcgcagcgt  13080
gtccagcacc atcaggcggc ggccctcggc ggcgcgcttg aggccgtcga accactccgg  13140
```

ggccatgatg ttgggcaggc tgccgatcag cggctggatc agcaggccgt cagccacggc 13200
ttgccgttcc tcggcgctga ggtgcgcccc aagggcgtgc aggcggtgat gaatggcggt 13260
gggcgggtct tcggcgggca ggtagatcac cgggccggtg ggcagttcgc ccacctccag 13320
cagatccggc ccgcctgcaa tctgtgcggc cagttgcagg gccagcatgg atttaccggc 13380
accaccgggc gacaccagcg ccccgaccgt accggccacc atgttgggca aaacgtagtc 13440
cagcggtggc ggcgctgctg cgaacgcctc cagaatattg ataggcttat gggtagccat 13500
tgattgcctc ctttgcaggc agttggtggt taggcgctgg cggggtcact acccccgccc 13560
tgcgccgctc tgagttcttc caggcactcg cgcagcgcct cgtattcgtc gtcggtcagc 13620
cagaacttgc gctgacgcat ccctttggcc ttcatgcgct cggcatatcg cgcttggcgt 13680
acagcgtcag ggctggccag caggtcgccg gtctgcttgt ccttttggtc tttcatatca 13740
gtcaccgaga aacttgccgg ggccgaaagg cttgtcttcg cggaacaagg acaaggtgca 13800
gccgtcaagg ttaaggctgg ccatatcagc gactgaaaag cggccagcct cggccttgtt 13860
tgacgtataa ccaaagccac cgggcaacca atagcccttg tcacttttga tcaggtagac 13920
cgaccctgaa gcgctttttt cgtattccat aaaacccccct tctgtgcgtg agtactcata 13980
gtataacagg cgtgagtacc aacgcaagca ctacatgctg aaatctggcc cgcccctgtc 14040
catgcctcgc tggcggggtg ccggtgcccg tgccagctcg gcccgcgcaa gctggacgct 14100
gggcagaccc atgaccttgc tgacggtgcg ctcgatgtaa tccgcttcgt ggccgggctt 14160
gcgctctgcc agcgctgggc tggcctcggc catggccttg ccgatttcct cggcactgcg 14220
gccccggctg gccagcttct gcgcggcgat aaagtcgcac ttgctgaggt catgaccgaa 14280
gcgcttgacc agcccggcca tctcgctgcg gtactcgtcc agcgccgtgc gccggtggcg 14340
gctaagctgc cgctcgggca gttcgaggct ggccagcctg cgggccttct cctgctgccg 14400
ctgggcctgc tcgatctgct ggccagcctg ctgcaccagc gccgggccag cggtggcggt 14460
cttgcccttg gattcacgca gcagcaccca cggctgataa ccggcgcggg tggtgtgctt 14520
gtccttgcgg ttggtgaagc ccgccaagcg gccatagtgg cggctgtcgg cgctggccgg 14580
gtcggcgtcg tactcgctgg ccagcgtccg ggcaatctgc ccccgaagtt caccgcctgc 14640
ggcgtcggcc accttgaccc atgcctgata gttcttcggg ctggtttcca ctaccagggc 14700
aggctcccgg ccctcggctt tcatgtcatc caggtcaaac tcgctgaggt cgtccaccag 14760
caccagacca tgccgctcct gctcggcggg cctgatatac acgtcattgc cctgggcatt 14820
catccgcttg agccatggcg tgttctggag cacttcggcg gctgaccatt cccggttcat 14880
catctggccg gtgggtgcgt ccctgacgcc gatatcgaag cgctcacagc ccatggcctt 14940
gagctgtcgg cctatggcct gcaaagtcct gtcgttcttc atcgggccac caagcgcagc 15000
cagatcgagc cgtcctcggt tgtcagtggc gtcaggtcga gcaagagcaa cgatgcgatc 15060
agcagcacca ccgtaggcat catggaagcc agcatcacgg ttagccatag cttccagtgc 15120
cacccccgcg acgcgctccg ggcgctctgc gcggcgctgc tcacctcggc ggctacctcc 15180
cgcaactctt tggccagctc cacccatgcc gcccctgtct ggcgctgggc tttcagccac 15240
tccgccgcct gcgcctcgct ggcctgcttg gtctggctca tgacctgccg ggcttcgtcg 15300
gccagtgtcg ccatgctctg ggccagcggt tcgatctgct ccgctaactc gttgatgcct 15360
ctggatttct tcactctgtc gattgcgttc atggtctatt gcctcccggt attcctgtaa 15420
gtcgatgatc tgggcgttgg cggtgtcgat gttcagggcc acgtctgccc ggtcggtgcg 15480
gatgccccgg ccttccatct ccaccacgtt cggccccagg tgaacaccgg gcaggcgctc 15540
gatgccctgc gcctcaagtg ttctgtggtc aatgcgggcg tcgtggccag cccgctctaa 15600
tgcccggttg gcatggtcgg cccatgcctc gcgggtctgc tcaagccatg ccttgggctt 15660
gagcgcttcg gtcttctgtg ccccgccctt ctccggggtc ttgccgttgt accgcttgaa 15720
ccactgagcg gcgggccgct cgatgccgtc attgatccgc tcggagatca tcaggtggca 15780
gtgcgggttc tcgccgccac cggcatggat ggccagcgta tacggcaggc gctcggcacc 15840
ggtcaggtgc tgggcgaact cggacgccag cgccttctgc tggtcgaggg tcagctcgac 15900
cggcagggca aattcgacct ccttgaacag ccgcccattg gcgcgttcat acaggtcggc 15960
agcatcccag tagtcggcgg gccgctcgac gaactccggc atgtgcccgg attcggcgtg 16020
caagacttca tccatgtcgc gggcatactt gccttcgcgc tggatgtagt cggccttggc 16080
cctggccgat tggccgcccg acctgctgcc ggttttcgcc gtaaggtgat aaatcgccat 16140
gctgcctcgc tgttgctttt gcttttcggc tccatgcaat ggccctcgga gagcgcaccg 16200
cccgaagggt ggccgttagg ccagtttctc gaagagaaac cggtaagtgc gccctcccct 16260
acaaagtagg gtcgggattg ccgccgctgt gcctccatga tagcctacga gacagcacat 16320
taacaatggg gtgtcaagat ggttaagggg agcaacaagg cggcggatcg gctggccaag 16380
ctcgaagaac aacgagcgcg aatcaatgcc gaaattcagc gggagcgggc aagggaacag 16440
cagcaagagc gcaagaacga aacaaggcgc aaggtgctgg tgggggccat gattttggcc 16500
aaggtgaaca gcagcgagtg gccggaggat cggctcatgg cggcaatgga tgcgtacctt 16560
gaacgcgacc acgaccgcgc cttgttcggt ctgccgccac gccagaagga tgagccgggc 16620
tgaatgatcg accgagacag gccctgcggg gctgcacacg cgcccccacc cttcgggtag 16680
ggggaaaggc cgctaaagcg gctaaaagcg ctccagcgta tttctgcggg gtttggtgtg 16740
gggtttagcg ggctttgccc gcctttcccc ctgccgcgca gcggtggggc ggtgtgtagc 16800
ctagcgcagc gaatagacca gctatccggc ctctggccgg gcatattggg caagggcagc 16860
agcgccccac aagggcgctg ataaccgcgc ctagtggatt attcttagat aatcatggat 16920
ggatttttcc aacaccccgc cagcccccgc ccctgctggg tttgcaggtt tgggggcgtg 16980
acagttattg caggggttcg tgacagttat tgcagggggg cgtgacagtt attgcagggg 17040
ttcgtgacag ttagtacggg agtgacgggc actggctggc aatgtctagc aacggcaggc 17100
atttcggctg agggtaaaag aactttccgc taagcgatag actgtatgta aacacagtat 17160
tgcaaggacg cggaacatgc ctcatgtggc ggccagga 17198

<210> SEQ ID NO 87
<211> LENGTH: 17712
<212> TYPE: DNA
<213> ORGANISM: Artificial Sequence
<220> FEATURE:
<223> OTHER INFORMATION: sequence of plasmid Sh-DP560

<400> SEQUENCE: 87
ctcgcgagaa ttaattcaga taaaaaaaat ccttagcttt cgctaaggat gatttctagc 60
gatgaccctg ctgattggtt cgctgaccat ttccgggtgc gggacggcgt taccagaaac 120
tcagaaggtt cgtccaacca aaccgactct gacggcagtt tacgagagag atgataggt 180 ctgcttcagt aagccagatg ctacacaatt aggcttgtac gggtactcga cctgcatccc 240
ttaacttact tattaaataa tttatagcta ttgaaaagag ataagaattg ttcaaagcta 300
atattgttta aatcgtcaat tcctgcatgt tttaaggaat tgttaaattg attttttgta 360

-continued

```
aatattttct tgtattcttt gttaaaataa aaaaggggac ctctagggtc cccaattaat    420
tagtaatata atctattaaa ggtcattcaa aaggtcatcc accggatcag cttagtaaag    480
ccctcgctag attttaatgc ggatgttgcg attacttcgc caactattgc gataacaaga    540
aaaagccagc ctttcatgat atatctccca atttgtgtag ggcttattat gcacgcttaa    600
aaataataaa agcagacttg acctgatagt ttggctgtga gcaattatgt gcttagtgca    660
tctaacgctt gagttaagcc gcgccgcgaa gcggcgtcgg cttgaacgaa ttgttagaca    720
ttatttgccg actaccttgg tgatctcgcc tttcacgtag tggacaaatt cttccaactg    780
atctgcgcgc gaggccaagc gatcttcttc ttgtccaaga taagcctgtc tagcttcaag    840
tatgacgggc tgatactggg ccggcaggcg ctccattgcc cagtcggcag cgacatcctt    900
cggcgcgatt ttgccggtta ctgcgctgta ccaaatgcgg gacaacgtaa gcactacatt    960
tcgctcatcg ccagcccagt cgggcggcga gttccatagc gttaaggttt catttagcgc   1020
ctcaaataga tcctgttcag gaaccggatc aaagagttcc tccgccgctg gacctaccaa   1080
ggcaacgcta tgttctcttg cttttgtcag caagatagcc agatcaatgt cgatcgtggc   1140
tggctcgaag atacctgcaa gaatgtcatt gcgctgccat tctccaaatt gcagttcgcg   1200
cttagctgga taacgccacg gaatgatgtc gtcgtgcaca acaatggtga cttctacagc   1260
gcggagaatc tcgctctctc caggggaagc cgaagtttcc aaaaggtcgt tgatcaaagc   1320
tcgccgcgtt gtttcatcaa gccttacggt caccgtaacc agcaaatcaa tatcactgtg   1380
tggcttcagg ccgccatcca ctgcggagcc gtacaaatgt acggccagca acgtcggttc   1440
gagatggcgc tcgatgacgc caactacctc tgatagttga gtcgatactt cggcgatcac   1500
cgcttccctc atgatgttta actttgtttt agggcgactg ccctgctgcg taacatcgtt   1560
gctgctccat aacatcaaac atcgacccac ggcgtaacgc gcttgctgct tggatgcccg   1620
aggcatagac tgtaccccaa aaaaacagtc ataacaagcc atgaaaaccg ccactgcgcc   1680
gttaccaccg ctgcgttcgg tcaaggttct ggaccagttg cgtgagcgca tacgctactt   1740
gcattacagc ttacgaaccg aacaggctta tgtccactgg gttcgtgcct tcatccgttt   1800
ccacggtgtg cgtcacccgg caaccttggg cagcagcgaa gtcgaggcat ttctgtcctg   1860
gctggcgaac gagcgcaagg tttcggtctc cacgcatcgt caggcattgg cggccttgct   1920
gttcttctac ggcaaggtgc tgtgcacgga tctgccctgg cttcaggaga tcggaagacc   1980
tcggccgtcg cggcgcttgc cggtggtgct gaccccggat gaagtggttc gcatcctcgg   2040
ttttctggaa ggcgagcatc gtttgttcgc ccagcttctg tatggaacgg gcggatcagt   2100
gagggtttgc aactgcgggt caaggatctg gatttcgatc acggcacgat catcgtgcgg   2160
gagggcaagg gctccaagga tcgggccttg atgttacccg agagcttggc acccagcctg   2220
cgcgagcagg ggaattgatc cggtggatga ccttttgaat gacctttaat agattatatt   2280
actaattaat tggggaccct agaggtcccc tttttttattt tctgaacggt ctggttatag   2340
gtacattgag caactgactg aaatgcctca aaatgttctt tacgatgcca ttgggatata   2400
tcaacggtgg tatatccagt gatttttttc tccattttag cttccttagc tcctgaaaat   2460
ctcgataact caaaaaatac gcccggtagt gatcttattt cattatggtg aaagttggaa   2520
cctcttacga gcggccgcat acgatttagg tgacactata ggatccctgc cggccggtcc   2580
ggcgcgcccg ggctcgagtg cacgtacgca ttgaattaat ctcctacttg actttatgag   2640
ttgggatttt cttaaacaca attcccccgg ataaactgag ggagtccaaa gtaatgaccc   2700
```

```
tagagttatt gttactgatc tccattaact ttcgttaact acccggggat ttatgagaga   2760
tattacctaa ataaatccag ggagaaacac ggaggcagcg acaagggcca ccgggatgct   2820
caaacagctc agcgcctagg cttgaatgct tttgcaatcc cacagttaac tttatacaac   2880
ggtgatggga cttatgtctg ttacatcttg ttaattttat tcctgctttt ttgttaagta   2940
atgttgcagg ggattctcag attgtcctgg attgggaagg gaagacaacc agtttcgttc   3000
agcttatgtt ttagggctaa aattatgcaa ttgatgttcg gtgcgaactt ttctcgtttt   3060
tttagtttcc agtggggtag ggaagactgt tgcctaggga accacagcct actttccttt   3120
ttgagctttt tatcccacca ttttgatatt cagggactct tctctacagg tggacgtcat   3180
gggtacacct cacgctactt ttgcagctac tgagacagca tttcatgtga cgggctacga   3240
aaagatagat tttagcctgg tttatgtgaa tggtgtattc aacatcaaaa acacagaaat   3300
tgctgatagt tatcagaagt ttggacgctg cttgactgtt gttgatcata atgtctaccg   3360
tttgtatgga gaccaaatta agtcatattt tcgttactac gacatagact taactgtgtt   3420
tccaattact attactgaac ctggcaaaac catgtcaact tttgaacaag tagttgatgc   3480
gtttgccgat tttggcttaa ttcgtaaaga accagtttta gtagttggtg gtggtttagt   3540
tactgatgtt gtaggttttg cttgtgcagc ttatcgtcgc agtactaact atattcgcat   3600
tcccacgact ttgattggtt tgatagatgc tggaattgcg attaaagtag cagtcaatca   3660
taaaaagctg aaaaatcgct tgggtgctta ccatgcaccg cagaaagtca ttctagactt   3720
ttcctttctc aagacactac caacagccca agtccggaat ggaatggcgg agttagtgaa   3780
aattgctgtg gtagcaaatg cagaagtttt taattggctg tatgagtacg gagaagattt   3840
actgcataca cactttggct atctcaacgg tacagaggaa ctgcaagaaa ttgctcacaa   3900
agttaactac gaagcaatta aaaccatgct ggagttagaa actccaaacc tgcatgagct   3960
agacttagat cgcgtcattg cttatggtca cacttggagt ccgacactag aattagcacc   4020
gcgggttcct ctgtatcatg gtcatgctgt caacatcgat atggcgctat cagcaactat   4080
tgctgaacga cggggatata ttactgtagc agaacgcgat cgcattcttg gattgatgag   4140
tcgtctaggt ttagcccttg atcatcccct tctagatagc gatttgttat ggtacgctac   4200
ccagtctatc acccagacaa gagacgggaa acaacgcgcc gccatgccaa aacctattgg   4260
tgagtgtttc tttgtcaatg acctaacccg tgaagaattg catcaagctt tgattgcaca   4320
caaggatgta tgtgcaacat atccccgtgg tggagatggg attgaagcct atatcagtgc   4380
agaacaatct gagatggtag gagtttagaa tcgtgactag cattgttgaa aagaacacag   4440
ctagacccgt aactccccac ggtatcttgg ttgaacagct acaaaaaact ctggctttgg   4500
cagaatcagg aaatacacct gaaactgttg tgactgcact acgacaggcg tatcaattag   4560
cggcgggttt agaaccttat attagtgaac acaccactac tgaatctgac gccttagcag   4620
cactggtaca aaaaactacc aaagaagact ggacaaaacg tttcactgat ggtgaaacag   4680
tgcgtcaact agaacaggaa atgctttctg gacacgtcga gggacaaacc ctgaaaatgt   4740
ttgttcacat gactaaagcc aagagtgttt tggaagtagg aatgttcacc gggtattctg   4800
ctttggcaat ggcagaggca ttacctgatg atggacgagt ggtagcatgt gaagtagact   4860
cttatgttgc tagctttgct caaacttgtt tccaaaactc gccccacggt cataaaatta   4920
ctgtggaagt tgcaccagcc ttggaaactc tgcaaaaact tgcagcagca ggtgaatcat   4980
ttgatttgat attcatcgat gctgacaaga aagagtatgt gcagtatttc cagatcatct   5040
tggataataa tctacttgca tctaacggca ttatttgtgt agataacact ttaatgcagg   5100
```

```
gacaggttta tctgccacca gaacaacgta cagctaatgg tgaagcgatc gctcaattta   5160
accaaatcat tacccaagat ccgcgtgtag aacaagttat actaccgctt cgtgatggtg   5220
tgactttaat tcggcggttg taggagctcc attgaattaa tctcctactt gactttatga   5280
gttgggattt tcttaaacac aattcccccg gataaactga gggagtccaa agtaatgacc   5340
ctagagttat tgttactgat ctccattaac tttcgttaac tacccgggga tttatgagag   5400
atattaccta aataaatcca gggagaaaca cggaggcagc gacaagggcc accgggatgc   5460
tcaaacagct cagcgcctag gcttgaatgc ttttgcaatc ccacagttaa ctttatacaa   5520
cggtgatggg acttatgtct gttacatctt gttaatttta ttcctgcttt tttgttaagt   5580
aatgttgcag ggattctca gattgtcctg gattgggaag ggaagacaac cagtttcgtt    5640
cagcttatgt tttagggcta aaattatgca attgatgttc ggtgcgaact tttctcgttt   5700
ttttagtttc cagtggggta gggaagactg ttgcctaggg aaccacagcc tactttcctt   5760
tttgagcttt ttatcccacc attttgatat tcagggactc ttctctacag gtgatgacac   5820
aatctatttc tgtggcttct gttggacaaa caactcagtc ggtgagcctg ggacttcgca   5880
tatctgcgtt gtggaaaagt ttagctacac ttgcactgct gttgttagta ttgccaatca   5940
atgctgcgat tgtgttggta tcgctgttat tgggtagtca atcgcaagcg atcgccaccg   6000
aacccaaaaa catcttgatt agtggcggta aaatgactaa ggcgttacaa ttagcccgta   6060
gttttcacgc cgccggacat cgagtggttt tagtagaaac tcacaaatac tggttaacgg   6120
gacaccgatt ttccaaagca gtaagtcgtt tctacactct accaacgccc caatctgatc   6180
ctgaagcata cacccaagcc ctattagata ttgttcaaaa agaaaatatc gatgtctatg   6240
tacccgtgtg cagtccggtt gctagttact acgactcttt agctaaaccc gtactgtcga   6300
agtactgcga ggtttttcac tgtgacgcag atgtcaccca aatgttggat gataaatacg   6360
cttttgctga gaaagcgcgg agtttggggt tatctgttcc caagtctttc aaaattactg   6420
acccggaaca ggtgagcaac tttgattttt ctcaagaaaa gcgtaaatac atcctcaaaa   6480
gcattcctta tgactctgtt cgtcgcttag atttaaccaa acttccttgt gagactcccg   6540
aagcaacagc agattttgtc aacagcttac ccatcagttc ccaaaagcca tggattatgc   6600
aagaattcat tcctggaaaa gaattttgca cccacagcac tgtccgcaat ggggagttga   6660
gaatgcattg ctgttgtgaa tcttcggcat ttcaagttaa ctatgagaat gtcgatcatc   6720
cccaaatttt ggaatgggtg cgacactttg tcaaagcatt aggtatcact ggacaggtat   6780
cttttgattt tatcgaagca caagatggca caatctacgc cattgaatgt aatccgcgta   6840
cccattctgc catcactatg ttctacaatc atccggatgt ggcaaatgct tatttgagtg   6900
aaattccaca agtagaacca attcaacctc tgattaatag taagcctacc tactggactt   6960
atcacgaaat ttggcgattg acaggaattc gttctttctc acagttgcaa acttggttga   7020
aaaacttttt tggtggaaaa gatgcgattt acagtttgag tgatcctcta cctttttaa    7080
cagttcatca ctggcaaatt cctttattat tgctacaaaa tttgcaacag ctaaaaggtt   7140
ggatcaggat agattttaat attgggaaat tggttgagtt tggtggcgat tagattcagt   7200
tatcagttat cagttatcag ttagtagctg ttcactgata atttatagat attgaatata   7260
tataagactc atatttgatt tctgaaatac acgtagggtg cgtgatagct acgccataac   7320
acaccctact ggcgcgtcaa gcctaaaatg ttgcaataaa tctctgattc tatctctgtg   7380
ttctctctct tgaaaagctt tgatcggagg aaacctccgc tcaaactttt cgctgcttcc   7440
```

-continued tctgcggttt attaatgcac tattttaagg ctgtcgcgcc ctttgttaaa gtcaaatttt 7500
tttatcaaac cgcagaggcg cagaggaatc agagagaagg aaataattct taattgaatt 7560
gtattaagtt ataaatcact atattttatc aaagatggaa ataataaact ttttagatga 7620
ttctctggaa attgaagaac agaagaaaaa ttgggaaaga caggtaggag atatttctga 7680
tctttctctg ctgagtttag aagaacagca aaaaatatta tttatatgga atcagacaga 7740
aagtaattat gatttgtcga tttgtctaca tgagttattt gcagcacagg tagagaaaac 7800
accagatgca aaagctctca agtttgctga tcaagaattg agttatcatc agttaaattg 7860
tcgggcgaat caactcgctc actatttgca atctttggga attgtaactg aagatttagt 7920
tgggatttgt gtggaacgtt ccctagaaat ggttgtgggg ttattgggta ttttgaaagc 7980
gggtgcggct tatgttccaa ttgatcctgg atatccccaa gaacgtttag gatatatgtt 8040
ggcggattcc caggtgtcgg tgttgttgac tcaaagtcat ttagtcgata gtttaccaac 8100
atgtccaacc catactattt gcttggatac tgactgggat ctgatttctc aatatagcga 8160
tcgcaatctc caaaatacaa cgacaccaga aaatctcgct tatgtaattt acacttctgg 8220
ttctactggt aaacctaaag gagcgatgaa tacccatcgc ggtatttgca atcgtctgtt 8280
atggatgcaa gatgcttatc aactcactca acaagatcgg gttctgcaaa aaactccctt 8340
tagttttgat gtctctgtct gggaattctt ttggccgttg attaccgggg cgcggctgat 8400
tatagcacaa ccaggtggac acaaggatag ttcttatcta attaatacaa ttatccaaga 8460
agaaattacc acattacatt ttgttccttc gatgttgcag gtatttttgc aagctaaagg 8520
agtggaaaat tgtcagtcat taaaacgggt aattactagt ggtgaagctt tacctgtgag 8580
tctgcaagaa cggtttttg aacgtttggg atgtgaactg cacaatcttt atggtcctac 8640
agaagcagcg atcgatgtta cgttttggca gtgtcaacct caaagtcaat atcaaacagt 8700
accgattggt cgtcccatcg ctaatactca aatatatata ttagatcaac atttgcaacc 8760
tgtgcctgtg ggtgttgtgg gtgaacttta tattggtggt gtgggagttg ccagaggtta 8820
ctggcgtcgt ccagaattaa ctacagaaag atttgtatct aatccctttg caacgggaca 8880
aatgtataaa actggtgact tggcgcgcta tttacctgat ggtaatatcg agtatgttgg 8940
cagaattgac gatcaagtta aaattcgcgg ttttcggatt gagttgggag aaattgagag 9000
tacgctgacg caacattccc agattagtca agctgtggtt gtcgcccaga cagataattt 9060
gaataataag catttaattg cttatattgt tccccaggga gaaccaccca caccaaccca 9120
actgcggaat ttccttcagg gtaagctacc tgaattcatg gttccctcag cttttgtctg 9180
cttaaattcc tttcctctca ctcctagtgg aaaaatagac aggcgatcgc ttcccaaacc 9240
tgatttttct aacttaatca ctcatgaaga ttttacgcct gcacgcaatg atttagagag 9300
aaaaatcgcg cagatttggt cagaaatttt acagatttcg gaaattgata ttagagataa 9360
ctttttgaa gttggtggta attccctttt agcattacat ttaatgaatg ccatcgaaca 9420
aaaatttggt cgagagttag cactgtcaac tttacttact aataactcaa ttgaaaaact 9480
agcagaaatt ctgcaaaacc ccacagatgt ttttcccaat tcacccatag tagcaattca 9540
gcccaaaggt acaaaacgtc cttttttctg catccatcca gccggcggac atgtactttg 9600
ctattttagt ttggcgcatt atttaggcac tgaccagcca ttttacggtt tacaagcaca 9660
gggtttttat ggtgaagaag aaccactaac tacagttgta gaaatggcta ggctttatgc 9720
tcaagctata caaacaattc aacccacagg gccatatcaa attggtggtt ggtcgtttgg 9780
tggtgtagtt gcctatgaaa cggctcaaca actacaccaa caaggaaaag aagtttcatt 9840

```
actagcaatt ttagattcct acgtgccaat tctgttagat aaaaataaaa aaattgatga   9900
tgtttattta gttggtgtac tatcccgtgt atttggcgga atgtttggtc aagataatct   9960
gatttcacta gcggaaatcg aaaatttaag tgtggaagaa agtttaaatt acatcatcga  10020
aaaagcacgc caagccaaaa tttttccgcc aggagtggaa cgtcacaaca atcgccgcat  10080
tttagatgtt ttagtcggaa ctttaaaagc cacttattct tatgaacgtt gtccctatcc  10140
tggcaaagtt actattttta gagccagaga aaaacatatc atggctcctg atcctacttt  10200
agtttgggta gaattatttt cagttttggc tgcggaggaa attgaaattc ataatgtccc  10260
cggtaatcac tattcatttg ttttagaacc tcacgtccaa gctttggctg aaagtttgca  10320
gaaatgtttg tgctgataca agatccccga cttctttgag gatgcagctg gcgaataggg  10380
ggtcaaaccc ctcgtgcgcc cacaaattgg ttgtagagac gcgccatggc gcgtctctac  10440
atctggtgga atgacgaaaa atctcggtga ggggtgtcac ccctgattcg ccagctgtat  10500
cctttgagaa gtcgggggta cccctagagt cgacctgcag ttcaatgcgg tccaatacct  10560
cccctgccca actgggtaag ctcgcggctc cactgagtaa tacagacaag gctaaacagg  10620
caaatttttt cattggtcaa ctcctagcac caatttccca agactacgga gggggcaatg  10680
aagtttcaat taattggggt cacaaaccac agcggcctat ggctctaatc aatggcacac  10740
tagaaaaaat gttgcagcat acttggctac caaaaccccc aaatttaacc ttattgtcag  10800
atgaagttca tctctggcgc attccccttg accaaccaga atcacagcta caggatttag  10860
ccgctacctt atctagtgac gaattagccc gtgcaaacag attttatttt cccgaacatc  10920
gccggcgttt tactgctggt cgtggtattc tccgcagtat cttgggggc tatttgggtg  10980
tggaaccagg gcaagttaaa tttgattatg aatcccgtgg taaaccaata ttaggcgatc  11040
gctttgccga gagtggttta ttatttaact tgtcacactc ccagaacttg gccttgtgtg  11100
cagtcaatta cacgcgccaa atcggcatcg atttagaata tctccgcccc acatctgatt  11160
tagaatccct tgccaaaagg ttctttttac cgcgagaata tgaattattg cgatcgctac  11220
ccgatgagca aaaacaaaaa attttctttc gttactggac ttgtaaagag gcttatctta  11280
aagcaacggg tgacggcatc gctaaattag aggaaattga aatagcacta actcccacag  11340
aaccagctaa gttacagaca gctccagcgt ggagtctcct agagctagtg ccagatgata  11400
attgtgttgc tgctgttgcc gtggcgggtt ttggctggca gccaaaattc tggcattatt  11460
gagcatgcaa gcttctccct atagtgagtc gtattagcgg ccgcatcgaa tataacttcg  11520
tataatgtat gctatacgaa gttattagcg atgaggacat gaggttgccc cgtattcagt  11580
gtcgctgatt tgtattgtct gaagttgttt ttacgttaag ttgatgcaga tcaattaata  11640
cgatacctgc gtcataattg attatttgac gtggtttgat ggcctccacg cacgttgtga  11700
tatgtagatg ataatcatta tcactttacg ggtcctttcc ggtgatccga caggttacgg  11760
ggcggcgacc tcgcgggttt tcgctattta tgaaaatttt ccggtttaag gcgtttccgt  11820
tcttcttcgt cataacttaa tgtttttatt taaaataccc tctgaaaaga aaggaaacga  11880
caggtgctga aagcgaggct tttggcctc tgtcgtttcc tttctctgtt tttgtccgtg  11940
gaatgaacaa tggaagtcct cgtctcgccc tcgaattagc ccgcctaatg agcgggcttt  12000
ttttgaatta attctcgcga gctggcacga caggtttccc gactggaaag cgggcagtga  12060
gcgcaacgca attaatgtaa gttagcgcga attgcaagct ggccgacgcg ctgggctacg  12120
tcttgctggc gttcgggagc agaagagcat acatctggaa gcaaagccag gaaagcggcc  12180
```

-continued

```
tatggagctg tgcggcagcg ctcagtaggc aatttttcaa aatattgtta agccttttct  12240
gagcatggta tttttcatgg tattaccaat tagcaggaaa ataagccatt gaatataaaa  12300
gataaaaatg tcttgtttac aatagagtgg ggggggtcag cctgccgcct tgggccgggt  12360
gatgtcgtac ttgcccgccg cgaactcggt taccgtccag cccagcgcga ccagctccgg  12420
caacgcctcg cgcacccgct tgcggcgctt gcgcatggtc gaaccactgg cctctgacgg  12480
ccagacatag ccgcacaagg tatctatgga agccttgccg gttttgccgg ggtcgatcca  12540
gccacacagc cgctggtgca gcaggcgggc ggtttcgctg tccagcgccc gcacctcgtc  12600
catgctgatg cgcacatgct ggccgccacc catgacggcc tgcgcgatca aggggttcag  12660
ggccacgtac aggcgcccgt ccgcctcgtc gctggcgtac tccgacagca gccgaaaccc  12720
ctgccgcttg cggccattct gggcgatgat ggataccttc caaaggcgct cgatgcagtc  12780
ctgtatgtgc ttgagcgccc caccactatc gacctctgcc ccgatttcct ttgccagcgc  12840
ccgatagcta cctttgacca catggcattc agcggtgacg gcctcccact tgggttccag  12900
gaacagccgg agctgccgtc cgccttcggt cttgggttcc gggccaagca ctaggccatt  12960
aggcccagcc atggccacca gcccttgcag gatgcgcaga tcatcagcgc ccagcggctc  13020
cgggccgctg aactcgatcc gcttgccgtc gccgtagtca tacgtcacgt ccagcttgct  13080
gcgcttgcgc tcgccccgct tgagggcacg gaacaggccg gggccagac agtgcgccgg  13140
gtcgtgccgg acgtggctga ggctgtgctt gttcttaggc ttcaccacgg ggcacccccct  13200
tgctcttgcg ctgcctctcc agcacggcgg gcttgagcac cccgccgtca tgccgcctga  13260
accaccgatc agcgaacggt gcgccatagt tggccttgct cacaccgaag cggacgaaga  13320
accggcgctg gtcgtcgtcc acaccccatt cctcggcctc ggcgctggtc atgctcgaca  13380
ggtaggactg ccagcggatg ttatcgacca gtaccgagct gccccggctg gcctgctgct  13440
ggtcgcctgc gcccatcatg gccgcgccct tgctggcatg gtgcaggaac acgatagagc  13500
acccggtatc ggcggcgatg gcctccatgc gaccgatgac ctgggccatg gggccgctgg  13560
cgttttcttc ctcgatgtgg aaccggcgca gcgtgtccag caccatcagg cggcggccct  13620
cggcggcgcg cttgaggccg tcgaaccact ccggggccat gatgttgggc aggctgccga  13680
tcagcggctg gatcagcagg ccgtcagcca cggcttgccg ttcctcggcg ctgaggtgcg  13740
ccccaagggc gtgcaggcgg tgatgaatgg cggtgggcgg gtcttcggcg ggcaggtaga  13800
tcaccgggcc ggtgggcagt tcgcccacct ccagcagatc cggcccgcct gcaatctgtg  13860
cggccagttg cagggccagc atggatttac cggcaccacc gggcgacacc agcgccccga  13920
ccgtaccggc caccatgttg ggcaaaacgt agtccagcgg tggcggcgct gctgcgaacg  13980
cctccagaat attgataggc ttatgggtag ccattgattg cctcctttgc aggcagttgg  14040
tggttaggcg ctggcggggt cactaccccc gccctgcgcc gctctgagtt cttccaggca  14100
ctcgcgcagc gcctcgtatt cgtcgtcggt cagccagaac ttgcgctgac gcatcccttt  14160
ggccttcatg cgctcggcat atcgcgcttg gcgtacagcg tcagggctgg ccagcaggtc  14220
gccggtctgc ttgtcctttt ggtctttcat atcagtcacc gagaaacttg ccggggccga  14280
aaggcttgtc ttcgcggaac aaggacaagg tgcagccgtc aaggttaagg ctggccatat  14340
cagcgactga aaagcggcca gcctcggcct tgtttgacgt ataaccaaag ccaccgggca  14400
accaatagcc cttgtcactt ttgatcaggt agaccgaccc tgaagcgctt ttttcgtatt  14460
ccataaaacc cccttctgtg cgtgagtact catagtataa caggcgtgag taccaacgca  14520
agcactacat gctgaaatct ggcccgcccc tgtccatgcc tcgctggcgg ggtgccggtg  14580
```

```
cccgtgccag ctcggcccgc gcaagctgga cgctgggcag acccatgacc ttgctgacgg  14640
tgcgctcgat gtaatccgct tcgtggccgg gcttgcgctc tgccagcgct gggctggcct  14700
cggccatggc cttgccgatt tcctcggcac tgcggccccg gctggccagc ttctgcgcgg  14760
cgataaagtc gcacttgctg aggtcatgac cgaagcgctt gaccagcccg gccatctcgc  14820
tgcggtactc gtccagcgcc gtgcgccggt ggcggctaag ctgccgctcg ggcagttcga  14880
ggctggccag cctgcgggcc ttctcctgct gccgctgggc ctgctcgatc tgctggccag  14940
cctgctgcac cagcgccggg ccagcggtgg cggtcttgcc cttggattca cgcagcagca  15000
cccacggctg ataaccggcg cgggtggtgt gcttgtcctt gcggttggtg aagcccgcca  15060
agcggccata gtggcggctg tcggcgctgg ccgggtcggc gtcgtactcg ctggccagcg  15120
tccgggcaat ctgcccccga agttcaccgc ctgcggcgtc ggccaccttg acccatgcct  15180
gatagttctt cgggctggtt tccactacca gggcaggctc ccggccctcg gctttcatgt  15240
catccaggtc aaactcgctg aggtcgtcca ccagcaccag accatgccgc tcctgctcgg  15300
cgggcctgat atacacgtca ttgccctggg cattcatccg cttgagccat ggcgtgttct  15360
ggagcacttc ggcggctgac cattcccggt tcatcatctg gccggtgggt gcgtccctga  15420
cgccgatatc gaagcgctca cagcccatgg ccttgagctg tcggcctatg gcctgcaaag  15480
tcctgtcgtt cttcatcggg ccaccaagcg cagccagatc gagccgtcct cggttgtcag  15540
tggcgtcagg tcgagcaaga gcaacgatgc gatcagcagc accaccgtag gcatcatgga  15600
agccagcatc acggttagcc atagcttcca gtgccacccc cgcgacgcgc tccgggcgct  15660
ctgcgcggcg ctgctcacct cggcggctac ctcccgcaac tctttggcca gctccaccca  15720
tgccgcccct gtctggcgct gggctttcag ccactccgcc gcctgcgcct cgctggcctg  15780
cttggtctgg ctcatgacct gccgggcttc gtcggccagt gtcgccatgc tctgggccag  15840
cggttcgatc tgctccgcta actcgttgat gcctctggat ttcttcactc tgtcgattgc  15900
gttcatggtc tattgcctcc cggtattcct gtaagtcgat gatctgggcg ttggcggtgt  15960
cgatgttcag ggccacgtct gcccggtcgg tgcggatgcc ccggccttcc atctccacca  16020
cgttcggccc caggtgaaca ccgggcaggc gctcgatgcc ctgcgcctca agtgttctgt  16080
ggtcaatgcg ggcgtcgtgg ccagcccgct ctaatgcccg gttggcatgg tcggcccatg  16140
cctcgcgggt ctgctcaagc catgccttgg gcttgagcgc ttcggtcttc tgtgccccgc  16200
ccttctccgg ggtcttgccg ttgtaccgct tgaaccactg agcggcgggc cgctcgatgc  16260
cgtcattgat ccgctcggag atcatcaggt ggcagtgcgg gttctcgccg ccaccggcat  16320
ggatggccag cgtatacggc aggcgctcgg caccggtcag gtgctgggcg aactcggacg  16380
ccagcgcctt ctgctggtcg agggtcagct cgaccggcag ggcaaattcg acctccttga  16440
acagccgccc attggcgcgt tcatacaggt cggcagcatc ccagtagtcg gcgggccgct  16500
cgacgaactc cggcatgtgc ccggattcgg cgtgcaagac ttcatccatg tcgcgggcat  16560
acttgccttc gcgctggatg tagtcggcct tggccctggc cgattggccg cccgacctgc  16620
tgccggtttt cgccgtaagg tgataaatcg ccatgctgcc tcgctgttgc ttttgctttt  16680
cggctccatg caatggccct cggagagcgc accgcccgaa gggtggccgt taggccagtt  16740
tctcgaagag aaaccggtaa gtgcgccctc ccctacaaag tagggtcggg attgccgccg  16800
ctgtgcctcc atgatagcct acgagacagc acattaacaa tggggtgtca agatggttaa  16860
ggggagcaac aaggcggcgg atcggctggc caagctcgaa gaacaacgag cgcgaatcaa  16920
```

tgccgaaatt cagcgggagc gggcaaggga acagcagcaa gagcgcaaga acgaaacaag 16980
gcgcaaggtg ctggtggggg ccatgatttt ggccaaggtg aacagcagcg agtggccgga 17040
ggatcggctc atggcggcaa tggatgcgta ccttgaacgc gaccacgacc gcgccttgtt 17100
cggtctgccg ccacgccaga aggatgagcc gggctgaatg atcgaccgag acaggccctg 17160
cggggctgca cacgcgcccc caccettcgg gtagggggaa aggccgctaa agcggctaaa 17220
agcgctccag cgtatttctg cggggtttgg tgtggggttt agcgggcttt gcccgccttt 17280
ccccctgccg cgcagcggtg gggcggtgtg tagcctagcg cagcgaatag accagctatc 17340
cggcctctgg ccgggcatat tgggcaaggg cagcagcgcc ccacaagggc gctgataacc 17400
gcgcctagtg gattattctt agataatcat ggatggattt ttccaacacc ccgccagccc 17460
ccgcccctgc tgggtttgca ggtttggggg cgtgacagtt attgcagggg ttcgtgacag 17520
ttattgcagg ggggcgtgac agttattgca ggggttcgtg acagttagta cgggagtgac 17580
gggcactggc tggcaatgtc tagcaacggc aggcatttcg gctgagggta aaagaacttt 17640
ccgctaagcg atagactgta tgtaaacaca gtattgcaag gacgcggaac atgcctcatg 17700
tggcggccag ga 17712

<210> SEQ ID NO 88
<211> LENGTH: 17869
<212> TYPE: DNA
<213> ORGANISM: Artificial Sequence
<220> FEATURE:
<223> OTHER INFORMATION: sequence of plasmid Sh-TP560

<400> SEQUENCE: 88
ctcgcgagaa ttaattcaga taaaaaaaat ccttagcttt cgctaaggat gatttctagc 60
gatgaccctg ctgattggtt cgctgaccat ttccgggtgc gggacggcgt taccagaaac 120
tcagaaggtt cgtccaacca aaccgactct gacggcagtt tacgagagag atgatagggt 180
ctgcttcagt aagccagatg ctacacaatt aggcttgtac gggtactcga cctgcatccc 240
ttaacttact tattaaataa tttatagcta ttgaaaagag ataagaattg ttcaaagcta 300
atattgttta aatcgtcaat tcctgcatgt tttaaggaat tgttaaattg attttttgta 360
aatattttct tgtattcttt gttaaaataa aaaaggggac ctctagggtc cccaattaat 420
tagtaatata atctattaaa ggtcattcaa aaggtcatcc accggatcag cttagtaaag 480
ccctcgctag attttaatgc ggatgttgcg attacttcgc caactattgc gataacaaga 540
aaaagccagc ctttcatgat atatctccca atttgtgtag ggcttattat gcacgcttaa 600
aaataataaa agcagacttg acctgatagt ttggctgtga gcaattatgt gcttagtgca 660
tctaacgctt gagttaagcc gcgccgcgaa gcggcgtcgg cttgaacgaa ttgttagaca 720
ttatttgccg actaccttgg tgatctcgcc tttcacgtag tggacaaatt cttccaactg 780
atctgcgcgc gaggccaagc gatcttcttc ttgtccaaga taagcctgtc tagcttcaag 840
tatgacgggc tgatactggg ccggcaggcg ctccattgcc cagtcggcag cgacatcctt 900
cggcgcgatt ttgccggtta ctgcgctgta ccaaatgcgg gacaacgtaa gcactacatt 960
tcgctcatcg ccagcccagt cgggcggcga gttccatagc gttaaggttt catttagcgc 1020
ctcaaataga tcctgttcag gaaccggatc aaagagttcc tccgccgctg gacctaccaa 1080
ggcaacgcta tgttctcttg cttttgtcag caagatagcc agatcaatgt cgatcgtggc 1140
tggctcgaag atacctgcaa gaatgtcatt gcgctgccat tctccaaatt gcagttcgcg 1200
cttagctgga taacgccacg gaatgatgtc gtcgtgcaca acaatggtga cttctacagc 1260

-continued

```
gcggagaatc tcgctctctc caggggaagc cgaagtttcc aaaaggtcgt tgatcaaagc   1320
tcgccgcgtt gtttcatcaa gccttacggt caccgtaacc agcaaatcaa tatcactgtg   1380
tggcttcagg ccgccatcca ctgcggagcc gtacaaatgt acggccagca acgtcggttc   1440
gagatggcgc tcgatgacgc caactacctc tgatagttga gtcgatactt cggcgatcac   1500
cgcttccctc atgatgttta actttgtttt agggcgactg ccctgctgcg taacatcgtt   1560
gctgctccat aacatcaaac atcgacccac ggcgtaacgc gcttgctgct tggatgcccg   1620
aggcatagac tgtaccccaa aaaaacagtc ataacaagcc atgaaaaccg ccactgcgcc   1680
gttaccaccg ctgcgttcgg tcaaggttct ggaccagttg cgtgagcgca tacgctactt   1740
gcattacagc ttacgaaccg aacaggctta tgtccactgg gttcgtgcct tcatccgttt   1800
ccacggtgtg cgtcacccgg caaccttggg cagcagcgaa gtcgaggcat ttctgtcctg   1860
gctggcgaac gagcgcaagg tttcggtctc cacgcatcgt caggcattgg cggccttgct   1920
gttcttctac ggcaaggtgc tgtgcacgga tctgccctgg cttcaggaga tcggaagacc   1980
tcggccgtcg cggcgcttgc cggtggtgct gaccccggat gaagtggttc gcatcctcgg   2040
ttttctggaa ggcgagcatc gtttgttcgc ccagcttctg tatggaacgg gcggatcagt   2100
gagggtttgc aactgcgggt caaggatctg gatttcgatc acggcacgat catcgtgcgg   2160
gagggcaagg gctccaagga tcgggccttg atgttacccg agagcttggc acccagcctg   2220
cgcgagcagg ggaattgatc cggtggatga cctttgaat gacctttaat agattatatt   2280
actaattaat tggggaccct agaggtcccc tttttattt tctgaacggt ctggttatag   2340
gtacattgag caactgactg aaatgcctca aaatgttctt tacgatgcca ttgggatata   2400
tcaacggtgg tatatccagt gatttttttc tccattttag cttccttagc tcctgaaaat   2460
ctcgataact caaaaaatac gcccggtagt gatcttattt cattatggtg aaagttggaa   2520
cctcttacga gcggccgcat acgatttagg tgacactata ggatccctgc cggccggtcc   2580
ggcgcgcccg ggctcgagtg cacgtacgca ttgaattaat ctcctacttg actttatgag   2640
ttgggatttt cttaaacaca attcccccgg ataaactgag ggagtccaaa gtaatgaccc   2700
tagagttatt gttactgatc tccattaact ttcgttaact acccggggat ttatgagaga   2760
tattacctaa ataaatccag ggagaaacac ggaggcagcg acaagggcca ccgggatgct   2820
caaacagctc agcgcctagg cttgaatgct tttgcaatcc cacagttaac tttatacaac   2880
ggtgatggga cttatgtctg ttacatcttg ttaattttat tcctgctttt ttgttaagta   2940
atgttgcagg ggattctcag attgtcctgg attgggaagg gaagacaacc agtttcgttc   3000
agcttatgtt ttagggctaa aattatgcaa ttgatgttcg gtgcgaactt ttctcgtttt   3060
tttagtttcc agtggggtag ggaagactgt tgcctaggga accacagcct actttccttt   3120
ttgagctttt tatcccacca ttttgatatt cagggactct tctctacagg tggacgtcat   3180
gggtacacct cacgctactt ttgcagctac tgagacagca tttcatgtga cgggctacga   3240
aaagatagat tttagcctgg tttatgtgaa tggtgtattc aacatcaaaa acacagaaat   3300
tgctgatagt tatcagaagt ttggacgctg cttgactgtt gttgatcata atgtctaccg   3360
tttgtatgga gaccaaatta agtcatattt tcgttactac gacatagact taactgtgtt   3420
tccaattact attactgaac ctggcaaaac catgtcaact tttgaacaag tagttgatgc   3480
gtttgccgat tttggcttaa ttcgtaaaga accagtttta gtagttggtg gtggtttagt   3540
tactgatgtt gtaggttttg cttgtgcagc ttatcgtcgc agtactaact atattcgcat   3600
```

-continued

```
tcccacgact ttgattggtt tgatagatgc tggaattgcg attaaagtag cagtcaatca   3660
taaaaagctg aaaaatcgct tgggtgctta ccatgcaccg cagaaagtca ttctagactt   3720
ttcctttctc aagacactac caacagccca agtccggaat ggaatggcgg agttagtgaa   3780
aattgctgtg gtagcaaatg cagaagtttt taattggctg tatgagtacg gagaagattt   3840
actgcataca cactttggct atctcaacgg tacagaggaa ctgcaagaaa ttgctcacaa   3900
agttaactac gaagcaatta aaaccatgct ggagttagaa actccaaacc tgcatgagct   3960
agacttagat cgcgtcattg cttatggtca cacttggagt ccgacactag aattagcacc   4020
gcgggttcct ctgtatcatg gtcatgctgt caacatcgat atggcgctat cagcaactat   4080
tgctgaacga cggggatata ttactgtagc agaacgcgat cgcattcttg gattgatgag   4140
tcgtctaggt ttagcccttg atcatcccct tctagatagc gatttgttat ggtacgctac   4200
ccagtctatc acccagacaa gagacgggaa acaacgcgcc gccatgccaa aacctattgg   4260
tgagtgtttc tttgtcaatg acctaacccg tgaagaattg catcaagctt tgattgcaca   4320
caaggatgta tgtgcaacat atccccgtgg tggagatggg attgaagcct atatcagtgc   4380
agaacaatct gagatggtag gagtttagaa tcgtgactag cattgttgaa aagaacacag   4440
ctagacccgt aactccccac ggtatcttgg ttgaacagct acaaaaaact ctggctttgg   4500
cagaatcagg aaatacacct gaaactgttg tgactgcact acgacaggcg tatcaattag   4560
cggcgggttt agaaccttat attagtgaac acaccactac tgaatctgac gccttagcag   4620
cactggtaca aaaaactacc aaagaagact ggacaaaacg tttcactgat ggtgaaacag   4680
tgcgtcaact agaacaggaa atgctttctg gacacgtcga gggacaaacc ctgaaaatgt   4740
ttgttcacat gactaaagcc aagagtgttt tggaagtagg aatgttcacc gggtattctg   4800
ctttggcaat ggcagaggca ttacctgatg atggacgagt ggtagcatgt gaagtagact   4860
cttatgttgc tagctttgct caaacttgtt tccaaaactc gccccacggt cataaaatta   4920
ctgtggaagt tgcaccagcc ttggaaactc tgcaaaaact tgcagcagca ggtgaatcat   4980
ttgatttgat attcatcgat gctgacaaga aagagtatgt gcagtatttc cagatcatct   5040
tggataataa tctacttgca tctaacggca ttatttgtgt agataacact ttaatgcagg   5100
gacaggttta tctgccacca gaacaacgta cagctaatgg tgaagcgatc gctcaattta   5160
accaaatcat tacccaagat ccgcgtgtag aacaagttat actaccgctt cgtgatggtg   5220
tgactttaat tcggcggttg taggagctcc attgaattaa tctcctactt gactttatga   5280
gttgggattt tcttaaacac aattccccccg gataaactga gggagtccaa agtaatgacc   5340
ctagagttat tgttactgat ctccattaac tttcgttaac tacccgggga tttatgagag   5400
atattaccta aataaatcca gggagaaaca cggaggcagc gacaagggcc accgggatgc   5460
tcaaacagct cagcgcctag gcttgaatgc ttttgcaatc ccacagttaa ctttatacaa   5520
cggtgatggg acttatgtct gttacatctt gttaatttta ttcctgcttt tttgttaagt   5580
aatgttgcag ggattctca gattgtcctg gattgggaag ggaagacaac cagtttcgtt   5640
cagcttatgt tttagggcta aaattatgca attgatgttc ggtgcgaact tttctcgttt   5700
ttttagtttc cagtggggta gggaagactg ttgcctaggg aaccacagcc tactttcctt   5760
tttgagcttt ttatcccacc attttgatat tcagggactc ttctctacag gtgatgacac   5820
aatctatttc tgtggcttct gttggacaaa caactcagtc ggtgagcctg ggacttcgca   5880
tatctgcgtt gtggaaaagt ttagctacac ttgcactgct gttgttagta ttgccaatca   5940
atgctgcgat tgtgttggta tcgctgttat tgggtagtca atcgcaagcg atcgccaccg   6000
```

-continued

```
aacccaaaaa catcttgatt agtggcggta aaatgactaa ggcgttacaa ttagcccgta   6060
gttttcacgc cgccggacat cgagtggttt tagtagaaac tcacaaatac tggttaacgg   6120
gacaccgatt ttccaaagca gtaagtcgtt tctacactct accaacgccc caatctgatc   6180
ctgaagcata cacccaagcc ctattagata ttgttcaaaa agaaaatatc gatgtctatg   6240
tacccgtgtg cagtccggtt gctagttact acgactcttt agctaaaccc gtactgtcga   6300
agtactgcga ggtttttcac tgtgacgcag atgtcaccca aatgttggat gataaatacg   6360
cttttgctga gaaagcgcgg agtttggggt tatctgttcc caagtctttc aaaattactg   6420
acccggaaca ggtgagcaac tttgattttt ctcaagaaaa gcgtaaatac atcctcaaaa   6480
gcattcctta tgactctgtt cgtcgcttag atttaaccaa acttccttgt gagactcccg   6540
aagcaacagc agattttgtc aacagcttac ccatcagttc ccaaaagcca tggattatgc   6600
aagaattcat tcctggaaaa gaattttgca cccacagcac tgtccgcaat ggggagttga   6660
gaatgcattg ctgttgtgaa tcttcggcat ttcaagttaa ctatgagaat gtcgatcatc   6720
cccaaatttt ggaatgggtg cgacactttg tcaaagcatt aggtatcact ggacaggtat   6780
cttttgattt tatcgaagca caagatggca caatctacgc cattgaatgt aatccgcgta   6840
cccattctgc catcactatg ttctacaatc atccggatgt ggcaaatgct tatttgagtg   6900
aaattccaca agtagaacca attcaacctc tgattaatag taagcctacc tactggactt   6960
atcacgaaat ttggcgattg acaggaattc gttctttctc acagttgcaa acttggttga   7020
aaaacttttt tggtggaaaa gatgcgattt acagtttgag tgatcctcta cctttttaa    7080
cagttcatca ctggcaaatt cctttattat tgctacaaaa tttgcaacag ctaaaaggtt   7140
ggatcaggat agattttaat attgggaaat tggttgagtt tggtggcgat tagggtaccc   7200
attgaattaa tctcctactt gactttatga gttgggattt tcttaaacac aattcccccg   7260
gataaactga gggagtccaa agtaatgacc ctagagttat tgttactgat ctccattaac   7320
tttcgttaac tacccgggga tttatgagag atattaccta aataaatcca gggagaaaca   7380
cggaggcagc gacaagggcc accgggatgc tcaaacagct cagcgcctag gcttgaatgc   7440
ttttgcaatc ccacagttaa ctttatacaa cggtgatggg acttatgtct gttacatctt   7500
gttaatttta ttcctgcttt tttgttaagt aatgttgcag ggattctca gattgtcctg    7560
gattgggaag ggaagacaac cagtttcgtt cagcttatgt tttagggcta aaattatgca   7620
attgatgttc ggtgcgaact tttctcgttt ttttagtttc cagtggggta gggaagactg   7680
ttgcctaggg aaccacagcc tactttcctt tttgagcttt ttatcccacc attttgatat   7740
tcagggactc ttctctacag gtgatggaaa taataaactt tttagatgat tctctggaaa   7800
ttgaagaaca gaagaaaaat tgggaaagac aggtaggaga tatttctgat ctttctctgc   7860
tgagtttaga agaacagcaa aaaatattat ttatatggaa tcagacagaa agtaattatg   7920
atttgtcgat ttgtctacat gagttatttg cagcacaggt agagaaaaca ccagatgcaa   7980
aagctctcaa gtttgctgat caagaattga gttatcatca gttaaattgt cgggcgaatc   8040
aactcgctca ctatttgcaa tctttgggaa ttgtaactga agatttagtt gggatttgtg   8100
tggaacgttc cctagaaatg gttgtggggt tattgggtat tttgaaagcg ggtgcggctt   8160
atgttccaat tgatcctgga tatccccaag aacgtttagg atatatgttg gcggattccc   8220
aggtgtcggt gttgttgact caaagtcatt tagtcgatag tttaccaaca tgtccaaccc   8280
atactatttg cttggatact gactgggatc tgatttctca atatagcgat cgcaatctcc   8340
```

```
aaaatacaac gacaccagaa aatctcgctt atgtaattta cacttctggt tctactggta   8400
aacctaaagg agcgatgaat acccatcgcg gtatttgcaa tcgtctgtta tggatgcaag   8460
atgcttatca actcactcaa caagatcggg ttctgcaaaa aactcccttt agttttgatg   8520
tctctgtctg ggaattcttt tggccgttga ttaccggggc gcggctgatt atagcacaac   8580
caggtggaca caaggatagt tcttatctaa ttaatacaat tatccaagaa gaaattacca   8640
cattacattt tgttccttcg atgttgcagg tatttttgca agctaaagga gtggaaaatt   8700
gtcagtcatt aaaacgggta attactagtg gtgaagcttt acctgtgagt ctgcaagaac   8760
ggtttttga acgtttggga tgtgaactgc acaatcttta tggtcctaca gaagcagcga   8820
tcgatgttac gttttggcag tgtcaacctc aaagtcaata tcaaacagta ccgattggtc   8880
gtcccatcgc taatactcaa atatatatat tagatcaaca tttgcaacct gtgcctgtgg   8940
gtgttgtggg tgaactttat attggtggtg tgggagttgc cagaggttac tggcgtcgtc   9000
cagaattaac tacagaaaga tttgtatcta atccctttgc aacgggacaa atgtataaaa   9060
ctggtgactt ggcgcgctat ttacctgatg gtaatatcga gtatgttggc agaattgacg   9120
atcaagttaa aattcgcggt tttcggattg agttgggaga aattgagagt acgctgacgc   9180
aacattccca gattagtcaa gctgtggttg tcgcccagac agataatttg aataataagc   9240
atttaattgc ttatattgtt ccccagggag aaccacccac accaacccaa ctgcggaatt   9300
tccttcaggg taagctacct gaattcatgg ttccctcagc ttttgtctgc ttaaattcct   9360
ttcctctcac tcctagtgga aaaatagaca ggcgatcgct tcccaaacct gatttttcta   9420
acttaatcac tcatgaagat tttacgcctg cacgcaatga tttagagaga aaaatcgcgc   9480
agatttggtc agaaatttta cagatttcgg aaattgatat tagagataac tttttgaag   9540
ttggtggtaa ttccctttta gcattacatt taatgaatgc catcgaacaa aaatttggtc   9600
gagagttagc actgtcaact ttacttacta ataactcaat tgaaaaacta gcagaaattc   9660
tgcaaaaccc cacagatgtt tttcccaatt cacccatagt agcaattcag cccaaaggta   9720
caaaacgtcc tttttctgc atccatccag ccggcggaca tgtactttgc tattttagtt   9780
tggcgcatta tttaggcact gaccagccat tttacggttt acaagcacag ggtttttatg   9840
gtgaagaaga accactaact acagttgtag aaatggctag gctttatgct caagctatac   9900
aaacaattca acccacaggg ccatatcaaa ttggtggttg gtcgtttggt ggtgtagttg   9960
cctatgaaac ggctcaacaa ctacaccaac aaggaaaaga agtttcatta ctagcaattt  10020
tagattccta cgtgccaatt ctgttagata aaaataaaaa aattgatgat gtttatttag  10080
ttggtgtact atcccgtgta tttggcggaa tgtttggtca agataatctg atttcactag  10140
cggaaatcga aaatttaagt gtggaagaaa gtttaaatta catcatcgaa aaagcacgcc  10200
aagccaaaat ttttccgcca ggagtggaac gtcacaacaa tcgccgcatt ttagatgttt  10260
tagtcggaac tttaaaagcc acttattctt atgaacgttg tccctatcct ggcaaagtta  10320
ctatttttag agccagagaa aaacatatca tggctcctga tcctacttta gtttgggtag  10380
aattatttc agttttggct gcggaggaaa ttgaaattca taatgtcccc ggtaatcact  10440
attcatttgt tttagaacct cacgtccaag ctttggctga aagtttgcag aaatgtttgt  10500
gctgatacaa gatccccgac ttctttgagg atgcagctgg cgaatagggg gtcaaacccc  10560
tcgtgcgccc acaaattggt tgtagagacg cgccatggcg cgtctctaca tctggtggaa  10620
tgacgaaaaa tctcggtgag ggtgtcaccc cctgattcgc cagctgtatc ctttgagaag  10680
tcggggtcga cctgcagttc aatgcggtcc aatacctccc ctgcccaact gggtaagctc  10740
```

-continued gcggctccac tgagtaatac agacaaggct aaacaggcaa attttttcat tggtcaactc 10800
ctagcaccaa tttcccaaga ctacggaggg ggcaatgaag tttcaattaa ttggggtcac 10860
aaaccacagc ggcctatggc tctaatcaat ggcacactag aaaaaatgtt gcagcatact 10920
tggctaccaa aacccccaaa tttaacctta ttgtcagatg aagttcatct ctggcgcatt 10980
ccccttgacc aaccagaatc acagctacag gatttagccg ctaccttatc tagtgacgaa 11040
ttagcccgtg caaacagatt ttattttccc gaacatcgcc ggcgttttac tgctggtcgt 11100
ggtattctcc gcagtatctt ggggggctat ttgggtgtgg aaccagggca agttaaattt 11160
gattatgaat cccgtggtaa accaatatta ggcgatcgct ttgccgagag tggtttatta 11220
tttaacttgt cacactccca gaacttggcc ttgtgtgcag tcaattacac gcgccaaatc 11280
ggcatcgatt tagaatatct ccgccccaca tctgatttag aatcccttgc caaaaggttc 11340
tttttaccgc gagaatatga attattgcga tcgctacccg atgagcaaaa acaaaaaatt 11400
ttctttcgtt actggacttg taaagaggct tatcttaaag caacgggtga cggcatcgct 11460
aaattagagg aaattgaaat agcactaact cccacagaac cagctaagtt acagacagct 11520
ccagcgtgga gtctcctaga gctagtgcca gatgataatt gtgttgctgc tgttgccgtg 11580
gcgggttttg gctggcagcc aaaattctgg cattattgag catgcaagct tctccctata 11640
gtgagtcgta ttagcggccg catcgaatat aacttcgtat aatgtatgct atacgaagtt 11700
attagcgatg aggacatgag gttgccccgt attcagtgtc gctgatttgt attgtctgaa 11760
gttgttttta cgttaagttg atgcagatca attaatacga tacctgcgtc ataattgatt 11820
atttgacgtg gtttgatggc ctccacgcac gttgtgatat gtagatgata atcattatca 11880
ctttacgggt cctttccggt gatccgacag gttacggggc ggcgacctcg cgggttttcg 11940
ctatttatga aaattttccg gtttaaggcg tttccgttct tcttcgtcat aacttaatgt 12000
ttttatttaa aataccctct gaaaagaaag gaaacgacag gtgctgaaag cgaggctttt 12060
tggcctctgt cgtttccttt ctctgttttt gtccgtggaa tgaacaatgg aagtcctcgt 12120
ctcgccctcg aattagcccg cctaatgagc gggctttttt tgaattaatt ctcgcgagct 12180
ggcacgacag gtttcccgac tggaaagcgg gcagtgagcg caacgcaatt aatgtaagtt 12240
agcgcgaatt gcaagctggc cgacgcgctg ggctacgtct tgctggcgtt cgggagcaga 12300
agagcataca tctggaagca aagccaggaa agcggcctat ggagctgtgc ggcagcgctc 12360
agtaggcaat ttttcaaaat attgttaagc cttttctgag catggtattt ttcatggtat 12420
taccaattag caggaaaata agccattgaa tataaaagat aaaaatgtct tgtttacaat 12480
agagtggggg gggtcagcct gccgccttgg gccgggtgat gtcgtacttg cccgccgcga 12540
actcggttac cgtccagccc agcgcgacca gctccggcaa cgcctcgcgc acccgcttgc 12600
ggcgcttgcg catggtcgaa ccactggcct ctgacggcca gacatagccg cacaaggtat 12660
ctatggaagc cttgccggtt ttgccggggt cgatccagcc acacagccgc tggtgcagca 12720
ggcgggcggt ttcgctgtcc agcgcccgca cctcgtccat gctgatgcgc acatgctggc 12780
cgccacccat gacggcctgc gcgatcaagg ggttcagggc cacgtacagg cgcccgtccg 12840
cctcgtcgct ggcgtactcc gacagcagcc gaaacccctg ccgcttgcgg ccattctggg 12900
cgatgatgga taccttccaa aggcgctcga tgcagtcctg tatgtgcttg agcgccccac 12960
cactatcgac ctctgccccg atttcctttg ccagcgcccg atagctacct ttgaccacat 13020
ggcattcagc ggtgacggcc tcccacttgg gttccaggaa cagccggagc tgccgtccgc 13080

-continued

```
cttcggtctt gggttccggg ccaagcacta ggccattagg cccagccatg gccaccagcc  13140
cttgcaggat gcgcagatca tcagcgccca gcggctccgg gccgctgaac tcgatccgct  13200
tgccgtcgcc gtagtcatac gtcacgtcca gcttgctgcg cttgcgctcg ccccgcttga  13260
gggcacggaa caggccgggg gccagacagt gcgccgggtc gtgccggacg tggctgaggc  13320
tgtgcttgtt cttaggcttc accacggggc accccccttgc tcttgcgctg cctctccagc  13380
acggcgggct tgagcacccc gccgtcatgc cgcctgaacc accgatcagc gaacggtgcg  13440
ccatagttgg ccttgctcac accgaagcgg acgaagaacc ggcgctggtc gtcgtccaca  13500
ccccattcct cggcctcggc gctggtcatg ctcgacaggt aggactgcca gcggatgtta  13560
tcgaccagta ccgagctgcc ccggctggcc tgctgctggt cgcctgcgcc catcatggcc  13620
gcgcccttgc tggcatggtg caggaacacg atagagcacc cggtatcggc ggcgatggcc  13680
tccatgcgac cgatgacctg ggccatgggg ccgctggcgt tttcttcctc gatgtggaac  13740
cggcgcagcg tgtccagcac catcaggcgg cggccctcgg cggcgcgctt gaggccgtcg  13800
aaccactccg gggccatgat gttgggcagg ctgccgatca gcggctggat cagcaggccg  13860
tcagccacgg cttgccgttc ctcggcgctg aggtgcgccc caagggcgtg caggcggtga  13920
tgaatggcgg tgggcgggtc ttcggcgggc aggtagatca ccgggccggt gggcagttcg  13980
cccacctcca gcagatccgg cccgcctgca atctgtgcgg ccagttgcag ggccagcatg  14040
gatttaccgg caccaccggg cgacaccagc gccccgaccg taccggccac catgttgggc  14100
aaaacgtagt ccagcggtgg cggcgctgct gcgaacgcct ccagaatatt gataggctta  14160
tgggtagcca ttgattgcct cctttgcagg cagttggtgg ttaggcgctg gcggggtcac  14220
taccccccgcc ctgcgccgct ctgagttctt ccaggcactc gcgcagcgcc tcgtattcgt  14280
cgtcggtcag ccagaacttg cgctgacgca tccctttggc cttcatgcgc tcggcatatc  14340
gcgcttggcg tacagcgtca gggctggcca gcaggtcgcc ggtctgcttg tccttttggt  14400
ctttcatatc agtcaccgag aaacttgccg gggccgaaag gcttgtcttc gcggaacaag  14460
gacaaggtgc agccgtcaag gttaaggctg gccatatcag cgactgaaaa gcggccagcc  14520
tcggccttgt ttgacgtata accaaagcca ccgggcaacc aatagccctt gtcacttttg  14580
atcaggtaga ccgaccctga agcgcttttt tcgtattcca taaaaccccc ttctgtgcgt  14640
gagtactcat agtataacag gcgtgagtac caacgcaagc actacatgct gaaatctggc  14700
ccgcccctgt ccatgcctcg ctggcggggt gccggtgccc gtgccagctc ggcccgcgca  14760
agctggacgc tgggcagacc catgaccttg ctgacggtgc gctcgatgta atccgcttcg  14820
tggccgggct tgcgctctgc cagcgctggg ctggcctcgg ccatggcctt gccgatttcc  14880
tcggcactgc ggccccggct ggccagcttc tgcgcggcga taaagtcgca cttgctgagg  14940
tcatgaccga agcgcttgac cagcccggcc atctcgctgc ggtactcgtc cagcgccgtg  15000
cgccggtggc ggctaagctg ccgctcgggc agttcgaggc tggccagcct gcgggccttc  15060
tcctgctgcc gctgggcctg ctcgatctgc tggccagcct gctgcaccag cgccgggcca  15120
gcggtggcgg tcttgccctt ggattcacgc agcagcaccc acggctgata accggcgcgg  15180
gtggtgtgct tgtccttgcg gttggtgaag cccgccaagc ggccatagtg gcggctgtcg  15240
gcgctggccg ggtcggcgtc gtactcgctg gccagcgtcc gggcaatctg cccccgaagt  15300
tcaccgcctg cggcgtcggc caccttgacc catgcctgat agttcttcgg gctggtttcc  15360
actaccaggg caggctcccg gccctcggct ttcatgtcat ccaggtcaaa ctcgctgagg  15420
tcgtccacca gcaccagacc atgccgctcc tgctcggcgg gcctgatata cacgtcattg  15480
```

-continued

```
ccctgggcat tcatccgctt gagccatggc gtgttctgga gcacttcggc ggctgaccat  15540
tcccggttca tcatctggcc ggtgggtgcg tccctgacgc cgatatcgaa gcgctcacag  15600
cccatggcct tgagctgtcg gcctatggcc tgcaaagtcc tgtcgttctt catcgggcca  15660
ccaagcgcag ccagatcgag ccgtcctcgg ttgtcagtgg cgtcaggtcg agcaagagca  15720
acgatgcgat cagcagcacc accgtaggca tcatggaagc cagcatcacg gttagcccata  15780
gcttccagtg ccaccccccgc gacgcgctcc gggcgctctg cgcggcgctg ctcacctcgg  15840
cggctacctc ccgcaactct ttggccagct ccacccatgc cgcccctgtc tggcgctggg  15900
ctttcagcca ctccgccgcc tgcgcctcgc tggcctgctt ggtctggctc atgacctgcc  15960
gggcttcgtc ggccagtgtc gccatgctct gggccagcgg ttcgatctgc tccgctaact  16020
cgttgatgcc tctggatttc ttcactctgt cgattgcgtt catggtctat tgcctcccgg  16080
tattcctgta agtcgatgat ctgggcgttg gcggtgtcga tgttcagggc cacgtctgcc  16140
cggtcggtgc ggatgccccg gccttccatc tccaccacgt tcggccccag gtgaacaccg  16200
ggcaggcgct cgatgccctg cgcctcaagt gttctgtggt caatgcgggc gtcgtggcca  16260
gcccgctcta atgcccggtt ggcatggtcg gcccatgcct cgcgggtctg ctcaagccat  16320
gccttgggct tgagcgcttc ggtcttctgt gccccgccct tctccggggt cttgccgttg  16380
taccgcttga accactgagc ggcgggccgc tcgatgccgt cattgatccg ctcggagatc  16440
atcaggtggc agtgcgggtt ctcgccgcca ccggcatgga tggccagcgt atacggcagg  16500
cgctcggcac cggtcaggtg ctgggcgaac tcggacgcca gcgccttctg ctggtcgagg  16560
gtcagctcga ccggcagggc aaattcgacc tccttgaaca gccgcccatt ggcgcgttca  16620
tacaggtcgg cagcatccca gtagtcggcg ggccgctcga cgaactccgg catgtgcccg  16680
gattcggcgt gcaagacttc atccatgtcg cgggcatact tgccttcgcg ctggatgtag  16740
tcggccttgg ccctggccga ttggccgccc gacctgctgc cggttttcgc cgtaaggtga  16800
taaatcgcca tgctgcctcg ctgttgcttt tgcttttcgg ctccatgcaa tggccctcgg  16860
agagcgcacc gcccgaaggg tggccgttag gccagtttct cgaagagaaa ccggtaagtg  16920
cgccctcccc tacaaagtag ggtcgggatt gccgccgctg tgcctccatg atagcctacg  16980
agacagcaca ttaacaatgg ggtgtcaaga tggttaaggg gagcaacaag gcggcggatc  17040
ggctggccaa gctcgaagaa caacgagcgc gaatcaatgc cgaaattcag cgggagcggg  17100
caagggaaca gcagcaagag cgcaagaacg aaacaaggcg caaggtgctg gtgggggcca  17160
tgattttggc caaggtgaac agcagcgagt ggccggagga tcggctcatg gcggcaatgg  17220
atgcgtacct tgaacgcgac cacgaccgcg ccttgttcgg tctgccgcca cgccagaagg  17280
atgagccggg ctgaatgatc gaccgagaca ggccctgcgg ggctgcacac gcgcccccac  17340
ccttcgggta gggggaaagg ccgctaaagc ggctaaaagc gctccagcgt atttctgcgg  17400
ggtttggtgt ggggtttagc gggctttgcc cgcctttccc cctgccgcgc agcggtgggg  17460
cggtgtgtag cctagcgcag cgaatagacc agctatccgg cctctggccg ggcatattgg  17520
gcaagggcag cagcgcccca caagggcgct gataaccgcg cctagtggat tattcttaga  17580
taatcatgga tggatttttc caacaccccg ccagcccccg cccctgctgg gtttgcaggt  17640
ttgggggcgt gacagttatt gcaggggttc gtgacagtta ttgcaggggg gcgtgacagt  17700
tattgcaggg gttcgtgaca gttagtacgg gagtgacggg cactggctgg caatgtctag  17760
caacggcagg catttcggct gagggtaaaa gaactttccg ctaagcgata gactgtatgt  17820
```

aaacacagta ttgcaaggac gcggaacatg cctcatgtgg cggccagga 17869

<210> SEQ ID NO 89
<211> LENGTH: 27
<212> TYPE: DNA
<213> ORGANISM: Artificial Sequence
<220> FEATURE:
<223> OTHER INFORMATION: Sfp-FW Primer

<400> SEQUENCE: 89
catgccatgg aaatttatgg gatttac 27

<210> SEQ ID NO 90
<211> LENGTH: 28
<212> TYPE: DNA
<213> ORGANISM: Artificial Sequence
<220> FEATURE:
<223> OTHER INFORMATION: Sfp-Rv Primer

<400> SEQUENCE: 90
ccgctcgagc tacaacagtt cttcatag 28

<210> SEQ ID NO 91
<211> LENGTH: 26
<212> TYPE: DNA
<213> ORGANISM: Artificial Sequence
<220> FEATURE:
<223> OTHER INFORMATION: MPPT-Fw Primer

<400> SEQUENCE: 91
catgccatgg ttatatctac cgatga 26

<210> SEQ ID NO 92
<211> LENGTH: 25
<212> TYPE: DNA
<213> ORGANISM: Artificial Sequence
<220> FEATURE:
<223> OTHER INFORMATION: MPPT-Rv Primer

<400> SEQUENCE: 92
ccgctcgagt agatcagaaa ggcca 25

<210> SEQ ID NO 93
<211> LENGTH: 26
<212> TYPE: DNA
<213> ORGANISM: Artificial Sequence
<220> FEATURE:
<223> OTHER INFORMATION: SPPT-Fw Primer

<400> SEQUENCE: 93
catgccatgg tcccccagcc ccaaat 26

<210> SEQ ID NO 94
<211> LENGTH: 25
<212> TYPE: DNA
<213> ORGANISM: Artificial Sequence
<220> FEATURE:
<223> OTHER INFORMATION: SPPT-Rv Primer

<400> SEQUENCE: 94
ccgctcgagg ggcaatgaat caagg 25

<210> SEQ ID NO 95
<211> LENGTH: 26
<212> TYPE: DNA
<213> ORGANISM: Artificial Sequence
<220> FEATURE:
<223> OTHER INFORMATION: SePPT-Fw Primer

<400> SEQUENCE: 95
catgccatgg aacgccccaa ccctag 26

<210> SEQ ID NO 96
<211> LENGTH: 28
<212> TYPE: DNA
<213> ORGANISM: Artificial Sequence
<220> FEATURE:
<223> OTHER INFORMATION: SePPT-Rv Primer

<400> SEQUENCE: 96
ccgctcgaga tgatttttcc ggattatg 28

<210> SEQ ID NO 97
<211> LENGTH: 25
<212> TYPE: DNA
<213> ORGANISM: Artificial Sequence
<220> FEATURE:
<223> OTHER INFORMATION: APPT-Fw Primer

<400> SEQUENCE: 97
catgccatgg tgcagcatac ttggc 25

<210> SEQ ID NO 98
<211> LENGTH: 26
<212> TYPE: DNA
<213> ORGANISM: Artificial Sequence
<220> FEATURE:
<223> OTHER INFORMATION: APPT-Rv Primer

<400> SEQUENCE: 98
ccgctcgaga taatgccaga attttg 26

<210> SEQ ID NO 99
<211> LENGTH: 28
<212> TYPE: DNA
<213> ORGANISM: Artificial Sequence
<220> FEATURE:
<223> OTHER INFORMATION: AvPPT-Fw Primer

<400> SEQUENCE: 99
catgccatgg tgcagcatac ttggctac 28

<210> SEQ ID NO 100
<211> LENGTH: 28
<212> TYPE: DNA
<213> ORGANISM: Artificial Sequence
<220> FEATURE:
<223> OTHER INFORMATION: AvPPT-Rv Primer

<400> SEQUENCE: 100
ccgctcgaga tactgccaga attttggc 28

<210> SEQ ID NO 101
<211> LENGTH: 26
<212> TYPE: DNA
<213> ORGANISM: Artificial Sequence
<220> FEATURE:
<223> OTHER INFORMATION: FPPT-Fw Primer

<400> SEQUENCE: 101
catgccatgg ggtctgagac taatca 26

```
<210> SEQ ID NO 102
<211> LENGTH: 27
<212> TYPE: DNA
<213> ORGANISM: Artificial Sequence
<220> FEATURE:
<223> OTHER INFORMATION: FPPT-Rv Primer

<400> SEQUENCE: 102

ccgctcgaga tactgccagt actttaa                                           27


<210> SEQ ID NO 103
<211> LENGTH: 26
<212> TYPE: DNA
<213> ORGANISM: Artificial Sequence
<220> FEATURE:
<223> OTHER INFORMATION: SFACP-Fw Primer

<400> SEQUENCE: 103

catgccatgg atcaggaaat ttttga                                            26


<210> SEQ ID NO 104
<211> LENGTH: 27
<212> TYPE: DNA
<213> ORGANISM: Artificial Sequence
<220> FEATURE:
<223> OTHER INFORMATION: SFACP-Rv Primer

<400> SEQUENCE: 104

ccgctcgagt ttactttcga tatgctc                                           27


<210> SEQ ID NO 105
<211> LENGTH: 23
<212> TYPE: DNA
<213> ORGANISM: Artificial Sequence
<220> FEATURE:
<223> OTHER INFORMATION: AFACP-Fw Primer

<400> SEQUENCE: 105

ggaattccat atgagccaat cag                                               23


<210> SEQ ID NO 106
<211> LENGTH: 27
<212> TYPE: DNA
<213> ORGANISM: Artificial Sequence
<220> FEATURE:
<223> OTHER INFORMATION: AFACP-Rv Primer

<400> SEQUENCE: 106

ccgctcgaga gctgatgcgg caacttg                                           27


<210> SEQ ID NO 107
<211> LENGTH: 29
<212> TYPE: DNA
<213> ORGANISM: Artificial Sequence
<220> FEATURE:
<223> OTHER INFORMATION: APACP-Fw Primer

<400> SEQUENCE: 107

catgccatgg gtctaaaaca aaattatag                                         29


<210> SEQ ID NO 108
<211> LENGTH: 30
<212> TYPE: DNA
<213> ORGANISM: Artificial Sequence
<220> FEATURE:
<223> OTHER INFORMATION: APACP-Rv Primer
```

<400> SEQUENCE: 108
ccgctcgaga gattgttctt ccaattcttc 30

<210> SEQ ID NO 109
<211> LENGTH: 28
<212> TYPE: DNA
<213> ORGANISM: Artificial Sequence
<220> FEATURE:
<223> OTHER INFORMATION: APNPCP-Fw Primer

<400> SEQUENCE: 109
catgccatgg aacaatctac aactaatc 28

<210> SEQ ID NO 110
<211> LENGTH: 27
<212> TYPE: DNA
<213> ORGANISM: Artificial Sequence
<220> FEATURE:
<223> OTHER INFORMATION: APNPCP-Rv Primer

<400> SEQUENCE: 110
ccgctcgaga tcagtaatag gcgattg 27

<210> SEQ ID NO 111
<211> LENGTH: 30
<212> TYPE: DNA
<213> ORGANISM: Artificial Sequence
<220> FEATURE:
<223> OTHER INFORMATION: FNPCP-Fw Primer

<400> SEQUENCE: 111
catgccatgg cccaacgccc tatcattatc 30

<210> SEQ ID NO 112
<211> LENGTH: 27
<212> TYPE: DNA
<213> ORGANISM: Artificial Sequence
<220> FEATURE:
<223> OTHER INFORMATION: FNPCP-Rv Primer

<400> SEQUENCE: 112
ccgctcgagt tcaacttcat cactatc 27

<210> SEQ ID NO 113
<211> LENGTH: 28
<212> TYPE: DNA
<213> ORGANISM: Artificial Sequence
<220> FEATURE:
<223> OTHER INFORMATION: FisPCP-Fw Primer

<400> SEQUENCE: 113
catgccatgg gatcgcttcc caaacctg 28

<210> SEQ ID NO 114
<211> LENGTH: 27
<212> TYPE: DNA
<213> ORGANISM: Artificial Sequence
<220> FEATURE:
<223> OTHER INFORMATION: FisPCP-Rv Primer

<400> SEQUENCE: 114
ccgctcgagt gaattgggaa aaacatc 27

<210> SEQ ID NO 115

<211> LENGTH: 27
<212> TYPE: DNA
<213> ORGANISM: Artificial Sequence
<220> FEATURE:
<223> OTHER INFORMATION: FNsACP-Fw Primer

<400> SEQUENCE: 115
catgccatgg cttttctaga agatgtc 27

<210> SEQ ID NO 116
<211> LENGTH: 27
<212> TYPE: DNA
<213> ORGANISM: Artificial Sequence
<220> FEATURE:
<223> OTHER INFORMATION: FNsACP-Rv Primer

<400> SEQUENCE: 116
ccgctcgagg gaattaccta gaaaagc 27

<210> SEQ ID NO 117
<211> LENGTH: 28
<212> TYPE: DNA
<213> ORGANISM: Artificial Sequence
<220> FEATURE:
<223> OTHER INFORMATION: AprACP-Fw Primer

<400> SEQUENCE: 117
catgccatgg aaatttttga acaggaat 28

<210> SEQ ID NO 118
<211> LENGTH: 27
<212> TYPE: DNA
<213> ORGANISM: Artificial Sequence
<220> FEATURE:
<223> OTHER INFORMATION: AprACP-Rv Primer

<400> SEQUENCE: 118
ccgctcgaga ctaaaattaa tatcttc 27

<210> SEQ ID NO 119
<211> LENGTH: 26
<212> TYPE: DNA
<213> ORGANISM: Artificial Sequence
<220> FEATURE:
<223> OTHER INFORMATION: MACP-Fw Primer

<400> SEQUENCE: 119
catgccatgg tgacaactgt tcaatc 26

<210> SEQ ID NO 120
<211> LENGTH: 25
<212> TYPE: DNA
<213> ORGANISM: Artificial Sequence
<220> FEATURE:
<223> OTHER INFORMATION: MACP-Rv Primer

<400> SEQUENCE: 120
ccgctcgaga agatataatt cccct 25

<210> SEQ ID NO 121
<211> LENGTH: 25
<212> TYPE: DNA
<213> ORGANISM: Artificial Sequence
<220> FEATURE:
<223> OTHER INFORMATION: ScACP-Fw Primer

<400> SEQUENCE: 121
catgccatgg agcagcggct ggctc 25

<210> SEQ ID NO 122
<211> LENGTH: 25
<212> TYPE: DNA
<213> ORGANISM: Artificial Sequence
<220> FEATURE:
<223> OTHER INFORMATION: ScACP-Rv Primer

<400> SEQUENCE: 122
ccgctcgagc tcctgctcgc cgaac 25

<210> SEQ ID NO 123
<211> LENGTH: 24
<212> TYPE: DNA
<213> ORGANISM: Artificial Sequence
<220> FEATURE:
<223> OTHER INFORMATION: SSPCP-Fw Primer

<400> SEQUENCE: 123
catgccatgg aggagatcct cgcc 24

<210> SEQ ID NO 124
<211> LENGTH: 26
<212> TYPE: DNA
<213> ORGANISM: Artificial Sequence
<220> FEATURE:
<223> OTHER INFORMATION: SSPCP-Rv Primer

<400> SEQUENCE: 124
ccgctcgagg gtacgcccgg ccaggc 26

<210> SEQ ID NO 125
<211> LENGTH: 27
<212> TYPE: DNA
<213> ORGANISM: Artificial Sequence
<220> FEATURE:
<223> OTHER INFORMATION: Ptrc-F Primer

<400> SEQUENCE: 125
ggatccattc tgaaatgagc tgttgac 27

<210> SEQ ID NO 126
<211> LENGTH: 26
<212> TYPE: DNA
<213> ORGANISM: Artificial Sequence
<220> FEATURE:
<223> OTHER INFORMATION: SHI-F Primer

<400> SEQUENCE: 126
ctcgagatgg gtacacctca cgctac 26

<210> SEQ ID NO 127
<211> LENGTH: 24
<212> TYPE: DNA
<213> ORGANISM: Artificial Sequence
<220> FEATURE:
<223> OTHER INFORMATION: SHI-R Primer

<400> SEQUENCE: 127
agatcttcag cacaaacatt tctg 24

<210> SEQ ID NO 128
<211> LENGTH: 24
<212> TYPE: DNA

<213> ORGANISM: Artificial Sequence
<220> FEATURE:
<223> OTHER INFORMATION: PRNPB-F Primer

<400> SEQUENCE: 128
agatctttca atgcggtcca atac 24

<210> SEQ ID NO 129
<211> LENGTH: 40
<212> TYPE: DNA
<213> ORGANISM: Artificial Sequence
<220> FEATURE:
<223> OTHER INFORMATION: PRNPB-R Primer

<400> SEQUENCE: 129
gttgatgcct accatcatat gtttttctag tgtgccattg 40

<210> SEQ ID NO 130
<211> LENGTH: 40
<212> TYPE: DNA
<213> ORGANISM: Artificial Sequence
<220> FEATURE:
<223> OTHER INFORMATION: FPPT-F Primer

<400> SEQUENCE: 130
tggcacacta gaaaaacata tgatggtagg catcaactat 40

<210> SEQ ID NO 131
<211> LENGTH: 26
<212> TYPE: DNA
<213> ORGANISM: Artificial Sequence
<220> FEATURE:
<223> OTHER INFORMATION: FPPT-R Primer

<400> SEQUENCE: 131
gagctctcac tctggccacc gccaac 26

<210> SEQ ID NO 132
<211> LENGTH: 40
<212> TYPE: DNA
<213> ORGANISM: Artificial Sequence
<220> FEATURE:
<223> OTHER INFORMATION: APPT-F Primer

<400> SEQUENCE: 132
tggcacacta gaaaaacata tgatgttgca gcatacttgg 40

<210> SEQ ID NO 133
<211> LENGTH: 27
<212> TYPE: DNA
<213> ORGANISM: Artificial Sequence
<220> FEATURE:
<223> OTHER INFORMATION: APPT-R Primer

<400> SEQUENCE: 133
gagctcataa tgccagaatt ttggctg 27

<210> SEQ ID NO 134
<211> LENGTH: 27
<212> TYPE: DNA
<213> ORGANISM: Artificial Sequence
<220> FEATURE:
<223> OTHER INFORMATION: SPPT-Up-F Primer

<400> SEQUENCE: 134
ccaagcttcc tggcagtagt gttggtg 27

<210> SEQ ID NO 135
<211> LENGTH: 40
<212> TYPE: DNA
<213> ORGANISM: Artificial Sequence
<220> FEATURE:
<223> OTHER INFORMATION: SPPT-Up-R Primer

<400> SEQUENCE: 135
ggtaacgaaa actagtcgta cgaggtcagt ttaaacagcg 40

<210> SEQ ID NO 136
<211> LENGTH: 40
<212> TYPE: DNA
<213> ORGANISM: Artificial Sequence
<220> FEATURE:
<223> OTHER INFORMATION: SPPT-Dn-F Primer

<400> SEQUENCE: 136
aaactgacct cgtacgacta gttttcgtta ccttgggccg 40

<210> SEQ ID NO 137
<211> LENGTH: 26
<212> TYPE: DNA
<213> ORGANISM: Artificial Sequence
<220> FEATURE:
<223> OTHER INFORMATION: SPPT-Dn-R Primer

<400> SEQUENCE: 137
gtgaattcgg gctacaccgt cgctac 26

<210> SEQ ID NO 138
<211> LENGTH: 35
<212> TYPE: DNA
<213> ORGANISM: Artificial Sequence
<220> FEATURE:
<223> OTHER INFORMATION: Syn-APPT-F Primer

<400> SEQUENCE: 138
taaagaggta tatattaatg ttgcagcata cttgg 35

<210> SEQ ID NO 139
<211> LENGTH: 86
<212> TYPE: DNA
<213> ORGANISM: Artificial Sequence
<220> FEATURE:
<223> OTHER INFORMATION: Syn-APPT-R Primer

<400> SEQUENCE: 139
catagctgtt tcctgtgtca aaaaacccct caagacccgt ttagaggccc caaggggtta 60
tgctagtcaa taatgccaga attttg 86

<210> SEQ ID NO 140
<211> LENGTH: 36
<212> TYPE: DNA
<213> ORGANISM: Artificial Sequence
<220> FEATURE:
<223> OTHER INFORMATION: Syn-MPPT-F Primer

<400> SEQUENCE: 140
taaagaggta tatattaatg tttatatcta ccgatg 36

<210> SEQ ID NO 141
<211> LENGTH: 84
<212> TYPE: DNA

<213> ORGANISM: Artificial Sequence
<220> FEATURE:
<223> OTHER INFORMATION: Syn-MPPT-R Primer

<400> SEQUENCE: 141
catagctgtt tcctgtgtca aaaaacccct caagacccgt ttagaggccc caaggggtta 60
tgctagtcat agatcagaaa ggcc 84

<210> SEQ ID NO 142
<211> LENGTH: 38
<212> TYPE: DNA
<213> ORGANISM: Artificial Sequence
<220> FEATURE:
<223> OTHER INFORMATION: Syn-SFP-F Primer

<400> SEQUENCE: 142
taaagaggta tatattaatg aaaatttatg ggatttac 38

<210> SEQ ID NO 143
<211> LENGTH: 85
<212> TYPE: DNA
<213> ORGANISM: Artificial Sequence
<220> FEATURE:
<223> OTHER INFORMATION: Syn-SFP-R Primer

<400> SEQUENCE: 143
catagctgtt tcctgtgtca aaaaacccct caagacccgt ttagaggccc caaggggtta 60
tgctagctac aacagttctt catag 85

<210> SEQ ID NO 144
<211> LENGTH: 27
<212> TYPE: DNA
<213> ORGANISM: Artificial Sequence
<220> FEATURE:
<223> OTHER INFORMATION: Ptrc-F Primer

<400> SEQUENCE: 144
ctcgtacgat tctgaaatga gctgttg 27

<210> SEQ ID NO 145
<211> LENGTH: 35
<212> TYPE: DNA
<213> ORGANISM: Artificial Sequence
<220> FEATURE:
<223> OTHER INFORMATION: Ptrc-APPT-R Primer

<400> SEQUENCE: 145
ccaagtatgc tgcaacatta atatatacct cttta 35

<210> SEQ ID NO 146
<211> LENGTH: 36
<212> TYPE: DNA
<213> ORGANISM: Artificial Sequence
<220> FEATURE:
<223> OTHER INFORMATION: Ptrc-MPPT-R Primer

<400> SEQUENCE: 146
catcggtaga tataaacatt aatatatacc tcttta 36

<210> SEQ ID NO 147
<211> LENGTH: 38
<212> TYPE: DNA
<213> ORGANISM: Artificial Sequence
<220> FEATURE:
<223> OTHER INFORMATION: Ptrc-SFP-R Primer

<400> SEQUENCE: 147
gtaaatccca taaattttca ttaatatata cctcttta 38

<210> SEQ ID NO 148
<211> LENGTH: 36
<212> TYPE: DNA
<213> ORGANISM: Artificial Sequence
<220> FEATURE:
<223> OTHER INFORMATION: Kana-F Primer

<400> SEQUENCE: 148
gtcttgaggg gtttttgac acaggaaaca gctatg 36

<210> SEQ ID NO 149
<211> LENGTH: 26
<212> TYPE: DNA
<213> ORGANISM: Artificial Sequence
<220> FEATURE:
<223> OTHER INFORMATION: Kana-R Primer

<400> SEQUENCE: 149
aaactagtaa acgacggcca gtgaat 26

<210> SEQ ID NO 150
<211> LENGTH: 19
<212> TYPE: DNA
<213> ORGANISM: Artificial Sequence
<220> FEATURE:
<223> OTHER INFORMATION: RT-rnpB-F Primer

<400> SEQUENCE: 150
cgtgaggaca gtgccacag 19

<210> SEQ ID NO 151
<211> LENGTH: 19
<212> TYPE: DNA
<213> ORGANISM: Artificial Sequence
<220> FEATURE:
<223> OTHER INFORMATION: RT-rnpB-R Primer

<400> SEQUENCE: 151
cgctcttacc gcacctttg 19

<210> SEQ ID NO 152
<211> LENGTH: 18
<212> TYPE: DNA
<213> ORGANISM: Artificial Sequence
<220> FEATURE:
<223> OTHER INFORMATION: RT-SPPT-F Primer

<400> SEQUENCE: 152
tttgattggc ttaagtac 18

<210> SEQ ID NO 153
<211> LENGTH: 18
<212> TYPE: DNA
<213> ORGANISM: Artificial Sequence
<220> FEATURE:
<223> OTHER INFORMATION: RT-SPPT-R Primer

<400> SEQUENCE: 153
aatgcttcct tcgctgtc 18

<210> SEQ ID NO 154

<211> LENGTH: 18
<212> TYPE: DNA
<213> ORGANISM: Artificial Sequence
<220> FEATURE:
<223> OTHER INFORMATION: RT-APPT-F Primer

<400> SEQUENCE: 154
atctagtgac gaattagc 18

<210> SEQ ID NO 155
<211> LENGTH: 17
<212> TYPE: DNA
<213> ORGANISM: Artificial Sequence
<220> FEATURE:
<223> OTHER INFORMATION: RT-APPT-R Primer

<400> SEQUENCE: 155
aataaaccac tctcggc 17

<210> SEQ ID NO 156
<211> LENGTH: 18
<212> TYPE: DNA
<213> ORGANISM: Artificial Sequence
<220> FEATURE:
<223> OTHER INFORMATION: RT-MPPT-F Primer

<400> SEQUENCE: 156
gtattaacta tcaattgc 18

<210> SEQ ID NO 157
<211> LENGTH: 18
<212> TYPE: DNA
<213> ORGANISM: Artificial Sequence
<220> FEATURE:
<223> OTHER INFORMATION: RT-MPPT-R Primer

<400> SEQUENCE: 157
aagctatcta aatctttc 18

<210> SEQ ID NO 158
<211> LENGTH: 18
<212> TYPE: DNA
<213> ORGANISM: Artificial Sequence
<220> FEATURE:
<223> OTHER INFORMATION: RT-Sfp-F Primer

<400> SEQUENCE: 158
tagtcattct ggtcgctg 18

<210> SEQ ID NO 159
<211> LENGTH: 18
<212> TYPE: DNA
<213> ORGANISM: Artificial Sequence
<220> FEATURE:
<223> OTHER INFORMATION: RT-Sfp-R Primer

<400> SEQUENCE: 159
ataaatcaga gtattcgg 18

<210> SEQ ID NO 160
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 160
ttgacagcta gctcagtcct aggtataatg ctagc 35

<210> SEQ ID NO 161
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 161
ttgacggcta gctcagtcct aggtacagtg ctagc 35

<210> SEQ ID NO 162
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 162
tttacagcta gctcagtcct aggtattatg ctagc 35

<210> SEQ ID NO 163
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 163
ttgacagcta gctcagtcct aggtactgtg ctagc 35

<210> SEQ ID NO 164
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 164
ctgatagcta gctcagtcct agggattatg ctagc 35

<210> SEQ ID NO 165
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 165
ttgacagcta gctcagtcct aggtattgtg ctagc 35

<210> SEQ ID NO 166
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 166
tttacggcta gctcagtcct aggtactatg ctagc 35

<210> SEQ ID NO 167
<211> LENGTH: 35
<212> TYPE: DNA

<213> ORGANISM: Artificial Sequence
<220> FEATURE:
<223> OTHER INFORMATION: Exemplary promoter from J23 library

<400> SEQUENCE: 167
tttacggcta gctcagtcct aggtatagtg ctagc 35

<210> SEQ ID NO 168
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 168
tttacggcta gctcagccct aggtattatg ctagc 35

<210> SEQ ID NO 169
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 169
ctgacagcta gctcagtcct aggtataatg ctagc 35

<210> SEQ ID NO 170
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 170
tttacagcta gctcagtcct agggactgtg ctagc 35

<210> SEQ ID NO 171
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 171
tttacggcta gctcagtcct aggtacaatg ctagc 35

<210> SEQ ID NO 172
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 172
ttgacggcta gctcagtcct aggtatagtg ctagc 35

<210> SEQ ID NO 173
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 173
ctgatagcta gctcagtcct agggattatg ctagc 35

<210> SEQ ID NO 174
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 174
ctgatggcta gctcagtcct agggattatg ctagc 35

<210> SEQ ID NO 175
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 175
tttatggcta gctcagtcct aggtacaatg ctagc 35

<210> SEQ ID NO 176
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 176
tttatagcta gctcagccct tggtacaatg ctagc 35

<210> SEQ ID NO 177
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 177
ttgacagcta gctcagtcct agggactatg ctagc 35

<210> SEQ ID NO 178
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 178
ttgacagcta gctcagtcct agggattgtg ctagc 35

<210> SEQ ID NO 179
<211> LENGTH: 35
<212> TYPE: DNA
<213> ORGANISM: Artificial Sequence
<220> FEATURE:
<223> OTHER INFORMATION: Exemplary promoter from J23 library

<400> SEQUENCE: 179
ttgacggcta gctcagtcct aggtattgtg ctagc 35